(12) United States Patent
Loew et al.

(10) Patent No.: US 11,667,691 B2
(45) Date of Patent: Jun. 6, 2023

(54) TREATMENT OF CANCER USING CHIMERIC CD3 RECEPTOR PROTEINS

(71) Applicants: Novartis AG, Basel (CH); The Trustees of the University of Pennsylvania, Philadelphia, PA (US)

(72) Inventors: Andreas Loew, Boston, MA (US); Brian Granda, Salisbury, MA (US); Melissa Ramones, Cambridge, MA (US)

(73) Assignees: Novartis AG, Basel (CH); The Trustees of the University of Pennsylvania, Philadelphia, PA (US)

(*) Notice: Subject to any disclaimer, the term of this patent is extended or adjusted under 35 U.S.C. 154(b) by 578 days.

(21) Appl. No.: 15/750,796

(22) PCT Filed: Aug. 5, 2016

(86) PCT No.: PCT/US2016/045816
§ 371 (c)(1),
(2) Date: Feb. 6, 2018

(87) PCT Pub. No.: WO2017/027392
PCT Pub. Date: Feb. 16, 2017

(65) Prior Publication Data
US 2018/0230193 A1 Aug. 16, 2018

Related U.S. Application Data

(60) Provisional application No. 62/202,446, filed on Aug. 7, 2015.

(51) Int. Cl.
C07K 14/725 (2006.01)
C07K 16/28 (2006.01)
C07K 16/30 (2006.01)
C07K 19/00 (2006.01)

(52) U.S. Cl.
CPC ...... *C07K 14/7051* (2013.01); *C07K 16/2803* (2013.01); *C07K 16/30* (2013.01); *C07K 19/00* (2013.01); *C07K 2317/622* (2013.01); *C07K 2317/73* (2013.01); *C07K 2319/03* (2013.01); *C07K 2319/70* (2013.01)

(58) Field of Classification Search
CPC . C07K 19/00; C07K 2319/03; C07K 2319/00
See application file for complete search history.

(56) References Cited

U.S. PATENT DOCUMENTS

| 5,359,046 A | 10/1994 | Capon et al. |
| 5,686,281 A | 11/1997 | Roberts |
| 5,712,149 A | 1/1998 | Roberts |
| 5,874,240 A | 2/1999 | Ni et al. |
| 5,906,936 A | 5/1999 | Eshhar et al. |
| 6,103,521 A | 8/2000 | Capon et al. |
| 6,319,494 B1 | 11/2001 | Capon et al. |
| 6,355,779 B1 | 3/2002 | Goodwin et al. |
| 6,410,319 B1 | 6/2002 | Raubitschek et al. |
| 6,569,997 B1 | 5/2003 | Kwon |
| 7,049,136 B2 | 5/2006 | Seed et al. |
| 7,052,906 B1 | 5/2006 | Lawson et al. |
| 7,070,995 B2 | 7/2006 | Jensen |
| 7,265,209 B2 | 9/2007 | Jensen |
| 7,319,143 B2 | 1/2008 | Gross et al. |
| 7,320,787 B2 | 1/2008 | Seed et al. |
| 7,446,190 B2 | 11/2008 | Sadelain et al. |
| 7,446,191 B2 | 11/2008 | Jensen |
| 7,514,537 B2 | 4/2009 | Jensen |
| 7,638,326 B2 | 12/2009 | June et al. |
| 7,741,465 B1 | 6/2010 | Eshhar et al. |
| 7,745,140 B2 | 6/2010 | June et al. |
| 7,754,482 B2 | 7/2010 | Riley et al. |
| 7,994,298 B2 | 8/2011 | Zhang et al. |
| 8,211,422 B2 | 7/2012 | Eshhar et al. |
| 8,252,914 B2 | 8/2012 | Zhang et al. |
| 8,389,282 B2 | 3/2013 | Sadelain et al. |
| 8,399,645 B2 | 3/2013 | Campana et al. |

(Continued)

FOREIGN PATENT DOCUMENTS

| EP | 0574512 A1 | 12/1993 |
| EP | 0871495 A1 | 10/1998 |

(Continued)

OTHER PUBLICATIONS

Kim et al. (J. Immunology 2010 185: 2951-2959) (Year: 2010).*
Halotag (Promega Corp. May 30, 2006) (Year: 2006).*
Snap-Tag (New England Biolabs Corp. May 12, 2020) (Year: 2020).*
Prazma and Tedder (Immunology Letters 2008, 115: 1-8) (Year: 2008).*
Inobe and Nukina (J. Bioscience and Bioengineering 122 (1): 40-46 2016) (Year: 2016).*

(Continued)

*Primary Examiner* — Peter J Reddig
(74) *Attorney, Agent, or Firm* — K&L Gates LLP

(57) ABSTRACT

The present disclosure features the use of chimeric CD3 proteins to modulate T cell Receptor (TCR) signaling. Specifically, the disclosure is based, in part, on the discovery that chimeric CD3 proteins (e.g., CD3delta, CD3gamma, and CD3epsilon) having all or most of their extracellular domain fused to an antigen binding domain can activate the TCR in the presence of a cognate antigen. The disclosure is further based on the observation that the above chimeric proteins can be potentiated through the inclusion of a co-stimulatory domain in the intracellular portion of the chimeric molecule. Thus, the preferred elements of the engineered signaling complexes of the disclosure include an antigen binding domain, an extracellular domain derived from one of the above CD3 proteins, and an intracellular co-stimulatory domain.

44 Claims, 40 Drawing Sheets
Specification includes a Sequence Listing.

(56) References Cited

U.S. PATENT DOCUMENTS

| | | |
|---|---|---|
| 8,465,743 B2 | 6/2013 | Rosenberg et al. |
| 8,637,307 B2 | 1/2014 | June et al. |
| 8,722,400 B2 | 5/2014 | Riley et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,394,368 B2 | 7/2016 | Brogdon et al. |
| 9,573,988 B2 | 2/2017 | Brogdon et al. |
| 9,745,368 B2 | 8/2017 | Milone et al. |
| 9,777,061 B2 | 10/2017 | Ebersbach et al. |
| 9,815,901 B2 | 11/2017 | Brogdon et al. |
| 2003/0060444 A1 | 3/2003 | Finney et al. |
| 2003/0077249 A1 | 4/2003 | Bebbington et al. |
| 2003/0148982 A1 | 8/2003 | Brenner et al. |
| 2003/0224520 A1 | 12/2003 | June et al. |
| 2004/0038886 A1 | 2/2004 | Finney et al. |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2007/0036773 A1 | 2/2007 | Cooper et al. |
| 2008/0131415 A1 | 6/2008 | Riddell et al. |
| 2009/0257994 A1 | 10/2009 | Jensen |
| 2011/0052554 A1 | 3/2011 | Zakrzewski et al. |
| 2012/0148552 A1 | 6/2012 | Jensen |
| 2012/0321667 A1 | 12/2012 | Sentman |
| 2013/0071409 A1 | 3/2013 | Riley et al. |
| 2013/0071414 A1 | 3/2013 | Dotti et al. |
| 2013/0149337 A1 | 6/2013 | Cooper et al. |
| 2013/0155909 A1 | 6/2013 | Jackson et al. |
| 2013/0287748 A1 | 10/2013 | June et al. |
| 2014/0050708 A1 | 2/2014 | Powell et al. |
| 2014/0099309 A1 | 4/2014 | Powell, Jr. et al. |
| 2014/0099340 A1 | 4/2014 | June et al. |
| 2014/0106449 A1 | 4/2014 | June et al. |
| 2014/0186947 A1 | 7/2014 | June et al. |
| 2014/0212446 A1 | 7/2014 | Riley et al. |
| 2014/0219975 A1 | 8/2014 | June et al. |
| 2014/0227237 A1 | 8/2014 | June et al. |
| 2014/0271635 A1 | 9/2014 | Brogdon et al. |
| 2014/0322169 A1 | 10/2014 | Harper et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0370045 A1 | 12/2014 | June et al. |
| 2015/0017141 A1 | 1/2015 | June et al. |
| 2015/0140019 A1 | 5/2015 | June et al. |
| 2015/0190428 A1 | 7/2015 | June et al. |
| 2015/0202286 A1 | 7/2015 | June et al. |
| 2015/0283178 A1 | 10/2015 | June et al. |
| 2015/0290244 A1 | 10/2015 | June et al. |
| 2015/0342994 A1 | 12/2015 | Riley et al. |
| 2016/0046724 A1 | 2/2016 | Brogdon et al. |
| 2016/0051651 A1 | 2/2016 | Brogdon et al. |
| 2016/0068601 A1 | 3/2016 | Brogdon et al. |
| 2016/0096892 A1 | 4/2016 | Brogdon et al. |
| 2016/0185861 A1 | 6/2016 | Bedoya et al. |
| 2016/0311907 A1 | 10/2016 | Brogdon et al. |
| 2016/0311917 A1 | 10/2016 | Beatty et al. |
| 2016/0340406 A1 | 11/2016 | Zhao et al. |
| 2016/0362472 A1 | 12/2016 | Bitter et al. |
| 2017/0008963 A1 | 1/2017 | Brogdon et al. |
| 2017/0081411 A1 | 3/2017 | Engels et al. |
| 2017/0137783 A1 | 5/2017 | Bedoya et al. |
| 2017/0183415 A1 | 6/2017 | Brogdon et al. |
| 2017/0209492 A1 | 7/2017 | June et al. |
| 2017/0211055 A1 | 7/2017 | Brogdon et al. |
| 2017/0226495 A1 | 8/2017 | Guimaraes |
| 2017/0239294 A1 | 8/2017 | Thomas-Tikhonenko et al. |
| 2017/0260268 A1 | 9/2017 | Beatty et al. |
| 2017/0274014 A1 | 9/2017 | Brogdon et al. |
| 2017/0306416 A1 | 10/2017 | Bedoya et al. |
| 2017/0335281 A1 | 11/2017 | Loew et al. |
| 2018/0022795 A1 | 1/2018 | Milone et al. |
| 2018/0044423 A1 | 2/2018 | Ebersbach et al. |
| 2018/0044424 A1 | 2/2018 | June et al. |
| 2018/0066034 A1* | 3/2018 | Ma .................. A61K 39/39 |
| 2018/0118834 A1 | 5/2018 | Brogdon et al. |
| 2018/0125892 A1 | 5/2018 | Brannetti et al. |
| 2018/0133296 A1 | 5/2018 | Barrett et al. |
| 2018/0140602 A1 | 5/2018 | Angst et al. |
| 2018/0252727 A1 | 9/2018 | Garfall et al. |
| 2018/0258149 A1 | 9/2018 | Motz et al. |
| 2018/0298068 A1 | 10/2018 | Albelda |
| 2018/0312595 A1 | 11/2018 | Brogdon et al. |
| 2019/0000880 A1 | 1/2019 | Motz et al. |
| 2019/0000944 A1 | 1/2019 | Brogdon et al. |
| 2019/0135940 A1 | 5/2019 | Brogdon et al. |
| 2019/0151365 A1 | 5/2019 | Anak et al. |
| 2019/0153061 A1 | 5/2019 | Brogdon et al. |
| 2019/0161542 A1 | 5/2019 | Gill et al. |
| 2019/0263914 A1 | 8/2019 | Brogdon et al. |
| 2019/0292238 A1 | 9/2019 | Bitter et al. |
| 2019/0292257 A1 | 9/2019 | Bedoya et al. |
| 2019/0298715 A1 | 10/2019 | Motz et al. |
| 2019/0330356 A1 | 10/2019 | Brogdon et al. |
| 2019/0336504 A1 | 11/2019 | Gill et al. |
| 2019/0375815 A1* | 12/2019 | Engels .............. C07K 16/2803 |
| 2019/0382500 A1 | 12/2019 | Abujoub et al. |
| 2019/0388471 A1 | 12/2019 | June et al. |
| 2019/0389928 A1 | 12/2019 | Posey et al. |
| 2020/0048359 A1 | 2/2020 | Albelda et al. |
| 2020/0055948 A1 | 2/2020 | Daley et al. |
| 2020/0061113 A1 | 2/2020 | Kassim et al. |
| 2020/0085869 A1 | 3/2020 | Schuster et al. |
| 2020/0087376 A1 | 3/2020 | Fraietta et al. |
| 2020/0113941 A1 | 4/2020 | Brannetti et al. |
| 2020/0179511 A1 | 6/2020 | Daley et al. |
| 2020/0215171 A1 | 7/2020 | Brogdon et al. |
| 2020/0281973 A1 | 9/2020 | Dranoff |
| 2020/0283729 A1 | 9/2020 | Loew et al. |
| 2020/0291354 A1 | 9/2020 | Johnson et al. |
| 2020/0339704 A1 | 10/2020 | Bradner et al. |
| 2020/0360431 A1 | 11/2020 | Garfall et al. |
| 2020/0368268 A1 | 11/2020 | Johnson et al. |
| 2020/0370012 A1 | 11/2020 | Fraietta et al. |
| 2020/0371091 A1 | 11/2020 | Pruteanu-Malinici et al. |
| 2020/0399383 A1 | 12/2020 | Scholler et al. |
| 2021/0002377 A1 | 1/2021 | Brogdon et al. |
| 2021/0047405 A1 | 2/2021 | Nobles et al. |
| 2021/0079073 A1 | 3/2021 | Milone et al. |
| 2021/0087279 A1 | 3/2021 | Engels et al. |
| 2021/0139595 A1 | 5/2021 | Ebersbach et al. |
| 2021/0171909 A1 | 6/2021 | Golovina |
| 2021/0172020 A1 | 6/2021 | Bedoya et al. |
| 2021/0177896 A1 | 6/2021 | Porter et al. |
| 2021/0177900 A1 | 6/2021 | Engels et al. |
| 2021/0213063 A1 | 7/2021 | Isaacs et al. |
| 2021/0220404 A1 | 7/2021 | Abujoub et al. |
| 2021/0246423 A1 | 8/2021 | Bedoya et al. |
| 2021/0284752 A1 | 9/2021 | Brogdon et al. |
| 2021/0317183 A1 | 10/2021 | Zhao et al. |
| 2021/0347851 A1 | 11/2021 | Isaacs et al. |
| 2021/0396739 A1 | 12/2021 | Pruteanu-Malinici et al. |
| 2022/0047633 A1 | 2/2022 | Grupp |
| 2022/0064316 A1 | 3/2022 | Brogdon et al. |
| 2022/0089750 A1 | 3/2022 | June et al. |
| 2022/0152150 A1 | 5/2022 | Koshy et al. |
| 2022/0168389 A1 | 6/2022 | Ghassemi et al. |
| 2022/0195010 A1 | 6/2022 | Bitter et al. |
| 2022/0251152 A1 | 8/2022 | Carbonneau et al. |

FOREIGN PATENT DOCUMENTS

| | | |
|---|---|---|
| EP | 1226244 A2 | 7/2002 |
| WO | 1992015322 A1 | 9/1992 |
| WO | 199530014 A1 | 11/1995 |
| WO | 9623814 A1 | 8/1996 |
| WO | 9624671 A1 | 8/1996 |
| WO | 1997015669 A1 | 5/1997 |
| WO | 9723613 A2 | 7/1997 |

(56) References Cited

FOREIGN PATENT DOCUMENTS

| | | | |
|---|---|---|---|
| WO | 9818809 A1 | 5/1998 | |
| WO | 9900494 A2 | 1/1999 | |
| WO | 9957268 A1 | 11/1999 | |
| WO | 0014257 A1 | 3/2000 | |
| WO | 2002033101 A1 | 4/2002 | |
| WO | 02077029 A2 | 10/2002 | |
| WO | 02088334 A1 | 11/2002 | |
| WO | 2003057171 A2 | 7/2003 | |
| WO | 2005019429 A2 | 3/2005 | |
| WO | 2005044996 A2 | 5/2005 | |
| WO | 2005/118788 A2 | 12/2005 | |
| WO | 2006060878 A1 | 6/2006 | |
| WO | 2008045437 A2 | 4/2008 | |
| WO | 2010085660 A2 | 7/2010 | |
| WO | 2011059836 A2 | 5/2011 | |
| WO | 2011097477 A1 | 8/2011 | |
| WO | 2012058460 A2 | 5/2012 | |
| WO | 2012079000 A1 | 6/2012 | |
| WO | 2012082841 A2 | 6/2012 | |
| WO | 2012/099973 A2 | 7/2012 | |
| WO | 2012127464 A2 | 9/2012 | |
| WO | 2012129514 A1 | 9/2012 | |
| WO | 2012135854 A2 | 10/2012 | |
| WO | 2012138858 A1 | 10/2012 | |
| WO | 2013019615 A2 | 2/2013 | |
| WO | 2013033626 A2 | 3/2013 | |
| WO | 2013040371 A2 | 3/2013 | |
| WO | 2013040557 A2 | 3/2013 | |
| WO | 2013059593 A1 | 4/2013 | |
| WO | 2013/126712 A1 | 8/2013 | |
| WO | 2013126729 A1 | 8/2013 | |
| WO | 2013126733 A1 | 8/2013 | |
| WO | 2014/011984 A1 | 1/2014 | |
| WO | 2014/011987 A1 | 1/2014 | |
| WO | 2014/011993 A2 | 1/2014 | |
| WO | 2014/012001 A2 | 1/2014 | |
| WO | 2014011988 A2 | 1/2014 | |
| WO | 2014011996 A1 | 1/2014 | |
| WO | 2014031687 A1 | 2/2014 | |
| WO | 2014039513 A2 | 3/2014 | |
| WO | 2014/055442 A2 | 4/2014 | |
| WO | 2014055657 A1 | 4/2014 | |
| WO | 2014130635 A1 | 8/2014 | |
| WO | WO-2014127261 A1 * | 8/2014 | ........... C07K 14/705 |
| WO | 2014/145252 A2 | 9/2014 | |
| WO | 2014183066 A2 | 11/2014 | |
| WO | 2015090229 A1 | 6/2015 | |
| WO | 2015090230 A1 | 6/2015 | |
| WO | 2015112626 A1 | 7/2015 | |
| WO | 2015/142661 A1 | 9/2015 | |
| WO | 2015142675 A2 | 9/2015 | |
| WO | 2015157252 A1 | 10/2015 | |
| WO | 2016014501 A1 | 1/2016 | |
| WO | 2016014530 A1 | 1/2016 | |
| WO | 2016014535 A1 | 1/2016 | |
| WO | 2016014553 A1 | 1/2016 | |
| WO | 2016014565 A2 | 1/2016 | |
| WO | 2016014576 A1 | 1/2016 | |
| WO | 2016019300 A1 | 2/2016 | |
| WO | 2016025880 A1 | 2/2016 | |
| WO | 2016028896 A1 | 2/2016 | |
| WO | 2016036746 A1 | 3/2016 | |
| WO | 2016044605 A1 | 3/2016 | |
| WO | 2016054520 A2 | 4/2016 | |
| WO | 2016130598 A1 | 8/2016 | |
| WO | 2016164731 | 10/2016 | |
| WO | 2016187349 A1 | 11/2016 | |
| WO | 2017027392 A1 | 2/2017 | |

OTHER PUBLICATIONS

Jena et al. (Blood Aug. 19, 2010 116(7): 1035-1044) (Year: 2010).*
Zufferey et al., "Multiply attenuated lentiviral vector achieves efficient gene delivery in vivo" Nature Biotechnology (1997) vol. 15 pp. 871-876.
Kim et al., "Human 4-1BB regulates CD28 co-stimulation to promote Th1 cell responses" Eur. J. Immunol. (1998) vol. 28 pp. 881-890.
Kloss et al. "Combinatorial antigen recognition with balanced signaling promostes selective tumor reradication by engineered T cells" Nature Biotechnology vol. 31, No. 1, pp. 71-75.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-Of-Hematology (ASH); Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 689-702.
Kochenderfer et al., "Eradication of B-lineage cells and regression of lymphoma in a patient treated with autologous T cells genetically-engineered to recognize CD19," Blood 116: 4099-4102 (2010).
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letoumeur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
MaCallan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
Manolios et al. "The T cell antigen receptor alpha and beta chains interact via distinct regions with CD3 chains" European Journal of Immunology (1994) vol. 24, No. 1, pp. 84-92.
McGuinness et al., "Anti-tumor activity of human T cells expressing the CC49-zeta chimeric immune receptor," Hum. Gene Ther. 10: 165-173 (1999).
Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).

(56) References Cited

OTHER PUBLICATIONS

Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).
Nolan et al. "Advances in Brief Bypassing Immunization: Optimized Design of "Designer T Cells" against Carcinoembryonic Antigen (CEA)-expressing Tumors, and Lack of Suppression by Soluble CEA 1" Clinical Cancer Research (1999) vol. 5, pp. 3931—Abstract.
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Van Der Stegen et al. "The pharmacology of second-generation chimeric antigen receptors" Nature Reviews Cancer Discovery (2015) vol. 14, No. 7, pp. 499-509.
Vinay & Kwon, "Role of 4-1BB in immune responses" Immunology (1998) vol. 10 pp. 481-489.
Willemsen et al., "Genetic Engineering of T Cell Specificity for Immunotherapy of Cancer" Human Immunology (2003) vol. 64 pp. 56-68.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
"Pilot Study of Autologous T-cells Redirected to Mesothelin and CD19 With a Chimeric Antigen Receptor in Patients With Metastatic Pancreatic Cancer (NCT02465983 on Jan. 20, 2016)" Clinicaltrials.gov Clinical Trial No. NCT02465983; Last Updated Jan. 20, 2016; Retrieved from the internet at http://clinicaltrials.gov/archive/NCT02365983/2016_01_20 on May 17, 2017.
Abate-Daga et al "CAR models: next-generation CAR modifications for enhanced T-cell function" Molecular Therapy—Oncolytics (2016) vol. 3, pp. 16014.
Baeksgaard & Sorensen, "Acute tumor lysis syndrome in solid tumors—a case report and review of the literature" Cancer Chemotherapy Pharmacology (2003) vol. 51 pp. 187-192.
Bondanza et al. "Suicide gene therapy of graft-versus-host disease induced by central memory human T lymphocytes" Blood (2006) vol. 107 No. 5 pp. 1828-1836.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interieukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Brocker and Karjalainen, "Signals through T Cell Receptor-Chain alone Are Insufficient to Prime Resting T Lymphocytes" J. Exp. Med. (1995) vol. 181 pp. 1653-1659.
Call & Wucherpfennig, "The T Cell Receptor: Critical Role of the Membrane Environment in Receptor Assembly and Function" Annu. Rev. Immunol. (2005) vol. 23 pp. 101-125.
Call et al. "The Organizing Principle in the Formation of the T Cell Receptor-CD3 Complex" Cell (2002) vol. 111, No. 7, pp. 967-979.
Carpenito et al. "Control of large, established tumor xenografts with genetically retargeted human T cells containing CD28 and CD 137 domains", Proc Natl Acad Sci USA (2009) vol. 106 pp. 3360-3365.
Davila et al. "B Cell Aplasia in a Patient with Relapsed B Cell Acute Lymphoblastic Leukemia Following Re-Induction and Consolida-

(56) References Cited

OTHER PUBLICATIONS tion with Autologous T Cells Genetically Targeted to the CD 19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dull et al, "A Third-Generation Lentivirus Vector with a Conditional Packaging System" Journal of Virology (1998) vol. 72 No. 11 pp. 8463-8471.
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).
Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).

Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors by Adoptive Transfer of Cytotoxic T Lymphocytes Reprogrammed by CD44V6-Specific SCFV:~-Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD 19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Search Report and Written Opinion for International Application No. PCT/US2016/045816 dated Oct. 25, 2016.
International Search Report and Written Opinion for International Application No. PCT/US2018/016139 dated Apr. 3, 2018.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Lloyd et al., "Modelling the human immune response: performance of a 10" human antibody repertoire against a broad panel of therapeutically relevant antigens," Protein Engineering, Design & Selection (2009) vol. 22, No. 3, pp. 159-168.

\* cited by examiner

SEQUENCE LISTING

<160> NUMBER OF SEQ ID NOS: 62

<210> SEQ ID NO 1
<211> LENGTH: 495
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

```
Gly Ser Ala Thr Met Ala Leu Pro Val Thr Ala Leu Leu Leu Pro Leu
1               5                   10                  15

Ala Leu Leu Leu His Ala Ala Arg Pro Glu Ile Val Met Thr Gln Ser
            20                  25                  30

Pro Ala Thr Leu Ser Leu Ser Pro Gly Glu Arg Ala Thr Leu Ser Cys
        35                  40                  45

Arg Ala Ser Gln Asp Ile Ser Lys Tyr Leu Asn Trp Tyr Gln Gln Lys
    50                  55                  60

Pro Gly Gln Ala Pro Arg Leu Leu Ile Tyr His Thr Ser Arg Leu His
65                  70                  75                  80

Ser Gly Ile Pro Ala Arg Phe Ser Gly Ser Gly Ser Gly Thr Asp Tyr
                85                  90                  95

Thr Leu Thr Ile Ser Ser Leu Gln Pro Glu Asp Phe Ala Val Tyr Phe
            100                 105                 110

Cys Gln Gln Gly Asn Thr Leu Pro Tyr Thr Phe Gly Gln Gly Thr Lys
        115                 120                 125

Leu Glu Ile Lys Gly Gly Gly Gly Ser Gly Gly Gly Gly Ser Gly Gly
    130                 135                 140

Gly Gly Ser Gly Gly Gly Gly Ser Gln Val Gln Leu Gln Glu Ser Gly
145                 150                 155                 160

Pro Gly Leu Val Lys Pro Ser Glu Thr Leu Ser Leu Thr Cys Thr Val
                165                 170                 175

Ser Gly Val Ser Leu Pro Asp Tyr Gly Val Ser Trp Ile Arg Gln Pro
            180                 185                 190

Pro Gly Lys Gly Leu Glu Trp Ile Gly Val Ile Trp Gly Ser Glu Thr
        195                 200                 205

Thr Tyr Tyr Asn Ser Ser Leu Lys Ser Arg Val Thr Ile Ser Lys Asp
    210                 215                 220

Asn Ser Lys Asn Gln Val Ser Leu Lys Leu Ser Ser Val Thr Ala Ala
225                 230                 235                 240

Asp Thr Ala Val Tyr Tyr Cys Ala Lys His Tyr Tyr Tyr Gly Gly Ser
                245                 250                 255

Tyr Ala Met Asp Tyr Trp Gly Gln Gly Thr Leu Val Thr Val Ser Ser
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350
```

```
Lys Gln Pro Phe Met Arg Pro Val Gln Thr Thr Gln Glu Glu Asp Gly
            355                 360                 365

Cys Ser Cys Arg Phe Pro Glu Glu Glu Gly Gly Cys Glu Leu Arg
        370                 375                 380

Val Lys Phe Ser Arg Ser Ala Asp Ala Pro Ala Tyr Lys Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
                420                 425                 430

Arg Arg Lys Asn Pro Gln Glu Gly Leu Tyr Asn Glu Leu Gln Lys Asp
                435                 440                 445

Lys Met Ala Glu Ala Tyr Ser Glu Ile Gly Met Lys Gly Glu Arg Arg
            450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 2
<211> LENGTH: 476
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gly Ser Ala Thr Met Ala Leu Pro Val Thr Ala Leu Leu Leu Pro Leu
1               5                   10                  15

Ala Leu Leu Leu His Ala Ala Arg Pro Glu Ile Val Met Thr Gln Ser
            20                  25                  30

Pro Ala Thr Leu Ser Leu Ser Pro Gly Glu Arg Ala Thr Leu Ser Cys
        35                  40                  45

Arg Ala Ser Gln Asp Ile Ser Lys Tyr Leu Asn Trp Tyr Gln Gln Lys
    50                  55                  60

Pro Gly Gln Ala Pro Arg Leu Leu Ile Tyr His Thr Ser Arg Leu His
65                  70                  75                  80

Ser Gly Ile Pro Ala Arg Phe Ser Gly Ser Gly Ser Gly Thr Asp Tyr
                85                  90                  95

Thr Leu Thr Ile Ser Ser Leu Gln Pro Glu Asp Phe Ala Val Tyr Phe
            100                 105                 110

Cys Gln Gln Gly Asn Thr Leu Pro Tyr Thr Phe Gly Gln Gly Thr Lys
        115                 120                 125

Leu Glu Ile Lys Gly Gly Gly Ser Gly Gly Gly Gly Ser Gly Gly
    130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Gly Val Ser Leu
                165                 170                 175

Pro Asp Tyr Gly Val Ser Trp Ile Arg Gln Pro Pro Gly Lys Gly Leu
            180                 185                 190

Glu Trp Ile Gly Val Ile Trp Gly Ser Glu Thr Thr Tyr Tyr Ser Ser
        195                 200                 205
```

Ser Leu Lys Ser Arg Val Thr Ile Ser Lys Asp Asn Ser Lys Asn Gln
210                 215                 220

Val Ser Leu Lys Leu Ser Ser Val Thr Ala Ala Asp Thr Ala Val Tyr
225                 230                 235                 240

Tyr Cys Ala Lys His Tyr Tyr Tyr Gly Gly Ser Tyr Ala Met Asp Tyr
            245                 250                 255

Trp Gly Gln Gly Thr Leu Val Thr Val Ser Ser Thr Thr Pro Ala
                260                 265                 270

Pro Arg Pro Pro Thr Pro Ala Pro Thr Ile Ala Ser Gln Pro Leu Ser
            275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Ser Leu Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
            355                 360                 365

Arg Phe Pro Glu Glu Glu Gly Gly Cys Glu Leu Met Phe Asn Ala
370                 375                 380

Lys Tyr Val Ala Glu Ala Thr Gly Asn Phe Ile Thr Val Met Asp Ala
385                 390                 395                 400

Leu Lys Leu Asn Tyr Asn Ala Lys Asp Gln Leu His Pro Leu Leu Ala
                405                 410                 415

Glu Leu Leu Ile Ser Ile Asn Arg Val Thr Arg Asp Phe Glu Asn
                420                 425                 430

Arg Ser Lys Leu Ile Asp Trp Ile Val Arg Ile Asn Lys Leu Ser Ile
            435                 440                 445

Gly Asp Thr Leu Thr Glu Thr Gln Ile Arg Glu Leu Leu Phe Asp Leu
            450                 455                 460

Glu Leu Ala Tyr Lys Ser Phe Tyr Ala Leu Leu Asp
465                 470                 475

<210> SEQ ID NO 3
<211> LENGTH: 295
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gly Ser Met Gln Ser Gly Thr His Trp Arg Val Leu Gly Leu Cys Leu
1               5                   10                  15

Leu Ser Val Gly Val Trp Gly Gln Asp Gly Asn Glu Glu Met Gly Gly
                20                  25                  30

Ile Thr Gln Thr Pro Tyr Lys Val Ser Ile Ser Gly Thr Thr Val Ile
            35                  40                  45

Leu Thr Cys Pro Gln Tyr Pro Gly Ser Glu Ile Leu Trp Gln His Asn
        50                  55                  60

Asp Lys Asn Ile Gly Gly Asp Glu Asp Lys Asn Ile Gly Ser Asp
65                  70                  75                  80

Glu Asp His Leu Ser Leu Lys Glu Phe Ser Glu Leu Glu Gln Ser Gly

```
                        85                  90                  95
Tyr Tyr Val Cys Tyr Pro Arg Gly Ser Lys Pro Glu Asp Ala Asn Phe
                100                 105                 110

Tyr Leu Tyr Leu Arg Ala Arg Val Cys Glu Asn Cys Met Glu Met Asp
            115                 120                 125

Val Met Ser Val Ala Thr Ile Val Val Asp Ile Cys Ile Thr Gly
130                 135                 140

Gly Leu Leu Leu Val Tyr Tyr Trp Ser Lys Asn Arg Lys Ala Lys
145                 150                 155                 160

Ala Lys Pro Val Thr Arg Gly Ala Gly Gly Arg Gln Arg Gly
                165                 170                 175

Gln Asn Lys Glu Arg Pro Pro Val Pro Asn Pro Asp Tyr Glu Pro
                180                 185                 190

Ile Arg Lys Gly Gln Arg Asp Leu Tyr Ser Gly Leu Asn Gln Arg Arg
                195                 200                 205

Ile Gly Ser Gly Ser Gly Ser Gly Ser Gly Gly Ser Gly Ser
    210                 215                 220

Gly Ser Ser Gly Ala Ser Ala Asp Val Val Ser Thr Trp Val Cys Pro
225                 230                 235                 240

Ile Cys Met Val Ser Asn Glu Thr Gln Gly Glu Phe Thr Lys Asp Thr
                245                 250                 255

Leu Pro Thr Pro Ile Cys Ile Asn Cys Gly Val Pro Ala Asp Tyr Glu
                260                 265                 270

Leu Thr Lys Ser Ser Ile Asn Cys Ser Asn Ala Ile Asp Pro Asn Ala
                275                 280                 285

Asn Pro Arg Asn Gln Phe Gly
                290                 295

<210> SEQ ID NO 4
<211> LENGTH: 417
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Gly Ser Ala Thr Met Ala Leu Pro Val Thr Ala Leu Leu Leu Pro Leu
1               5                   10                  15

Ala Leu Leu Leu His Ala Ala Arg Pro Glu Ile Val Met Thr Gln Ser
            20                  25                  30

Pro Ala Thr Leu Ser Leu Ser Pro Gly Glu Arg Ala Thr Leu Ser Cys
        35                  40                  45

Arg Ala Ser Gln Asp Ile Ser Lys Tyr Leu Asn Trp Tyr Gln Gln Lys
    50                  55                  60

Pro Gly Gln Ala Pro Arg Leu Leu Ile Tyr His Thr Ser Arg Leu His
65                  70                  75                  80

Ser Gly Ile Pro Ala Arg Phe Ser Gly Ser Gly Ser Gly Thr Asp Tyr
                85                  90                  95

Thr Leu Thr Ile Ser Ser Leu Gln Pro Glu Asp Phe Ala Val Tyr Phe
            100                 105                 110

Cys Gln Gln Gly Asn Thr Leu Pro Tyr Thr Phe Gly Gln Gly Thr Lys
        115                 120                 125

Leu Glu Ile Lys Gly Gly Gly Gly Ser Gly Gly Gly Gly Ser Gly Gly
    130                 135                 140
```

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Gly Val Ser Leu
                165                 170                 175

Pro Asp Tyr Gly Val Ser Trp Ile Arg Gln Pro Pro Lys Gly Leu
            180                 185                 190

Glu Trp Ile Gly Val Ile Trp Gly Ser Glu Thr Thr Tyr Tyr Ser Ser
            195                 200                 205

Ser Leu Lys Ser Arg Val Thr Ile Ser Lys Asp Asn Ser Lys Asn Gln
210                 215                 220

Val Ser Leu Lys Leu Ser Ser Val Thr Ala Ala Asp Thr Ala Val Tyr
225                 230                 235                 240

Tyr Cys Ala Lys His Tyr Tyr Gly Gly Ser Tyr Ala Met Asp Tyr
                245                 250                 255

Trp Gly Gln Gly Thr Leu Val Thr Val Ser Ser Thr Thr Thr Pro Ala
                260                 265                 270

Pro Arg Pro Pro Thr Pro Ala Pro Thr Ile Ala Ser Gln Pro Leu Ser
                275                 280                 285

Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Ser Leu Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
                355                 360                 365

Arg Phe Pro Glu Glu Glu Glu Gly Gly Cys Glu Leu Arg Ile Ala Arg
370                 375                 380

Leu Glu Glu Glu Val Lys Thr Leu Glu Ala Gln Asn Ser Glu Leu Ala
385                 390                 395                 400

Ser Thr Ala Asn Met Leu Glu Glu Gln Val Ala Gln Leu Lys Gln Lys
                405                 410                 415

Val

<210> SEQ ID NO 5
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gly Ser Met Gln Ser Gly Thr His Trp Arg Val Leu Gly Leu Cys Leu
1               5                   10                  15

Leu Ser Val Gly Val Trp Gly Gln Asp Gly Asn Glu Met Gly Gly
                20                  25                  30

Ile Thr Gln Thr Pro Tyr Lys Val Ser Ile Ser Gly Thr Thr Val Ile
                35                  40                  45

Leu Thr Cys Pro Gln Tyr Pro Gly Ser Glu Ile Leu Trp Gln His Asn
50                  55                  60

Asp Lys Asn Ile Gly Gly Asp Glu Asp Asp Lys Asn Ile Gly Ser Asp

```
65                  70                  75                  80
Glu Asp His Leu Ser Leu Lys Glu Phe Ser Glu Leu Glu Gln Ser Gly
                85                  90                  95
Tyr Tyr Val Cys Tyr Pro Arg Gly Ser Lys Pro Glu Asp Ala Asn Phe
              100                 105                 110
Tyr Leu Tyr Leu Arg Ala Arg Val Cys Glu Asn Cys Met Glu Met Asp
          115                 120                 125
Val Met Ser Val Ala Thr Ile Val Ile Val Asp Ile Cys Ile Thr Gly
      130                 135                 140
Gly Leu Leu Leu Val Tyr Tyr Trp Ser Lys Asn Arg Lys Ala Lys
145                 150                 155                 160
Ala Lys Pro Val Thr Arg Gly Ala Gly Ala Gly Arg Gln Arg Gly
                165                 170                 175
Gln Asn Lys Glu Arg Pro Pro Val Pro Asn Pro Asp Tyr Glu Pro
              180                 185                 190
Ile Arg Lys Gly Gln Arg Asp Leu Tyr Ser Gly Leu Asn Gln Arg Arg
          195                 200                 205
Ile Gly Ser Gly Ser Gly Ser Leu Thr Asp Thr Leu Gln Ala Lys
      210                 215                 220
Thr Asp Gln Leu Lys Asp Glu Lys Ser Ala Leu Gln Thr Lys Ile Ala
225                 230                 235                 240
Asn Leu Leu Lys Glu Lys Glu Lys Leu Glu Phe Ile Leu
                245                 250

<210> SEQ ID NO 6
<211> LENGTH: 281
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gly Ser Met Gln Ser Gly Thr His Trp Arg Val Leu Gly Leu Cys Leu
1               5                   10                  15
Leu Ser Val Gly Val Trp Gly Gln Asp Gly Asn Glu Glu Met Gly Gly
                20                  25                  30
Ile Thr Gln Thr Pro Tyr Lys Val Ser Ile Ser Gly Thr Thr Val Ile
            35                  40                  45
Leu Thr Cys Pro Gln Tyr Pro Gly Ser Glu Ile Leu Trp Gln His Asn
        50                  55                  60
Asp Lys Asn Ile Gly Gly Asp Glu Asp Lys Asn Ile Gly Ser Asp
65                  70                  75                  80
Glu Asp His Leu Ser Leu Lys Glu Phe Ser Glu Leu Glu Gln Ser Gly
                85                  90                  95
Tyr Tyr Val Cys Tyr Pro Arg Gly Ser Lys Pro Glu Asp Ala Asn Phe
              100                 105                 110
Tyr Leu Tyr Leu Arg Ala Arg Val Cys Glu Asn Cys Met Glu Met Asp
          115                 120                 125
Val Met Ser Val Ala Thr Ile Val Ile Val Asp Ile Cys Ile Thr Gly
      130                 135                 140
Gly Leu Leu Leu Val Tyr Tyr Trp Ser Arg Ser Lys Arg Ser Arg
145                 150                 155                 160
Leu Leu His Ser Asp Tyr Met Asn Met Thr Pro Arg Arg Pro Gly Pro
                165                 170                 175
```

```
Thr Arg Lys His Tyr Gln Pro Tyr Ala Pro Arg Asp Phe Ala Ala
            180                 185                 190

Tyr Arg Ser Gly Ser Gly Ser Gly Ser Gly Ser Gly Gly Gly Ser
            195                 200                 205

Gly Ser Gly Ser Ser Gly Ala Ser Ala Asp Val Val Ser Thr Trp Val
210                 215                 220

Cys Pro Ile Cys Met Val Ser Asn Glu Thr Gln Gly Glu Phe Thr Lys
225                 230                 235                 240

Asp Thr Leu Pro Thr Pro Ile Cys Ile Asn Cys Gly Val Pro Ala Asp
                245                 250                 255

Tyr Glu Leu Thr Lys Ser Ser Ile Asn Cys Ser Asn Ala Ile Asp Pro
                260                 265                 270

Asn Ala Asn Pro Arg Asn Gln Phe Gly
                275                 280

<210> SEQ ID NO 7
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gly Ser Ala Thr Met Ala Leu Pro Val Thr Ala Leu Leu Leu Pro Leu
1               5                   10                  15

Ala Leu Leu Leu His Ala Ala Arg Pro Glu Ile Val Met Thr Gln Ser
                20                  25                  30

Pro Ala Thr Leu Ser Leu Ser Pro Gly Glu Arg Ala Thr Leu Ser Cys
            35                  40                  45

Arg Ala Ser Gln Asp Ile Ser Lys Tyr Leu Asn Trp Tyr Gln Gln Lys
        50                  55                  60

Pro Gly Gln Ala Pro Arg Leu Leu Ile Tyr His Thr Ser Arg Leu His
65                  70                  75                  80

Ser Gly Ile Pro Ala Arg Phe Ser Gly Ser Gly Ser Gly Thr Asp Tyr
                85                  90                  95

Thr Leu Thr Ile Ser Ser Leu Gln Pro Glu Asp Phe Ala Val Tyr Phe
            100                 105                 110

Cys Gln Gln Gly Asn Thr Leu Pro Tyr Thr Phe Gly Gln Gly Thr Lys
        115                 120                 125

Leu Glu Ile Lys Gly Gly Gly Gly Ser Gly Gly Gly Ser Gly Gly
130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Gly Val Ser Leu
                165                 170                 175

Pro Asp Tyr Gly Val Ser Trp Ile Arg Gln Pro Pro Gly Lys Gly Leu
            180                 185                 190

Glu Trp Ile Gly Val Ile Trp Gly Ser Glu Thr Thr Tyr Tyr Ser Ser
        195                 200                 205

Ser Leu Lys Ser Arg Val Thr Ile Ser Lys Asp Asn Ser Lys Asn Gln
    210                 215                 220

Val Ser Leu Lys Leu Ser Ser Val Thr Ala Ala Asp Thr Ala Val Tyr
225                 230                 235                 240
```

```
Tyr Cys Ala Lys His Tyr Tyr Gly Gly Ser Tyr Ala Met Asp Tyr
                245                 250                 255

Trp Gly Gln Gly Thr Leu Val Thr Val Ser Ser Gly Gly Gly Ser
            260                 265                 270

Asp Gly Asn Glu Glu Met Gly Gly Ile Thr Gln Thr Pro Tyr Lys Val
        275                 280                 285

Ser Ile Ser Gly Thr Thr Val Ile Leu Thr Cys Pro Gln Tyr Pro Gly
    290                 295                 300

Ser Glu Ile Leu Trp Gln His Asn Asp Lys Asn Ile Gly Gly Asp Glu
305                 310                 315                 320

Asp Asp Lys Asn Ile Gly Ser Asp Glu Asp His Leu Ser Leu Lys Glu
                325                 330                 335

Phe Ser Glu Leu Glu Gln Ser Gly Tyr Tyr Val Cys Tyr Pro Arg Gly
            340                 345                 350

Ser Lys Pro Glu Asp Ala Asn Phe Tyr Leu Tyr Leu Arg Ala Arg Val
        355                 360                 365

Cys Glu Asn Cys Met Glu Met Asp Val Met Ser Val Ala Thr Ile Val
    370                 375                 380

Ile Val Asp Ile Cys Ile Thr Gly Gly Leu Leu Leu Leu Val Tyr Tyr
385                 390                 395                 400

Trp Ser Lys Asn Arg Lys Ala Lys Ala Lys Pro Val Thr Arg Gly Ala
                405                 410                 415

Gly Ala Gly Gly Arg Gln Arg Gly Gln Asn Lys Glu Arg Pro Pro Pro
            420                 425                 430

Val Pro Asn Pro Asp Tyr Glu Pro Ile Arg Lys Gly Gln Arg Asp Leu
        435                 440                 445

Tyr Ser Gly Leu Asn Gln Arg Arg Ile
    450                 455

<210> SEQ ID NO 8
<211> LENGTH: 506
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gly Ser Ala Thr Met Ala Leu Pro Val Thr Ala Leu Leu Leu Pro Leu
1               5                   10                  15

Ala Leu Leu Leu His Ala Ala Arg Pro Glu Ile Val Met Thr Gln Ser
                20                  25                  30

Pro Ala Thr Leu Ser Leu Ser Pro Gly Glu Arg Ala Thr Leu Ser Cys
            35                  40                  45

Arg Ala Ser Gln Asp Ile Ser Lys Tyr Leu Asn Trp Tyr Gln Gln Lys
        50                  55                  60

Pro Gly Gln Ala Pro Arg Leu Leu Ile Tyr His Thr Ser Arg Leu His
65                  70                  75                  80

Ser Gly Ile Pro Ala Arg Phe Ser Gly Ser Gly Ser Gly Thr Asp Tyr
                85                  90                  95

Thr Leu Thr Ile Ser Ser Leu Gln Pro Glu Asp Phe Ala Val Tyr Phe
            100                 105                 110

Cys Gln Gln Gly Asn Thr Leu Pro Tyr Thr Phe Gly Gln Gly Thr Lys
        115                 120                 125

Leu Glu Ile Lys Gly Gly Gly Gly Ser Gly Gly Gly Gly Ser Gly Gly
```

```
             130                 135                 140
Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Gly Val Ser Leu
                165                 170                 175

Pro Asp Tyr Gly Val Ser Trp Ile Arg Gln Pro Pro Gly Lys Gly Leu
            180                 185                 190

Glu Trp Ile Gly Val Ile Trp Gly Ser Glu Thr Thr Tyr Tyr Ser Ser
        195                 200                 205

Ser Leu Lys Ser Arg Val Thr Ile Ser Lys Asp Asn Ser Lys Asn Gln
    210                 215                 220

Val Ser Leu Lys Leu Ser Ser Val Thr Ala Ala Asp Thr Ala Val Tyr
225                 230                 235                 240

Tyr Cys Ala Lys His Tyr Tyr Gly Gly Ser Tyr Ala Met Asp Tyr
                245                 250                 255

Trp Gly Gln Gly Thr Leu Val Thr Val Ser Ser Gly Gly Gly Gly Ser
                260                 265                 270

Asp Gly Asn Glu Glu Met Gly Gly Ile Thr Gln Thr Pro Tyr Lys Val
            275                 280                 285

Ser Ile Ser Gly Thr Thr Val Ile Leu Thr Cys Pro Gln Tyr Pro Gly
        290                 295                 300

Ser Glu Ile Leu Trp Gln His Asn Asp Lys Asn Ile Gly Gly Asp Glu
305                 310                 315                 320

Asp Asp Lys Asn Ile Gly Ser Asp Glu Asp His Leu Ser Leu Lys Glu
                325                 330                 335

Phe Ser Glu Leu Glu Gln Ser Gly Tyr Tyr Val Cys Tyr Pro Arg Gly
                340                 345                 350

Ser Lys Pro Glu Asp Ala Asn Phe Tyr Leu Tyr Leu Arg Ala Arg Val
            355                 360                 365

Cys Glu Asn Cys Met Glu Met Asp Val Met Ser Val Ala Thr Ile Val
        370                 375                 380

Ile Val Asp Ile Cys Ile Thr Gly Gly Leu Leu Leu Val Tyr Tyr
385                 390                 395                 400

Trp Ser Lys Asn Arg Lys Ala Lys Ala Lys Pro Val Thr Arg Gly Ala
                405                 410                 415

Gly Ala Gly Gly Arg Gln Arg Gly Gln Asn Lys Glu Arg Pro Pro
            420                 425                 430

Val Pro Asn Pro Asp Tyr Glu Pro Ile Arg Lys Gly Gln Arg Asp Leu
            435                 440                 445

Tyr Ser Gly Leu Asn Gln Arg Arg Ile Gly Ser Gly Ser Gly Gly Ser
    450                 455                 460

Lys Arg Gly Arg Lys Lys Leu Leu Tyr Ile Phe Lys Gln Pro Phe Met
465                 470                 475                 480

Arg Pro Val Gln Thr Thr Gln Glu Glu Asp Gly Cys Ser Cys Arg Phe
                485                 490                 495

Pro Glu Glu Glu Glu Gly Gly Cys Glu Leu
                500                 505

<210> SEQ ID NO 9
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 9

```
Gly Ser Ala Thr Met Ala Leu Pro Val Thr Ala Leu Leu Leu Pro Leu
1               5                   10                  15

Ala Leu Leu Leu His Ala Arg Pro Glu Ile Val Met Thr Gln Ser
            20                  25                  30

Pro Ala Thr Leu Ser Leu Ser Pro Gly Glu Arg Ala Thr Leu Ser Cys
            35                  40                  45

Arg Ala Ser Gln Asp Ile Ser Lys Tyr Leu Asn Trp Tyr Gln Gln Lys
        50                  55                  60

Pro Gly Gln Ala Pro Arg Leu Leu Ile Tyr His Thr Ser Arg Leu His
65                  70                  75                  80

Ser Gly Ile Pro Ala Arg Phe Ser Gly Ser Gly Ser Gly Thr Asp Tyr
                85                  90                  95

Thr Leu Thr Ile Ser Ser Leu Gln Pro Glu Asp Phe Ala Val Tyr Phe
            100                 105                 110

Cys Gln Gln Gly Asn Thr Leu Pro Tyr Thr Phe Gly Gln Gly Thr Lys
            115                 120                 125

Leu Glu Ile Lys Gly Gly Gly Gly Ser Gly Gly Gly Gly Ser Gly Gly
        130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Gly Val Ser Leu
                165                 170                 175

Pro Asp Tyr Gly Val Ser Trp Ile Arg Gln Pro Pro Gly Lys Gly Leu
            180                 185                 190

Glu Trp Ile Gly Val Ile Trp Gly Ser Glu Thr Thr Tyr Tyr Ser Ser
        195                 200                 205

Ser Leu Lys Ser Arg Val Thr Ile Ser Lys Asp Asn Ser Lys Asn Gln
    210                 215                 220

Val Ser Leu Lys Leu Ser Ser Val Thr Ala Ala Asp Thr Ala Val Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Leu Val Thr Val Ser Ser Gly Gly Gly Gly Ser
            260                 265                 270

Asp Gly Asn Glu Glu Met Gly Gly Ile Thr Gln Thr Pro Tyr Lys Val
        275                 280                 285

Ser Ile Ser Gly Thr Thr Val Ile Leu Thr Cys Pro Gln Tyr Pro Gly
    290                 295                 300

Ser Glu Ile Leu Trp Gln His Asn Asp Lys Asn Ile Gly Gly Asp Glu
305                 310                 315                 320

Asp Asp Lys Asn Ile Gly Ser Asp Glu Asp His Leu Ser Leu Lys Glu
                325                 330                 335

Phe Ser Glu Leu Glu Gln Ser Gly Tyr Tyr Val Cys Tyr Pro Arg Gly
            340                 345                 350

Ser Lys Pro Glu Asp Ala Asn Phe Tyr Leu Tyr Leu Arg Ala Arg Val
        355                 360                 365

Cys Glu Asn Cys Met Glu Met Asp Val Met Ser Val Ala Thr Ile Val
        370                 375                 380

Ile Val Asp Ile Cys Ile Thr Gly Gly Leu Leu Leu Leu Val Tyr Tyr
385                 390                 395                 400
```

```
Trp Ser Lys Arg Gly Arg Lys Lys Leu Leu Tyr Ile Phe Lys Gln Pro
                405                 410                 415

Phe Met Arg Pro Val Gln Thr Thr Gln Glu Glu Asp Gly Cys Ser Cys
            420                 425                 430

Arg Phe Pro Glu Glu Glu Glu Gly Gly Cys Glu Leu
        435                 440

<210> SEQ ID NO 10
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
            20                  25                  30

Thr Leu Ser Leu Ser Pro Gly Glu Arg Ala Thr Leu Ser Cys Arg Ala
        35                  40                  45

Ser Gln Asp Ile Ser Lys Tyr Leu Asn Trp Tyr Gln Gln Lys Pro Gly
    50                  55                  60

Gln Ala Pro Arg Leu Leu Ile Tyr His Thr Ser Arg Leu His Ser Gly
65                  70                  75                  80

Ile Pro Ala Arg Phe Ser Gly Ser Gly Ser Gly Thr Asp Tyr Thr Leu
                85                  90                  95

Thr Ile Ser Ser Leu Gln Pro Glu Asp Phe Ala Val Tyr Phe Cys Gln
            100                 105                 110

Gln Gly Asn Thr Leu Pro Tyr Thr Phe Gly Gln Gly Thr Lys Leu Glu
        115                 120                 125

Ile Lys Gly Gly Gly Gly Ser Gly Gly Gly Gly Ser Gly Gly Gly Gly
    130                 135                 140

Ser Gly Gly Gly Gly Ser Gln Val Gln Leu Gln Glu Ser Gly Pro Gly
145                 150                 155                 160

Leu Val Lys Pro Ser Glu Thr Leu Ser Leu Thr Cys Thr Val Ser Gly
                165                 170                 175

Val Ser Leu Pro Asp Tyr Gly Val Ser Trp Ile Arg Gln Pro Pro Gly
            180                 185                 190

Lys Gly Leu Glu Trp Ile Gly Val Ile Trp Gly Ser Glu Thr Thr Tyr
        195                 200                 205

Tyr Asn Ser Ser Leu Lys Ser Arg Val Thr Ile Ser Lys Asp Asn Ser
    210                 215                 220

Lys Asn Gln Val Ser Leu Lys Leu Ser Ser Val Thr Ala Ala Asp Thr
225                 230                 235                 240

Ala Val Tyr Tyr Cys Ala Lys His Tyr Tyr Gly Gly Ser Tyr Ala
                245                 250                 255

Met Asp Tyr Trp Gly Gln Gly Thr Leu Val Thr Val Ser Ser Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
```

```
                305                 310                 315                 320
        Pro Leu Ala Gly Thr Cys Gly Val Leu Leu Leu Ser Leu Val Ile Thr
                        325                 330                 335

Leu Tyr Cys Arg Val Lys Phe Ser Arg Ser Ala Asp Ala Pro Ala Tyr
                        340                 345                 350

Lys Gln Gly Gln Asn Gln Leu Tyr Asn Glu Leu Asn Leu Gly Arg Arg
                        355                 360                 365

Glu Glu Tyr Asp Val Leu Asp Lys Arg Gly Arg Asp Pro Glu Met
                370                 375                 380

Gly Gly Lys Pro Arg Arg Lys Asn Pro Gln Glu Gly Leu Tyr Asn Glu
        385                 390                 395                 400

Leu Gln Lys Asp Lys Met Ala Glu Ala Tyr Ser Glu Ile Gly Met Lys
                        405                 410                 415

Gly Glu Arg Arg Arg Gly Lys Gly His Asp Gly Leu Tyr Gln Gly Leu
                        420                 425                 430

Ser Thr Ala Thr Lys Asp Thr Tyr Asp Ala Leu His Met Gln Ala Leu
                        435                 440                 445

Pro Pro Arg
                450

<210> SEQ ID NO 11
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gly Ser Met Ala Leu Pro Val Thr Ala Leu Leu Leu Pro Leu Ala Leu
        1               5                   10                  15

Leu Leu His Ala Ala Arg Pro Glu Ile Val Met Thr Gln Ser Pro Ala
                        20                  25                  30

Thr Leu Ser Leu Ser Pro Gly Glu Arg Ala Thr Leu Ser Cys Arg Ala
                        35                  40                  45

Ser Gln Asp Ile Ser Lys Tyr Leu Asn Trp Tyr Gln Gln Lys Pro Gly
                50                  55                  60

Gln Ala Pro Arg Leu Leu Ile Tyr His Thr Ser Arg Leu His Ser Gly
        65                  70                  75                  80

Ile Pro Ala Arg Phe Ser Gly Ser Gly Ser Gly Thr Asp Tyr Thr Leu
                        85                  90                  95

Thr Ile Ser Ser Leu Gln Pro Glu Asp Phe Ala Val Tyr Phe Cys Gln
                        100                 105                 110

Gln Gly Asn Thr Leu Pro Tyr Thr Phe Gly Gln Gly Thr Lys Leu Glu
                        115                 120                 125

Ile Lys Gly Gly Gly Gly Ser Gly Gly Gly Gly Ser Gly Gly Gly Gly
                        130                 135                 140

Ser Gly Gly Gly Gly Ser Gln Val Gln Leu Gln Glu Ser Gly Pro Gly
        145                 150                 155                 160

Leu Val Lys Pro Ser Glu Thr Leu Ser Leu Thr Cys Thr Val Ser Gly
                        165                 170                 175

Val Ser Leu Pro Asp Tyr Gly Val Ser Trp Ile Arg Gln Pro Pro Gly
                        180                 185                 190

Lys Gly Leu Glu Trp Ile Gly Val Ile Trp Gly Ser Glu Thr Thr Tyr
                        195                 200                 205
```

```
Tyr Asn Ser Ser Leu Lys Ser Arg Val Thr Ile Ser Lys Asp Asn Ser
    210                 215                 220

Lys Asn Gln Val Ser Leu Lys Leu Ser Ser Val Thr Ala Ala Asp Thr
225                 230                 235                 240

Ala Val Tyr Tyr Cys Ala Lys His Tyr Tyr Gly Gly Ser Tyr Ala
                245                 250                 255

Met Asp Tyr Trp Gly Gln Gly Thr Leu Val Thr Val Ser Ser Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Arg Val Lys Phe Ser Arg Ser Ala Asp Ala Pro Ala Phe
            340                 345                 350

Lys Gln Gly Gln Asn Gln Leu Phe Asn Glu Leu Asn Leu Gly Arg Arg
        355                 360                 365

Glu Glu Phe Asp Val Leu Asp Lys Arg Arg Gly Arg Asp Pro Glu Met
370                 375                 380

Gly Gly Lys Pro Arg Arg Lys Asn Pro Gln Glu Gly Leu Phe Asn Glu
385                 390                 395                 400

Leu Gln Lys Asp Lys Met Ala Glu Ala Phe Ser Glu Ile Gly Met Lys
                405                 410                 415

Gly Glu Arg Arg Arg Gly Lys Gly His Asp Gly Leu Phe Gln Gly Leu
            420                 425                 430

Ser Thr Ala Thr Lys Asp Thr Phe Asp Ala Leu His Met Gln Ala Leu
        435                 440                 445

Pro Pro Arg
    450

<210> SEQ ID NO 12
<211> LENGTH: 381
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
                20                  25                  30

Thr Leu Ser Leu Ser Pro Gly Glu Arg Ala Thr Leu Ser Cys Arg Ala
            35                  40                  45

Ser Gln Asp Ile Ser Lys Tyr Leu Asn Trp Tyr Gln Gln Lys Pro Gly
        50                  55                  60

Gln Ala Pro Arg Leu Leu Ile Tyr His Thr Ser Arg Leu His Ser Gly
65                  70                  75                  80

Ile Pro Ala Arg Phe Ser Gly Ser Gly Ser Gly Thr Asp Tyr Thr Leu
                85                  90                  95
```

```
Thr Ile Ser Ser Leu Gln Pro Glu Asp Phe Ala Val Tyr Phe Cys Gln
                100                 105                 110

Gln Gly Asn Thr Leu Pro Tyr Thr Phe Gly Gln Gly Thr Lys Leu Glu
            115                 120                 125

Ile Lys Gly Gly Gly Gly Ser Gly Gly Gly Gly Ser Gly Gly Gly Gly
130                 135                 140

Ser Gly Gly Gly Gly Ser Gln Val Gln Leu Gln Glu Ser Gly Pro Gly
145                 150                 155                 160

Leu Val Lys Pro Ser Glu Thr Leu Ser Leu Thr Cys Thr Val Ser Gly
                165                 170                 175

Val Ser Leu Pro Asp Tyr Gly Val Ser Trp Ile Arg Gln Pro Pro Gly
            180                 185                 190

Lys Gly Leu Glu Trp Ile Gly Val Ile Trp Gly Ser Glu Thr Thr Tyr
        195                 200                 205

Tyr Asn Ser Ser Leu Lys Ser Arg Val Thr Ile Ser Lys Asp Asn Ser
    210                 215                 220

Lys Asn Gln Val Ser Leu Lys Leu Ser Ser Val Thr Ala Ala Asp Thr
225                 230                 235                 240

Ala Val Tyr Tyr Cys Ala Lys His Tyr Tyr Gly Gly Ser Tyr Ala
                245                 250                 255

Met Asp Tyr Trp Gly Gln Gly Thr Leu Val Thr Val Ser Ser Thr Thr
            260                 265                 270

Thr Pro Ala Pro Arg Pro Pro Thr Pro Ala Pro Thr Ile Ala Ser Gln
                275                 280                 285

Pro Leu Ser Leu Arg Pro Glu Ala Cys Arg Pro Ala Ala Gly Gly Ala
290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu
    370                 375                 380

<210> SEQ ID NO 13
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
            20                  25                  30

Thr Leu Ser Leu Ser Pro Gly Glu Arg Ala Thr Leu Ser Cys Arg Ala
        35                  40                  45

Ser Gln Asp Ile Ser Lys Tyr Leu Asn Trp Tyr Gln Gln Lys Pro Gly
    50                  55                  60

Gln Ala Pro Arg Leu Leu Ile Tyr His Thr Ser Arg Leu His Ser Gly
```

```
             65                  70                  75                  80
        Ile Pro Ala Arg Phe Ser Gly Ser Gly Ser Gly Thr Asp Tyr Thr Leu
                         85                  90                  95
        Thr Ile Ser Ser Leu Gln Pro Glu Asp Phe Ala Val Tyr Phe Cys Gln
                        100                 105                 110
        Gln Gly Asn Thr Leu Pro Tyr Thr Phe Gly Gln Gly Thr Lys Leu Glu
                        115                 120                 125
        Ile Lys Gly Gly Gly Gly Ser Gly Gly Gly Gly Ser Gly Gly Gly Gly
        130                 135                 140
        Ser Gln Val Gln Leu Gln Glu Ser Gly Pro Gly Leu Val Lys Pro Ser
        145                 150                 155                 160
        Glu Thr Leu Ser Leu Thr Cys Thr Val Ser Gly Val Ser Leu Pro Asp
                        165                 170                 175
        Tyr Gly Val Ser Trp Ile Arg Gln Pro Pro Gly Lys Gly Leu Glu Trp
                        180                 185                 190
        Ile Gly Val Ile Trp Gly Ser Glu Thr Thr Tyr Tyr Ser Ser Ser Leu
                        195                 200                 205
        Lys Ser Arg Val Thr Ile Ser Lys Asp Asn Ser Lys Asn Gln Val Ser
        210                 215                 220
        Leu Lys Leu Ser Ser Val Thr Ala Ala Asp Thr Ala Val Tyr Tyr Cys
        225                 230                 235                 240
        Ala Lys His Tyr Tyr Tyr Gly Gly Ser Tyr Ala Met Asp Tyr Trp Gly
                        245                 250                 255
        Gln Gly Thr Leu Val Thr Val Ser Ser Gly Gly Gly Ser Asp Gly
                        260                 265                 270
        Asn Glu Glu Met Gly Gly Ile Thr Gln Thr Pro Tyr Lys Val Ser Ile
                        275                 280                 285
        Ser Gly Thr Thr Val Ile Leu Thr Cys Pro Gln Tyr Pro Gly Ser Glu
                        290                 295                 300
        Ile Leu Trp Gln His Asn Asp Lys Asn Ile Gly Gly Asp Glu Asp Asp
        305                 310                 315                 320
        Lys Asn Ile Gly Ser Asp Glu Asp His Leu Ser Leu Lys Glu Phe Ser
                        325                 330                 335
        Glu Leu Glu Gln Ser Gly Tyr Tyr Val Cys Tyr Pro Arg Gly Ser Lys
                        340                 345                 350
        Pro Glu Asp Ala Asn Phe Tyr Leu Tyr Leu Arg Ala Arg Val Cys Glu
                        355                 360                 365
        Asn Cys Met Glu Met Asp Val Met Ser Val Ala Thr Ile Val Ile Val
                        370                 375                 380
        Asp Ile Cys Ile Thr Gly Gly Leu Leu Leu Leu Val Tyr Tyr Trp Ser
        385                 390                 395                 400
        Lys Asn Arg Lys Ala Lys Ala Lys Pro Val Thr Arg Gly Ala Gly Ala
                        405                 410                 415
        Gly Gly Arg Gln Arg Gly Gln Asn Lys Glu Arg Pro Pro Pro Val Pro
                        420                 425                 430
        Asn Pro Asp Phe Glu Pro Ile Arg Lys Gly Gln Arg Asp Leu Phe Ser
                        435                 440                 445
        Gly Leu Asn Gln Arg Arg Ile
                450                 455

<210> SEQ ID NO 14
<211> LENGTH: 488
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 14

Gly Ser Ala Thr Met Ala Leu Pro Val Thr Ala Leu Leu Leu Pro Leu
1               5                   10                  15

Ala Leu Leu Leu His Ala Ala Arg Pro Glu Ile Val Met Thr Gln Ser
            20                  25                  30

Pro Ala Thr Leu Ser Leu Ser Pro Gly Glu Arg Ala Thr Leu Ser Cys
        35                  40                  45

Arg Ala Ser Gln Asp Ile Ser Lys Tyr Leu Asn Trp Tyr Gln Gln Lys
    50                  55                  60

Pro Gly Gln Ala Pro Arg Leu Leu Ile Tyr His Thr Ser Arg Leu His
65                  70                  75                  80

Ser Gly Ile Pro Ala Arg Phe Ser Gly Ser Gly Ser Gly Thr Asp Tyr
                85                  90                  95

Thr Leu Thr Ile Ser Ser Leu Gln Pro Glu Asp Phe Ala Val Tyr Phe
            100                 105                 110

Cys Gln Gln Gly Asn Thr Leu Pro Tyr Thr Phe Gly Gln Gly Thr Lys
        115                 120                 125

Leu Glu Ile Lys Gly Gly Gly Gly Ser Gly Gly Gly Gly Ser Gly Gly
130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Gly Val Ser Leu
                165                 170                 175

Pro Asp Tyr Gly Val Ser Trp Ile Arg Gln Pro Pro Gly Lys Gly Leu
            180                 185                 190

Glu Trp Ile Gly Val Ile Trp Gly Ser Glu Thr Thr Tyr Tyr Ser Ser
        195                 200                 205

Ser Leu Lys Ser Arg Val Thr Ile Ser Lys Asp Asn Ser Lys Asn Gln
    210                 215                 220

Val Ser Leu Lys Leu Ser Ser Val Thr Ala Ala Asp Thr Ala Val Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Leu Val Thr Val Ser Ser Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Ser Leu Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Met Gly Val Gln
    370                 375                 380
```

```
Val Glu Thr Ile Ser Pro Gly Asp Gly Arg Thr Phe Pro Lys Arg Gly
385                 390                 395                 400

Gln Thr Cys Val Val His Tyr Thr Gly Met Leu Glu Asp Gly Lys Lys
                405                 410                 415

Phe Asp Ser Ser Arg Asp Arg Asn Lys Pro Phe Lys Phe Met Leu Gly
            420                 425                 430

Lys Gln Glu Val Ile Arg Gly Trp Glu Glu Gly Val Ala Gln Met Ser
        435                 440                 445

Val Gly Gln Arg Ala Lys Leu Thr Ile Ser Pro Asp Tyr Ala Tyr Gly
    450                 455                 460

Ala Thr Gly His Pro Gly Ile Ile Pro Pro His Ala Thr Leu Val Phe
465                 470                 475                 480

Asp Val Glu Leu Leu Lys Leu Glu
                485

<210> SEQ ID NO 15
<211> LENGTH: 309
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gly Ser Met Gln Ser Gly Thr His Trp Arg Val Leu Gly Leu Cys Leu
1               5                   10                  15

Leu Ser Val Gly Val Trp Gly Gln Asp Gly Asn Glu Glu Met Gly Gly
            20                  25                  30

Ile Thr Gln Thr Pro Tyr Lys Val Ser Ile Ser Gly Thr Thr Val Ile
        35                  40                  45

Leu Thr Cys Pro Gln Tyr Pro Gly Ser Glu Ile Leu Trp Gln His Asn
    50                  55                  60

Asp Lys Asn Ile Gly Gly Asp Glu Asp Lys Asn Ile Gly Ser Asp
65                  70                  75                  80

Glu Asp His Leu Ser Leu Lys Glu Phe Ser Glu Leu Glu Gln Ser Gly
                85                  90                  95

Tyr Tyr Val Cys Tyr Pro Arg Gly Ser Lys Pro Glu Asp Ala Asn Phe
                100                 105                 110

Tyr Leu Tyr Leu Arg Ala Arg Val Cys Glu Asn Cys Met Glu Met Asp
            115                 120                 125

Val Met Ser Val Ala Thr Ile Val Ile Val Asp Ile Cys Ile Thr Gly
        130                 135                 140

Gly Leu Leu Leu Leu Val Tyr Tyr Trp Ser Lys Asn Arg Lys Ala Lys
145                 150                 155                 160

Ala Lys Pro Val Thr Arg Gly Ala Gly Ala Gly Gly Arg Gln Arg Gly
                165                 170                 175

Gln Asn Lys Glu Arg Pro Pro Pro Val Pro Asn Pro Asp Tyr Glu Pro
            180                 185                 190

Ile Arg Lys Gly Gln Arg Asp Leu Tyr Ser Gly Leu Asn Gln Arg Arg
        195                 200                 205

Ile Gly Ser Gly Ser Gly Gly Ser Ile Leu Trp His Glu Met Trp His
    210                 215                 220

Glu Gly Leu Ile Glu Ala Ser Arg Leu Tyr Phe Gly Glu Arg Asn Val
225                 230                 235                 240

Lys Gly Met Phe Glu Val Leu Glu Pro Leu His Ala Met Met Glu Arg
```

```
                        245                 250                 255

Gly Pro Gln Thr Leu Lys Glu Thr Ser Phe Asn Gln Ala Tyr Gly Arg
            260                 265                 270

Asp Leu Met Glu Ala Gln Glu Trp Cys Arg Lys Tyr Met Lys Ser Gly
        275                 280                 285

Asn Val Lys Asp Leu Leu Gln Ala Trp Asp Leu Tyr Tyr His Val Phe
    290                 295                 300

Arg Arg Ile Ser Lys
305

<210> SEQ ID NO 16
<211> LENGTH: 309
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gly Ser Met Gln Ser Gly Thr His Trp Arg Val Leu Gly Leu Cys Leu
1               5                   10                  15

Leu Ser Val Gly Val Trp Gly Gln Asp Gly Asn Glu Glu Met Gly Gly
            20                  25                  30

Ile Thr Gln Thr Pro Tyr Lys Val Ser Ile Ser Gly Thr Thr Val Ile
        35                  40                  45

Leu Thr Cys Pro Gln Tyr Pro Gly Ser Glu Ile Leu Trp Gln His Asn
    50                  55                  60

Asp Lys Asn Ile Gly Gly Asp Glu Asp Lys Asn Ile Gly Ser Asp
65                  70                  75                  80

Glu Asp His Leu Ser Leu Lys Glu Phe Ser Glu Leu Glu Gln Ser Gly
                85                  90                  95

Tyr Tyr Val Cys Tyr Pro Arg Gly Ser Lys Pro Glu Asp Ala Asn Phe
            100                 105                 110

Tyr Leu Tyr Leu Arg Ala Arg Val Cys Glu Asn Cys Met Glu Met Asp
        115                 120                 125

Val Met Ser Val Ala Thr Ile Val Ile Val Asp Ile Cys Ile Thr Gly
    130                 135                 140

Gly Leu Leu Leu Leu Val Tyr Tyr Trp Ser Lys Asn Arg Lys Ala Lys
145                 150                 155                 160

Ala Lys Pro Val Thr Arg Gly Ala Gly Ala Gly Gly Arg Gln Arg Gly
                165                 170                 175

Gln Asn Lys Glu Arg Pro Pro Pro Val Pro Asn Pro Asp Tyr Glu Pro
            180                 185                 190

Ile Arg Lys Gly Gln Arg Asp Leu Tyr Ser Gly Leu Asn Gln Arg Arg
        195                 200                 205

Ile Gly Ser Gly Ser Gly Gly Ser Ile Leu Trp His Glu Met Trp His
    210                 215                 220

Glu Gly Leu Ile Glu Ala Ser Arg Leu Tyr Phe Gly Glu Arg Asn Val
225                 230                 235                 240

Lys Gly Met Phe Glu Val Leu Glu Pro Leu His Ala Met Met Glu Arg
                245                 250                 255

Gly Pro Gln Thr Leu Lys Glu Thr Ser Phe Asn Gln Ala Tyr Gly Arg
            260                 265                 270

Asp Leu Met Glu Ala Gln Glu Trp Cys Arg Lys Tyr Met Lys Ser Gly
        275                 280                 285
```

Asn Val Lys Asp Leu Leu Gln Ala Trp Asp Leu Tyr Tyr His Val Phe
            290                 295                 300

Arg Arg Ile Ser Lys
305

<210> SEQ ID NO 17
<211> LENGTH: 362
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gly Ser Ala Thr Met Ala Leu Pro Val Thr Ala Leu Leu Leu Pro Leu
1               5                   10                  15

Ala Leu Leu Leu His Ala Ala Arg Pro Glu Ile Val Met Thr Gln Ser
                20                  25                  30

Pro Ala Thr Leu Ser Leu Ser Pro Gly Glu Arg Ala Thr Leu Ser Cys
            35                  40                  45

Arg Ala Ser Gln Asp Ile Ser Lys Tyr Leu Asn Trp Tyr Gln Gln Lys
    50                  55                  60

Pro Gly Gln Ala Pro Arg Leu Leu Ile Tyr His Thr Ser Arg Leu His
65                  70                  75                  80

Ser Gly Ile Pro Ala Arg Phe Ser Gly Ser Gly Ser Gly Thr Asp Tyr
                85                  90                  95

Thr Leu Thr Ile Ser Ser Leu Gln Pro Glu Asp Phe Ala Val Tyr Phe
            100                 105                 110

Cys Gln Gln Gly Asn Thr Leu Pro Tyr Thr Phe Gly Gln Gly Thr Lys
        115                 120                 125

Leu Glu Ile Lys Gly Gly Gly Ser Gly Gly Gly Ser Gly Gly
    130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Gly Val Ser Leu
                165                 170                 175

Pro Asp Tyr Gly Val Ser Trp Ile Arg Gln Pro Pro Gly Lys Gly Leu
            180                 185                 190

Glu Trp Ile Gly Val Ile Trp Gly Ser Glu Thr Thr Tyr Tyr Ser Ser
        195                 200                 205

Ser Leu Lys Ser Arg Val Thr Ile Ser Lys Asp Asn Ser Lys Asn Gln
    210                 215                 220

Val Ser Leu Lys Leu Ser Ser Val Thr Ala Ala Asp Thr Ala Val Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Leu Val Thr Val Ser Ser Gly Gly Gly Gly Ser
            260                 265                 270

Pro Glu Asp Ala Asn Phe Tyr Leu Tyr Leu Arg Ala Arg Val Cys Glu
        275                 280                 285

Asn Cys Met Glu Met Asp Val Met Ser Val Ala Thr Ile Val Ile Val
    290                 295                 300

Asp Ile Cys Ile Thr Gly Gly Leu Leu Leu Leu Val Tyr Tyr Trp Ser
305                 310                 315                 320

-continued

```
Lys Arg Gly Arg Lys Lys Leu Leu Tyr Ile Phe Lys Gln Pro Phe Met
                325                 330                 335
Arg Pro Val Gln Thr Thr Gln Glu Glu Asp Gly Cys Ser Cys Arg Phe
            340                 345                 350
Pro Glu Glu Glu Glu Gly Gly Cys Glu Leu
        355                 360

<210> SEQ ID NO 18
<211> LENGTH: 362
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gly Ser Ala Thr Met Ala Leu Pro Val Thr Ala Leu Leu Leu Pro Leu
1               5                   10                  15
Ala Leu Leu Leu His Ala Ala Arg Pro Glu Ile Val Met Thr Gln Ser
            20                  25                  30
Pro Ala Thr Leu Ser Leu Ser Pro Gly Glu Arg Ala Thr Leu Ser Cys
        35                  40                  45
Arg Ala Ser Gln Asp Ile Ser Lys Tyr Leu Asn Trp Tyr Gln Gln Lys
    50                  55                  60
Pro Gly Gln Ala Pro Arg Leu Leu Ile Tyr His Thr Ser Arg Leu His
65                  70                  75                  80
Ser Gly Ile Pro Ala Arg Phe Ser Gly Ser Gly Ser Gly Thr Asp Tyr
                85                  90                  95
Thr Leu Thr Ile Ser Ser Leu Gln Pro Glu Asp Phe Ala Val Tyr Phe
            100                 105                 110
Cys Gln Gln Gly Asn Thr Leu Pro Tyr Thr Phe Gly Gln Gly Thr Lys
        115                 120                 125
Leu Glu Ile Lys Gly Gly Gly Gly Ser Gly Gly Gly Gly Ser Gly Gly
    130                 135                 140
Gly Gly Ser Gln Val Gln Leu Gln Glu Ser Gly Pro Gly Leu Val Lys
145                 150                 155                 160
Pro Ser Glu Thr Leu Ser Leu Thr Cys Thr Val Ser Gly Val Ser Leu
                165                 170                 175
Pro Asp Tyr Gly Val Ser Trp Ile Arg Gln Pro Pro Gly Lys Gly Leu
            180                 185                 190
Glu Trp Ile Gly Val Ile Trp Gly Ser Glu Thr Thr Tyr Tyr Ser Ser
        195                 200                 205
Ser Leu Lys Ser Arg Val Thr Ile Ser Lys Asp Asn Ser Lys Asn Gln
    210                 215                 220
Val Ser Leu Lys Leu Ser Ser Val Thr Ala Ala Asp Thr Ala Val Tyr
225                 230                 235                 240
Tyr Cys Ala Lys His Tyr Tyr Tyr Gly Gly Ser Tyr Ala Met Asp Tyr
                245                 250                 255
Trp Gly Gln Gly Thr Leu Val Thr Val Ser Ser Gly Gly Gly Gly Ser
            260                 265                 270
Pro Glu Asp Ala Asn Phe Tyr Leu Tyr Leu Arg Ala Arg Val Ser Glu
        275                 280                 285
Asn Cys Met Glu Met Asp Val Met Ser Val Ala Thr Ile Val Ile Val
    290                 295                 300
Asp Ile Cys Ile Thr Gly Gly Leu Leu Leu Leu Val Tyr Tyr Trp Ser
```

```
                    305                 310                 315                 320
Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
            340                 345                 350

Pro Glu Glu Glu Glu Gly Gly Cys Glu Leu
        355                 360

<210> SEQ ID NO 19
<211> LENGTH: 362
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gly Ser Ala Thr Met Ala Leu Pro Val Thr Ala Leu Leu Leu Pro Leu
1               5                   10                  15

Ala Leu Leu Leu His Ala Ala Arg Pro Glu Ile Val Met Thr Gln Ser
            20                  25                  30

Pro Ala Thr Leu Ser Leu Ser Pro Gly Glu Arg Ala Thr Leu Ser Cys
        35                  40                  45

Arg Ala Ser Gln Asp Ile Ser Lys Tyr Leu Asn Trp Tyr Gln Gln Lys
    50                  55                  60

Pro Gly Gln Ala Pro Arg Leu Leu Ile Tyr His Thr Ser Arg Leu His
65                  70                  75                  80

Ser Gly Ile Pro Ala Arg Phe Ser Gly Ser Gly Ser Gly Thr Asp Tyr
                85                  90                  95

Thr Leu Thr Ile Ser Ser Leu Gln Pro Glu Asp Phe Ala Val Tyr Phe
            100                 105                 110

Cys Gln Gln Gly Asn Thr Leu Pro Tyr Thr Phe Gly Gln Gly Thr Lys
        115                 120                 125

Leu Glu Ile Lys Gly Gly Gly Ser Gly Gly Gly Ser Gly Gly
    130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Gly Val Ser Leu
                165                 170                 175

Pro Asp Tyr Gly Val Ser Trp Ile Arg Gln Pro Pro Gly Lys Gly Leu
            180                 185                 190

Glu Trp Ile Gly Val Ile Trp Gly Ser Glu Thr Thr Tyr Tyr Ser Ser
        195                 200                 205

Ser Leu Lys Ser Arg Val Thr Ile Ser Lys Asp Asn Ser Lys Asn Gln
    210                 215                 220

Val Ser Leu Lys Leu Ser Ser Val Thr Ala Ala Asp Thr Ala Val Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Leu Val Thr Val Ser Ser Gly Gly Gly Gly Ser
            260                 265                 270

Pro Glu Asp Ala Asn Phe Tyr Leu Tyr Leu Arg Ala Arg Val Cys Glu
        275                 280                 285

Asn Ser Met Glu Met Asp Val Met Ser Val Ala Thr Ile Val Ile Val
    290                 295                 300
```

```
Asp Ile Cys Ile Thr Gly Gly Leu Leu Leu Val Tyr Tyr Trp Ser
305                 310                 315                 320

Lys Arg Gly Arg Lys Leu Leu Tyr Ile Phe Lys Gln Pro Phe Met
            325                 330                 335

Arg Pro Val Gln Thr Thr Gln Glu Glu Asp Gly Cys Ser Cys Arg Phe
            340                 345                 350

Pro Glu Glu Glu Glu Gly Gly Cys Glu Leu
        355                 360
```

<210> SEQ ID NO 20  
<211> LENGTH: 362  
<212> TYPE: PRT  
<213> ORGANISM: Artificial Sequence  
<220> FEATURE:  
<221> NAME/KEY: source  
<223> OTHER INFORMATION: /note="Description of Artificial Sequence: Synthetic polypeptide"

<400> SEQUENCE: 20

```
Gly Ser Ala Thr Met Ala Leu Pro Val Thr Ala Leu Leu Leu Pro Leu
1               5                   10                  15

Ala Leu Leu Leu His Ala Ala Arg Pro Glu Ile Val Met Thr Gln Ser
            20                  25                  30

Pro Ala Thr Leu Ser Leu Ser Pro Gly Glu Arg Ala Thr Leu Ser Cys
        35                  40                  45

Arg Ala Ser Gln Asp Ile Ser Lys Tyr Leu Asn Trp Tyr Gln Gln Lys
50                  55                  60

Pro Gly Gln Ala Pro Arg Leu Leu Ile Tyr His Thr Ser Arg Leu His
65                  70                  75                  80

Ser Gly Ile Pro Ala Arg Phe Ser Gly Ser Gly Ser Gly Thr Asp Tyr
                85                  90                  95

Thr Leu Thr Ile Ser Ser Leu Gln Pro Glu Asp Phe Ala Val Tyr Phe
            100                 105                 110

Cys Gln Gln Gly Asn Thr Leu Pro Tyr Thr Phe Gly Gln Gly Thr Lys
        115                 120                 125

Leu Glu Ile Lys Gly Gly Gly Gly Ser Gly Gly Gly Gly Ser Gly Gly
130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Gly Val Ser Leu
                165                 170                 175

Pro Asp Tyr Gly Val Ser Trp Ile Arg Gln Pro Pro Gly Lys Gly Leu
            180                 185                 190

Glu Trp Ile Gly Val Ile Trp Gly Ser Glu Thr Thr Tyr Tyr Ser Ser
        195                 200                 205

Ser Leu Lys Ser Arg Val Thr Ile Ser Lys Asp Asn Ser Lys Asn Gln
210                 215                 220

Val Ser Leu Lys Leu Ser Ser Val Thr Ala Ala Asp Thr Ala Val Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Leu Val Thr Val Ser Ser Gly Gly Gly Gly Ser
            260                 265                 270

Pro Glu Asp Ala Asn Phe Tyr Leu Tyr Leu Arg Ala Arg Val Ser Glu
        275                 280                 285
```

```
Asn Ser Met Glu Met Asp Val Met Ser Val Ala Thr Ile Val Ile Val
    290                 295                 300

Asp Ile Cys Ile Thr Gly Gly Leu Leu Leu Val Tyr Tyr Trp Ser
305                 310                 315                 320

Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
                340                 345                 350

Pro Glu Glu Glu Glu Gly Gly Cys Glu Leu
                355                 360

<210> SEQ ID NO 21
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
                20                  25                  30

Thr Leu Ser Leu Ser Pro Gly Glu Arg Ala Thr Leu Ser Cys Arg Ala
                35                  40                  45

Ser Gln Asp Ile Ser Lys Tyr Leu Asn Trp Tyr Gln Gln Lys Pro Gly
50                  55                  60

Gln Ala Pro Arg Leu Leu Ile Tyr His Thr Ser Arg Leu His Ser Gly
65                  70                  75                  80

Ile Pro Ala Arg Phe Ser Gly Ser Gly Ser Gly Thr Asp Tyr Thr Leu
                85                  90                  95

Thr Ile Ser Ser Leu Gln Pro Glu Asp Phe Ala Val Tyr Phe Cys Gln
                100                 105                 110

Gln Gly Asn Thr Leu Pro Tyr Thr Phe Gly Gln Gly Thr Lys Leu Glu
                115                 120                 125

Ile Lys Gly Gly Gly Gly Ser Gly Gly Gly Ser Gly Gly Gly Gly
                130                 135                 140

Ser Gln Val Gln Leu Gln Glu Ser Gly Pro Gly Leu Val Lys Pro Ser
145                 150                 155                 160

Glu Thr Leu Ser Leu Thr Cys Thr Val Ser Gly Val Ser Leu Pro Asp
                165                 170                 175

Tyr Gly Val Ser Trp Ile Arg Gln Pro Pro Gly Lys Gly Leu Glu Trp
                180                 185                 190

Ile Gly Val Ile Trp Gly Ser Glu Thr Thr Tyr Tyr Ser Ser Ser Leu
                195                 200                 205

Lys Ser Arg Val Thr Ile Ser Lys Asp Asn Ser Lys Asn Gln Val Ser
                210                 215                 220

Leu Lys Leu Ser Ser Val Thr Ala Ala Asp Thr Ala Val Tyr Tyr Cys
225                 230                 235                 240

Ala Lys His Tyr Tyr Tyr Gly Gly Ser Tyr Ala Met Asp Tyr Trp Gly
                245                 250                 255

Gln Gly Thr Leu Val Thr Val Ser Ser Gly Gly Gly Gly Ser Asp Gly
                260                 265                 270

Asn Glu Glu Met Gly Gly Ile Thr Gln Thr Pro Tyr Lys Val Ser Ile
```

```
                    275                 280                 285
Ser Gly Thr Thr Val Ile Leu Thr Cys Pro Gln Tyr Pro Gly Ser Glu
    290                 295                 300

Ile Leu Trp Gln His Asn Asp Lys Asn Ile Gly Gly Asp Glu Asp Asp
305                 310                 315                 320

Lys Asn Ile Gly Ser Asp Glu Asp His Leu Ser Leu Lys Glu Phe Ser
                325                 330                 335

Glu Leu Glu Gln Ser Gly Tyr Tyr Val Cys Tyr Pro Arg Gly Ser Lys
            340                 345                 350

Pro Glu Asp Ala Asn Phe Tyr Leu Tyr Leu Arg Ala Arg Val Cys Glu
        355                 360                 365

Asn Cys Met Glu Met Asp Val Met Ser Val Ala Thr Ile Val Ile Val
    370                 375                 380

Asp Ile Cys Ile Thr Gly Gly Leu Leu Leu Val Tyr Tyr Trp Ser
385                 390                 395                 400

Gln Arg Arg Lys Tyr Arg Ser Asn Lys Gly Glu Ser Pro Val Glu Pro
                405                 410                 415

Ala Glu Pro Cys His Tyr Ser Cys Pro Arg Glu Glu Glu Gly Ser Thr
            420                 425                 430

Ile Pro Ile Gln Glu Asp Tyr Arg Lys Pro Glu Pro Ala Cys Ser Pro
        435                 440                 445

<210> SEQ ID NO 22
<211> LENGTH: 441
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
                20                  25                  30

Thr Leu Ser Leu Ser Pro Gly Glu Arg Ala Thr Leu Ser Cys Arg Ala
            35                  40                  45

Ser Gln Asp Ile Ser Lys Tyr Leu Asn Trp Tyr Gln Gln Lys Pro Gly
        50                  55                  60

Gln Ala Pro Arg Leu Leu Ile Tyr His Thr Ser Arg Leu His Ser Gly
65                  70                  75                  80

Ile Pro Ala Arg Phe Ser Gly Ser Gly Ser Gly Thr Asp Tyr Thr Leu
                85                  90                  95

Thr Ile Ser Ser Leu Gln Pro Glu Asp Phe Ala Val Tyr Phe Cys Gln
            100                 105                 110

Gln Gly Asn Thr Leu Pro Tyr Thr Phe Gly Gln Gly Thr Lys Leu Glu
        115                 120                 125

Ile Lys Gly Gly Gly Gly Ser Gly Gly Gly Ser Gly Gly Gly Gly
    130                 135                 140

Ser Gln Val Gln Leu Gln Glu Ser Gly Pro Gly Leu Val Lys Pro Ser
145                 150                 155                 160

Glu Thr Leu Ser Leu Thr Cys Thr Val Ser Gly Val Ser Leu Pro Asp
                165                 170                 175

Tyr Gly Val Ser Trp Ile Arg Gln Pro Pro Gly Lys Gly Leu Glu Trp
            180                 185                 190
```

```
Ile Gly Val Ile Trp Gly Ser Glu Thr Thr Tyr Tyr Ser Ser Ser Leu
        195                 200                 205

Lys Ser Arg Val Thr Ile Ser Lys Asp Asn Ser Lys Asn Gln Val Ser
    210                 215                 220

Leu Lys Leu Ser Ser Val Thr Ala Ala Asp Thr Ala Val Tyr Tyr Cys
225                 230                 235                 240

Ala Lys His Tyr Tyr Tyr Gly Gly Ser Tyr Ala Met Asp Tyr Trp Gly
                245                 250                 255

Gln Gly Thr Leu Val Thr Val Ser Ser Gly Gly Gly Ser Asp Gly
                260                 265                 270

Asn Glu Glu Met Gly Gly Ile Thr Gln Thr Pro Tyr Lys Val Ser Ile
            275                 280                 285

Ser Gly Thr Thr Val Ile Leu Thr Cys Pro Gln Tyr Pro Gly Ser Glu
        290                 295                 300

Ile Leu Trp Gln His Asn Asp Lys Asn Ile Gly Gly Asp Glu Asp Asp
305                 310                 315                 320

Lys Asn Ile Gly Ser Asp Glu Asp His Leu Ser Leu Lys Glu Phe Ser
                325                 330                 335

Glu Leu Glu Gln Ser Gly Tyr Tyr Val Cys Tyr Pro Arg Gly Ser Lys
            340                 345                 350

Pro Glu Asp Ala Asn Phe Tyr Leu Tyr Leu Arg Ala Arg Val Cys Glu
        355                 360                 365

Asn Cys Met Glu Met Asp Val Met Ser Val Ala Thr Ile Val Ile Val
    370                 375                 380

Asp Ile Cys Ile Thr Gly Gly Leu Leu Leu Leu Val Tyr Tyr Trp Ser
385                 390                 395                 400

Arg Ser Lys Arg Ser Arg Leu Leu His Ser Asp Tyr Met Asn Met Thr
                405                 410                 415

Pro Arg Arg Pro Gly Pro Thr Arg Lys His Tyr Gln Pro Tyr Ala Pro
            420                 425                 430

Pro Arg Asp Phe Ala Ala Tyr Arg Ser
        435                 440

<210> SEQ ID NO 23
<211> LENGTH: 437
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
                20                  25                  30

Thr Leu Ser Leu Ser Pro Gly Glu Arg Ala Thr Leu Ser Cys Arg Ala
            35                  40                  45

Ser Gln Asp Ile Ser Lys Tyr Leu Asn Trp Tyr Gln Gln Lys Pro Gly
        50                  55                  60

Gln Ala Pro Arg Leu Leu Ile Tyr His Thr Ser Arg Leu His Ser Gly
65                  70                  75                  80

Ile Pro Ala Arg Phe Ser Gly Ser Gly Ser Gly Thr Asp Tyr Thr Leu
                85                  90                  95
```

Thr Ile Ser Ser Leu Gln Pro Glu Asp Phe Ala Val Tyr Phe Cys Gln
            100                 105                 110

Gln Gly Asn Thr Leu Pro Tyr Thr Phe Gly Gln Gly Thr Lys Leu Glu
        115                 120                 125

Ile Lys Gly Gly Gly Gly Ser Gly Gly Gly Gly Ser Gly Gly Gly Gly
    130                 135                 140

Ser Gln Val Gln Leu Gln Glu Ser Gly Pro Gly Leu Val Lys Pro Ser
145                 150                 155                 160

Glu Thr Leu Ser Leu Thr Cys Thr Val Ser Gly Val Ser Leu Pro Asp
                165                 170                 175

Tyr Gly Val Ser Trp Ile Arg Gln Pro Pro Lys Gly Leu Glu Trp
            180                 185                 190

Ile Gly Val Ile Trp Gly Ser Glu Thr Thr Tyr Tyr Ser Ser Ser Leu
    195                 200                 205

Lys Ser Arg Val Thr Ile Ser Lys Asp Asn Ser Lys Asn Gln Val Ser
210                 215                 220

Leu Lys Leu Ser Ser Val Thr Ala Ala Asp Thr Ala Val Tyr Tyr Cys
225                 230                 235                 240

Ala Lys His Tyr Tyr Tyr Gly Gly Ser Tyr Ala Met Asp Tyr Trp Gly
            245                 250                 255

Gln Gly Thr Leu Val Thr Val Ser Ser Gly Gly Gly Ser Asp Gly
        260                 265                 270

Asn Glu Glu Met Gly Gly Ile Thr Gln Thr Pro Tyr Lys Val Ser Ile
    275                 280                 285

Ser Gly Thr Thr Val Ile Leu Thr Cys Pro Gln Tyr Pro Gly Ser Glu
290                 295                 300

Ile Leu Trp Gln His Asn Asp Lys Asn Ile Gly Gly Asp Glu Asp Asp
305                 310                 315                 320

Lys Asn Ile Gly Ser Asp Glu Asp His Leu Ser Leu Lys Glu Phe Ser
            325                 330                 335

Glu Leu Glu Gln Ser Gly Tyr Tyr Val Cys Tyr Pro Arg Gly Ser Lys
        340                 345                 350

Pro Glu Asp Ala Asn Phe Tyr Leu Tyr Leu Arg Ala Arg Val Cys Glu
        355                 360                 365

Asn Cys Met Glu Met Asp Val Met Ser Val Ala Thr Ile Val Ile Val
370                 375                 380

Asp Ile Cys Ile Thr Gly Gly Leu Leu Leu Leu Val Tyr Tyr Trp Ser
385                 390                 395                 400

Arg Arg Asp Gln Arg Leu Pro Pro Asp Ala His Lys Pro Pro Gly Gly
            405                 410                 415

Gly Ser Phe Arg Thr Pro Ile Gln Glu Glu Gln Ala Asp Ala His Ser
        420                 425                 430

Thr Leu Ala Lys Ile
        435

<210> SEQ ID NO 24
<211> LENGTH: 435
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gly Ser Met Ala Leu Pro Val Thr Ala Leu Leu Leu Pro Leu Ala Leu

-continued

```
1               5                   10                  15
Leu Leu His Ala Ala Arg Pro Glu Ile Val Met Thr Gln Ser Pro Ala
                20                  25                  30
Thr Leu Ser Leu Ser Pro Gly Glu Arg Ala Thr Leu Ser Cys Arg Ala
                35                  40                  45
Ser Gln Asp Ile Ser Lys Tyr Leu Asn Trp Tyr Gln Gln Lys Pro Gly
                50                  55                  60
Gln Ala Pro Arg Leu Leu Ile Tyr His Thr Ser Arg Leu His Ser Gly
 65                 70                  75                  80
Ile Pro Ala Arg Phe Ser Gly Ser Gly Ser Gly Thr Asp Tyr Thr Leu
                    85                  90                  95
Thr Ile Ser Ser Leu Gln Pro Glu Asp Phe Ala Val Tyr Phe Cys Gln
                100                 105                 110
Gln Gly Asn Thr Leu Pro Tyr Thr Phe Gly Gln Gly Thr Lys Leu Glu
                115                 120                 125
Ile Lys Gly Gly Gly Gly Ser Gly Gly Gly Gly Ser Gly Gly Gly Gly
            130                 135                 140
Ser Gln Val Gln Leu Gln Glu Ser Gly Pro Gly Leu Val Lys Pro Ser
145                 150                 155                 160
Glu Thr Leu Ser Leu Thr Cys Thr Val Ser Gly Val Ser Leu Pro Asp
                165                 170                 175
Tyr Gly Val Ser Trp Ile Arg Gln Pro Pro Gly Lys Gly Leu Glu Trp
                180                 185                 190
Ile Gly Val Ile Trp Gly Ser Glu Thr Thr Tyr Tyr Ser Ser Ser Leu
                195                 200                 205
Lys Ser Arg Val Thr Ile Ser Lys Asp Asn Ser Lys Asn Gln Val Ser
210                 215                 220
Leu Lys Leu Ser Ser Val Thr Ala Ala Asp Thr Ala Val Tyr Tyr Cys
225                 230                 235                 240
Ala Lys His Tyr Tyr Tyr Gly Gly Ser Tyr Ala Met Asp Tyr Trp Gly
                245                 250                 255
Gln Gly Thr Leu Val Thr Val Ser Ser Gly Gly Gly Gly Ser Asp Gly
                260                 265                 270
Asn Glu Glu Met Gly Gly Ile Thr Gln Thr Pro Tyr Lys Val Ser Ile
                275                 280                 285
Ser Gly Thr Thr Val Ile Leu Thr Cys Pro Gln Tyr Pro Gly Ser Glu
                290                 295                 300
Ile Leu Trp Gln His Asn Asp Lys Asn Ile Gly Gly Asp Glu Asp Asp
305                 310                 315                 320
Lys Asn Ile Gly Ser Asp Glu Asp His Leu Ser Leu Lys Glu Phe Ser
                    325                 330                 335
Glu Leu Glu Gln Ser Gly Tyr Tyr Val Cys Tyr Pro Arg Gly Ser Lys
                340                 345                 350
Pro Glu Asp Ala Asn Phe Tyr Leu Tyr Leu Arg Ala Arg Val Cys Glu
                355                 360                 365
Asn Cys Met Glu Met Asp Val Met Ser Val Ala Thr Ile Val Ile Val
                370                 375                 380
Asp Ile Cys Ile Thr Gly Gly Leu Leu Leu Leu Val Tyr Tyr Trp Ser
385                 390                 395                 400
Thr Lys Lys Lys Tyr Ser Ser Ser Val His Asp Pro Asn Gly Glu Tyr
                    405                 410                 415
Met Phe Met Arg Ala Val Asn Thr Ala Lys Lys Ser Arg Leu Thr Asp
                420                 425                 430
```

Val Thr Leu
        435

<210> SEQ ID NO 25
<211> LENGTH: 516
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
            20                  25                  30

Thr Leu Ser Leu Ser Pro Gly Glu Arg Ala Thr Leu Ser Cys Arg Ala
        35                  40                  45

Ser Gln Asp Ile Ser Lys Tyr Leu Asn Trp Tyr Gln Gln Lys Pro Gly
    50                  55                  60

Gln Ala Pro Arg Leu Leu Ile Tyr His Thr Ser Arg Leu His Ser Gly
65                  70                  75                  80

Ile Pro Ala Arg Phe Ser Gly Ser Gly Ser Gly Thr Asp Tyr Thr Leu
                85                  90                  95

Thr Ile Ser Ser Leu Gln Pro Glu Asp Phe Ala Val Tyr Phe Cys Gln
            100                 105                 110

Gln Gly Asn Thr Leu Pro Tyr Thr Phe Gly Gln Gly Thr Lys Leu Glu
        115                 120                 125

Ile Lys Gly Gly Gly Gly Ser Gly Gly Gly Gly Ser Gly Gly Gly Gly
    130                 135                 140

Ser Gln Val Gln Leu Gln Glu Ser Gly Pro Gly Leu Val Lys Pro Ser
145                 150                 155                 160

Glu Thr Leu Ser Leu Thr Cys Thr Val Ser Gly Val Ser Leu Pro Asp
                165                 170                 175

Tyr Gly Val Ser Trp Ile Arg Gln Pro Pro Gly Lys Gly Leu Glu Trp
            180                 185                 190

Ile Gly Val Ile Trp Gly Ser Glu Thr Thr Tyr Tyr Ser Ser Ser Leu
        195                 200                 205

Lys Ser Arg Val Thr Ile Ser Lys Asp Asn Ser Lys Asn Gln Val Ser
    210                 215                 220

Leu Lys Leu Ser Ser Val Thr Ala Ala Asp Thr Ala Val Tyr Tyr Cys
225                 230                 235                 240

Ala Lys His Tyr Tyr Tyr Gly Gly Ser Tyr Ala Met Asp Tyr Trp Gly
                245                 250                 255

Gln Gly Thr Leu Val Thr Val Ser Ser Gly Gly Gly Gly Ser Asp Gly
            260                 265                 270

Asn Glu Glu Met Gly Gly Ile Thr Gln Thr Pro Tyr Lys Val Ser Ile
        275                 280                 285

Ser Gly Thr Thr Val Ile Leu Thr Cys Pro Gln Tyr Pro Gly Ser Glu
    290                 295                 300

Ile Leu Trp Gln His Asn Asp Lys Asn Ile Gly Gly Asp Glu Asp Asp
305                 310                 315                 320

Lys Asn Ile Gly Ser Asp Glu Asp His Leu Ser Leu Lys Glu Phe Ser
                325                 330                 335

Glu Leu Glu Gln Ser Gly Tyr Tyr Val Cys Tyr Pro Arg Gly Ser Lys
                340                 345                 350

Pro Glu Asp Ala Asn Phe Tyr Leu Tyr Leu Arg Ala Arg Val Cys Glu
            355                 360                 365

Asn Cys Met Glu Met Asp Val Met Ser Val Ala Thr Ile Val Ile Val
        370                 375                 380

Asp Ile Cys Ile Thr Gly Gly Leu Leu Leu Val Tyr Tyr Trp Ser
385                 390                 395                 400

Lys Arg Lys Lys Gln Arg Ser Arg Arg Asn Asp Glu Glu Leu Glu Thr
                405                 410                 415

Arg Ala His Arg Val Ala Thr Glu Glu Arg Gly Arg Lys Pro His Gln
            420                 425                 430

Ile Pro Ala Ser Thr Pro Gln Asn Pro Ala Thr Ser Gln His Pro Pro
            435                 440                 445

Pro Pro Pro Gly His Arg Ser Gln Ala Pro Ser His Arg Pro Pro Pro
        450                 455                 460

Pro Gly His Arg Val Gln His Gln Pro Gln Lys Arg Pro Pro Ala Pro
465                 470                 475                 480

Ser Gly Thr Gln Val His Gln Gln Lys Gly Pro Pro Leu Pro Arg Pro
                485                 490                 495

Arg Val Gln Pro Lys Pro Pro His Gly Ala Ala Glu Asn Ser Leu Ser
            500                 505                 510

Pro Ser Ser Asn
        515

<210> SEQ ID NO 26
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
                20                  25                  30

Thr Leu Ser Leu Ser Pro Gly Glu Arg Ala Thr Leu Ser Cys Arg Ala
            35                  40                  45

Ser Gln Asp Ile Ser Lys Tyr Leu Asn Trp Tyr Gln Gln Lys Pro Gly
    50                  55                  60

Gln Ala Pro Arg Leu Leu Ile Tyr His Thr Ser Arg Leu His Ser Gly
65                  70                  75                  80

Ile Pro Ala Arg Phe Ser Gly Ser Gly Ser Gly Thr Asp Tyr Thr Leu
                85                  90                  95

Thr Ile Ser Ser Leu Gln Pro Glu Asp Phe Ala Val Tyr Phe Cys Gln
            100                 105                 110

Gln Gly Asn Thr Leu Pro Tyr Thr Phe Gly Gln Gly Thr Lys Leu Glu
        115                 120                 125

Ile Lys Gly Gly Gly Gly Ser Gly Gly Gly Gly Ser Gly Gly Gly Gly
    130                 135                 140

Ser Gln Val Gln Leu Gln Glu Ser Gly Pro Gly Leu Val Lys Pro Ser
145                 150                 155                 160

Glu Thr Leu Ser Leu Thr Cys Thr Val Ser Gly Val Ser Leu Pro Asp

-continued

```
                165                 170                 175
Tyr Gly Val Ser Trp Ile Arg Gln Pro Gly Lys Gly Leu Glu Trp
                180                 185                 190

Ile Gly Val Ile Trp Gly Ser Glu Thr Thr Tyr Tyr Ser Ser Leu
                195                 200                 205

Lys Ser Arg Val Thr Ile Ser Lys Asp Asn Ser Lys Asn Gln Val Ser
210                 215                 220

Leu Lys Leu Ser Ser Val Thr Ala Ala Asp Thr Ala Val Tyr Tyr Cys
225                 230                 235                 240

Ala Lys His Tyr Tyr Gly Gly Ser Tyr Ala Met Asp Tyr Trp Gly
                245                 250                 255

Gln Gly Thr Leu Val Thr Val Ser Ser Gly Gly Gly Ser Gly Gly
                260                 265                 270

Gly Gly Ser Asp Gly Asn Glu Glu Met Gly Gly Ile Thr Gln Thr Pro
                275                 280                 285

Tyr Lys Val Ser Ile Ser Gly Thr Thr Val Ile Leu Thr Cys Pro Gln
290                 295                 300

Tyr Pro Gly Ser Glu Ile Leu Trp Gln His Asn Asp Lys Asn Ile Gly
305                 310                 315                 320

Gly Asp Glu Asp Asp Lys Asn Ile Gly Ser Asp Glu Asp His Leu Ser
                325                 330                 335

Leu Lys Glu Phe Ser Glu Leu Glu Gln Ser Gly Tyr Tyr Val Cys Tyr
                340                 345                 350

Pro Arg Gly Ser Lys Pro Glu Asp Ala Asn Phe Tyr Leu Tyr Leu Arg
                355                 360                 365

Ala Arg Val Cys Glu Asn Cys Met Glu Met Asp Val Met Ser Val Ala
                370                 375                 380

Thr Ile Val Ile Val Asp Ile Cys Ile Thr Gly Gly Leu Leu Leu Leu
385                 390                 395                 400

Val Tyr Tyr Trp Ser Lys Arg Gly Arg Lys Lys Leu Leu Tyr Ile Phe
                405                 410                 415

Lys Gln Pro Phe Met Arg Pro Val Gln Thr Thr Gln Glu Glu Asp Gly
                420                 425                 430

Cys Ser Cys Arg Phe Pro Glu Glu Glu Glu Gly Gly Cys Glu Leu
                435                 440                 445
```

<210> SEQ ID NO 27
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 27

```
Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
                20                  25                  30

Thr Leu Ser Leu Ser Pro Gly Glu Arg Ala Thr Leu Ser Cys Arg Ala
                35                  40                  45

Ser Gln Asp Ile Ser Lys Tyr Leu Asn Trp Tyr Gln Gln Lys Pro Gly
50                  55                  60

Gln Ala Pro Arg Leu Leu Ile Tyr His Thr Ser Arg Leu His Ser Gly
65                  70                  75                  80
```

Ile Pro Ala Arg Phe Ser Gly Ser Gly Ser Gly Thr Asp Tyr Thr Leu
               85                  90                  95

Thr Ile Ser Ser Leu Gln Pro Glu Asp Phe Ala Val Tyr Phe Cys Gln
            100                 105                 110

Gln Gly Asn Thr Leu Pro Tyr Thr Phe Gly Gln Gly Thr Lys Leu Glu
        115                 120                 125

Ile Lys Gly Gly Gly Gly Ser Gly Gly Gly Gly Ser Gly Gly Gly Gly
    130                 135                 140

Ser Gln Val Gln Leu Gln Glu Ser Gly Pro Gly Leu Val Lys Pro Ser
145                 150                 155                 160

Glu Thr Leu Ser Leu Thr Cys Thr Val Ser Gly Val Ser Leu Pro Asp
                165                 170                 175

Tyr Gly Val Ser Trp Ile Arg Gln Pro Pro Gly Lys Gly Leu Glu Trp
            180                 185                 190

Ile Gly Val Ile Trp Gly Ser Glu Thr Thr Tyr Tyr Ser Ser Ser Leu
        195                 200                 205

Lys Ser Arg Val Thr Ile Ser Lys Asp Asn Ser Lys Asn Gln Val Ser
    210                 215                 220

Leu Lys Leu Ser Ser Val Thr Ala Ala Asp Thr Ala Val Tyr Tyr Cys
225                 230                 235                 240

Ala Lys His Tyr Tyr Gly Gly Ser Tyr Ala Met Asp Tyr Trp Gly
                245                 250                 255

Gln Gly Thr Leu Val Thr Val Ser Ser Gly Gly Gly Ser Gly Gly
            260                 265                 270

Gly Gly Ser Gly Gly Gly Ser Gly Gly Gly Ser Asp Gly Asn
        275                 280                 285

Glu Glu Met Gly Gly Ile Thr Gln Thr Pro Tyr Lys Val Ser Ile Ser
290                 295                 300

Gly Thr Thr Val Ile Leu Thr Cys Pro Gln Tyr Pro Gly Ser Glu Ile
305                 310                 315                 320

Leu Trp Gln His Asn Asp Lys Asn Ile Gly Gly Asp Glu Asp Asp Lys
                325                 330                 335

Asn Ile Gly Ser Asp Glu Asp His Leu Ser Leu Lys Glu Phe Ser Glu
            340                 345                 350

Leu Glu Gln Ser Gly Tyr Tyr Val Cys Tyr Pro Arg Gly Ser Lys Pro
        355                 360                 365

Glu Asp Ala Asn Phe Tyr Leu Tyr Leu Arg Ala Arg Val Cys Glu Asn
    370                 375                 380

Cys Met Glu Met Asp Val Met Ser Val Ala Thr Ile Val Ile Val Asp
385                 390                 395                 400

Ile Cys Ile Thr Gly Gly Leu Leu Leu Leu Val Tyr Tyr Trp Ser Lys
                405                 410                 415

Arg Gly Arg Lys Lys Leu Leu Tyr Ile Phe Lys Gln Pro Phe Met Arg
            420                 425                 430

Pro Val Gln Thr Thr Gln Glu Glu Asp Gly Cys Ser Cys Arg Phe Pro
        435                 440                 445

Glu Glu Glu Glu Gly Gly Cys Glu Leu
    450                 455

<210> SEQ ID NO 28
<211> LENGTH: 419
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 28

```
Gly Ser Ala Thr Met Ala Leu Pro Val Thr Ala Leu Leu Leu Pro Leu
1               5                   10                  15

Ala Leu Leu Leu His Ala Ala Arg Pro Glu Ile Val Met Thr Gln Ser
            20                  25                  30

Pro Ala Thr Leu Ser Leu Ser Pro Gly Glu Arg Ala Thr Leu Ser Cys
        35                  40                  45

Arg Ala Ser Gln Asp Ile Ser Lys Tyr Leu Asn Trp Tyr Gln Gln Lys
    50                  55                  60

Pro Gly Gln Ala Pro Arg Leu Leu Ile Tyr His Thr Ser Arg Leu His
65                  70                  75                  80

Ser Gly Ile Pro Ala Arg Phe Ser Gly Ser Gly Ser Gly Thr Asp Tyr
                85                  90                  95

Thr Leu Thr Ile Ser Ser Leu Gln Pro Glu Asp Phe Ala Val Tyr Phe
            100                 105                 110

Cys Gln Gln Gly Asn Thr Leu Pro Tyr Thr Phe Gly Gln Gly Thr Lys
        115                 120                 125

Leu Glu Ile Lys Gly Gly Gly Gly Ser Gly Gly Gly Gly Ser Gly Gly
    130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Gly Val Ser Leu
                165                 170                 175

Pro Asp Tyr Gly Val Ser Trp Ile Arg Gln Pro Pro Gly Lys Gly Leu
            180                 185                 190

Glu Trp Ile Gly Val Ile Trp Gly Ser Glu Thr Thr Tyr Tyr Ser Ser
        195                 200                 205

Ser Leu Lys Ser Arg Val Thr Ile Ser Lys Asp Asn Ser Lys Asn Gln
    210                 215                 220

Val Ser Leu Lys Leu Ser Ser Val Thr Ala Ala Asp Thr Ala Val Tyr
225                 230                 235                 240

Tyr Cys Ala Lys His Tyr Tyr Gly Gly Ser Tyr Ala Met Asp Tyr
                245                 250                 255

Trp Gly Gln Gly Thr Leu Val Thr Val Ser Ser Gly Gly Gly Gly Ser
            260                 265                 270

Phe Lys Ile Pro Ile Glu Glu Leu Glu Asp Arg Val Phe Val Asn Cys
        275                 280                 285

Asn Thr Ser Ile Thr Trp Val Glu Gly Thr Val Gly Thr Leu Leu Ser
    290                 295                 300

Asp Ile Thr Arg Leu Asp Leu Gly Lys Arg Ile Leu Asp Pro Arg Gly
305                 310                 315                 320

Ile Tyr Arg Cys Asn Gly Thr Asp Ile Tyr Lys Asp Lys Glu Ser Thr
                325                 330                 335

Val Gln Val His Tyr Arg Met Cys Gln Ser Cys Val Glu Leu Asp Pro
            340                 345                 350

Ala Thr Val Ala Gly Ile Ile Val Thr Asp Val Ile Ala Thr Leu Leu
        355                 360                 365

Leu Ala Leu Gly Val Phe Cys Phe Ala Lys Arg Gly Arg Lys Lys Leu
    370                 375                 380

Leu Tyr Ile Phe Lys Gln Pro Phe Met Arg Pro Val Gln Thr Thr Gln
```

```
                385                 390                 395                 400
Glu Glu Asp Gly Cys Ser Cys Arg Phe Pro Glu Glu Glu Gly Gly
                    405                 410                 415

Cys Glu Leu

<210> SEQ ID NO 29
<211> LENGTH: 422
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
                20                  25                  30

Thr Leu Ser Leu Ser Pro Gly Glu Arg Ala Thr Leu Ser Cys Arg Ala
            35                  40                  45

Ser Gln Asp Ile Ser Lys Tyr Leu Asn Trp Tyr Gln Gln Lys Pro Gly
        50                  55                  60

Gln Ala Pro Arg Leu Leu Ile Tyr His Thr Ser Arg Leu His Ser Gly
65                  70                  75                  80

Ile Pro Ala Arg Phe Ser Gly Ser Gly Ser Gly Thr Asp Tyr Thr Leu
                85                  90                  95

Thr Ile Ser Ser Leu Gln Pro Glu Asp Phe Ala Val Tyr Phe Cys Gln
            100                 105                 110

Gln Gly Asn Thr Leu Pro Tyr Thr Phe Gly Gln Gly Thr Lys Leu Glu
        115                 120                 125

Ile Lys Gly Gly Gly Gly Ser Gly Gly Gly Gly Ser Gly Gly Gly Gly
130                 135                 140

Ser Gln Val Gln Leu Gln Glu Ser Gly Pro Gly Leu Val Lys Pro Ser
145                 150                 155                 160

Glu Thr Leu Ser Leu Thr Cys Thr Val Ser Gly Val Ser Leu Pro Asp
                165                 170                 175

Tyr Gly Val Ser Trp Ile Arg Gln Pro Pro Gly Lys Gly Leu Glu Trp
            180                 185                 190

Ile Gly Val Ile Trp Gly Ser Glu Thr Thr Tyr Tyr Ser Ser Ser Leu
        195                 200                 205

Lys Ser Arg Val Thr Ile Ser Lys Asp Asn Ser Lys Asn Gln Val Ser
    210                 215                 220

Leu Lys Leu Ser Ser Val Thr Ala Ala Asp Thr Ala Val Tyr Tyr Cys
225                 230                 235                 240

Ala Lys His Tyr Tyr Tyr Gly Gly Ser Tyr Ala Met Asp Tyr Trp Gly
                245                 250                 255

Gln Gly Thr Leu Val Thr Val Ser Ser Gly Gly Gly Gly Ser Gly Gly
            260                 265                 270

Gly Gly Ser Phe Lys Ile Pro Ile Glu Glu Leu Glu Asp Arg Val Phe
        275                 280                 285

Val Asn Cys Asn Thr Ser Ile Thr Trp Val Glu Gly Thr Val Gly Thr
    290                 295                 300

Leu Leu Ser Asp Ile Thr Arg Leu Asp Leu Gly Lys Arg Ile Leu Asp
305                 310                 315                 320
```

```
Pro Arg Gly Ile Tyr Arg Cys Asn Gly Thr Asp Ile Tyr Lys Asp Lys
                325                 330                 335

Glu Ser Thr Val Gln Val His Tyr Arg Met Cys Gln Ser Cys Val Glu
            340                 345                 350

Leu Asp Pro Ala Thr Val Ala Gly Ile Ile Val Thr Asp Val Ile Ala
        355                 360                 365

Thr Leu Leu Leu Ala Leu Gly Val Phe Cys Phe Ala Lys Arg Gly Arg
    370                 375                 380

Lys Lys Leu Leu Tyr Ile Phe Lys Gln Pro Phe Met Arg Pro Val Gln
385                 390                 395                 400

Thr Thr Gln Glu Glu Asp Gly Cys Ser Cys Arg Phe Pro Glu Glu Glu
                405                 410                 415

Glu Gly Gly Cys Glu Leu
            420

<210> SEQ ID NO 30
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
            20                  25                  30

Thr Leu Ser Leu Ser Pro Gly Glu Arg Ala Thr Leu Ser Cys Arg Ala
        35                  40                  45

Ser Gln Asp Ile Ser Lys Tyr Leu Asn Trp Tyr Gln Gln Lys Pro Gly
    50                  55                  60

Gln Ala Pro Arg Leu Leu Ile Tyr His Thr Ser Arg Leu His Ser Gly
65                  70                  75                  80

Ile Pro Ala Arg Phe Ser Gly Ser Gly Ser Gly Thr Asp Tyr Thr Leu
                85                  90                  95

Thr Ile Ser Ser Leu Gln Pro Glu Asp Phe Ala Val Tyr Phe Cys Gln
            100                 105                 110

Gln Gly Asn Thr Leu Pro Tyr Thr Phe Gly Gln Gly Thr Lys Leu Glu
        115                 120                 125

Ile Lys Gly Gly Gly Gly Ser Gly Gly Gly Ser Gly Gly Gly Gly
    130                 135                 140

Ser Gln Val Gln Leu Gln Glu Ser Gly Pro Gly Leu Val Lys Pro Ser
145                 150                 155                 160

Glu Thr Leu Ser Leu Thr Cys Thr Val Ser Gly Val Ser Leu Pro Asp
                165                 170                 175

Tyr Gly Val Ser Trp Ile Arg Gln Pro Pro Gly Lys Gly Leu Glu Trp
            180                 185                 190

Ile Gly Val Ile Trp Gly Ser Glu Thr Thr Tyr Tyr Ser Ser Ser Leu
        195                 200                 205

Lys Ser Arg Val Thr Ile Ser Lys Asp Asn Ser Lys Asn Gln Val Ser
    210                 215                 220

Leu Lys Leu Ser Ser Val Thr Ala Ala Asp Thr Ala Val Tyr Tyr Cys
225                 230                 235                 240

Ala Lys His Tyr Tyr Tyr Gly Gly Ser Tyr Ala Met Asp Tyr Trp Gly
```

-continued

```
                245                 250                 255
Gln Gly Thr Leu Val Thr Val Ser Ser Gly Gly Gly Ser Gly Gly
            260                 265                 270

Gly Gly Ser Gly Gly Gly Ser Gly Gly Gly Ser Phe Lys Ile
        275                 280                 285

Pro Ile Glu Glu Leu Glu Asp Arg Val Phe Val Asn Cys Asn Thr Ser
    290                 295                 300

Ile Thr Trp Val Glu Gly Thr Val Gly Thr Leu Leu Ser Asp Ile Thr
305                 310                 315                 320

Arg Leu Asp Leu Gly Lys Arg Ile Leu Asp Pro Arg Gly Ile Tyr Arg
                325                 330                 335

Cys Asn Gly Thr Asp Ile Tyr Lys Asp Lys Glu Ser Thr Val Gln Val
            340                 345                 350

His Tyr Arg Met Cys Gln Ser Cys Val Glu Leu Asp Pro Ala Thr Val
        355                 360                 365

Ala Gly Ile Ile Val Thr Asp Val Ile Ala Thr Leu Leu Leu Ala Leu
    370                 375                 380

Gly Val Phe Cys Phe Ala Lys Arg Gly Arg Lys Lys Leu Leu Tyr Ile
385                 390                 395                 400

Phe Lys Gln Pro Phe Met Arg Pro Val Gln Thr Thr Gln Glu Glu Asp
                405                 410                 415

Gly Cys Ser Cys Arg Phe Pro Glu Glu Glu Glu Gly Gly Cys Glu Leu
            420                 425                 430
```

<210> SEQ ID NO 31
<211> LENGTH: 429
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 31

```
Gly Ser Ala Thr Met Ala Leu Pro Val Thr Ala Leu Leu Leu Pro Leu
1               5                   10                  15

Ala Leu Leu Leu His Ala Ala Arg Pro Glu Ile Val Met Thr Gln Ser
                20                  25                  30

Pro Ala Thr Leu Ser Leu Ser Pro Gly Glu Arg Ala Thr Leu Ser Cys
            35                  40                  45

Arg Ala Ser Gln Asp Ile Ser Lys Tyr Leu Asn Trp Tyr Gln Gln Lys
    50                  55                  60

Pro Gly Gln Ala Pro Arg Leu Leu Ile Tyr His Thr Ser Arg Leu His
65                  70                  75                  80

Ser Gly Ile Pro Ala Arg Phe Ser Gly Ser Gly Ser Gly Thr Asp Tyr
                85                  90                  95

Thr Leu Thr Ile Ser Ser Leu Gln Pro Glu Asp Phe Ala Val Tyr Phe
            100                 105                 110

Cys Gln Gln Gly Asn Thr Leu Pro Tyr Thr Phe Gly Gln Gly Thr Lys
        115                 120                 125

Leu Glu Ile Lys Gly Gly Gly Gly Ser Gly Gly Gly Gly Ser Gly Gly
    130                 135                 140

Gly Gly Ser Gln Val Gln Leu Gln Glu Ser Gly Pro Gly Leu Val Lys
145                 150                 155                 160

Pro Ser Glu Thr Leu Ser Leu Thr Cys Thr Val Ser Gly Val Ser Leu
                165                 170                 175
```

Pro Asp Tyr Gly Val Ser Trp Ile Arg Gln Pro Pro Gly Lys Gly Leu
            180                 185                 190

Glu Trp Ile Gly Val Ile Trp Gly Ser Glu Thr Thr Tyr Tyr Ser Ser
        195                 200                 205

Ser Leu Lys Ser Arg Val Thr Ile Ser Lys Asp Asn Ser Lys Asn Gln
    210                 215                 220

Val Ser Leu Lys Leu Ser Ser Val Thr Ala Ala Asp Thr Ala Val Tyr
225                 230                 235                 240

Tyr Cys Ala Lys His Tyr Tyr Gly Gly Ser Tyr Ala Met Asp Tyr
                245                 250                 255

Trp Gly Gln Gly Thr Leu Val Thr Val Ser Ser Gly Gly Gly Gly Ser
            260                 265                 270

Gln Ser Ile Lys Gly Asn His Leu Val Lys Val Tyr Asp Tyr Gln Glu
        275                 280                 285

Asp Gly Ser Val Leu Leu Thr Cys Asp Ala Glu Ala Lys Asn Ile Thr
    290                 295                 300

Trp Phe Lys Asp Gly Lys Met Ile Gly Phe Leu Thr Glu Asp Lys Lys
305                 310                 315                 320

Lys Trp Asn Leu Gly Ser Asn Ala Lys Asp Pro Arg Gly Met Tyr Gln
                325                 330                 335

Cys Lys Gly Ser Gln Asn Lys Ser Lys Pro Leu Gln Val Tyr Tyr Arg
            340                 345                 350

Met Cys Gln Asn Cys Ile Glu Leu Asn Ala Ala Thr Ile Ser Gly Phe
        355                 360                 365

Leu Phe Ala Glu Ile Val Ser Ile Phe Val Leu Ala Val Gly Val Tyr
    370                 375                 380

Phe Ile Ala Lys Arg Gly Arg Lys Lys Leu Leu Tyr Ile Phe Lys Gln
385                 390                 395                 400

Pro Phe Met Arg Pro Val Gln Thr Thr Gln Glu Glu Asp Gly Cys Ser
                405                 410                 415

Cys Arg Phe Pro Glu Glu Glu Glu Gly Gly Cys Glu Leu
            420                 425

<210> SEQ ID NO 32
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
            20                  25                  30

Thr Leu Ser Leu Ser Pro Gly Glu Arg Ala Thr Leu Ser Cys Arg Ala
        35                  40                  45

Ser Gln Asp Ile Ser Lys Tyr Leu Asn Trp Tyr Gln Gln Lys Pro Gly
    50                  55                  60

Gln Ala Pro Arg Leu Leu Ile Tyr His Thr Ser Arg Leu His Ser Gly
65                  70                  75                  80

Ile Pro Ala Arg Phe Ser Gly Ser Gly Ser Gly Thr Asp Tyr Thr Leu
                85                  90                  95

```
Thr Ile Ser Ser Leu Gln Pro Glu Asp Phe Ala Val Tyr Phe Cys Gln
                100                 105                 110

Gln Gly Asn Thr Leu Pro Tyr Thr Phe Gly Gln Gly Thr Lys Leu Glu
            115                 120                 125

Ile Lys Gly Gly Gly Gly Ser Gly Gly Gly Gly Ser Gly Gly Gly Gly
        130                 135                 140

Ser Gln Val Gln Leu Gln Glu Ser Gly Pro Gly Leu Val Lys Pro Ser
145                 150                 155                 160

Glu Thr Leu Ser Leu Thr Cys Thr Val Ser Gly Val Ser Leu Pro Asp
                165                 170                 175

Tyr Gly Val Ser Trp Ile Arg Gln Pro Pro Gly Lys Gly Leu Glu Trp
            180                 185                 190

Ile Gly Val Ile Trp Gly Ser Glu Thr Thr Tyr Tyr Ser Ser Ser Leu
        195                 200                 205

Lys Ser Arg Val Thr Ile Ser Lys Asp Asn Ser Lys Asn Gln Val Ser
210                 215                 220

Leu Lys Leu Ser Ser Val Thr Ala Ala Asp Thr Ala Val Tyr Tyr Cys
225                 230                 235                 240

Ala Lys His Tyr Tyr Tyr Gly Gly Ser Tyr Ala Met Asp Tyr Trp Gly
                245                 250                 255

Gln Gly Thr Leu Val Thr Val Ser Ser Gly Gly Gly Ser Gly Gly Gly
            260                 265                 270

Gly Ser Gln Ser Ile Lys Gly Asn His Leu Val Lys Val Tyr Asp Tyr
        275                 280                 285

Gln Glu Asp Gly Ser Val Leu Leu Thr Cys Asp Ala Glu Ala Lys Asn
290                 295                 300

Ile Thr Trp Phe Lys Asp Gly Lys Met Ile Gly Phe Leu Thr Glu Asp
305                 310                 315                 320

Lys Lys Lys Trp Asn Leu Gly Ser Asn Ala Lys Asp Pro Arg Gly Met
                325                 330                 335

Tyr Gln Cys Lys Gly Ser Gln Asn Lys Ser Lys Pro Leu Gln Val Tyr
            340                 345                 350

Tyr Arg Met Cys Gln Asn Cys Ile Glu Leu Asn Ala Ala Thr Ile Ser
        355                 360                 365

Gly Phe Leu Phe Ala Glu Ile Val Ser Ile Phe Val Leu Ala Val Gly
370                 375                 380

Val Tyr Phe Ile Ala Lys Arg Gly Arg Lys Lys Leu Leu Tyr Ile Phe
385                 390                 395                 400

Lys Gln Pro Phe Met Arg Pro Val Gln Thr Thr Gln Glu Glu Asp Gly
                405                 410                 415

Cys Ser Cys Arg Phe Pro Glu Glu Glu Glu Gly Gly Cys Glu Leu
            420                 425                 430
```

<210> SEQ ID NO 33
<211> LENGTH: 442
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 33

```
Gly Ser Met Ala Leu Pro Val Thr Ala Leu Leu Leu Pro Leu Ala Leu
1               5                   10                  15

Leu Leu His Ala Ala Arg Pro Glu Ile Val Met Thr Gln Ser Pro Ala
```

```
            20                  25                  30
Thr Leu Ser Leu Ser Pro Gly Glu Arg Ala Thr Leu Ser Cys Arg Ala
        35                  40                  45

Ser Gln Asp Ile Ser Lys Tyr Leu Asn Trp Tyr Gln Gln Lys Pro Gly
 50                  55                  60

Gln Ala Pro Arg Leu Leu Ile Tyr His Thr Ser Arg Leu His Ser Gly
 65                  70                  75                  80

Ile Pro Ala Arg Phe Ser Gly Ser Gly Ser Gly Thr Asp Tyr Thr Leu
                 85                  90                  95

Thr Ile Ser Ser Leu Gln Pro Glu Asp Phe Ala Val Tyr Phe Cys Gln
            100                 105                 110

Gln Gly Asn Thr Leu Pro Tyr Thr Phe Gly Gln Gly Thr Lys Leu Glu
        115                 120                 125

Ile Lys Gly Gly Gly Gly Ser Gly Gly Gly Gly Ser Gly Gly Gly Gly
    130                 135                 140

Ser Gln Val Gln Leu Gln Glu Ser Gly Pro Gly Leu Val Lys Pro Ser
145                 150                 155                 160

Glu Thr Leu Ser Leu Thr Cys Thr Val Ser Gly Val Ser Leu Pro Asp
                165                 170                 175

Tyr Gly Val Ser Trp Ile Arg Gln Pro Pro Gly Lys Gly Leu Glu Trp
            180                 185                 190

Ile Gly Val Ile Trp Gly Ser Glu Thr Thr Tyr Tyr Ser Ser Ser Leu
        195                 200                 205

Lys Ser Arg Val Thr Ile Ser Lys Asp Asn Ser Lys Asn Gln Val Ser
    210                 215                 220

Leu Lys Leu Ser Ser Val Thr Ala Ala Asp Thr Ala Val Tyr Tyr Cys
225                 230                 235                 240

Ala Lys His Tyr Tyr Tyr Gly Gly Ser Tyr Ala Met Asp Tyr Trp Gly
                245                 250                 255

Gln Gly Thr Leu Val Thr Val Ser Ser Gly Gly Gly Gly Ser Gly Gly
            260                 265                 270

Gly Gly Ser Gly Gly Gly Gly Ser Gly Gly Gly Gly Ser Gln Ser Ile
        275                 280                 285

Lys Gly Asn His Leu Val Lys Val Tyr Asp Tyr Gln Glu Asp Gly Ser
    290                 295                 300

Val Leu Leu Thr Cys Asp Ala Glu Ala Lys Asn Ile Thr Trp Phe Lys
305                 310                 315                 320

Asp Gly Lys Met Ile Gly Phe Leu Thr Glu Asp Lys Lys Lys Trp Asn
                325                 330                 335

Leu Gly Ser Asn Ala Lys Asp Pro Arg Gly Met Tyr Gln Cys Lys Gly
            340                 345                 350

Ser Gln Asn Lys Ser Lys Pro Leu Gln Val Tyr Tyr Arg Met Cys Gln
        355                 360                 365

Asn Cys Ile Glu Leu Asn Ala Ala Thr Ile Ser Gly Phe Leu Phe Ala
    370                 375                 380

Glu Ile Val Ser Ile Phe Val Leu Ala Val Gly Val Tyr Phe Ile Ala
385                 390                 395                 400

Lys Arg Gly Arg Lys Lys Leu Leu Tyr Ile Phe Lys Gln Pro Phe Met
                405                 410                 415

Arg Pro Val Gln Thr Thr Gln Glu Glu Asp Gly Cys Ser Cys Arg Phe
            420                 425                 430

Pro Glu Glu Glu Glu Gly Gly Cys Glu Leu
        435                 440
```

<210> SEQ ID NO 34
<211> LENGTH: 342
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 34

```
Gly Ser Met Ala Leu Pro Val Thr Ala Leu Leu Pro Leu Ala Leu
1               5                   10                  15

Leu Leu His Ala Ala Arg Pro Glu Ile Val Met Thr Gln Ser Pro Ala
                20                  25                  30

Thr Leu Ser Leu Ser Pro Gly Glu Arg Ala Thr Leu Ser Cys Arg Ala
            35                  40                  45

Ser Gln Asp Ile Ser Lys Tyr Leu Asn Trp Tyr Gln Gln Lys Pro Gly
        50                  55                  60

Gln Ala Pro Arg Leu Leu Ile Tyr His Thr Ser Arg Leu His Ser Gly
65                  70                  75                  80

Ile Pro Ala Arg Phe Ser Gly Ser Gly Ser Gly Thr Asp Tyr Thr Leu
                85                  90                  95

Thr Ile Ser Ser Leu Gln Pro Glu Asp Phe Ala Val Tyr Phe Cys Gln
            100                 105                 110

Gln Gly Asn Thr Leu Pro Tyr Thr Phe Gly Gln Gly Thr Lys Leu Glu
        115                 120                 125

Ile Lys Gly Gly Gly Gly Ser Gly Gly Gly Gly Ser Gly Gly Gly Gly
130                 135                 140

Ser Gln Val Gln Leu Gln Glu Ser Gly Pro Gly Leu Val Lys Pro Ser
145                 150                 155                 160

Glu Thr Leu Ser Leu Thr Cys Thr Val Ser Gly Val Ser Leu Pro Asp
                165                 170                 175

Tyr Gly Val Ser Trp Ile Arg Gln Pro Pro Gly Lys Gly Leu Glu Trp
            180                 185                 190

Ile Gly Val Ile Trp Gly Ser Glu Thr Thr Tyr Tyr Ser Ser Ser Leu
        195                 200                 205

Lys Ser Arg Val Thr Ile Ser Lys Asp Asn Ser Lys Asn Gln Val Ser
210                 215                 220

Leu Lys Leu Ser Ser Val Thr Ala Ala Asp Thr Ala Val Tyr Tyr Cys
225                 230                 235                 240

Ala Lys His Tyr Tyr Gly Gly Ser Tyr Ala Met Asp Tyr Trp Gly
                245                 250                 255

Gln Gly Thr Leu Val Thr Val Ser Ser Gly Gly Gly Ser Gln Ser
            260                 265                 270

Phe Gly Leu Leu Asp Pro Lys Leu Cys Tyr Leu Leu Asp Gly Ile Leu
        275                 280                 285

Phe Ile Tyr Gly Val Ile Leu Thr Ala Leu Phe Leu Lys Arg Gly Arg
        290                 295                 300

Lys Lys Leu Leu Tyr Ile Phe Lys Gln Pro Phe Met Arg Pro Val Gln
305                 310                 315                 320

Thr Thr Gln Glu Glu Asp Gly Cys Ser Cys Arg Phe Pro Glu Glu Glu
                325                 330                 335

Glu Gly Gly Cys Glu Leu
            340
```

```
<210> SEQ ID NO 35
<211> LENGTH: 487
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gly Ser Met Ala Leu Pro Val Thr Ala Leu Leu Leu Pro Leu Ala Leu
1               5                   10                  15

Leu Leu His Ala Ala Arg Pro Gln Val Gln Leu Val Gln Ser Gly Ala
            20                  25                  30

Glu Val Glu Lys Pro Gly Ala Ser Val Lys Val Ser Cys Lys Ala Ser
        35                  40                  45

Gly Tyr Thr Phe Thr Asp Tyr Tyr Met His Trp Val Arg Gln Ala Pro
    50                  55                  60

Gly Gln Gly Leu Glu Trp Met Gly Trp Ile Asn Pro Asn Ser Gly Gly
65                  70                  75                  80

Thr Asn Tyr Ala Gln Lys Phe Gln Gly Arg Val Thr Met Thr Arg Asp
                85                  90                  95

Thr Ser Ile Ser Thr Ala Tyr Met Glu Leu Ser Arg Leu Arg Ser Asp
            100                 105                 110

Asp Thr Ala Val Tyr Tyr Cys Ala Ser Gly Trp Asp Phe Asp Tyr Trp
        115                 120                 125

Gly Gln Gly Thr Leu Val Thr Val Ser Ser Gly Gly Gly Gly Ser Gly
    130                 135                 140

Gly Gly Ser Gly Gly Gly Ser Gly Gly Gly Gly Ser Asp Ile
145                 150                 155                 160

Val Met Thr Gln Ser Pro Ser Ser Leu Ser Ala Ser Val Gly Asp Arg
                165                 170                 175

Val Thr Ile Thr Cys Arg Ala Ser Gln Ser Ile Arg Tyr Tyr Leu Ser
            180                 185                 190

Trp Tyr Gln Gln Lys Pro Gly Lys Ala Pro Lys Leu Leu Ile Tyr Thr
        195                 200                 205

Ala Ser Ile Leu Gln Asn Gly Val Pro Ser Arg Phe Ser Gly Ser Gly
    210                 215                 220

Ser Gly Thr Asp Phe Thr Leu Thr Ile Ser Ser Leu Gln Pro Glu Asp
225                 230                 235                 240

Phe Ala Thr Tyr Tyr Cys Leu Gln Thr Tyr Thr Thr Pro Asp Phe Gly
                245                 250                 255

Pro Gly Thr Lys Val Glu Ile Lys Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
```

```
                355                 360                 365
Glu Glu Gly Gly Cys Glu Leu Arg Val Lys Phe Ser Arg Ser Ala Asp
            370                 375                 380

Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
                435                 440                 445

Ile Gly Met Lys Gly Glu Arg Arg Arg Gly Lys Gly His Asp Gly Leu
            450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 36
<211> LENGTH: 441
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Gly Ser Met Ala Leu Pro Val Thr Ala Leu Leu Leu Pro Leu Ala Leu
1               5                   10                  15

Leu Leu His Ala Ala Arg Pro Gln Val Gln Leu Val Gln Ser Gly Ala
                20                  25                  30

Glu Val Glu Lys Pro Gly Ala Ser Val Lys Val Ser Cys Lys Ala Ser
            35                  40                  45

Gly Tyr Thr Phe Thr Asp Tyr Tyr Met His Trp Val Arg Gln Ala Pro
        50                  55                  60

Gly Gln Gly Leu Glu Trp Met Gly Trp Ile Asn Pro Asn Ser Gly Gly
65                  70                  75                  80

Thr Asn Tyr Ala Gln Lys Phe Gln Gly Arg Val Thr Met Thr Arg Asp
                85                  90                  95

Thr Ser Ile Ser Thr Ala Tyr Met Glu Leu Ser Arg Leu Arg Ser Asp
            100                 105                 110

Asp Thr Ala Val Tyr Tyr Cys Ala Ser Gly Trp Asp Phe Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Gly Gly Gly Gly Ser Asp Ile
145                 150                 155                 160

Val Met Thr Gln Ser Pro Ser Ser Leu Ser Ala Ser Val Gly Asp Arg
                165                 170                 175

Val Thr Ile Thr Cys Arg Ala Ser Gln Ser Ile Arg Tyr Tyr Leu Ser
            180                 185                 190

Trp Tyr Gln Gln Lys Pro Gly Lys Ala Pro Lys Leu Leu Ile Tyr Thr
        195                 200                 205

Ala Ser Ile Leu Gln Asn Gly Val Pro Ser Arg Phe Ser Gly Ser Gly
    210                 215                 220
```

```
Ser Gly Thr Asp Phe Thr Leu Thr Ile Ser Ser Leu Gln Pro Glu Asp
225                 230                 235                 240

Phe Ala Thr Tyr Tyr Cys Leu Gln Thr Tyr Thr Pro Asp Phe Gly
            245                 250                 255

Pro Gly Thr Lys Val Glu Ile Lys Gly Gly Gly Ser Asp Gly Asn
        260                 265                 270

Glu Glu Met Gly Gly Ile Thr Gln Thr Pro Tyr Lys Val Ser Ile Ser
            275                 280                 285

Gly Thr Thr Val Ile Leu Thr Cys Pro Gln Tyr Pro Gly Ser Glu Ile
            290                 295                 300

Leu Trp Gln His Asn Asp Lys Asn Ile Gly Gly Asp Glu Asp Lys
305                 310                 315                 320

Asn Ile Gly Ser Asp Glu Asp His Leu Ser Leu Lys Glu Phe Ser Glu
            325                 330                 335

Leu Glu Gln Ser Gly Tyr Tyr Val Cys Tyr Pro Arg Gly Ser Lys Pro
            340                 345                 350

Glu Asp Ala Asn Phe Tyr Leu Tyr Leu Arg Ala Arg Val Cys Glu Asn
            355                 360                 365

Cys Met Glu Met Asp Val Met Ser Val Ala Thr Ile Val Ile Val Asp
            370                 375                 380

Ile Cys Ile Thr Gly Gly Leu Leu Leu Val Tyr Tyr Trp Ser Lys
385                 390                 395                 400

Arg Gly Arg Lys Lys Leu Leu Tyr Ile Phe Lys Gln Pro Phe Met Arg
            405                 410                 415

Pro Val Gln Thr Thr Gln Glu Glu Asp Gly Cys Ser Cys Arg Phe Pro
            420                 425                 430

Glu Glu Glu Glu Gly Gly Cys Glu Leu
            435                 440
```

<210> SEQ ID NO 37
<211> LENGTH: 482
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

```
Gly Ser Met Ala Leu Pro Val Thr Ala Leu Leu Leu Pro Leu Ala Leu
1               5                   10                  15

Leu Leu His Ala Ala Arg Pro Gln Val Gln Leu Val Gln Ser Gly Ala
            20                  25                  30

Glu Val Glu Lys Pro Gly Ala Ser Val Lys Val Ser Cys Lys Ala Ser
        35                  40                  45

Gly Tyr Thr Phe Thr Asp Tyr Tyr Met His Trp Val Arg Gln Ala Pro
    50                  55                  60

Gly Gln Gly Leu Glu Trp Met Gly Trp Ile Asn Pro Asn Ser Gly Gly
65                  70                  75                  80

Thr Asn Tyr Ala Gln Lys Phe Gln Gly Arg Val Thr Met Thr Arg Asp
            85                  90                  95

Thr Ser Ile Ser Thr Ala Tyr Met Glu Leu Ser Arg Leu Arg Ser Asp
            100                 105                 110

Asp Thr Ala Val Tyr Tyr Cys Ala Ser Gly Trp Asp Phe Asp Tyr Trp
            115                 120                 125
```

```
Gly Gln Gly Thr Leu Val Thr Val Ser Ser Gly Gly Gly Ser Gly
    130                 135                 140
Gly Gly Gly Ser Gly Gly Gly Ser Gly Gly Gly Ser Asp Ile
145                 150                 155                 160
Val Met Thr Gln Ser Pro Ser Ser Leu Ser Ala Ser Val Gly Asp Arg
                165                 170                 175
Val Thr Ile Thr Cys Arg Ala Ser Gln Ser Ile Arg Tyr Tyr Leu Ser
            180                 185                 190
Trp Tyr Gln Gln Lys Pro Gly Lys Ala Pro Lys Leu Leu Ile Tyr Thr
        195                 200                 205
Ala Ser Ile Leu Gln Asn Gly Val Pro Ser Arg Phe Ser Gly Ser Gly
210                 215                 220
Ser Gly Thr Asp Phe Thr Leu Thr Ile Ser Ser Leu Gln Pro Glu Asp
225                 230                 235                 240
Phe Ala Thr Tyr Tyr Cys Leu Gln Thr Tyr Thr Thr Pro Asp Phe Gly
                245                 250                 255
Pro Gly Thr Lys Val Glu Ile Lys Thr Thr Thr Pro Ala Pro Arg Pro
            260                 265                 270
Pro Thr Pro Ala Pro Thr Ile Ala Ser Gln Pro Leu Ser Leu Arg Pro
        275                 280                 285
Glu Ala Ser Arg Pro Ala Ala Gly Gly Ala Val His Thr Arg Gly Leu
290                 295                 300
Asp Thr Gly Gly Gly Ser Asp Gly Asn Glu Glu Met Gly Gly Ile Thr
305                 310                 315                 320
Gln Thr Pro Tyr Lys Val Ser Ile Ser Gly Thr Thr Val Ile Leu Thr
                325                 330                 335
Cys Pro Gln Tyr Pro Gly Ser Glu Ile Leu Trp Gln His Asn Asp Lys
            340                 345                 350
Asn Ile Gly Gly Asp Glu Asp Asp Lys Asn Ile Gly Ser Asp Glu Asp
        355                 360                 365
His Leu Ser Leu Lys Glu Phe Ser Glu Leu Glu Gln Ser Gly Tyr Tyr
370                 375                 380
Val Cys Tyr Pro Arg Gly Ser Lys Pro Glu Asp Ala Asn Phe Tyr Leu
385                 390                 395                 400
Tyr Leu Arg Ala Arg Val Cys Glu Asn Cys Met Glu Met Asp Val Met
                405                 410                 415
Ser Val Ala Thr Ile Val Ile Val Asp Ile Cys Ile Thr Gly Gly Leu
            420                 425                 430
Leu Leu Leu Val Tyr Tyr Trp Ser Lys Arg Gly Arg Lys Lys Leu Leu
        435                 440                 445
Tyr Ile Phe Lys Gln Pro Phe Met Arg Pro Val Gln Thr Thr Gln Glu
450                 455                 460
Glu Asp Gly Cys Ser Cys Arg Phe Pro Glu Glu Glu Gly Gly Cys
465                 470                 475                 480
Glu Leu
```

<210> SEQ ID NO 38
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

-continued

```
Gly Ser Met Ala Leu Pro Val Thr Ala Leu Leu Pro Leu Ala Leu
1               5                   10                  15

Leu Leu His Ala Ala Arg Pro Gln Val Gln Leu Val Gln Ser Gly Ala
            20                  25                  30

Glu Val Glu Lys Pro Gly Ala Ser Val Lys Val Ser Cys Lys Ala Ser
            35                  40                  45

Gly Tyr Thr Phe Thr Asp Tyr Tyr Met His Trp Val Arg Gln Ala Pro
        50                  55                  60

Gly Gln Gly Leu Glu Trp Met Gly Trp Ile Asn Pro Asn Ser Gly Gly
65                  70                  75                  80

Thr Asn Tyr Ala Gln Lys Phe Gln Gly Arg Val Thr Met Thr Arg Asp
                85                  90                  95

Thr Ser Ile Ser Thr Ala Tyr Met Glu Leu Ser Arg Leu Arg Ser Asp
            100                 105                 110

Asp Thr Ala Val Tyr Tyr Cys Ala Ser Gly Trp Asp Phe Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Ser Gly Gly Gly Ser Asp Ile
145                 150                 155                 160

Val Met Thr Gln Ser Pro Ser Ser Leu Ser Ala Ser Val Gly Asp Arg
                165                 170                 175

Val Thr Ile Thr Cys Arg Ala Ser Gln Ser Ile Arg Tyr Tyr Leu Ser
            180                 185                 190

Trp Tyr Gln Gln Lys Pro Gly Lys Ala Pro Lys Leu Leu Ile Tyr Thr
        195                 200                 205

Ala Ser Ile Leu Gln Asn Gly Val Pro Ser Arg Phe Ser Gly Ser Gly
210                 215                 220

Ser Gly Thr Asp Phe Thr Leu Thr Ile Ser Ser Leu Gln Pro Glu Asp
225                 230                 235                 240

Phe Ala Thr Tyr Tyr Cys Leu Gln Thr Tyr Thr Thr Pro Asp Phe Gly
                245                 250                 255

Pro Gly Thr Lys Val Glu Ile Lys Gly Gly Gly Gly Ser Asp Gly Asn
            260                 265                 270

Glu Glu Met Gly Gly Ile Thr Gln Thr Pro Tyr Lys Val Ser Ile Ser
        275                 280                 285

Gly Thr Thr Val Ile Leu Thr Cys Pro Gln Tyr Pro Gly Ser Glu Ile
    290                 295                 300

Leu Trp Gln His Asn Asp Lys Asn Ile Gly Asp Glu Asp Lys
305                 310                 315                 320

Asn Ile Gly Ser Asp Glu Asp His Leu Ser Leu Lys Glu Phe Ser Glu
                325                 330                 335

Leu Glu Gln Ser Gly Tyr Tyr Val Cys Tyr Pro Arg Gly Ser Lys Pro
            340                 345                 350

Glu Asp Ala Asn Phe Tyr Leu Tyr Leu Arg Ala Arg Val Cys Glu Asn
        355                 360                 365

Cys Met Glu Met Asp Val Met Ser Val Ala Thr Ile Val Ile Val Asp
    370                 375                 380

Ile Cys Ile Thr Gly Gly Leu Leu Leu Leu Val Tyr Tyr Trp Ser Gln
385                 390                 395                 400

Arg Arg Lys Tyr Arg Ser Asn Lys Gly Glu Ser Pro Val Glu Pro Ala
                405                 410                 415
```

Glu Pro Cys His Tyr Ser Cys Pro Arg Glu Glu Glu Gly Ser Thr Ile
            420                 425                 430

Pro Ile Gln Glu Asp Tyr Arg Lys Pro Glu Pro Ala Cys Ser Pro
        435                 440                 445

<210> SEQ ID NO 39
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Arg Gly Asp Ser
1

<210> SEQ ID NO 40
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(21)
<223> OTHER INFORMATION: /note="Variant residues given in the sequence
      have no preference with respect to those in the annotations for
      variant positions"

<400> SEQUENCE: 40

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 41
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(22)
<223> OTHER INFORMATION: /note="Variant residues given in the sequence
      have no preference with respect to those in the annotations for
      variant positions"

<400> SEQUENCE: 41

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 42

```
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(23)
<223> OTHER INFORMATION: /note="Variant residues given in the sequence
      have no preference with respect to those in the annotations for
      variant positions"

<400> SEQUENCE: 42

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 43
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(3)
<223> OTHER INFORMATION: /replace=" "
<220> FEATURE:
<221> NAME/KEY: MISC_FEATURE
<222> LOCATION: (1)..(25)
<223> OTHER INFORMATION: /note="Variant residues given in the sequence
      have no preference with respect to those in the annotations for
      variant positions"

<400> SEQUENCE: 43

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 44
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Gly Gly Ser
1

<210> SEQ ID NO 45
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 45

Gly Gly Gly Gly Ser Gly Gly Gly Gly Ser Gly Gly Gly Gly Ser Gly
1               5                   10                  15

Gly Gly Gly Ser
            20

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gly Gly Gly Gly Ser Gly Gly Gly Gly Ser Gly Gly Gly Gly Ser
1               5                   10                  15

<210> SEQ ID NO 47
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47

| | | |
|---|---|---|
| cgtgaggctc cggtgcccgt cagtgggcag agcgcacatc gcccacagtc cccgagaagt | 60 |
| tgggggagg ggtcggcaat tgaaccggtg cctagagaag gtgcgcggg gtaaactggg | 120 |
| aaagtgatgt cgtgtactgg ctccgccttt ttcccgaggg tgggggagaa ccgtatataa | 180 |
| gtgcagtagt cgccgtgaac gttcttttc gcaacgggtt tgccgccaga acacaggtaa | 240 |
| gtgccgtgtg tggttcccgc gggcctggcc tctttacggg ttatggccct tgcgtgcctt | 300 |
| gaattacttc cacctggctg cagtacgtga ttcttgatcc cgagcttcgg gttggaagtg | 360 |
| ggtgggagag ttcgaggcct tgcgcttaag gagccccttc gcctcgtgct tgagttgagg | 420 |
| cctggcctgg gcgctggggc cgccgcgtgc gaatctggtg gcaccttcgc gcctgtctcg | 480 |
| ctgctttcga taagtctcta gccatttaaa attttttgatg acctgctgcg acgctttttt | 540 |
| tctggcaaga tagtccttgta aatgcgggcc aagatctgca cactggtatt tcggttttg | 600 |
| gggccgcggg cggcgacggg gcccgtgcgt cccagcgcac atgttcggcg aggcggggcc | 660 |
| tgcgagcgcg gccaccgaga atcggacggg ggtagtctca agctggccgg cctgctctgg | 720 |
| tgcctggcct cgcgccgccg tgtatcgccc cgccctgggc ggcaaggctg gcccggtcgg | 780 |
| caccagttgc gtgagcggaa agatggccgc ttccggccc tgctgcaggg agctcaaaat | 840 |
| ggaggacgcg gcgctcggga gagcgggcgg gtgagtcacc cacacaaagg aaaagggcct | 900 |
| ttccgtcctc agccgtcgct tcatgtgact ccacggagta ccgggcgccg tccaggcacc | 960 |
| tcgattagtt ctcgagcttt tggagtacgt cgtctttagg ttgggggag gggttttatg | 1020 |
| cgatggagtt tccccacact gagtgggtgg agactgaagt taggccagct tggcacttga | 1080 |
| tgtaattctc cttggaattt gccctttttg agtttggatc ttggttcatt ctcaagcctc | 1140 |
| agacagtggt tcaaagtttt tttcttccat ttcaggtgtc gtga | 1184 |

<210> SEQ ID NO 48
<211> LENGTH: 21
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Met Ala Leu Pro Val Thr Ala Leu Leu Leu Pro Leu Ala Leu Leu Leu
1               5                   10                  15

His Ala Ala Arg Pro
            20

<210> SEQ ID NO 49
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
atggccctgc ctgtgacagc cctgctgctg cctctggctc tgctgctgca tgccgctaga      60
ccc                                                                   63

<210> SEQ ID NO 50
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 51
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 52
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 52

Gly Gly Gly Gly Ser
1               5

<210> SEQ ID NO 53
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Asp Val Pro Asp Tyr Ala Ser Leu Gly Gly Pro Ser Ser Pro Lys Lys
1               5                   10                  15

Lys Arg Lys Val Ser Arg Gly Val Gln Val Glu Thr Ile Ser Pro Gly
                20                  25                  30

Asp Gly Arg Thr Phe Pro Lys Arg Gly Gln Thr Cys Val Val His Tyr
            35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Thr Ser Tyr
    130

<210> SEQ ID NO 54
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
                20                  25                  30

Lys Lys Phe Asp Ser Ser Arg Asp Arg Asn Lys Pro Phe Lys Phe Met
            35                  40                  45

Leu Gly Lys Gln Glu Val Ile Arg Gly Trp Glu Glu Gly Val Ala Gln
    50                  55                  60

Met Ser Val Gly Gln Arg Ala Lys Leu Thr Ile Ser Pro Asp Tyr Ala
65                  70                  75                  80

Tyr Gly Ala Thr Gly His Pro Gly Ile Ile Pro Pro His Ala Thr Leu
                85                  90                  95

Val Phe Asp Val Glu Leu Leu Lys Leu Glu Thr Ser
            100                 105

<210> SEQ ID NO 55
```

```
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys
                85                  90

<210> SEQ ID NO 56
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95

<210> SEQ ID NO 57
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45
```

```
Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Thr Gln Ala
 65                  70                  75                  80

Trp Asp Leu Tyr Tyr His Val Phe Arg Arg Ile Ser Lys Thr Ser
                 85                  90                  95

<210> SEQ ID NO 58
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Ile Leu Trp His Glu Met Trp His Glu Gly Leu Glu Glu Ala Ser Arg
 1               5                  10                  15

Leu Tyr Phe Gly Glu Arg Asn Val Lys Gly Met Phe Glu Val Leu Glu
                 20                  25                  30

Pro Leu His Ala Met Met Glu Arg Gly Pro Gln Thr Leu Lys Glu Thr
             35                  40                  45

Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Leu Gln Ala
 65                  70                  75                  80

Trp Asp Leu Tyr Tyr His Val Phe Arg Arg Ile Ser Lys Thr Ser
                 85                  90                  95

<210> SEQ ID NO 59
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (78)..(78)
<223> OTHER INFORMATION: Any amino acid

<400> SEQUENCE: 59

Ile Leu Trp His Glu Met Trp His Glu Gly Leu Xaa Glu Ala Ser Arg
 1               5                  10                  15

Leu Tyr Phe Gly Glu Arg Asn Val Lys Gly Met Phe Glu Val Leu Glu
                 20                  25                  30

Pro Leu His Ala Met Met Glu Arg Gly Pro Gln Thr Leu Lys Glu Thr
             35                  40                  45

Ser Phe Asn Gln Ala Tyr Gly Arg Asp Leu Met Glu Ala Gln Glu Trp
 50                  55                  60

Cys Arg Lys Tyr Met Lys Ser Gly Asn Val Lys Asp Leu Xaa Gln Ala
 65                  70                  75                  80

Trp Asp Leu Tyr Tyr His Val Phe Arg Arg Ile Ser Lys Thr Ser
                 85                  90                  95

<210> SEQ ID NO 60
```

<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 60

```
Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95
```

<210> SEQ ID NO 61
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

```
Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys Thr Ser
                85                  90                  95
```

<210> SEQ ID NO 62
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 62

```
Gly Gly Gly Gly Ser Gly Gly Gly Gly Ser
1               5                   10
```

TREATMENT OF CANCER USING CHIMERIC CD3 RECEPTOR PROTEINS

CROSS REFERENCE TO RELATED APPLICATIONS

This application is a U.S. national phase application and claims the benefit of priority under 35 U.S.C. § 371 of International Application No. PCT/US2016/045816, filed Aug. 5, 2016, which claims benefit of U.S. Provisional Application No. 62/202,446, filed Aug. 7, 2015, the entire contents of each of which is hereby incorporated by reference.

SEQUENCE LISTING

The instant application contains a Sequence Listing which has been submitted electronically in ASCII format and is hereby incorporated by reference in its entirety. Said ASCII copy, created on Aug. 5, 2016, is named PAT057024-WO-PCT_SL.txt and is 158,755 bytes in size.

FIELD OF THE INVENTION

The present invention relates generally to the use of immune effector cells (e.g., T cells, NK cells) engineered to express a Chimeric Membrane Proteins to treat a disease associated with expression of a tumor antigen.

BACKGROUND OF THE INVENTION

Adoptive cell transfer (ACT) therapy with autologous T-cells, especially with T-cells transduced with Chimeric Antigen Receptors (CARs), has shown promise in hematologic cancer trials. There is a need in the art for improved chimeric molecules for use in ACT

SUMMARY OF THE INVENTION

The present invention pertains, at least in part, to the use of immune effector cells (e.g., T cells, NK cells) engineered to express a chimeric polypeptide that binds to a tumor antigen as described herein to treat cancer associated with expression of said tumor antigen.

In one aspect, the invention features a chimeric membrane protein including a CD3 gamma, delta, or epsilon domain and an intracellular co-stimulatory domain, wherein the CD3 domain includes an extracellular domain derived from the extracellular domain of CD3 gamma, delta, or epsilon and the intracellular co-stimulatory domain is not derived from CD3 gamma, delta, or epsilon.

In a related aspect, the invention features a chimeric membrane protein including a CD3 gamma, delta, or epsilon domain and a first intracellular dimerization domain, wherein the CD3 gamma, delta, or epsilon domain includes an extracellular domain derived from the extracellular domain of CD3 gamma, delta, or epsilon. In this aspect, the protein can, optionally, further includes an intracellular co-stimulatory domain.

In yet another aspect, the invention features a chimeric membrane protein including an antigen binding domain and a CD3 gamma, delta, or epsilon domain, wherein the CD3 gamma, delta, or epsilon domain includes an extracellular domain derived from the extracellular domain of CD3 gamma, delta, or epsilon.

In any of the foregoing aspects, CD3 gamma, delta, or epsilon domain includes the entire CD3 gamma, delta, or epsilon extracellular domain (e.g., the entire protein) or a portion of the CD3 gamma, delta, or epsilon domain. In certain aspects where it is only a portion of the extracellular domain, the truncated domain retains the ability to associate with the remaining TCR polypeptides. In certain aspects, the the chimeric protein does not include any intracellular and/or transmembrane domains derived from CD3 gamma, delta, or epsilon.

In any of the foregoing aspects, the protein also includes an antigen binding domain located N-terminal to the CD3 gamma, delta, or epsilon domain.

In another aspect, the invention features a cell (e.g., a NK cell or T cell) including any one of the foregoing chimeric membrane proteins.

In another aspect, the invention features a nucleic acid (e.g., a DNA or mRNA) encoding any one of the foregoing chimeric membrane proteins. The invention also feature vectors (e.g., a lentiviral, adenoviral, or retroviral) vector including such nucleic acids.

In certain of any of the foregoing cells, the chimeric membrane protein includes the CD3 gamma, delta, or epsilon domain and intracellular dimerization domain, and the cell further includes a second chimeric protein, the second chimeric protein including an intracellular costimulatory domain and a second intracellular dimerization domain. In certain embodiments, the first and second dimerization domains make up a heterodimerization pair and heterodimerize when expressed in the cell (e.g., p53 and MDM2, mFos and mJun Coils, and VPS36 and VPS28). In other embodiments, the first and second dimerization domain make up a heterodimerization pair and heterodimerize when expressed in the cell only in the presence of a dimerization compound. For example, one of the first and second dimerization domains can include a rapamycin analog binding sequence having at least 85% identity with FKBP, and, optionally, the other of the first and second dimerization domains includes a rapamycin analog binding sequence having at least 85% identity with FRP. In another example, one of the first and second dimerization domains includes a rapamycin analog binding sequence from FKBP. Here, the other of the first and second dimerization domain can optionally include a rapamycin analog binding sequence from FRP. In certain embodiments, the rapamycin analog binding sequence includes an AP21967 binding sequence from FKBP or FRP. Other exemplary heterodimerizatoin pairs include a GyrB-GyrB based switch, a GAI-GID1 based switch, or a HALOTAG®/SNAPTAG® based switch.

The second chimeric protein can be, e.g., a chimeric membrane protein and can, e.g., further include an extracellular antigen-binding domain. In other aspects, certain of the foregoing cells can, e.g., include the CD3 gamma, delta, or epsilon domain and intracellular dimerization domain, and the cell can, e.g., further include a second chimeric protein (e.g., a chimeric membrane protein), the second chimeric protein including an extracellular antigen binding domain, an intracellular costimulatory domain, and a CD3 gamma, delta, or epsilon binding domain (which, e.g., binds the intracellular or extracellular CD3 domain). Such binding domains can be, e.g., derived from an anti-CD3 gamma, delta, or epsilon antibody (e.g., an scFv or Vhh domain). In certain of these embodiments, the extracellular antigen-binding domain (e.g., the antigen binding domain of an antibody or fragment thereof.) of the second chimeric protein is heterologous to the intracellular costimulatory signaling domain of the second chimeric protein and/or is the extracellular domain of an inhibitory molecule. Alternatively, the extracellular antigen-binding domain of the second chimeric protein is naturally associated with the intracellular costimulatory signaling domain of the second chimeric protein.

In certain of the above aspects, the second chimeric protein can be, e.g., expressed as an intracellular protein.

In certain of the foregoing aspects, the first and second chimeric protein both include an intracellular co-stimulatory domain derived from the same or different endogenous protein.

In another aspect, the invention features a nucleic acid encoding any of the foregoing first and second chimeric proteins and a vector including such a nucleic acid. Such vectors can be configure such that, upon expression of the first and second chimeric proteins, the proteins are expressed as a single mRNA transcript, e.g., where the first and second chimeric proteins are separated by a nucleic acid encoding a self-cleavage site or an internal ribosomal entry site.

In any of the foregoing embodiments, one or more of the intracellular co-stimulatory domains is a functional signaling domain of a protein selected from the group including of: an MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In yet another aspect, the invention features the treatment of a subject (e.g., a human) with any of the foregoing cells (e.g., wherein the subject has a proliferative disorders (e.g., cancer). In certain embodiments the subject has a tumor and the administration provides the subject with immunity against the tumor. The cell can be, e.g., a T cell or NK cell autologous or allogeneic to the subject.

Chimeric Protein Encoding Nucleic Acids

Accordingly, in one aspect, the invention pertains to an isolated nucleic acid molecule encoding a chimeric membrane protein that comprises one or more of the following: an antigen binding domain (e.g., antibody or antibody fragment. TCR or TCR fragment) that binds to a tumor antigen as described herein, a transmembrane domain (e.g., a transmembrane domain described herein), and an intracellular signaling domain (e.g., an intracellular signaling domain comprising a costimulatory domain (e.g., a costimulatory domain described herein) and/or a primary signaling domain (e.g., a primary signaling domain described herein). In some embodiments, the tumor antigen is chosen from one or more of: CD19: CD123; CD22; CD30: CD171; CS-1 (also referred to as CD2 subset 1, CRACC, SLAMF7, CD319, and 19A24): C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1) Cer); TNF receptor family member B cell maturation (BCMA); Tn antigen ((Tn Ag) or (GalNAcα-Ser/Thr)); prostate-specific membrane antigen (PSMA), Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21): vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu): Mucin 1, cell surface associated (MUC1); epidermal growth factor receptor (EGFR); neural cell adhesion molecule (NCAM): Prostase: prostatic acid phosphatase (PAP); elongation factor 2 mutated (ELF2M); Ephrin B2; fibroblast activation protein alpha (FAP): insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid: placenta-specific 1 (PLAC1); hexasaccharide portion of globoH glycoceramide (GloboH): mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP): Wilms tumor protein (WT1); Cancer/testis antigen 1 (NY-ESO-1): Cancer/testis antigen 2 (LAGE-1a) Melanoma-associated antigen 1 (MAGE-A1); ETS translocation-variant gene 6, located on chromosome 12p (ETV6-AML): sperm protein 17 (SPA 17): X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT): sarcoma translocation breakpoints; melanoma inhibitor of apoptosis (ML-IAP): ERG (transmembrane protease, serine 2 (TMPRSS2) ETS fusion gene); N-Acetyl glucosaminyl-transferase V (NA17); paired box protein Pax-3 (PAX3); Androgen receptor: Cyclin B1; v-myc avian myelocytomatosis viral oncogene neuroblastoma derived homolog (MYCN); Ras Homolog Family Member C (RhoC): Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2): CD79a: CD79b; CD72: Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF): C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, tumor antigen bound by the encoded molecule is chosen from one or more of: TSHR, CD171, CS-1, CLL-I, GD3, Tn Ag, FLT3, CD38, CD44v6, B7H3, KIT, IL-13Ra2, IL-11Ra, PSCA, PRSS21, VEGFR2, LewisY, CD24, PDGFR-beta, SSEA-4, MUC1, EGFR, NCAM, CAIX, LMP2, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, ETV6-AML, sperm protein 17, XAGE1, Tie 2, MAD-CT-1, MAD-CT-2, Fos-related antigen 1, p53 mutant, hTERT, sarcoma translocation breakpoints, ML-IAP, ERG (TMPRSS2 ETS fusion gene), NA17, PAX3, Androgen receptor, Cyclin B1, MYCN, RhoC, CYP1B1, BORIS, SART3, PAX5, OY-TES1, LCK, AKAP-4, SSX2, CD79a, CD79b, CD72, LAIR1, FCAR, LILRA2, CD300LF, CLEC12A, BST2, EMR2, LY75, GPC3, FCRL5, and IGLL1.

In certain embodiments, the tumor antigen bound by the encoded CAR molecule is chosen from one or more of: TSHR, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, and OR51E2.

In some embodiments, the antigen binding domain of the encoded CAR molecule comprises an antibody, an antibody fragment, an scFv, a Fv, a Fab, a (Fab')2, a single domain antibody (SDAB), a VH or VL domain, or a camelid VHH domain.

In some embodiments, the transmembrane domain of the encoded molecule comprises a transmembrane domain chosen from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

In other embodiments, the nucleic acid molecule encodes an intracellular signaling domain comprising a sequence encoding a primary signaling domain and/or a sequence encoding a costimulatory signaling domain. In some embodiments, the intracellular signaling domain comprises a sequence encoding a primary signaling domain. In some embodiments, the intracellular signaling domain comprises a sequence encoding a costimulatory signaling domain. In some embodiments, the intracellular signaling domain comprises a sequence encoding a primary signaling domain and a sequence encoding a costimulatory signaling domain.

In certain embodiments, the encoded primary signaling domain comprises a functional signaling domain of a protein selected from the group consisting of CD3 zeta, CD3 gamma, CD3 delta, CD3 epsilon, common FcR gamma (FCER1G), FcR beta (Fc Epsilon R1b), CD79a, CD79b, Fcgamma RIIa, DAP10, and DAP12.

In one embodiment, the encoded primary signaling domain comprises a functional signaling domain of CD3 zeta.

In certain preferred embodiments, the encoded intracellular signaling domain comprises a sequence encoding a costimulatory signaling domain. For example, the intracellular signaling domain can comprise a sequence encoding a primary signaling domain and a sequence encoding a costimulatory signaling domain. In some embodiments, the encoded costimulatory signaling domain comprises a functional signaling domain of a protein chosen from one or more of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D.

In some embodiments, the nucleic acid molecule further comprises a leader sequence.

In certain embodiments, the encoded antigen binding domain has a binding affinity KD of $10^{-4}$ M to $10^{-8}$ M.

In one embodiment, the encoded antigen binding domain is an antigen binding domain described herein, e.g., an antigen binding domain described herein for a target provided above.

In one embodiment, the encoded molecule comprises an antigen binding domain that has a binding affinity KD of $10^{-4}$ M to $10^{-8}$ M. e.g., $10^{-5}$ M to $10^{-7}$ M, e.g., $10^{-6}$ M or $10^{-7}$ M, for the target antigen. In one embodiment, the antigen binding domain has a binding affinity that is at least five-fold, 10-fold, 20-fold, 30-fold, 50-fold, 100-fold or 1,000-fold less than a reference antibody, e.g., an antibody described herein. In one embodiment, the encoded antigen binding domain has a binding affinity at least 5-fold less than a reference antibody (e.g., an antibody from which the antigen binding domain is derived).

Vectors

In another aspect, the invention pertains to a vector comprising a nucleic acid sequence encoding a chimeric polypeptide described herein. In one embodiment, the vector is chosen from a DNA vector, an RNA vector, a plasmid, a lentivirus vector, adenoviral vector, or a retrovirus vector. In one embodiment, the vector is a lentivirus vector.

In an embodiment, the vector comprises a nucleic acid sequence that encodes a chimeric protein, e.g., as described herein, and a nucleic acid sequence that encodes an inhibitory molecule comprising: an inhKIR cytoplasmic domain; a transmembrane domain, e.g., a KIR transmembrane domain; and an inhibitor cytoplasmic domain, e.g., an ITIM domain, e.g., an inhKIR ITIM domain. In an embodiment the inhibitory molecule is a naturally occurring inhKIR, or a sequence sharing at least 50, 60, 70, 80, 85, 90, 95, or 99% homology with, or that differs by no more than 1, 2, 3, 4, 5, 6, 7, 8, 9, 10, 15, or 20 residues from, a naturally occurring inhKIR.

In an embodiment, the nucleic acid sequence that encodes an inhibitory molecule comprises: a SLAM family cytoplasmic domain; a transmembrane domain, e.g., a SLAM family transmembrane domain; and an inhibitor cytoplasmic domain, e.g., a SLAM family domain, e.g., an SLAM family ITIM domain. In an embodiment the inhibitory molecule is a naturally occurring SLAM family member, or a sequence sharing at least 50, 60, 70, 80, 85, 90, 95, or 99% homology with, or that differs by no more than 1, 2, 3, 4, 5, 6, 7, 8, 9, 10, 15, or 20 residues from, a naturally occurring SLAM family member.

In one embodiment, the vector further comprises a promoter. In some embodiments, the promoter is chosen from an EF-1 promoter, a CMV IE gene promoter, an EF-1α promoter, an ubiquitin C promoter, or a phosphoglycerate kinase (PGK) promoter. In one embodiment, the promoter is an EF-1 promoter.

In one embodiment, the vector is an in vitro transcribed vector, e.g., a vector that transcribes RNA of a nucleic acid molecule described herein. In one embodiment, the nucleic acid sequence in the vector further comprises a poly(A) tail, e.g., a poly A tail described herein, e.g., comprising about 150 adenosine bases. In one embodiment, the nucleic acid sequence in the vector further comprises a 3'UTR. e.g., a 3' UTR described herein, e.g., comprising at least one repeat of a 3'UTR derived from human beta-globulin. In one embodiment, the nucleic acid sequence in the vector further comprises promoter, e.g., a T2A promoter.

Polypeptides

In another aspect, the invention features one or more isolated polypeptide molecules comprising one or more of an antigen binding domain, a transmembrane domain, and an intracellular signaling domain, wherein said antigen binding domain binds to a tumor antigen chosen from one or more of: CD19, CD123, CD22, CD30, CD171, CS-1, CLL-1 (CLECL1), CD33, EGFRvIII, GD2, GD3, BCMA, Tn Ag, PSMA, ROR1, FLT3, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, FAP, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Polysialic acid, PLAC1, GloboH, NY-BR-1. UPK2, HAVCR1, ADRB3, PANX3, GPR20, LY6K, OR51E2, TARP, WT1, NY-ESO-1. LAGE-1a, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, legumain, HPV E6, E7, intestinal carboxyl esterase, mut hsp70-2, CD79a, CD79b, CD72, LAIR, FCAR, LILRA2, CD300LF, CLEC12A, BST2, EMR2, LY75, GPC3, FCRL5, and IGLL1.

In some embodiments, the antigen binding domain of the polypeptide molecule binds to a tumor antigen chosen from one or more of: TSHR, CD171, CS-1, CLL-1, GD3, Tn Ag, FLT3, CD38, CD44v6, B7H3, KIT, IL-13Ra2, IL-11Ra, PSCA, PRSS21, VEGFR2, LewisY, CD24, PDGFR-beta, SSEA-4, MUC1, EGFR, NCAM, CAIX, LMP2, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, ETV6-AML, sperm protein 17, XAGE1, Tie 2, MAD-CT-1, MAD-CT-2, Fos-related antigen 1, p53 mutant, hTERT, sarcoma translocation breakpoints, ML-IAP, ERG (TMPRSS2 ETS fusion gene), NA17, PAX3, Androgen receptor, Cyclin B1, MYCN, RhoC, CYP1B1, BORIS, SART3, PAX5, OY-TES1, LCK, AKAP-4, SSX2, CD79a, CD79b, CD72, LAIR1, FCAR, LILRA2, CD300LF, CLEC12A, BST2, EMR2, LY75, GPC3, FCRL5, and IGLL1.

In some embodiments, the antigen binding domain of the polypeptide molecule binds to a tumor antigen chosen from one or more of: TSHR, CLDN6, GPRC5D, CXORF61, CD97, CD179a, ALK, polysialic acid, PLAC1, GloboH, NY-BR-1. UPK2, HAVCR1, ADRB3, PANX3, GPR20, LY6K, and OR51E2.

In some embodiments, the antigen binding domain of the polypeptide molecule comprises an antibody, an antibody fragment, an scFv, a Fv, a Fab, a (Fab')2, a single domain antibody (SDAB), a VH or VL domain, or a camelid VHH domain.

In some embodiments, the antigen binding domain of the polypeptide molecule comprises a transmembrane domain of a protein chosen from an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

In other embodiments, the intracellular signaling domain of the polypeptide molecule comprises a primary signaling domain and/or a costimulatory signaling domain. In other embodiments, the intracellular signaling domain of the polypeptide molecule comprises a primary signaling domain. In other preferred embodiments, the intracellular signaling domain of the polypeptide molecule comprises a costimulatory signaling domain. In yet other embodiments, the intracellular signaling domain of the polypeptide molecule comprises a primary signaling domain and a costimulatory signaling domain.

In other embodiments, the primary signaling domain of the CAR polypeptide molecule comprises a functional signaling domain of a protein selected from the group consisting of CD3 zeta, CD3 gamma, CD3 delta, CD3 epsilon, common FcR gamma (FCER1G), FcR beta (Fc Epsilon R1b), CD79a, CD79b, Fcgamma RIIa, DAP10, and DAP12. In one embodiment, the primary signaling domain comprises a functional signaling domain of CD3 zeta.

In preferred embodiments, the intracellular signaling domain of the CAR polypeptide molecule comprises a sequence encoding a costimulatory signaling domain. For example, the intracellular signaling domain can comprise a sequence encoding a primary signaling domain and a sequence encoding a costimulatory signaling domain. In some embodiments, the encoded costimulatory signaling domain comprises a functional signaling domain of a protein chosen from one or more of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D.

In some embodiments, the CAR polypeptide molecule further comprises a leader sequence.

In certain embodiments, the antigen binding domain of the polypeptide molecule has a binding affinity KD of $10^{-4}$ M to $10^{-8}$ M. In one embodiment, the antigen binding domain is an antigen binding domain described herein, e.g., an antigen binding domain described herein for a target provided above. In one embodiment, the CAR molecule comprises an antigen binding domain that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen. In one embodiment, the antigen binding domain has a binding affinity that is at least five-fold, 10-fold, 20-fold, 30-fold, 50-fold, 100-fold or 1.000-fold less than a reference antibody, e.g., an antibody described herein. In one embodiment, the encoded antigen binding domain has a binding affinity at least 5-fold less than a reference antibody (e.g., an antibody from which the antigen binding domain is derived).

In another aspect, the invention features an isolated polypeptide molecule comprising an antigen binding domain, a transmembrane domain, and an intracellular signaling domain, wherein said antigen binding domain binds to a tumor-supporting antigen (e.g., a tumor-supporting antigen as described herein). In some embodiments, the tumor-supporting antigen is an antigen present on a stromal cell or a myeloid-derived suppressor cell (MDSC).

Chimeric Protein-Expressing Cells

In another aspect, the invention pertains to a cell, e.g., an immune effector cell, (e.g., a population of cells, e.g., a population of immune effector cells) comprising a nucleic acid molecule, one or more chimeric polypeptide molecules, or a vector as described herein.

In one embodiment, the cell is a human T cell. In one embodiment, the cell is a cell described herein, e.g., a human T cell, e.g., a human T cell described herein; or a human NK cell, e.g., a human NK cell described herein. In one embodiment, the human T cell is a CD8+ T cell. In one embodiment, the cell is a T cell and the T cell is diaglycerol kinase (DGK) deficient. In one embodiment, the cell is a T cell and the T cell is Ikaros deficient. In one embodiment, the cell is a T cell and the T cell is both DGK and Ikaros deficient.

In another embodiment, a chimeric protein-expressing immune effector cell described herein can further express another agent, e.g., an agent which enhances the activity of a cell. For example, in one embodiment, the agent can be an agent which inhibits an inhibitory molecule. Examples of inhibitory molecules include PD-1, PD-L1, CTLA-4, TIM-3, CEACAM (e.g., CEACAM-1, CEACAM-3 and/or CEACAM-5), LAG-3, VISTA, BTLA, TIG1T, LAIR1, CD160, 2B4 and TGF beta, e.g., as described herein. In one embodiment, the agent that inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, PD-L1, CTLA-4, TIM-3, CEACAM (e.g., CEACAM-1, CEACAM-3 and/or CEACAM-5), LAG-3, VISTA, BTLA, TIG1T, LAIR1, CD160, 2B4 or TGF beta, or a fragment of any of these, and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD-i or a fragment thereof, and a second polypeptide of an intracellular signaling domain described herein (e.g., a CD28, CD27, OX40 or 4-IBB signaling domain described herein and/or a CD3 zeta signaling domain described herein).

In one embodiment, the cell further comprises an inhibitory molecule comprising: an inhKIR cytoplasmic domain, a transmembrane domain, e.g., a KIR transmembrane domain; and an inhibitor cytoplasmic domain, e.g., an ITIM domain, e.g., an inhKIR ITIM domain. In an embodiment the inhibitory molecule is a naturally occurring inhKIR, or a sequence sharing at least 50, 60, 70, 80, 85, 90, 95, or 99% homology with, or that differs by no more than 1, 2, 3, 4, 5, 6, 7, 8, 9, 10, 15, or 20 residues from, a naturally occurring inhKIR.

In one embodiment, the cell further comprises an inhibitory molecule comprising: a SLAM family cytoplasmic domain; a transmembrane domain, e.g., a SLAM family transmembrane domain; and an inhibitor cytoplasmic domain, e.g., a SLAM family domain, e.g., an SLAM family ITIM domain. In an embodiment the inhibitory molecule is a naturally occurring SLAM family member, or a sequence sharing at least 50, 60, 70, 80, 85, 90, 95, or 99% homology with, or that differs by no more than 1, 2, 3, 4, 5, 6, 7, 8, 9, 10, 15, or 20 residues from, a naturally occurring SLAM family member.

In one embodiment, the second CAR in the cell is an inhibitory CAR, wherein the inhibitory CAR comprises an antigen binding domain, a transmembrane domain, and an intracellular domain of an inhibitory molecule. The inhibitory molecule can be chosen from one or more of: PD1, PD-L1, CTLA-4, TIM-3, LAG-3, VISTA, BTLA, TIGIT, LAIR1, CD160, 2B4, TGF beta, CEACAM-1, CEACAM-3, and CEACAM-5. In one embodiment, the second CAR molecule comprises the extracellular domain of PD1 or a fragment thereof.

In embodiments, the second CAR molecule in the cell further comprises an intracellular signaling domain comprising a primary signaling domain and/or an intracellular signaling domain.

In other embodiments, the intracellular signaling domain in the cell comprises a primary signaling domain comprising the functional domain of CD3 zeta and a costimulatory signaling domain comprising the functional domain of 4-1BB.

In certain embodiments, the antigen binding domain of the first CAR molecule comprises a scFv and the antigen binding domain of the second CAR molecule does not comprise a scFv. For example, the antigen binding domain of the first CAR molecule comprises a scFv and the antigen binding domain of the second CAR molecule comprises a camelid VHH domain.

Methods of Treatment/Combination Therapies

In another aspect, the present invention provides a method comprising administering a polypeptide, e.g., as described herein, or a cell comprising one or more nucleic acids encoding a polypeptide, e.g., as described herein. In one embodiment, the subject has a disorder described herein, e.g., the subject has cancer, e.g., the subject has a cancer which expresses a target antigen described herein. In one embodiment, the subject is a human.

In another aspect, the invention pertains to a method of treating a subject having a disease associated with expression of a cancer associated antigen as described herein comprising administering to the subject an effective amount of a cell comprising a polypeptide, e.g., as described herein.

In yet another aspect, the invention features a method of treating a subject having a disease associated with expression of a tumor antigen, comprising administering to the subject an effective amount of a cell, e.g., an immune effector cell (e.g., a population of immune effector cells) comprising a chimeric molecule as described herein.

In a related aspect, the invention features a method of treating a subject having a disease associated with expression of a tumor antigen. The method comprises administering to the subject an effective amount of a cell, e.g., an immune effector cell (e.g., a population of immune effector cells) comprising a chimeric molecule, in combination with an agent that increases the efficacy of the immune cell, wherein:

In another aspect, the invention features a composition comprising an immune effector cell (e.g., a population of immune effector cells) comprising a polypeptide, e.g., as described herein for use in the treatment of a subject having a disease associated with expression of a tumor antigen, e.g., a disorder as described herein.

In certain embodiments of any of the aforesaid methods or uses, the disease associated with a tumor antigen, e.g., a tumor antigen described herein, is selected from a proliferative disease such as a cancer or malignancy or a precancerous condition such as a myelodysplasia, a myelodysplastic syndrome or a preleukemia, or is a non-cancer related indication associated with expression of a tumor antigen described herein. In one embodiment, the disease is a cancer described herein, e.g., a cancer described herein as being associated with a target described herein. In one embodiment, the disease is a hematologic cancer. In one embodiment, the hematologic cancer is leukemia. In one embodiment, the cancer is selected from the group consisting of one or more acute leukemias including but not limited to B-cell acute lymphoid leukemia ("BALL"), T-cell acute lymphoid leukemia ("TALL"), acute lymphoid leukemia (ALL); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myclodysplastic syndrome, non-Hodgkin lymphoma, Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and to disease associated with expression of a tumor antigen described herein include, but not limited to, atypical and/or non-classical cancers, malignancies, precancerous conditions or proliferative diseases expressing a tumor antigen as described herein, and any combination thereof. In another embodiment, the disease associated with a tumor antigen described herein is a solid tumor.

In certain embodiments of any of the aforesaid methods or uses, the tumor antigen associated with the disease is chosen from one or more of: CD19, CD123, CD22, CD30, CD171, CS-1, CLL-1 (CLECL1), CD33, EGFRvIII, GD2, GD3, BCMA, Tn Ag, PSMA, ROR1, FLT3, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, FAP, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248. TEM7R, CLDN6, TSHR, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, legumain, HPV E6, E7, intestinal carboxyl esterase, mut hsp70-2, CD79a. CD79b, CD72, LAIR1, FCAR, LILRA2, CD300LF, CLEC12A, BST2, EMR2, LY75. GPC3, FCRL5, and IGLL1.

In other embodiments of any of the aforesaid methods or uses, the tumor antigen associated with the disease is chosen from one or more of: TSHR, TSHR, CD171, CS-1, CLL-1, GD3. Tn Ag, FLT3, CD38, CD44v6, B7H3, KIT, IL-13Ra2, IL-11Ra, PSCA, PRSS21, VEGFR2, LewisY, CD24, PDGFR-beta, SSEA-4, MUC1, EGFR, NCAM, CAIX, LMP2, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, ETV6-AML, sperm protein 17, XAGE1, Tie 2, MAD-CT-1, MAD-CT-2, Fos-related antigen 1, p53 mutant, hTERT, sarcoma translocation breakpoints, ML-IAP, ERG (TMPRSS2 ETS fusion gene). NA17, PAX3, Androgen receptor, Cyclin B1, MYCN. RhoC, CYP1B1, BORIS, SART3, PAX5, OY-TES1, LCK, AKAP-4, SSX2, CD79a, CD79b, CD72, LAIR1, FCAR, LILRA2, CD300LF, CLEC12A, BST2, EMR2, LY75, GPC3, FCRL5, and IGLL1.

In other embodiments of any of the aforesaid methods or uses, the tumor antigen associated with the disease is chosen from one or more of: TSHR, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, and OR51E2.

In certain embodiments, the methods or uses are carried out in combination with an agent that increases the efficacy of the immune effector cell, e.g., an agent as described herein.

In any of the aforesaid methods or uses, the disease associated with expression of the tumor antigen is selected from the group consisting of a proliferative disease, a precancerous condition, a cancer, and a non-cancer related indication associated with expression of the tumor antigen.

The cancer can be a hematologic cancer, e.g., a cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or preleukemia.

The cancer can also be chosen from colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma pituitary adenoma, Kaposi's sarcoma, epidermoid cancer, squamous cell cancer, T-cell lymphoma, environmentally induced cancers, combinations of said cancers, and metastatic lesions of said cancers.

In certain embodiments of the methods or uses described herein, the chimeric molecule is administered in combination with an agent that increases the efficacy of the immune effector cell, e.g., one or more of a protein phosphatase inhibitor, a kinase inhibitor, a cytokine, an inhibitor of an immune inhibitory molecule, or an agent that decreases the level or activity of a $T_{REG}$ cell.

In certain embodiments of the methods or uses described herein, the protein phosphatase inhibitor is a SHP-1 inhibitor and/or an SHP-2 inhibitor.

In other embodiments of the methods or uses described herein, kinase inhibitor is chosen from one or more of a CDK4 inhibitor, a CDK4/6 inhibitor (e.g., palbociclib), a BTK inhibitor (e.g., ibrutinib or RN-486), an mTOR inhibitor (e.g., rapamycin or everolimus (RAD001)), an MNK inhibitor, or a dual P13K/mTOR inhibitor. In one embodiment, the BTK inhibitor does not reduce or inhibit the kinase activity of interleukin-2-inducible kinase (ITK).

In other embodiments of the methods or uses described herein, the agent that inhibits the immune inhibitory molecule comprises an antibody or antibody fragment, an inhibitory nucleic acid, a clustered regularly interspaced short palindromic repeats (CRISPR), a transcription-activator like effector nuclease (TALEN), or a zinc finger endonuclease (ZFN) that inhibits the expression of the inhibitory molecule.

In other embodiments of the methods or uses described herein, the agent that decreases the level or activity of the $T_{REG}$ cells is chosen from cyclophosphamide, anti-GITR antibody, CD25-depletion, or a combination thereof.

In certain embodiments of the methods or uses described herein, the immune inhibitory molecule is selected from the group consisting of PD1, PD-L1, CTLA-4, TIM-3, LAG-3, VISTA, BTLA, TIGIT, LAIR1, CD160, 2B4, TGF beta, CEACAM-1, CEACAM-3, and CEACAM-5.

In other embodiments, the agent that inhibits the inhibitory molecule comprises a first polypeptide comprising an inhibitory molecule or a fragment thereof and a second polypeptide that provides a positive signal to the cell, and wherein the first and second polypeptides are expressed on the CAR-containing immune cells, wherein (i) the first polypeptide comprises PD1, PD-L1, CTLA-4, TIM-3, LAG3, VISTA, BTLA, TIGIT, LAIR1, CD160, 2B4, TGF beta, CEACAM-1, CEACAM-3, and CEACAM-5 or a fragment thereof, and/or (ii) the second polypeptide comprises an intracellular signaling domain comprising a primary signaling domain and/or a costimulatory signaling domain. In one embodiment, the primary signaling domain comprises a functional domain of CD3 zeta; and/or the costimulatory signaling domain comprises a functional domain of a protein selected from 41BB, CD27 and CD28.

In other embodiments, cytokine is chosen from IL-7, IL-15 or IL-21, or both.

In other embodiments, the immune effector cell and a second, e.g., any of the combination therapies disclosed herein (e.g., the agent that that increases the efficacy of the immune effector cell) are administered substantially simultaneously or sequentially.

In one embodiment, lymphocyte infusion, for example allogeneic lymphocyte infusion, is used in the treatment of the cancer, wherein the lymphocyte infusion comprises at least one cell of the present invention. In one embodiment, autologous lymphocyte infusion is used in the treatment of the cancer, wherein the autologous lymphocyte infusion comprises at least one cell described herein.

In one embodiment, the cell is a T cell and the T cell is diaglycerol kinase (DGK) deficient. In one embodiment, the cell is a T cell and the T cell is Ikaros deficient. In one embodiment, the cell is a T cell and the T cell is both DGK and Ikaros deficient.

In one embodiment, the method includes administering a cell expressing the cell as described herein, in combination with an agent which enhances the activity of such a cell, wherein the agent is a cytokine, e.g., IL-7, IL-15, IL-21, or a combination thereof. The cytokine can be delivered in combination with, e.g., simultaneously or shortly after, administration of the cell. Alternatively, the cytokine can be delivered after a prolonged period of time after administration of the cell, e.g., after assessment of the subject's response to the cell. In one embodiment the cytokine is administered to the subject simultaneously (e.g., administered on the same day) with or shortly after administration (e.g., administered 1 day, 2 days, 3 days, 4 days, 5 days, 6 days, or 7 days after administration) of the cell or population of cells of any of claims 61-80. In other embodiments, the cytokine is administered to the subject after a prolonged period of time (e.g., e.g., at least 2 weeks, 3 weeks, 4 weeks, 6 weeks, 8 weeks, 10 weeks, or more) after administration of the cell or population of cells of any of claims 61-80, or after assessment of the subject's response to the cell.

In other embodiments, the cells are administered in combination with an agent that ameliorates one or more side effects associated with administration of a cell. Side effects associated with the cell can be chosen from cytokine release syndrome (CRS) or hemophagocytic lymphohistiocytosis (HLH).

In embodiments of any of the aforesaid methods or uses, the cells expressing the molecule are administered in combination with an agent that treats the disease associated with expression of the tumor antigen, e.g., any of the second or third therapies disclosed herein.

Additional exemplary combinations include one or more of the following.

In another embodiment, the cell expressing the molecule, e.g., as described herein, can be administered in combination with another agent, e.g., a kinase inhibitor and/or checkpoint inhibitor described herein. In an embodiment, a cell can further express another agent, e.g., an agent which enhances the activity of a chimeric protein-expressing cell.

For example, in one embodiment, the agent that enhances the activity of a cell can be an agent which inhibits an inhibitory molecule (e.g., an immune inhibitor molecule). Examples of inhibitory molecules include PD1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGF beta.

In one embodiment, the agent that inhibits the inhibitory molecule is an inhibitory nucleic acid is a dsRNA, a siRNA, or a shRNA. In embodiments, the inhibitory nucleic acid is linked to the nucleic acid that encodes a component of the chimeric molecule. For example, the inhibitory molecule can be expressed on the cell.

In another embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 or TGF beta, or a fragment of any of these (e.g., at least a portion of the extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one embodiment, the immune effector cell of the present invention, e.g., T cell or NK cell, is administered to a subject that has received a previous stem cell transplantation, e.g., autologous stem cell transplantation.

In one embodiment, the immune effector cell of the present invention, e.g., T cell or NK cells, is administered to a subject that has received a previous dose of melphalan.

In one embodiment, the cell described herein is administered in combination with an agent that increases the efficacy of a cell, e.g., an agent described herein.

In one embodiment, the cells described herein are administered in combination with a low, immune enhancing dose of an mTOR inhibitor. While not wishing to be bound by theory, it is believed that treatment with a low, immune enhancing, dose (e.g., a dose that is insufficient to completely suppress the immune system but sufficient to improve immune function) is accompanied by a decrease in PD-1 positive T cells or an increase in PD-1 negative cells. PD-1 positive T cells, but not PD-1 negative T cells, can be exhausted by engagement with cells which express a PD-1 ligand, e.g., PD-L1 or PD-L2.

In an embodiment, administration of a low, immune enhancing, dose of an mTOR inhibitor, e.g., an allosteric inhibitor, e.g., RAD001, or a catalytic inhibitor, is initiated prior to administration of a cell described herein, e.g., T cells or NK cells. In an embodiment, the cells are administered after a sufficient time, or sufficient dosing, of an mTOR inhibitor, such that the level of PD1 negative immune effector cells, e.g., T cells or NK cells, or the ratio of PD1 negative immune effector cells, e.g., T cells/PD1 positive immune effector cells, e.g., T cells, has been, at least transiently, increased.

In one embodiment, the cell described herein is administered at a dose and/or dosing schedule described herein.

In another aspect, the invention pertains to the isolated nucleic acid molecule encoding one or more chimeric proteins of the invention, the isolated polypeptide molecule of one or more chimeric proteins of the invention, the vector comprising a nucleic acid encoding one or more chimeric proteins of the invention, and the cell comprising one or more chimeric proteins of the invention for use as a medicament.

In any of the aforesaid methods or uses, the disease associated with expression of the tumor-supporting antigen is selected from the group consisting of a proliferative disease, a precancerous condition, a cancer, and a non-cancer related indication associated with expression of the tumor-supporting antigen. In an embodiment, the disease associated with a tumor-supporting antigen described herein is a solid tumor.

In one embodiment of the methods or uses described herein, the polypeptide described herein is administered in combination with another agent. In one embodiment, the agent can be a kinase inhibitor, e.g., a CDK4/6 inhibitor, a BTK inhibitor, an mTOR inhibitor, a MNK inhibitor, or a dual PI3K/mTOR inhibitor, and combinations thereof. In one embodiment, the kinase inhibitor is a CDK4 inhibitor, e.g., a CDK4 inhibitor described herein, e.g., a CD4/6 inhibitor, such as, e.g., 6-Acetyl-8-cyclopentyl-5-methyl-2-

(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor. e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo [3,4-d] pyrimidine. The MNK inhibitor can be, e.g., a MNK1a, MNK1b, MNK2a and/or MNK2b inhibitor. The dual PI3K/mTOR inhibitor can be, e.g., PF-04695102.

In one embodiment of the methods or uses described herein, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00): 1-methyl-5-[[2-[5-(trifluoromethyl)-1H-imidazol-2-yl]-4-pyridinyl] oxy]-N-[4-(trifluoromethyl)phenyl]-1H-benzimidazol-2-amine (RAF265); indisulam (E7070); roscovitine (CYC202): palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054): 5-[3-(4,6-difluoro-1H-benzimidazol-2-yl)-1H-indazol-5-yl]-N-ethyl-4-methyl-3-pyridinemethanamine (AG-024322): 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment of the methods or uses described herein, the kinase inhibitor is an mTOR inhibitor selected from temsirolimus; ridaforolimus (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis [(3S)-3-methylmorpholin-4-yl]pyrido[2,3-d]pyrimidin-7-yl}-2-methoxyphenyl)methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartyl-L-serine-("RGDS" disclosed as SEQ ID NO: 39), inner salt (SF1126); and XL765.

In one embodiment of the methods or uses described herein, the kinase inhibitor is an MNK inhibitor selected from CGP052088; 4-amino-3-(p-fluorophenylamino)-pyrazolo [3,4-d]pyrimidine (CGP57380); cercosporamide; ETC-1780445-2; and 4-amino-5-(4-fluoroanilino)-pyrazolo [3,4-d] pyrimidine.

In one embodiment of the methods or uses described herein, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7 (8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl] phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl] phenol (PI-103): 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In one embodiment of the methods or uses described herein, an immune effector cell described herein is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor.

In one embodiment of the methods or uses described herein, the chimeric molecule is administered in combination with another agent, and the agent is a cytokine. The cytokine can be, e.g., IL-7, IL-15, IL-21, or a combination thereof. In another embodiment, the CAR molecule is administered in combination with a checkpoint inhibitor, e.g., a checkpoint inhibitor described herein. For example, in one embodiment, the check point inhibitor inhibits an inhibitory molecule selected from PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGF beta.

Methods of Making Chimeric Protein-Expressing Cells

In another aspect, the invention pertains to a method of making a cell (e.g., an immune effector cell or population thereof) comprising introducing into (e.g., transducing) a cell, e.g., a T cell or a NK cell described herein, with a vector of comprising a nucleic acid encoding a polypeptide, e.g., as described herein, or a nucleic acid encoding a polypeptide, e.g., as described herein.

The cell in the methods is an immune effector cell (e.g., a T cell or a NK cell, or a combination thereof). In some embodiments, the cell in the methods is diaglycerol kinase (DGK) and/or Ikaros deficient.

In some embodiment, the introducing the nucleic acid molecule comprises transducing a vector comprising the nucleic acid molecule encoding a polypeptide, e.g., as described herein, or transfecting the nucleic acid molecule encoding a polypeptide, e.g., as described herein, wherein the nucleic acid molecule is an in vitro transcribed RNA.

In other embodiments, the population of cells is expanded by culturing the cells in the presence of an agent that stimulates a CD3/TCR complex associated signal and/or a ligand that stimulates a costimulatory molecule on the surface of the cells. The agent can be a bead conjugated with anti-CD3 antibody, or a fragment thereof, and/or anti-CD28 antibody, or a fragment thereof.

In other embodiments, the population of cells is expanded in an appropriate media that includes one or more interleukin that result in at least a 200-fold, 250-fold, 300-fold, or 350-fold increase in cells over a 14 day expansion period, as measured by flow cytometry.

In other embodiments, the population of cells is expanded in the presence IL-15 and/or IL-7.

In certain embodiments, the method further includes cryopreserving the population of cells after the appropriate expansion period.

In yet other embodiments, the method of making disclosed herein further comprises contacting the population of immune effector cells with a nucleic acid encoding a telomerase subunit, e.g., hTERT. The the nucleic acid encoding the telomerase subunit can be DNA.

The present invention also provides a method of generating a population of RNA-engineered cells, e.g., cells described herein, e.g., immune effector cells (e.g., T cells, NK cells), transiently expressing exogenous RNA.

In another aspect, the invention pertains to a method of providing an anti-tumor immunity in a subject comprising administering to the subject an effective amount of a cell as described herein. In one embodiment, the cell is an autologous T cell or NK cell. In one embodiment, the cell is an allogeneic T cell or NK cell. In one embodiment, the subject is a human.

In one aspect, the invention includes a population of autologous cells that are transfected or transduced with a vector comprising a nucleic acid molecule as described herein. In one embodiment, the vector is a retroviral vector. In one embodiment, the vector is a self-inactivating lentiviral vector as described elsewhere herein. In one embodiment, the vector is delivered (e.g., by transfecting or electroporating) to a cell, e.g., a T cell or a NK cell, wherein the vector comprises a nucleic acid molecule encoding a polypeptide as described herein, which is transcribed as an mRNA molecule, and the chimeric proteins of the present invention is translated from the RNA molecule and expressed on the surface of the cell.

In one embodiment, the nucleic acid molecule of the present invention molecule, e.g., as described herein, is expressed as an mRNA molecule. In one embodiment, the present invention-expressing cells, e.g., immune effector cells (e.g., T cells, NK cells), can be generated by transfecting or electroporating an RNA molecule encoding the desired proteins (e.g., without a vector sequence) into the cell. In one embodiment, a chimeric protein of the present invention molecule is translated from the RNA molecule once it is incorporated and expressed on the surface of the recombinant cell.

In certain aspects, the foregoing chimeric proteins are encoded by a single nucleic molecule in the same frame and as a single polypeptide chain. In this aspect, the proteins can, e.g., be separated by one or more peptide cleavage sites. (e.g., an auto-cleavage site or a substrate for an intracellular protease). Examples of peptide cleavage sites include the following, wherein the GSG residues are optional:

T2A:
(SEQ ID NO: 40)
(GSG) E G R G S L L T C G D V E E N P G P

P2A:
(SEQ ID NO: 41)
(GSG) A T N F S L L K Q A G D V E E N P G P

E2A:
(SEQ ID NO: 42)
(GSG) Q C T N Y A L L K L A G D V E S N P G P

F2A:
(SEQ ID NO: 43)
(GSG) V K Q T L N F D L L K L A G D V E S N P G P

In a related aspect, the invention features a single protein, as described above, encoding a two chimeric polypeptide.

In other aspects, the foregoing polypeptides are encoded by a single, or multiple, nucleic molecules and are not expressed as a single polypeptide. Here, e.g., the polypeptides can be controlled by a common promoter or be separated by an internal ribosomal entry site. Alternatively, the expression of the two proteins can be, e.g., controlled by separate promoters.

In yet another aspect, the invention features one or more vectors (e.g., any of the vectors described above) including the foregoing nucleic acid molecules encoding different chimeric proteins.

BRIEF DESCRIPTION OF THE DRAWINGS

FIG. 36, right panels are a series of graphs showing number of cells expressing the indicated construct under the indicated expression conditions.

DETAILED DESCRIPTION

Figure 1:
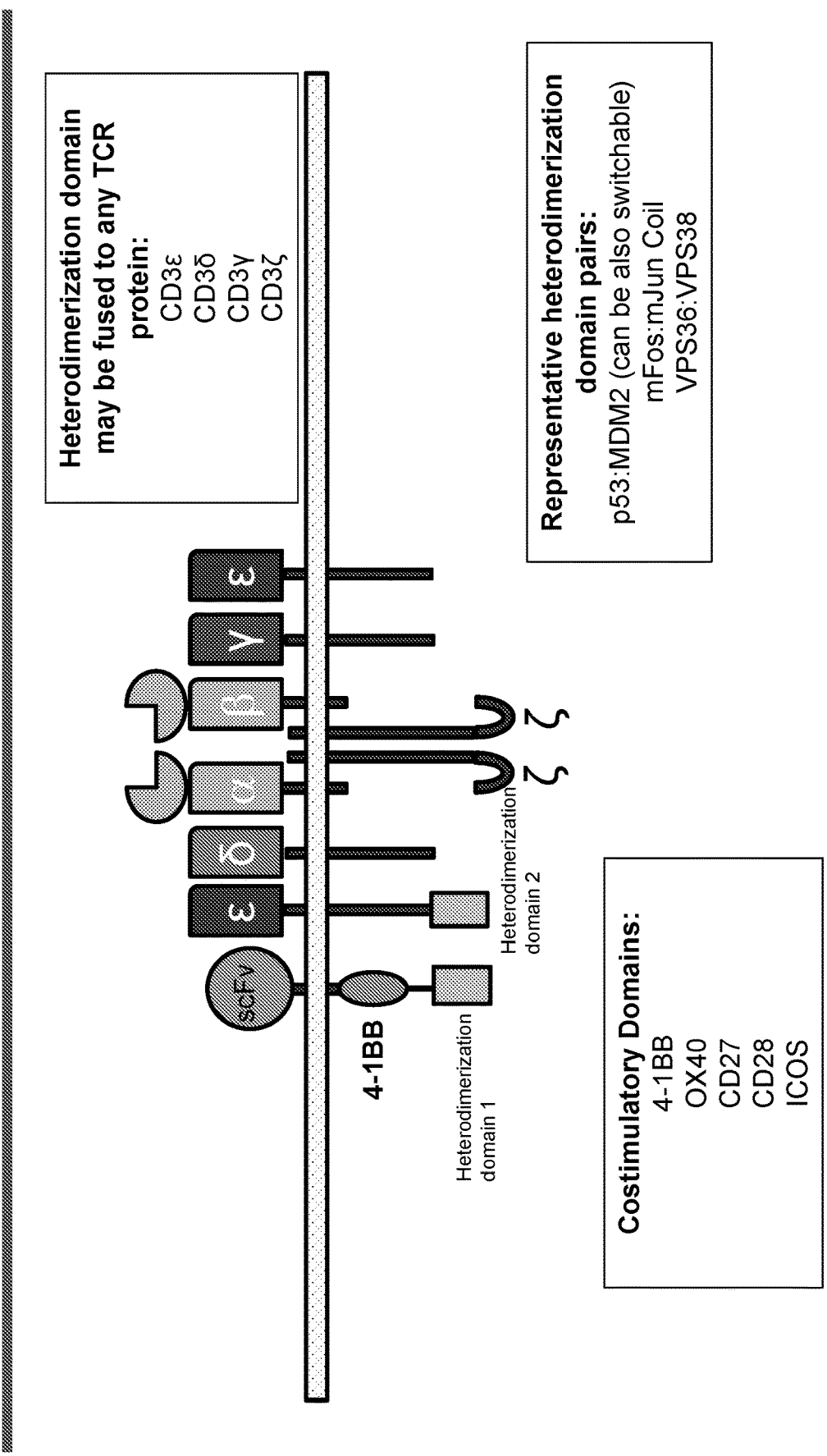
FIG. 1 is a schematic showing constitutively active TCR-based Chimeric Antigen Receptor (TCAR). A targeting and costimulatory domain are embedded into the TCR complex by fusion with an intracellular heterodimerization domain and co-transfection/co-transduction with an endogenous TCR complex member such as CD3 epsilon fused to a second heterodimerization domain.

The present invention features the use of chimeric CD3 proteins to modulate T cell Receptor (TCR) signaling. Specifically, the invention is based, in part, on the discovery that chimeric CD3 proteins (e.g., CD3delta. CD3gamma, and CD3 epsilon) having all or most of their extracellular domain fused to an antigen binding domain can activate the TCR in the presence of a cognate antigen. The invention is further based on the observation that the above chimeric proteins can be potentiated through the inclusion of a co-stimulatory domain in the intracellular portion of the chimeric molecule. Thus, the preferred elements of the engineered signaling complexes of the invention include an antigen binding domain, an extracellular domain derived from one of the above CD3 proteins, and an intracellular co-stimulatory domain. Interestingly, the invention is further based up on the discovery that these elements need not be present in a single polypeptide in order to achieve antigen based-TCR signaling. Indeed, any of the antigen binding domain and/or costimulatory domain can be engineered into a second chimeric molecule and still effectuate signaling provided that the second chimeric molecule and CD3 molecule are coupled either via an inducible or constitutive dimerization domain, as described herein.

TCR-based Chimeric Antigen Receptors (TCARs) may provide intrinsic advantages versus traditional chimeric antigen receptors. Traditional chimeric antigen receptors are single contiguous chain molecules comprising a targeting domain followed by a hinge, a transmembrane domain, one or more costimulatory domains and a signaling domain such as CD3zeta. By making the targeting domain a part of the TCR complex, signaling induced by the TCAR utilizes the entire pathway of accessory proteins within the TCR complex and is not limited to the exclusive signaling provided by a traditional CAR from, for example, CD3zeta on the CAR chain. In the natural pathways for T-cell activation and proliferation, the responsible intracellular pathway members are membrane proximal; while this is not possible for both the costimulatory and signaling domains in the traditional CAR format, TCARs enable the optimal orientation to be engineered into the T-cell.

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances 1%, or in some instances ±0.1% from the specified value, as such variations are appropriate to perform the disclosed methods.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically The term "xenogeneic" refers to a graft derived from an animal of a different species.

The term "cancer" refers to a disease characterized by the uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

The phrase "disease associated with expression of a tumor antigen as described herein" includes, but is not limited to, a disease associated with expression of a tumor antigen as described herein or condition associated with cells which express a tumor antigen as described herein including, e.g., proliferative diseases such as a cancer or malignancy or a precancerous condition such as a myelodysplasia, a myelodysplastic syndrome or a preleukemia; or a noncancer related indication associated with cells which express a tumor antigen as described herein. In one aspect, a cancer associated with expression of a tumor antigen as described herein is a hematological cancer. In one aspect, a cancer associated with expression of a tumor antigen as described herein is a solid cancer. Further diseases associated with expression of a tumor antigen described herein include, but not limited to, e.g., atypical and/or non-classical cancers, malignancies, precancerous conditions or proliferative diseases associated with expression of a tumor antigen as described herein. Non-cancer related indications associated with expression of a tumor antigen as described herein include, but are not limited to, e.g., autoimmune disease, (e.g., lupus), inflammatory disorders (allergy and asthma)

and transplantation. In some embodiments, the tumor antigen-expressing cells express, or at any time expressed, mRNA encoding the tumor antigen. In an embodiment, the tumor antigen-expressing cells produce the tumor antigen protein (e.g., wild-type or mutant), and the tumor antigen protein may be present at normal levels or reduced levels. In an embodiment, the tumor antigen-expressing cells produced detectable levels of a tumor antigen protein at one point, and subsequently produced substantially no detectable tumor antigen protein.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation," refers to a primary response induced by binding of a stimulatory molecule (e.g., a TCR/CD3 complex) with its cognate ligand (or tumor antigen in the case of a CAR) thereby mediating a signal transduction event, such as, but not limited to, signal transduction via the TCR/CD3 complex or signal transduction via the appropriate NK receptor or signaling domains. Stimulation can mediate altered expression of certain molecules.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloic-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX® vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The terms "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+ T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5): 1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The term "tumor-supporting antigen" or "cancer-supporting antigen" interchangeably refer to a molecule (typically a protein, carbohydrate or lipid) that is expressed on the surface of a cell that is, itself, not cancerous, but supports the cancer cells, e.g., by promoting their growth or survival e.g., resistance to immune cells. Exemplary cells of this type include stromal cells and myeloid-derived suppressor cells (MDSCs). The tumor-supporting antigen itself need not play a role in supporting the tumor cells so long as the antigen is present on a cell that supports cancer cells.

The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)n, where n is a positive integer equal to or greater than 1 (SEQ ID NO: 44). For example, n=1, n=2, n=3, n=4, n=5 and n=6, n=7, n=8, n=9 and n=10. In one embodiment, the flexible polypeptide linkers include, but are not limited to, (Gly4 Ser)4 (SEQ ID NO: 45) or (Gly4 Ser)3 (SEQ ID NO: 46). In another embodiment, the linkers include multiple repeats of (Gly2Ser), (GlySer) or (Gly3Ser) (SEQ ID NO: 44). Also included within the scope of the invention are linkers described in WO2012/138475, incorporated herein by reference).

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies. In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin lymphoma, Hodgkin lymphoma, leukemias, uterine cancer, cervical cancer, bladder cancer, kidney cancer and adenocarcinomas such as breast cancer, prostate cancer, ovarian cancer, pancreatic cancer, and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a binding partner (e.g., a tumor antigen) protein present in a sample, but which antibody or ligand does not substantially recognize or bind other molecules in the sample.

"Membrane anchor" or "membrane tethering domain", as that term is used herein, refers to a polypeptide or moiety, e.g., a myristoyl group, sufficient to anchor an extracellular or intracellular domain to the plasma membrane.

By "membrane protein" is meant a protein that comprises a transmembrane domain and, when expressed in a target cell, is anchored in, or traverses the cell membrane.

By "CD3 delta, gamma, or epsilon domain" is meant a domain that is derived from, and retains at least one endogenous activity of, CD3 delta gamma or epsilon.

The term "signaling domain" refers to the functional portion of a protein which acts by transmitting information within the cell to regulate cellular activity via defined signaling pathways by generating second messengers or functioning as effectors by responding to such messengers.

By "intracellular co-stimulatory domain" is meant the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment or derivative thereof.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an extracellular domain that is derived from a CD3 epsilon molecule, the extracellular domain retains sufficient CD3 epsilon structure such that is has the required function, namely, the ability to generate a signal under the appropriate conditions. It does not connotate or include a limitation to a particular process of producing the extracellular domain, e.g., it does not mean that, to provide the extracellular domain, one must start with a CD3 epsilon sequence and delete unwanted sequence, or impose mutations, to arrive at the extracellular domain. By "extracellular domain" is meant the domain of a transmembrane protein that is expressed outside the cell.

By "dimerization domain" is meant a domain that binds a cognate dimerization domain either constitutively or inducibly. Such cognate dimerization domains may be the same or similar to the initial dimerization domain ("homodimerization domains") or may be heterologous to the initial dimerization domain ("heterodimerization domains"). In cases where the domains constitutively dimerize, such dimerization will typically occur provided that both domains are expressed in the same cellular compartment. In cases where the domains inducibly dimerize, such dimerization will only occur in the presence of a "dimerization molecule."

"Dimerization molecule," as that term is used herein, refers to a molecule that promotes the association of a first dimerization domain with a second dimerization domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g., RAD001.

As used herein, the term "antigen binding domain" refers to a polypeptide capable of binding a second polypeptide. Such antigen binding domains include antibody molecules. Furthermore, the term "antigen binding domain" also includes polypeptides not derived from an antibody molecule (e.g., polypeptides that natively bind a cognate polypeptide or molecule, including the extracellular domains of receptor proteins).

As used herein, the term "antibody molecule" refers to an immunoglobulin chain or fragment thereof, comprising at least one immunoglobulin variable domain sequence. The term "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The portion of the chimeric proteins of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody, or bispecific antibody (Harlow et al., 1999, In: Using Antibodies: A Laboratory Manual, Cold Spring Harbor Laboratory Press, NY; Harlow et al., 1989. In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a composition of the invention comprises an antibody fragment. In a further aspect, the protein comprises an antibody fragment that comprises a scFv.

The antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of the invention comprises an antibody fragment. In a further aspect, the protein comprises an antibody fragment that comprises a scFv. The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), or a combination thereof.

The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like. In one aspect, the "4-1BB costimulatory domain" is the sequence provided as herein or the equivalent residues from a non-human species, e.g., mouse, rodent, monkey, ape and the like.

The term "bioequivalent" refers to an amount of an agent other than the reference compound (e.g., RAD001), required to produce an effect equivalent to the effect produced by the reference dose or reference amount of the reference compound (e.g., RAD001). In an embodiment the effect is the level of mTOR inhibition, e.g., as measured by P70 S6 kinase inhibition, e.g., as evaluated in an in vivo or in vitro assay, e.g., as measured by an assay described herein, e.g., the Boulay assay. In an embodiment, the effect is alteration of the ratio of PD-1 positive/PD-1 negative T cells, as measured by cell sorting. In an embodiment a bioequivalent amount or dose of an mTOR inhibitor is the amount or dose that achieves the same level of P70 S6 kinase inhibition as does the reference dose or reference amount of a reference compound. In an embodiment, a bioequivalent amount or dose of an mTOR inhibitor is the amount or dose that achieves the same level of alteration in the ratio of PD-1 positive/PD-1 negative T cells as does the reference dose or reference amount of a reference compound.

The term "low, immune enhancing, dose" when used in conjunction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-i negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

an increase in the expression of one or more of the following markers: $CD62L^{high}$, $CD127^{high}$, $CD27^+$, and BCL2, e.g., on memory T cells, e.g., memory T cell precursors; a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$, increased $CD27^+$, decreased KLRG1, and increased BCL2; wherein any of the changes described above occurs, e.g., at least transiently, e.g., as compared to a non-treated subject.

"Refractory" as used herein refers to a disease, e.g., cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

"Relapsed" as used herein refers to the return of a disease (e.g., cancer) or the signs and symptoms of a disease such as cancer after a period of improvement, e.g., after prior treatment of a therapy, e.g., cancer therapy Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Description

Provided herein are compositions of matter and methods of use for the treatment of a disease such as cancer using immune effector cells (e.g., T cells. NK cells) engineered with chimeric proteins of the invention.

Sequences of some examples of various components of the instant invention is listed in Table 1, where aa stands for amino acids, and na stands for nucleic acids that encode the corresponding peptide.

TABLE 1

Sequences of various components of CAR (aa- amino acids, na- nucleic acids that encodes the corresponding protein)

| description | Sequence |
|---|---|
| EF-1 promoter | CGTGAGGCTCCGGTGCCCGTCAGTGGGCAG AGCGCACATCGCCCACAGTCCCCGAGAAGT TGGGGGGAGGGGTCGGCAATTGAACCGGTG CCTAGAGAAGGTGGCGCGGGGTAAACTGGG AAAGTGATGTCGTGTACTGGCTCCGCCTTT TTCCCGAGGGTGGGGAGAACCGTATATAA GTGCAGTAGTCGCCGTGAACGTTCTTTTTC GCAACGGGTTTGCCGCCAGAACACAGGTAA GTGCCGTGTGTGGTTCCCGCGGGCCTGGCC TCTTTACGGGTTATGCCCTTGCGTGCCTT GAATTACTTCCACCTGGCTGCAGTACGTGA TTCTTGATCCCGAGCTTCGGGTTGGAAGTG GGTGGGAGAGTTCGAGGCCTTGCGCTTAAG GAGCCCCTTCGCCTCGTGCTTGAGTTGAGG CCTGGCCTGGGCGCTGGGGCCGCCGCGTGC GAATCTGGTGGCACCTTCGCGCCTGTCTCG CTGCTTTCGATAAGTCTCTAGCCATTTAAA ATTTTTGATGACCTGCTGCGACGCTTTTTT TCTGGCAAGATAGTCTTGTAAATGCGGGCC AAGATCTGCACACTGGTATTTCGGTTTTTG GGGCCGCGGGCGGCGACGGGGCCCGTGCGT CCCAGCGCACATGTTCGGCGAGGCGGGCC TGCGAGCGCGGCCACCGAGAATCGGACGGG GGTAGTCTCAAGCTGGCCGGCCTGCTCTGG TGCCTGGCCTCGCGCCGCCGTGTATCGCCC |

TABLE 1-continued

Sequences of various components of CAR (aa- amino acids, na- nucleic acids that encodes the corresponding protein)

| description | Sequence |
|---|---|
| | CGCCCTGGGCGGCAAGGCTGGCCCGGTCGG CACCAGTTGCGTGAGCGGAAAGATGGCCGC TTCCCGGCCCTGCTGCAGGGAGCTCAAAAT GGAGGACGCGGCGCTCGGGAGAGCGGGCGG GTGAGTCACCCACACAAAGGAAAAGGGCCT TTCCGTCCTCAGCCGTCGCTTCATGTGACT CCACGGAGTACCGGGCGCCGTCCAGGCACC TCGATTAGTTCTCGAGCTTTTGGAGTACGT CGTCTTTAGGTTGGGGGGAGGGGTTTTATG CGATGGAGTTTCCCCACACTGAGTGGGTGG AGACTGAAGTTAGGCCAGCTTGGCACTTGA TGTAATTCTCCTTGGAATTTGCCCTTTTTG AGTTTGGATCTTGGTTCATTCTCAAGCCTC AGACAGTGGTTCAAAGTTTTTTTCTTCCAT TTCAGGTGTCGTGA (SEQ ID NO: 47) |
| Leader (aa) | MALPVTALLLPLALLLHAARP (SEQ ID NO: 48) |
| Leader (na) | ATGGCCCTGCCTGTGACAGCCCTGCTGCTG CCTCTGGCTCTGCTGCTGCATGCCGCTAGA CCC (SEQ ID NO: 49) |
| 4-1BB intracellular domain (aa) | KRGRKKLLYIFKQPFMRPVQTTQEEDGCSC RFPEEEEGGCEL (SEQ ID NO: 50) |
| 4-1BB intracellular domain (na) | AAACGGGGCAGAAAGAAACTCCTGTATATA TTCAAACAACCATTTATGAGACCAGTACAA ACTACTCAAGAGGAAGATGGCTGTAGCTGC CGATTTCCAGAAGAAGAAGGAGGATGT GAACTG (SEQ ID NO: 51) |

Cancer Associated Antigens

The present invention provides immune effector cells (e.g., T cells, NK cells) that are engineered to contain one or more chimeric proteins that direct the immune effector cells to cancer. This is achieved through an antigen binding domain on the protein that is specific for a cancer associated antigen. There are two classes of cancer associated antigens (tumor antigens) that can be targeted by the proteins of the instant invention: (1) cancer associated antigens that are expressed on the surface of cancer cells; and (2) cancer associated antigens that itself is intracellar, however, a fragment of such antigen (peptide) is presented on the surface of the cancer cells by MHC (major histocompatibility complex).

Accordingly, the present invention provides proteins that target the following cancer associated antigens (tumor antigens): CD19, CD123, CD22, CD30, CD171, CS-1, CLL-1 (CLECL1), CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, PRSS21, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Polysialic acid, PLAC1, GloboH, NY-BR-1, UPK2, HAVCR1, ADRB3, PANX3, GPR20. LY6K, OR51E2, TARP, WT1, NY-ESO-1, LAGE-1a, legumain, HPV E6, E7, MAGE-A1, MAGE A1, ETV6-AML, sperm protein 17, XAGE1, Tie 2, MAD-CT-I, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

Tumor-Supporting Antigens

A chimeric proteins described herein can comprise an antigen binding domain (e.g., antibody or antibody fragment, TCR or TCR fragment) that binds to a tumor-supporting antigen (e.g., a tumor-supporting antigen as described herein). In some embodiments, the tumor-supporting antigen is an antigen present on a stromal cell or a myeloid-derived suppressor cell (MDSC). Stromal cells can secrete growth factors to promote cell division in the microenvironment. MDSC cells can inhibit T cell proliferation and activation.

In embodiments, the stromal cell antigen is chosen from one or more of: bone marrow stromal cell antigen 2 (BST2), fibroblast activation protein (FAP) and tenascin. In an embodiment, the FAP-specific antibody is, competes for binding with, or has the same CDRs as, sibrotuzumab. In embodiments, the MDSC antigen is chosen from one or more of: CD33, CD11b, C14, CD15, and CD66b. Accordingly, in some embodiments, the tumor-supporting antigen is chosen from one or more of: bone marrow stromal cell antigen 2 (BST2), fibroblast activation protein (FAP) or tenascin, CD33, CD11b, C14, CD15, and CD66b.

Chimeric Proteins of the Invention

The invention features one or more chimeric proteins. Generally, the invention features s first chimeric membrane protein that includes all or a functional portion of the extracellular domain of CD3 delta, gamma, or epsilon. These chimeric proteins can further include one or more of the following, an antigen binding domain, an intracellular co-stimulatory domain, and/or dimerization domain. In certain embodiments. e.g., where the first chimeric molecule does not include an antigen binding domain, the invention features a second chimeric membrane protein, this protein having an extracellular antigen binding domain and a dimerization domain. Optionally, this second protein can further include an intracellular co-stimulatory domain (whether or not the first chimeric protein has such a domain).

Alternatively, the second chimeric protein can include a domain which binds a domain (e.g., extracellular or intracellular domain) of the first chimeric protein and a co-stimulatory domain, antigen binding domain, or both.

Antigen Binding Domain

In one aspect, certain chimeric proteins of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in a protein of the invention include those associated with viral, bacterial and parasitic infections, autoimmune disease and cancer cells.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, e.g., single chain TCR, and the like.

In one embodiment, an antigen binding domain against CD22 is an antigen binding portion, e.g., CDRs, of an antibody described in, e.g., Haso et al., Blood, 121(7): 1165-1174 (2013); Wayne et al., Clin Cancer Res 16(6): 1894-1903 (2010); Kato et al., Leuk Res 37(1):83-88 (2013); Creative BioMart (creativebiomart.net): MOM-18047-S(P).

In one embodiment, an antigen binding domain against CS-1 is an antigen binding portion, e.g., CDRs, of Elotuzumab (BMS), see e.g., Tai et al., 2008. Blood 112(4): 1329-37; Tai et al., 2007, Blood, 110(5):1656-63.

In one embodiment, an antigen binding domain against CLL-1 is an antigen binding portion, e.g., CDRs, of an antibody available from R&D, ebiosciences, Abcam, for example, PE-CLL1-hu Cat #353604 (BioLegend); and PE-CLL1 (CLEC12A) Cat #562566 (BD).

In one embodiment, an antigen binding domain against CD33 is an antigen binding portion, e.g., CDRs, of an antibody described in, e.g., Bross et al., Clin Cancer Res 7(6): 1490-1496 (2001) (Gemtuzumab Ozogamicin, hP67.6), Caron et al., Cancer Res 52(24):6761-6767 (1992) (Lintuzumab, HuM195), Lapusan et al., Invest New Drugs 30(3):1121-1131 (2012) (AVE9633), Aigner et al., Leukemia 27(5): 1107-1115 (2013) (AMG330, CD33 BiTE), Dutour et al., Adv hematol 2012:683065 (2012), and Pizzitola et al., Leukemia doi:10.1038/Lue.2014.62 (2014).

In one embodiment, an antigen binding domain against GD2 is an antigen binding portion, e.g., CDRs, of an antibody described in, e.g., Mujoo et al., Cancer Res. 47(4): 1098-1104 (1987); Cheung et al., Cancer Res 45(6):2642-2649 (1985), Cheung et al., J Clin Oncol 5(9):1430-1440 (1987), Cheung et al., J Clin Oncol 16(9):3053-3060 (1998), Handgretinger et al., Cancer Immunol Immunother 35(3): 199-204 (1992). In some embodiments, an antigen binding domain against GD2 is an antigen binding portion of an antibody selected from mAb 14.18, 14G2a, ch14.18, hu14.18, 3F8, hu3F8, 3G6, 8B6, 60C3, 10B8, ME36.1, and 8H9, see e.g., WO2012033885, WO2013040371, WO2013192294, WO2013061273, WO2013123061, WO2013074916, and WO201385552. In some embodiments, an antigen binding domain against GD2 is an antigen binding portion of an antibody described in US Publication No.: 20100150910 or PCT Publication No.: WO 2011160119.

In one embodiment an antigen binding domain against BCMA is an antigen binding portion, e.g., CDRs, of an antibody described in, e.g., WO2012163805. WO200112812, and WO2003062401.

In one embodiment, an antigen binding domain against Tn antigen is an antigen binding portion, e.g., CDRs, of an antibody described in, e.g., U.S. Pat. No. 8,440,798, Brooks et al., PNAS 107(22): 10056-10061 (2010), and Stone et al., OncoImmunology 1(6):863-873(2012).

In one embodiment, an antigen binding domain against PSMA is an antigen binding portion, e.g., CDRs, of an antibody described in, e.g., Parker et al., Protein Expr Purif 89(2): 136-145 (2013), US 20110268656 (J591 ScFv); Frigerio et al, European J Cancer 49(9):2223-2232 (2013)

(scFvD2B); WO 2006125481 (mAbs 3/A12, 3/E7 and 3/F11) and single chain antibody fragments (scFv A5 and D7).

In one embodiment an antigen binding domain against ROR1 is an antigen binding portion, e.g., CDRs, of an antibody described in, e.g., Hudecek et al., Clin Cancer Res 19(12):3153-3164 (2013); WO 2011159847; and US20130101607.

In one embodiment, an antigen binding domain against FLT3 is an antigen binding portion, e.g., CDRs, of an antibody described in, e.g., WO2011076922. U.S. Pat. No. 5,777,084, EP0754230, US20090297529, and several commercial catalog antibodies (R&D, ebiosciences, Abcam).

In one embodiment, an antigen binding domain against TAG72 is an antigen binding portion, e.g., CDRs, of an antibody described in, e.g., Hombach et al., Gastroenterology 113(4):1163-1170 (1997); and Abcam ab691.

In one embodiment, an antigen binding domain against FAP is an antigen binding portion, e.g., CDRs, of an antibody described in, e.g., Ostermann et al., Clinical Cancer Research 14:4584-4592 (2008) (FAP5), US Pat. Publication No. 2009/0304718; sibrotuzumab (see e.g., Hofheinz et al., Oncology Research and Treatment 26(1), 2003); and Tran et al., J Exp Med 210(6): 1125-1135 (2013).

In one embodiment an antigen binding domain against CD38 is an antigen binding portion, e.g., CDRs, of daratumumab (see, e.g., Groen et al., Blood 116(21):1261-1262 (2010); MOR202 (see, e.g., U.S. Pat. No. 8,263,746); or antibodies described in U.S. Pat. No. 8,362,211.

In one embodiment, an antigen binding domain against CD44v6 is an antigen binding portion, e.g., CDRs, of an antibody described in, e.g., Casucci et al., Blood 122(20): 3461-3472 (2013).

In one embodiment, an antigen binding domain against CEA is an antigen binding portion, e.g., CDRs, of an antibody described in, e.g., Chmielewski et al., Gastoenterology 143(4):1095-1107 (2012).

In one embodiment, an antigen binding domain against EPCAM is an antigen binding portion, e.g., CDRS, of an antibody selected from MT110, EpCAM-CD3 bispecific Ab (see, e.g., clinicaltrials.gov/ct2/show/NCT00635596); Edrecolomab; 3622W94; ING-1; and adecatumumab (MT201).

In one embodiment, an antigen binding domain against PRSS21 is an antigen binding portion, e.g., CDRs, of an antibody described in U.S. Pat. No. 8,080,650.

In one embodiment, an antigen binding domain against B7H3 is an antigen binding portion. e.g., CDRs, of an antibody MGA271 (Macrogenics).

In one embodiment, an antigen binding domain against KIT is an antigen binding portion, e.g., CDRs, of an antibody described in, e.g., U.S. Pat. No. 7,915,391, US20120288506, and several commercial catalog antibodies.

In one embodiment, an antigen binding domain against IL-13Ra2 is an antigen binding portion, e.g., CDRs, of an antibody described in, e.g., WO2008/146911, WO2004087758, several commercial catalog antibodies, and WO2004087758.

In one embodiment, an antigen binding domain against CD30 is an antigen binding portion, e.g., CDRs, of an antibody described in. e.g., U.S. Pat. No. 7,090,843 B1, and EP0805871.

In one embodiment, an antigen binding domain against GD3 is an antigen binding portion, e.g., CDRs, of an antibody described in, e.g., U.S. Pat. No. 7,253,263: U.S. Pat. No. 8,207,308; US 20120276046; EP1013761; WO2005035577; and U.S. Pat. No. 6,437,098.

In one embodiment, an antigen binding domain against CD171 is an antigen binding portion, e.g., CDRs, of an antibody described in, e.g., Hong et al., J Immunother 37(2):93-104 (2014).

In one embodiment, an antigen binding domain against IL-11Ra is an antigen binding portion, e.g., CDRs, of an antibody available from Abcam (cat # ab55262) or Novus Biologicals (cat # EPR5446). In another embodiment, an antigen binding domain again IL-11Ra is a peptide, see, e.g., Huang et al., Cancer Res 72(1):271-281 (2012).

In one embodiment, an antigen binding domain against PSCA is an antigen binding portion, e.g., CDRs, of an antibody described in, e.g., Morgenroth et al., Prostate 67(10):1121-1131 (2007) (scFv 7F5); Nejatollahi et al., J of Oncology 2013(2013), article ID 839831 (scFv C5-II); and US Pat Publication No. 20090311181.

In one embodiment, an antigen binding domain against VEGFR2 is an antigen binding portion, e.g., CDRs, of an antibody described in, e.g., Chinnasamy et al., J Clin Invest 120(11):3953-3968 (2010).

In one embodiment, an antigen binding domain against LewisY is an antigen binding portion, e.g., CDRs, of an antibody described in, e.g., Kelly et al., Cancer Biother Radiopharm 23(4):411-423 (2008) (hu3S193 Ab (scFvs)); Dolezal et al., Protein Engineering 16(1):47-56 (2003) (NC 10 scFv).

In one embodiment, an antigen binding domain against CD24 is an antigen binding portion. e.g., CDRs, of an antibody described in, e.g., Maliar et al., Gastroenterology 143(5): 1375-1384 (2012).

In one embodiment, an antigen binding domain against PDGFR-beta is an antigen binding portion, e.g., CDRs, of an antibody Abcam ab32570.

In one embodiment, an antigen binding domain against SSEA-4 is an antigen binding portion, e.g., CDRs, of antibody MC813 (Cell Signaling), or other commercially available antibodies.

In one embodiment, an antigen binding domain against CD20 is an antigen binding portion, e.g., CDRs, of the antibody Rituximab. Ofatumumab, Ocrelizumab, Veltuzumab, or GA 101.

In one embodiment, an antigen binding domain against Folate receptor alpha is an antigen binding portion, e.g., CDRs, of the antibody IMGN853, or an antibody described in US20120009181; U.S. Pat. No. 4,851,332, LK26: U.S. Pat. No. 5,952,484.

In one embodiment, an antigen binding domain against ERBB2 (Her2/neu) is an antigen binding portion, e.g., CDRs, of the antibody trastuzumab, or pertuzumab.

In one embodiment, an antigen binding domain against MUC1 is an antigen binding portion, e.g., CDRs, of the antibody SAR566658.

In one embodiment, the antigen binding domain against EGFR is antigen binding portion, e.g., CDRs, of the antibody cetuximab, panitumumab, zalutumumab, nimotuzumab, or matuzumab.

In one embodiment, an antigen binding domain against NCAM is an antigen binding portion, e.g., CDRs, of the antibody clone 2-2B; MAB5324 (EMD Millipore)

In one embodiment, an antigen binding domain against Ephrin B2 is an antigen binding portion, e.g., CDRs, of an antibody described in, e.g., Abengozar et al., Blood 119(19): 4565-4576 (2012).

In one embodiment, an antigen binding domain against IGF-I receptor is an antigen binding portion, e.g., CDRs, of an antibody described in, e.g., U.S. Pat. No. 8,344,112 B2; EP2322550 A1; WO 2006/138315, or PCT/US2006/022995.

In one embodiment, an antigen binding domain against CAIX is an antigen binding portion, e.g., CDRs, of the antibody clone 303123 (R&D Systems).

In one embodiment an antigen binding domain against LMP2 is an antigen binding portion, e.g., CDRs, of an antibody described in, e.g., U.S. Pat. No. 7,410,640, or US20050129701.

In one embodiment, an antigen binding domain against gp100 is an antigen binding portion, e.g., CDRs, of the antibody HMB45, NKIbetaB, or an antibody described in WO2013165940, or US20130295007

In one embodiment an antigen binding domain against tyrosinase is an antigen binding portion, e.g., CDRs, of an antibody described in, e.g., U.S. Pat. No. 5,843,674; or US19950504048.

In one embodiment, an antigen binding domain against EphA2 is an antigen binding portion, e.g., CDRs, of an antibody described in, e.g., Yu et al., Mol Ther 22(1):102-111 (2014).

In one embodiment, an antigen binding domain against GD3 is an antigen binding portion, e.g., CDRs, of an antibody described in, e.g., U.S. Pat. Nos. 7,253,263; 8,207,308; US 20120276046; EP1013761 A3; 20120276046; WO2005035577; or U.S. Pat. No. 6,437,098.

In one embodiment, an antigen binding domain against fucosyl GM1 is an antigen binding portion, e.g., CDRs, of an antibody described in, e.g., US20100297138; or WO2007/067992.

In one embodiment, an antigen binding domain against sLe is an antigen binding portion, e.g., CDRs, of the antibody G193 (for lewis Y), see Scott A M et al, Cancer Res 60: 3254-61 (2000), also as described in Neeson et al, J Immunol May 2013 190 (Meeting Abstract Supplement) 177.10.

In one embodiment, an antigen binding domain against GM3 is an antigen binding portion, e.g., CDRs, of the antibody CA 2523449 (mAb 14F7).

In one embodiment, an antigen binding domain against HMWMAA is an antigen binding portion, e.g., CDRs, of an antibody described in, e.g., Kmiecik et al., Oncoimmunology 3(1): e27185 (2014) (PMID: 24575382) (mAb9.2.27); U.S. Pat. No. 6,528,481; WO2010033866; or US 20140004124.

In one embodiment, an antigen binding domain against o-acetyl-GD2 is an antigen binding portion, e.g., CDRs, of the antibody 8B6.

In one embodiment, an antigen binding domain against TEM1/CD248 is an antigen binding portion, e.g., CDRs, of an antibody described in, e.g., Marty et al., Cancer Lett 235(2):298-308 (2006); Zhao et al., J Immunol Methods 363(2):221-232 (2011).

In one embodiment, an antigen binding domain against CLDN6 is an antigen binding portion, e.g., CDRs, of the antibody IMAB027 (Ganymed Pharmaceuticals), see e.g., clinicaltrial.gov/show/NCT02054351.

In one embodiment, an antigen binding domain against TSHR is an antigen binding portion. e.g., CDRs, of an antibody described in, e.g., U.S. Pat. Nos. 8,603,466; 8,501,415; or U.S. Pat. No. 8,309,693.

In one embodiment, an antigen binding domain against GPRC5D is an antigen binding portion, e.g., CDRs, of the antibody FAB6300A (R&D Systems); or LS-A4180 (Lifespan Biosciences).

In one embodiment, an antigen binding domain against CD97 is an antigen binding portion, e.g., CDRs, of an antibody described in, e.g., U.S. Pat. No. 6,846,911; de Groot et al., J Immunol 183(6):4127-4134 (2009); or an antibody from R&D:MAB3734.

In one embodiment, an antigen binding domain against ALK is an antigen binding portion, e.g., CDRs, of an antibody described in, e.g., Mino-Kenudson et al., Clin Cancer Res 16(5):1561-1571 (2010).

In one embodiment, an antigen binding domain against polysialic acid is an antigen binding portion, e.g., CDRs, of an antibody described in, e.g., Nagae et al., J Biol Chem 288(47):33784-33796 (2013).

In one embodiment, an antigen binding domain against PLAC is an antigen binding portion, e.g., CDRs, of an antibody described in, e.g., Ghods et al., Biotechnol Appl Biochem 2013 doi: 10.1002/bab.1177.

In one embodiment, an antigen binding domain against GloboH is an antigen binding portion of the antibody VK9; or an antibody described in, e.g., Kudryashov V et al, Glycoconj J, 15(3):243-9 (1998). Lou et al., Proc Natl Acad Sci USA 111(7):2482-2487 (2014); MBrI: Bremer E-G et al. J Biol Chem 259:14773-14777 (1984).

In one embodiment, an antigen binding domain against NY-BR-1 is an antigen binding portion, e.g., CDRs of an antibody described in, e.g., Jager et al., Appl Immunohistochem Mol Morphol 15(1):77-83 (2007).

In one embodiment, an antigen binding domain against WT-1 is an antigen binding portion, e.g., CDRs, of an antibody described in, e.g., Dao et al., Sci Transl Med 5(176): 176ra33 (2013); or WO2012/135854.

In one embodiment, an antigen binding domain against MAGE-A1 is an antigen binding portion, e.g., CDRs, of an antibody described in, e.g., Willemsen et al., J Immunol 174(12):7853-7858 (2005) (TCR-like scFv).

In one embodiment, an antigen binding domain against sperm protein 17 is an antigen binding portion, e.g., CDRs, of an antibody described in, e.g., Song et al., Target Oncol 2013 Aug. 14 (PMID: 23943313); Song et al., Med Oncol 29(4):2923-2931 (2012).

In one embodiment, an antigen binding domain against Tie 2 is an antigen binding portion, e.g., CDRs, of the antibody AB33 (Cell Signaling Technology).

In one embodiment, an antigen binding domain against MAD-CT-2 is an antigen binding portion, e.g., CDRs, of an antibody described in, e.g., PMID: 2450952; U.S. Pat. No. 7,635,753.

In one embodiment, an antigen binding domain against Fos-related antigen 1 is an antigen binding portion, e.g., CDRs, of the antibody 12F9 (Novus Biologicals).

In one embodiment, an antigen binding domain against MelanA/MART1 is an antigen binding portion, e.g., CDRs, of an antibody described in, EP2514766 A2; or U.S. Pat. No. 7,749,719.

In one embodiment, an antigen binding domain against sarcoma translocation breakpoints is an antigen binding portion, e.g., CDRs, of an antibody described in, e.g., Luo et al, EMBO Mol. Med. 4(6):453-461 (2012).

In one embodiment an antigen binding domain against TRP-2 is an antigen binding portion, e.g., CDRs, of an antibody described in, e.g., Wang et al, J Exp Med. 184(6): 2207-16 (1996).

In one embodiment, an antigen binding domain against CYP1B1 is an antigen binding portion, e.g., CDRs, of an antibody described in, e.g., Maecker et al, Blood 102 (9): 3287-3294 (2003).

In one embodiment an antigen binding domain against RAGE-1 is an antigen binding portion, e.g., CDRs, of the antibody MAB5328 (EMD Millipore).

In one embodiment, an antigen binding domain against human telomerase reverse transcriptase is an antigen binding portion, e.g., CDRs, of the antibody cat no: LS-B95-100 (Lifespan Biosciences)

In one embodiment an antigen binding domain against intestinal carboxyl esterase is an antigen binding portion, e.g., CDRs, of the antibody 4F12: cat no: LS-B6190-50 (Lifespan Biosciences).

In one embodiment, an antigen binding domain against mut hsp70-2 is an antigen binding portion, e.g., CDRs, of the antibody Lifespan Biosciences: monoclonal: cat no: LS-C133261-100 (Lifespan Biosciences).

In one embodiment, an antigen binding domain against CD79a is an antigen binding portion, e.g., CDRs, of the antibody Anti-CD79a antibody [HM47/A9] (ab3121), available from Abcam; antibody CD79A Antibody #3351 available from Cell Signalling Technology; or antibody HPA017748—Anti-CD79A antibody produced in rabbit, available from Sigma Aldrich.

In one embodiment, an antigen binding domain against CD79b is an antigen binding portion, e.g., CDRs, of the antibody polatuzumab vedotin, anti-CD79b described in Doman et al., "Therapeutic potential of an anti-CD79b antibody-drug conjugate, anti-CD79b-vc-MMAE, for the treatment of non-Hodgkin lymphoma" Blood, 2009 Sep. 24; 114(13):2721-9. doi: 10.1182/blood-2009-02-205500. Epub 2009 Jul. 24, or the bispecific antibody Anti-CD79b/CD3 described in "4507 Pre-Clinical Characterization of T Cell-Dependent Bispecific Antibody Anti-CD79b/CD3 As a Potential Therapy for B Cell Malignancies" Abstracts of $56^{th}$ ASH Annual Meeting and Exposition, San Francisco, Calif. Dec. 6-9 2014.

In one embodiment, an antigen binding domain against CD72 is an antigen binding portion, e.g., CDRs, of the antibody J3-109 described in Myers, and Uckun, "An anti-CD72 immunotoxin against therapy-refractory B-lineage acute lymphoblastic leukemia." Leuk Lymphoma, 1995 June; 18(1-2): 119-22, or anti-CD72 (10D6.8.1, mIgG1) described in Polson et al., "Antibody-Drug Conjugates for the Treatment of Non-Hodgkin's Lymphoma: Target and Linker-Drug Selection" Cancer Res Mar. 15, 2009 69; 2358.

In one embodiment, an antigen binding domain against LAIR1 is an antigen binding portion, e.g., CDRs, of the antibody ANT-301 LAIR1 antibody, available from ProSpec; or anti-human CD305 (LAIR1) Antibody, available from BioLegend.

In one embodiment, an antigen binding domain against FCAR is an antigen binding portion, e.g., CDRs, of the antibody CD89/FCAR Antibody (Catalog #10414-H08H), available from Sino Biological Inc.

In one embodiment, an antigen binding domain against LILRA2 is an antigen binding portion, e.g., CDRs, of the antibody LILRA2 monoclonal antibody (M17), clone 3C7, available from Abnova, or Mouse Anti-LILRA2 antibody, Monoclonal (2D7), available from Lifespan Biosciences.

In one embodiment, an antigen binding domain against CD300LF is an antigen binding portion, e.g., CDRs, of the antibody Mouse Anti-CMRF35-like molecule 1 antibody, Monoclonal[UP-D2], available from BioLegend, or Rat Anti-CMRF35-like molecule 1 antibody, Monoclonal [234903], available from R&D Systems.

In one embodiment, an antigen binding domain against CLEC12A is an antigen binding portion, e.g., CDRs, of the antibody Bispecific T cell Engager (BiTE) scFv-antibody and ADC described in Noordhuis et al., "Targeting of CLEC12A In Acute Myeloid Leukemia by Antibody-Drug-Conjugates and Bispecific CLL-1×CD3 BiTE Antibody" $53^{rd}$ ASH Annual Meeting and Exposition, Dec. 10-13, 2011, and MCLA-117 (Merus).

In one embodiment, an antigen binding domain against BST2 (also called CD317) is an antigen binding portion, e.g., CDRs, of the antibody Mouse Anti-CD317 antibody, Monoclonal[3H4], available from Antibodies-Online or Mouse Anti-CD317 antibody, Monoclonal[696739], available from R&D Systems.

In one embodiment, an antigen binding domain against EMR2 (also called CD312) is an antigen binding portion, e.g., CDRs, of the antibody Mouse Anti-CD312 antibody, Monoclonal[LS-B8033] available from Lifespan Biosciences, or Mouse Anti-CD312 antibody, Monoclonal [494025] available from R&D Systems.

In one embodiment, an antigen binding domain against LY75 is an antigen binding portion, e.g., CDRs, of the antibody Mouse Anti-Lymphocyte antigen 75 antibody, Monoclonal[HD30] available from EMD Millipore or Mouse Anti-Lymphocyte antigen 75 antibody, Monoclonal [A15797] available from Life Technologies.

In one embodiment, an antigen binding domain against GPC3 is an antigen binding portion, e.g., CDRs, of the antibody hGC33 described in Nakano K, Ishiguro T, Konishi H, et al.

Generation of a humanized anti-glypican 3 antibody by CDR grafting and stability optimization. Anticancer Drugs, 2010 November; 21(10):907-916, or MDX-1414, HN3, or YP7, all three of which are described in Feng et al., "Glypican-3 antibodies: a new therapeutic target for liver cancer." FEBS Lett. 2014 Jan. 21; 588(2):377-82.

In one embodiment, an antigen binding domain against FCRL5 is an antigen binding portion, e.g., CDRs, of the anti-FcRL5 antibody described in Elkins et al., "FcRL5 as a target of antibody-drug conjugates for the treatment of multiple myeloma" Mol Cancer Ther. 2012 October; 11(10): 2222-32.

In one embodiment, an antigen binding domain against IGLL1 is an antigen binding portion, e.g., CDRs, of the antibody Mouse Anti-Immunoglobulin lambda-like polypeptide 1 antibody, Monoclonal[ATIG4] available from Lifespan Biosciences, Mouse Anti-Immunoglobulin lambda-like polypeptide 1 antibody, Monoclonal[HSL11] available from BioLegend.

In one embodiment, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed above.

In another aspect, the antigen binding domain comprises a humanized antibody or an antibody fragment. In some aspects, a non-human antibody is humanized, where specific sequences or regions of the antibody are modified to increase similarity to an antibody naturally produced in a human or fragment thereof. In one aspect, the antigen binding domain is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886. International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp): 5973s-5977s (1995), Couto et al., Cancer Res., 55(8): 1717-22 (1995). Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized antibodies and antibody fragments, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991. Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (see, e.g., Nicholson et al. Mol. Immun. 34 (16-17): 1157-1165 (1997); Carter et al., Proc. Natl. Acad. Sci. USA, 89:4285 (1992); Presta et al., J. Immunol., 151:2623 (1993), the contents of which are incorporated herein by reference herein in their entirety). In some embodiments, the framework region, e.g., all four framework regions, of the heavy chain variable region are derived from a VH4_4-59 germline sequence. In one embodiment, the framework region can comprise, one, two, three, four or five modifications, e.g., substitutions, e.g., from the amino acid at the corresponding murine sequence. In one embodiment, the framework region, e.g., all four framework regions of the light chain variable region are derived from a VK3_1.25 germline sequence. In one embodiment, the framework region can comprise, one, two, three, four or five modifications, e.g., substitutions, e.g., from the amino acid at the corresponding murine sequence.

In some aspects, the antibody fragment is humanized with retention of high affinity for the target antigen and other favorable biological properties. According to one aspect of the invention, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

A humanized antibody or antibody fragment may retain a similar antigenic specificity as the original antibody, e.g., in the present invention, the ability to bind human a cancer associated antigen as described herein. In some embodiments, a humanized antibody or antibody fragment may have improved affinity and/or specificity of binding to human a cancer associated antigen as described herein.

In one aspect, the antigen binding domain of the invention is characterized by particular functional features or properties of an antibody or antibody fragment. For example, in one aspect, the antigen binding domain specifically binds a tumor antigen as described herein.

In one aspect, the anti-cancer associated antigen as described herein binding domain is a fragment, e.g., a single chain variable fragment (scFv). In one aspect, the anti-cancer associated antigen as described herein binding domain is a Fv, a Fab, a (Fab')2, or a bi-functional (e.g. bi-specific) hybrid antibody (e.g., Lanzavecchia et al., Eur. J. Immunol. 17, 105 (1987)). In one aspect, the antibodies and fragments thereof of the invention binds a cancer associated antigen as described herein protein with wild-type or enhanced affinity.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as (Gly$_4$Ser)n, where n is a positive integer equal to or greater than 1 (SEQ ID NO: 52). In one embodiment, the linker can be (Gly$_4$Ser)$_4$ (SEQ ID NO: 45) or (Gly$_4$Ser)$_3$ (SEQ ID NO: 46). Variation in the linker length may retain or enhance activity, giving rise to superior efficacy in activity studies.

In another aspect, the antigen binding domain is a T cell receptor ("TCR"), or a fragment thereof, for example, a single chain TCR (scTCR). Methods to make such TCRs are known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracellar, however, a fragment of such antigen (peptide) is presented on the surface of the cancer cells by MHC.

Transmembrane Domain

With respect to the transmembrane domain, in various embodiments, a chimeric protein can be designed to comprise a transmembrane domain that is attached to the extracellular domain of the chimeric protein. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the chimeric molecule, e.g., in one embodiment, the transmembrane domain may be from the same protein that the signaling domain, costimulatory domain, the hinge domain, or the extracellular domain is derived from. In another aspect, the transmembrane domain is not derived from the same protein that any other domain of the chimeric protein is derived from.

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Cytoplasmic Domain

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of CD3 zeta, common FcR gamma (FCER1G), Fc gamma RIIa, FcR beta (Fe Epsilon Rib), CD3 gamma, CD3 delta, CD3 epsilon, CD79a, CD79b, DAP10, and DAP12. In one embodiment, a CAR of the invention comprises an intracellular signaling domain, e.g., a primary signaling domain of CD3-zeta.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), NKG2D, CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

Regulatable Chimeric Antigen Receptors

In some embodiments, a regulatable CAR (RCAR) where the CAR activity can be controlled is desirable to optimize the safety and efficacy of a CAR therapy. There are many ways CAR activities can be regulated. For example, inducible apoptosis using, e.g., a caspase fused to a dimerization domain (see, e.g., Di et al., N Engl. J. Med. 2011 Nov. 3; 365(18):1673-1683), can be used as a safety switch in the CAR therapy of the instant invention. In an aspect, a RCAR comprises a set of polypeptides, typically two in the simplest embodiments, in which the components of a standard CAR described herein, e.g., an antigen binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signaling domain.

Dimerization Switches

Dimerization switches can be non-covalent or covalent. In a non-covalent dimerization switch, the dimerization molecule promotes a non-covalent interaction between the switch domains. In a covalent dimerization switch, the dimerization molecule promotes a covalent interaction between the switch domains.

In an embodiment, the RCAR comprises a FKBP/FRAP, or FKBP/FRB, -based dimerization switch. FKBP12 (FKBP, or FK506 binding protein) is an abundant cytoplasmic protein that serves as the initial intracellular target for the natural product immunosuppressive drug, rapamycin. Rapamycin binds to FKBP and to the large PI3K homolog FRAP (RAFT, mTOR). FRB is a 93 amino acid portion of FRAP, that is sufficient for binding the FKBP-rapamycin complex (Chen, J., Zheng, X. F., Brown, E. J. & Schreiber, S. L. (1995) Identification of an 11-kDa FKBP12-rapamycin-binding domain within the 289-kDa FKBP12-rapamycin-associated protein and characterization of a critical serine residue. Proc Natl Acad Sci USA 92: 4947-51.)

In embodiments, an FKBP/FRAP, e.g., an FKBP/FRB, based switch can use a dimerization molecule, e.g., rapamycin or a rapamycin analog.

The amino acid sequence of FKBP is as follows:

```
                                        (SEQ ID NO: 53)
DVPDYASLGGPSSPKKKRKVSRGVQ

VETISPGDGRTFPKRGQTCVVHYTG

MLEDGKKFDSSRDRNKPFKFMLGKQ

EVIRGWEEGVAQMSVGQRAKLTISP

DYAYGATGHPGIIPPHATLVFDVEL

LKLETSY
```

In embodiments, an FKBP switch domain can comprise a fragment of FKBP having the ability to bind with FRB, or a fragment or analog thereof, in the presence of rapamycin or a rapalog, e.g., the underlined portion, which is:

```
                                        (SEQ ID NO: 54)
VQVETISPGDGRTFPKRGQTCVVHY

TGMLEDGKKFDSSRDRNKPFKIFML

GKQEVIRGWEEGVAQMSVGQRAKLT

ISPDYAYGAIGHPGIIPPHATLVFD

VELLKLETS
```

The amino acid sequence of FRB is as follows:

```
                                        (SEQ ID NO: 55)
ILWHEMWHEG LEENSRLYFG ERNVKGMFEV LEPLHAMMER

GPQTLKETSF NQAYGRDLME AQEWCRKYMK SGNVKDLTQA

WDLYYHNTRR ISK
```

In embodiments, the FKBP/FRB dimerization switch comprises a modified FRB switch domain that exhibits altered, e.g., enhanced, complex formation between an FRB-based switch domain, e.g., the modified FRB switch domain, a FKBP-based switch domain, and the dimerization molecule, e.g., rapamycin or a rapalogue, e.g., RAD001. In an embodiment, the modified FRB switch domain comprises one or more mutations, e.g., 2, 3, 4, 5, 6, 7, 8, 9, 10 or more, selected from mutations at amino acid position(s) L2031, E2032, S2035, R2036, F2039, G2040, T2098, W2101, D2102, Y2105, and F2108, where the wild-type amino acid is mutated to any other naturally-occurring amino acid. In an embodiment, a mutant FRB comprises a mutation at E2032, where E2032 is mutated to phenylalanine (E2032F), methionine (E2032M), arginine (E2032R), valine (E2032V), tyrosine (E2032Y), isoleucine (E2032I), or leucine (E2032L). In an embodiment, a mutant FRB comprises a mutation at T2098, where T2098 is mutated to phenylalanine (T2098F) or leucine (T2098L). In an embodiment, a mutant FRB comprises a mutation at E2032 and at T2098, where E2032 is mutated to any amino acid, and where T2098 is mutated to any amino acid. In an embodiment, a mutant FRB comprises an E2032I and a T2098L mutation. In an embodiment, a mutant FRB comprises an E2032L and a T2098L mutation.

TABLE 10

Exemplary mutant FRB having increased affinity for a dimerization molecule.

| FRB mutant | Amino Acid Sepence |
| --- | --- |
| E2032I mutant | ILWHEMWHEGLIEASRLYFGERNVKG MFEVLEPLHAMMERGPQTLKETSFNQ AYGRDLMEAQEWCRKYMKSGNVKDLT QAWDLYYHVFRRISKTS (SEQ ID NO: 56) |
| E2032L mutant | ILWHEMWHEGLLEASRLYFGERNVKG MFEVLEPLHAMMERGPQTLKETSFNQ AYGRDLMEAQEWCRKYMKSGNVKDLT QAWDLYYHVFRRISKTS (SEQ ID NO: 57) |
| T2098L mutant | ILWHEMWHEGLEEASRLYFGERNVKG MFEVLEPLHAMMERGPQTLKETSFNQ AYGRDLMEAQEWCRKYMKSGNVKDLL QAWDLYYHVFRRISKTS (SEQ ID NO: 58) |
| E2032, T2098 | ILWHEMWHEGLXEASRLYFGERNVKG MFEVLEPLHAMMERGPQTLKETSFNQ |

TABLE 10-continued

Exemplary mutant FRB having increased
affinity for a dimerization molecule.

| FRB mutant | Amino Acid Sepence |
|---|---|
| mutant | AYGRDLMEAQEWCRKYMKSGNVKDL<u>X</u><br>QAWDLYYHVFRRISKTS<br>(SEQ ID NO: 59) |
| E2032I,<br>T2098L<br>mutant | ILWHEMWHEGLIEASRLYFGERNVKG<br>MFEVLEPLHAMMERGPQTLKETSFNQ<br>AYGRDLMEAQEWCRKYMKSGNVKDLL<br>QAWDLYYHVFRRISKTS<br>(SEQ ID NO: 60) |
| E2032L,<br>T2098L<br>mutant | ILWHEMWHEGLLEASRLYFGERNVKG<br>MFEVLEPLHAMMERGPQTLKETSFNQ<br>AYGRDLMEAQEWCRKYMKSGNVKDLL<br>QAWDLYYHVFRRISKTS<br>(SEQ ID NO: 61) |

Other suitable dimerization switches include a GyrB-GyrB based dimerization switch, a Gibberellin-based dimerization switch, a tag/binder dimerization switch, and a HALOTAG®/SNAPTAG® dimerization switch. Following the guidance provided herein, such switches and relevant dimerization molecules will be apparent to one of ordinary skill.

Dimerization Molecule

Association between the switch domains is promoted by the dimerization molecule. In the presence of dimerization molecule interaction or association between switch domains allows for signal transduction between a polypeptide associated with, e.g., fused to, a first switch domain, and a polypeptide associated with, e.g., fused to, a second switch domain. In the presence of non-limiting levels of dimerization molecule signal transduction is increased by 1.1, 1.2, 1.3, 1.4, 1.5, 1.6, 1.7, 1.8, 1.9, 2, 5, 10, 50, 100 fold, e.g., as measured in a system described herein.

Rapamycin and rapamycin analogs (sometimes referred to as rapalogues), e.g., RAD001, can be used as dimerization molecules in a FKBP/FRB-based dimerization switch described herein. In an embodiment the dimerization molecule can be selected from rapamycin (sirolimus), RAD001 (everolimus), zotarolimus, temsirolimus, AP-23573 (ridaforolimus), biolimus and AP21967. Additional rapamycin analogs suitable for use with FKBP/FRB-based dimerization switches are further described in the section entitled "Combination Therapies", or in the subsection entitled "Exemplary mTOR inhibitors".

Nucleic Acid Constructs Encoding a CAR

The present invention also provides nucleic acid molecules encoding one or more chimeric protein constructs described herein. In one aspect, the nucleic acid molecule is provided as a messenger RNA transcript. In one aspect, the nucleic acid molecule is provided as a DNA construct.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (ψ), a primer binding site (PBS), one or more (e.g., two) long terminal repeats (LTR), and a transgene of interest, e.g., a gene encoding a chimeric protein. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the invention is an adenoviral vector (A5/35). In another embodiment, the expression of nucleic acids encoding chimeric proteins can be accomplished using of transposons such as sleeping beauty, crisper, CAS9, and zinc finger nucleases. See below June et al. 2009 Nature Reviews Immunology 9.10: 704-716, is incorporated herein by reference.

Sources of Cells

Prior to expansion and genetic modification or other modification, a source of cells, e.g., T cells or natural killer (NK) cells, can be obtained from a subject. The term "subject" is intended to include living organisms in which an immune response can be elicited (e.g., mammals). Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain aspects of the present disclosure, immune effector cells, e.g., T cells, can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer.

Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" Clinical & Translational Immunology (2015) 4, e31; doi: 10.1038/cti.2014.31.

In one aspect, T cells are isolated from peripheral blood lymphocytes by lysing the red blood cells and depleting the monocytes, for example, by centrifugation through a PERCOLL™ gradient or by counterflow centrifugal elutriation.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6 \times 10^9$ CD25+ T cells. In other aspects, the population of immune effector cells to be depleted include about $1 \times 10^9$ to $1 \times 10^{10}$ CD25+ T cell, and any integer value in between. In one embodiment, the resulting population T regulatory depleted cells has $2 \times 10^9$ T regulatory cells, e.g., CD25+ cells, or less (e.g., $1 \times 10^9$, $5 \times 10^8$, $1 \times 10^8$, $5 \times 10^7$, $1 \times 10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a chimeric protein-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the chimeric protein-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the chimeric protein-expressing cell (e.g., T cell, NK cell) product.

In an embodiment, a subject is pre-treated with one or more therapies that reduce $T_{REG}$ cells prior to collection of cells, thereby reducing the risk of subject relapse to cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the cell product.

In one embodiment, the population of cells to be removed are neither the regulatory T cells or tumor cells, but cells that otherwise negatively affect the expansion and/or function of cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a chimeric protein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include B7-H1, B7-1, CD160, P1H, 2B4, PD1, TIM3, CEACAM (e.g., CEACAM- 1, CEACAM-3 and/or CEACAM-5), LAG3, TIGIT, CTLA-4, BTLA and LAIR1. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

Methods described herein can include a positive selection step. For example, T cells can be isolated by incubation with anti-CD3/anti-CD28 (e.g., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours, e.g., 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 10 billion cells/ml, 9 billion/ml, 8 billion/ml, 7 billion/ml, 6 billion/ml, or 5 billion/ml is used. In one aspect, a concentration of 1 billion cells/ml is used. In yet one aspect, a concentration of cells from 75, 80, 85, 90, 95, or 100 million cells/ml is used. In further aspects, concentrations of 125 or 150 million cells/ml can be used.

Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is $5\times10^6$/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 10 per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells. e.g., T cells, in the subject or harvested from the subject has been, at least transiently, increased.

In other embodiments, population of immune effector cells can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In one embodiment, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Allogeneic Cells

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR or engineered such that it produces very little functional TCR on its surface. Alternatively, the T cell can express a substantially impaired TCR. e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class 1 and/or HLA class II, is downregulated.

In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not express or expresses at low levels an inhibitory molecule, e.g. by any method described herein. For example, the cell can be a cell that does not express or expresses at low levels an inhibitory molecule. Examples of inhibitory molecules include PD1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4 and TGF beta. Inhibition of an inhibitory molecule, e.g., by inhibition at the DNA, RNA or protein level, can optimize a cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA in a T cell.

Expression of siRNA and shRNAs in T cells can be achieved using any conventional expression system, e.g., such as a lentiviral expression system.

Exemplary shRNAs that downregulate expression of components of the TCR are described, e.g., in US Publication No.: 2012/0321667. Exemplary siRNA and shRNA that downregulate expression of HLA class I and/or HLA class II genes are described, e.g., in U.S. publication No.: US 2007/0036773.

CRISPR to inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene.

Naturally-occurring CRISPR/Cas systems are found in approximately 40% of sequenced eubacteria genomes and 90% of sequenced archaea. Grissa et al. (2007) BMC Bioinformatics 8: 172. This system is a type of prokaryotic immune system that confers resistance to foreign genetic elements such as plasmids and phages and provides a form of acquired immunity. Barrangou et al. (2007) Science 315: 1709-1712; Marragini et al. (2008) Science 322: 1843-1845.

The CRISPR/Cas system can thus be used to edit a TCR and/or HLA gene (adding or deleting a basepair), or introducing a premature stop which thus decreases expression of a TCR and/or HLA. The CRISPR/Cas system can alternatively be used like RNA interference, turning off TCR and/or HLA gene in a reversible fashion. In a mammalian cell, for example, the RNA can guide the Cas protein to a TCR and/or HLA promoter, sterically blocking RNA polymerases.

Artificial CRISPR/Cas systems can be generated which inhibit TCR and/or HLA, using technology known in the art, e.g., that described in U.S. Publication No. 20140068797, and Cong (2013) Science 339: 819-823. Other artificial CRISPR/Cas systems that are known in the art may also be generated which inhibit TCR and/or HLA, e.g., that described in Tsai (2014) Nature Biotechnol., 32:6 569-576, U.S. Pat. Nos. 8,871,445; 8,865,406; 8,795,965; 8,771,945; and 8,697,359.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene.

Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) Genetics Society of America 188: 773-782; and Kim et al. (1996) Proc. Natl. Acad. Sci. USA 93: 1156-1160.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a chimeric protein.

Activation and Expansion of Immune Effector Cells (e.g., T Cells)

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, a population of immune effector cells e.g., T regulatory cell depleted cells, may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998: Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect, more anti-CD28 antibody is bound to the particles than anti-CD3 antibody, i.e., the ratio of CD3:CD28 is less than one. In certain aspects, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle:cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 10 billion cells/ml, 9 billion/ml, 8 billion/ml, 7 billion/ml, 6 billion/ml, 5 billion/ml, or 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days).

Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence of IL-15 and/or IL-7 (e.g., IL-15 and IL-7).

In embodiments, methods described herein comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the cell, e.g., ex vivo. In embodiments, a cell described herein is contacted with a composition comprising a IL-15 polypeptide during the manufacturing of the cell, e.g., ex vivo. In embodiments, a cell described herein is contacted with a composition comprising a combination of both a IL-15 polypeptide and a IL-15 Ra polypeptide during the manufacturing of the cell, e.g., ex vivo.

In one embodiment the cell described herein is contacted with a composition comprising hetIL-15 during ex vivo expansion. In an embodiment, the cell described herein is contacted with a composition comprising an IL-15 polypeptide during ex vivo expansion. In an embodiment, the cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In another aspect, a method of treating a subject, e.g., reducing or ameliorating, a hyperproliferative condition or disorder (e.g., a cancer), e.g., solid tumor, a soft tissue tumor, or a metastatic lesion, in a subject is provided. As used herein, the term "cancer" is meant to include all types of cancerous growths or oncogenic processes, metastatic tissues or malignantly transformed cells, tissues, or organs, irrespective of histopathologic type or stage of invasiveness. Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention. Examples of other cancers that can be treated include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin Disease, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. Treatment of metastatic cancers, e.g., metastatic cancers that express PD-L1 (Iwai et al. (2005) Int. Immunol. 17:133-144) can be effected using the antibody molecules described herein.

Exemplary cancers whose growth can be inhibited include cancers typically responsive to immunotherapy. Non-limiting examples of cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, refractory or recurrent malignancies can be treated using the molecules described herein.

In one aspect, the invention pertains to a method of treating cancer in a subject. The method comprises administering to the subject cell of the present invention such that the cancer is treated in the subject. In one aspect, the cancer associated with expression of a cancer associate antigen as described herein is a hematological cancer. In one aspect, the hematological cancer is a leukemia or a lymphoma. In one aspect, a cancer associated with expression of a cancer associate antigen as described herein includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of a cancer associate antigen as described herein include, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma. Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with a cancer associate antigen as described herein expression include, but not limited to, e.g., atypical and/or non-classical cancers, malignancies, precancerous conditions or proliferative diseases associated with expression of a cancer associate antigen as described herein.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of immune effector cells (e.g., T cells, NK cells) comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Hematologic Cancer

Hematological cancer conditions are the types of cancer such as leukemia, lymphoma, and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

Lymphoma is a group of blood cell tumors that develop from lymphocytes. Exemplary lymphomas include non-Hodgkin lymphoma and Hodgkin lymphoma.

The present invention provides for compositions and methods for treating cancer. In one aspect, the cancer is a hematologic cancer including but is not limited to hematolical cancer is a leukemia or a lymphoma. In one aspect, the cells of the invention may be used to treat cancers and malignancies such as, but not limited to, e.g., acute leukemias including but not limited to, e.g., B-cell acute lymphoid leukemia ("BALL"), T-cell acute lymphoid leukemia ("TALL"), acute lymphoid leukemia (ALL): one or more chronic leukemias including but not limited to, e.g., chronic myclogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with a cancer associate antigen as described herein expression includes, but not limited to, e.g., atypical and/or non-classical cancers, malignancies, precancerous conditions or proliferative diseases expressing a cancer associate antigen as described herein.

The present invention also provides methods for preventing, treating and/or managing a disease associated with a cancer associated antigen as described herein-expressing cells (e.g., a hematologic cancer or atypical cancer expressing a cancer associated antigen as described herein), the methods comprising administering to a subject in need a T cell or NK cell of the invention that binds to a cancer associated antigen as described herein-expressing cell. In one aspect, the subject is a human. Non-limiting examples of disorders associated with a cancer associated antigen as described herein-expressing cells include autoimmune disorders (such as lupus), inflammatory disorders (such as allergies and asthma) and cancers (such as hematological cancers or atypical cancers expressing a cancer associated antigen as described herein).

The present invention also provides methods for preventing, treating and/or managing a disease associated with a cancer associated antigen as described herein-expressing cells, the methods comprising administering to a subject in need a T cell or NK cell of the invention that binds to a cancer associated antigen as described herein-expressing cell. In one aspect, the subject is a human.

The present invention provides methods for preventing relapse of cancer associated with a cancer associated antigen as described herein-expressing cells, the methods comprising administering to a subject in need thereof a T cell or NK cell of the invention that binds to a cancer associated antigen as described herein-expressing cell. In one aspect, the methods comprise administering to the subject in need thereof an effective amount of a T cell or NK cell described herein that binds to a cancer associated antigen as described herein-expressing cell in combination with an effective amount of another therapy.

Pharmaceutical Compositions and Treatments

Pharmaceutical compositions of the present invention may comprise a chimeric protein-expressing cell, e.g., a plurality of chimeric protein-expressing cells, as described herein, in combination with one or more pharmaceutically or physiologically acceptable carriers, diluents or excipients. Such compositions may comprise buffers such as neutral buffered saline, phosphate buffered saline and the like;

carbohydrates such as glucose, mannose, sucrose or dextrans, mannitol, proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus* influenza. *Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the immune effector cells (e.g., T cells, NK cells) described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated immune effector cells (e.g., T cells, NK cells) to a subject and then subsequently redraw blood (or have an apheresis performed), activate immune effector cells (e.g., T cells, NK cells) therefrom according to the present invention, and reinfuse the patient with these activated and expanded immune effector cells (e.g., T cells, NK cells). This process can be carried out multiple times every few weeks. In certain aspects, immune effector cells (e.g., T cells, NK cells) can be activated from blood draws of from 10 cc to 400 cc. In certain aspects, immune effector cells (e.g., T cells, NK cells) are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In one aspect, the T cell compositions of the present invention are administered by i.v. injection. The compositions of immune effector cells (e.g., T cells, NK cells) may be injected directly into a tumor, lymph node, or site of infection.

In a particular exemplary aspect, subjects may undergo leukapheresis, wherein leukocytes are collected, enriched, or depleted ex vivo to select and/or isolate the cells of interest. e.g., T cells. These T cell isolates may be expanded by methods known in the art and treated such that one or more constructs of the invention may be introduced, thereby creating a T cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded T cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices.

The dose for CAMPATH, for example, will generally be in the range 1 to about 100 mg for an adult patient, usually administered daily for a period between 1 and 30 days. The preferred daily dose is 1 to 10 mg per day although in some instances larger doses of up to

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Constitutively Active TCARs Using Intracellular Heterodimerization Domains Transient Expression and Activation Assays
Materials and Methods
Synthesis of Constitutively Active TCAR Constructs
Pairs of plasmid DNA were synthesized externally by DNA2.0. The nominal non-regulatable CAR construct, CD19scFv-BBZ, SEQ ID NO: 1, was used as a control. For the TCAR, various intracellular heterodimerization domains can be linked to different domains of the TCAR constructs as shown in FIG. 1.

"TCAR1" comprises a pair of constructs. In the first construct, the CD19 scFv was cloned with CD8 hinge and transmembrane domain followed by the costimulatory domain 4-1BB and the heterodimerization domain VPS28 at the C-terminus (SEQ ID NO: 2). The corresponding second construct was designed by fusing the heterodimerization domain VPS36 to a linker at the C-terminus of CD3 epsilon (SEQ ID NO: 3). "TCAR2" comprises a pair of constructs. In the first construct, the CD19 scFv was cloned with CD8 hinge and transmembrane domain followed by the costimulatory domain 4-1BB and the heterodimerization domain mJUN at the C-terminus (SEQ ID NO: 4). The corresponding second construct was designed by fusing the heterodimerization domain mFos to a linker at the C-terminus of CD3 epsilon (SEQ ID NO:5).

CD19scFv-BBZ (SEQ ID NO: 1)
GSATMALPVTALLLPLALLLHAARPEIVMTQSPATLSLSPGERATLSCR

ASQDISKYLNWYQQKPGQAPRLLIYHTSRLHSGIPARFSGSGSGTDYTL

TISSLQPEDFAVYTCQQCFNTLPYTFGQGTKLEIKGGGGSGGGGSGGGG

SGGGGSQVQLQESGPGLVKPSETLSLTCTVSGVSLPDYGVSWIRQPPGK

GLEWIGVIWGSETTYYNSSLKSRVTISKDNSKNQVSLKLSSVTAADTAV

YYCAKHYYYGGSYAMDYWGQGTLVTVSSTTTPAPRPPTPAPTIASQPLS

LRPEACRPAAGGAVHTRGLDFACDIYIWAPLAGTCGVLLLSLVITLYCK

RGRKKLLYIFKQPFMRPVQTTQEEDGCSCRFPEEEEGGCELRVKFSRSA

DAPAYKQGQNQLYNELNLGRREEYDVLDKRRGRDPEMGGKPRRKNPQEG

LYNELQKDKMAEAYSEIGMKGERRRGKGHDGLYQGLSTATKDTYDALHM

QALPPR

CD19scFV-BB-VPS28

(SEQ ID NO: 2)
GSATMALPVTALLLPLALLLHAARPEIVMTQSPATLSLSPGERATLSCR

ASQPISKYLNWYQQKPGQAPRLLIYHTSRLHSGIPARFSGSGSGTDYTL

TISSLQPEDFAVYKQQGNTLPYTFGQGTKLEIKGGGGSGGGGSGGGGSQ

VQLQESGPGLVKPSETLSLTCTVSGVSLPDYGVSWIRQPPGKGLEWIGV

IWGSETTYYSSSLKSRVTISKDNSKNQVSLKLSSVTAADTAVYYCAKHY

YYGGSYAMDYWGQGTLVTVSSTTTPAPRPPTPAPTIASQPLSLPSEACR

PAAGGAVHTRGLDFACDIYIWAPLAGTCGVLLLSLVITLYCSLKRGRKK

LLYIFKQPEMRPVQTTQEEDGCSCRFPEEEEGGCELMFNAKYVAEATGN

FITVMDALKLNYNAKDQLHPLLAELLISINRVTRDDFENRSKLIDWIVR

INKLSIGDTLTETQIRELLFDLELAYKSFYALLD

CD3e-VPS36

(SEQ ID NO: 3)
GSMQSGTHWRVLGLCLLSVGVWGQDGNEEMGGITQTPYKVSISGTTVIL

TCPQYPGSEILWQHNDKNIGGDEDDKNIGSDEDHLSLKEFSELEQSGYY

VCYPRGSKPEDANFYLYLRARVCENCMEMDVMSVATIVIVDICITGGLL

LLVYNAVSKNRKAKAKPVTRGAGAGGRQRGQNKERPPPVPNPDYEPIRK

GQRDLYSGLNQRRIGSGSGGSGSGGGSGSGSSGASADVVSTWVCPICNI

VSNETQGEFTKDTLPTPICINCGVPADYELTKSSINCSNAIDPNANPRN

QFG

CD19scFV-BB-mJUN (SEQ ID NO: 4)
GSATMALPVTALLLPLALLLHAARPEIVMTQSPATLSLSPGERATLSCR

ASQDISKYLNWYQQKPGQAPRLLIYHTSRLHSGIPARFSGSGSGTDYTL

TISSLQPEDFAVYFCQQGNTLPYTFGQGTKLEIKGGGGSGGGGSGGGGS

QVQLQESGPGLVKPSETLSLTCTVSGVSLPDYGVSWIRQPPGKGLEWIG

VIWGSETTYYSSSLKSRVTISKDNSKNQVSLKLSSVTAADTAVYYCAKH

MGGSYAMDYWGQGTLVTVSSTTTPAPRPPTPAPTIASQPLSLRPEACRP

AAGGAVHTRGLDFACDIYIWAPLAGTCGVLLLSLVITLYCSLKRGRKKL

LYIFKQPFMRPVQTTQEEDGCSCRFPEEEEGGCELRIARLEEEVKTLEA

QNSELASTANMLEEQVAQLKQKV

CD3e-mFos (SEQ ID NO: 5)
GSMQSGTHWRVLGLCLLSVGVWGQDGNEEMGGITQTPYKVSISGTTVIL

TCPQYPGSEILWQHNDKNIGGDEDDKNIGSDEDHLSLKEFSELEQSGYY

VCYPRGSKPEDANFYLYLRARVCENCMEMDVMSVATIVIVDICITGGLL

LLVYYWSKNRKAKAKPVTRGAGAGGRQRGQNKERPPPVPNPDYEPIRKG

QRDLYSGLNQRRIGSGSGGSLTDTLQAKTDQLKDEKSALQTKIANLLKE

KEKLEFIL

Generation of Jurkat Reporter Cell Line for Initial Characterization of CAR Function As an alternative to primary T cell transduction and activation, a Jurkat-NFAT reporter cell line can be used to evaluate the functional activity of CAR constructs. The Jurkat T cell line (E6-1) was transfected with a NFAT-luciferase reporter construct and a stable, clonal cell line Jurkat cells with NFAT-LUC reporter (JNL), was selected for further characterization based on strong induction of the NFAT reporter following PMA and ionomycin stimulation.

Transfection of Jurkat reporter cell line and activation of NFAT.

Jurkat cells with NFAT-LUC reporter (JNL) were grown to the density of $0.5\text{-}1.0\times10^6$/ml in RPMI-1640 media containing 2 mM glutamine and 10% fetal bovine serum with puromycin at 0.5 µg/ml. For each transfection $2.0\times10^6$ cells were spin down at 100 g for 10 minutes. 1 µg DNA each for co-transfection or 2 µg for single transfection of the control CAR were used per transfection. Amaxa Nucleofector solution V and supplement I was mixed and 100 µl was added into the tube with DNA construct. The mixture was then added to the cells and transferred to the electroporation cuvette. Electroporation was done under setting X-001 using Amaxa Nucleofector II Device. 0.4 ml of RPMI-1640 media containing 2 mM glutamine and 10% FBS was added immediately after electroporation and the mixture was transferred into 0.25 ml growth media in one well of the 6-well plate and allowed to recover for at least 3 hours. During cell recovery, white solid bottom tissue culture treated plates were coated with either anti-CD19 idiotype antibody or irrelevant human IgG1-Fc negative control for 2 hours followed by blocking with 5% BSA in FBS for 30 minutes at 37° C., 5% $CO_2$. The blocking buffer was then aspirated. 100 µL of each of the transfected Jurkat constructs was plated in triplicate. After an overnight incubation 100 µL of One-Glo Luciferase (Promega) reagent was added to each well. To determine the relative-fold activation of the anti-idiotype wells to the negative control wells, the plate was then incubated for 5 min to allow for equilibrium of the luciferase signal and read using an Envision multilabel reader.

IL-2 Expression in Transfected Jurkat (JNL) Cells

Transfection of JNL cells and activation was performed as described above in the JNL RGA assay excepting incubation which was for 40-48 hours at 37° C., 5% $CO_2$. Supernatant was collected from the cells by centrifuging at 300×g for 10 minutes. Levels of IL-2 expression were measured using Mesoscale Discovery Human IL-2 kit (Mesoscale). All provided reagents were prepared according to manufacturer's instructions. 50 µL of collected supernatant (neat) and prepared standard were added to the pre-coated MSD plate and incubated at room temperature with shaking for two hours. The plate was washed 3× with 300 µL PBS+Tween 20 and 25 µL detection antibody solution was added to each well. The plate was incubated again at room temperature with shaking for 2 hours and washed with the previous conditions and 150 μL 2× Read Buffer T was added to each well. The plate was immediately read on the MSD instrument for human IL-2 levels.

Transient Expression Results

Figure 2:
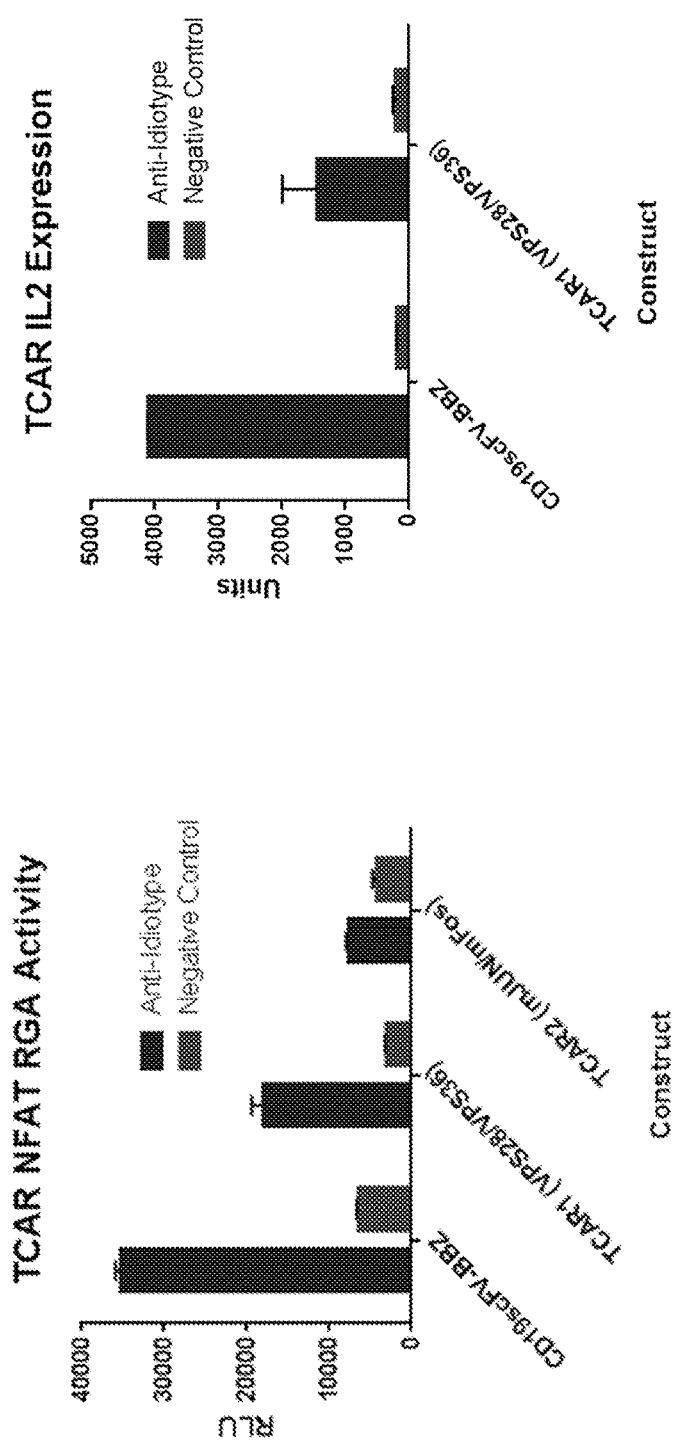
FIG. 2 is a pair of graphs showing JNL signaling and IL2 expression of antigen activated TCARs with intracellular heterodimerization domains.

Transient transfection via electroporation of JNL cells of TCAR1 and TCAR2 demonstrated antigen-dependent signaling in the reporter gene assay as shown in FIG. 2. TCAR1, VPS28/VPS36-based heterodimers, demonstrated similar fold over background activation compared to the positive control CAR, CD19scFV-BBZ in the RGA assay. Expression of IL2 after 40 hours of activation was also evaluated. Antigen dependent IL2 expression was also observed for TCAR1; due to the low intrinsic signal in the JNL RGA assay, TCAR2 was not assessed. Further enhancements in signaling and IL2 expression would be expected by optimizing the orientation of the heterodimerization domains via linker length, enhancing the affinity of the heterodimerization domains to one another and/or enhancing the affinity of the CD3 epsilon interface to the remainder of the TCR complex.

Production of Lentiviral Transduced Primary Human T-Cells

TCAR1 was also evaluated in vitro using primary human T-cells produced via lentiviral transduction in comparison to CD19scFv-BBZ.

Lentivirus Production

Lenti-X 293T cells (Clontech), grown in DMEM supplemented with 10% FBS and Non-essential amino acids were co-transfected with lentiviral vector plasmids along with the pRSV.rev, pMDL.g/p.rre and pVSVg packaging plasmids using Lipofectamine 2000 (Invitrogen) transfection reagent. Lentivirus vector containing supernatants were harvested 48 hours after transfection, and concentrated using Lenti-X Concentrator (Clontech) and centrifugation at 1,500×g for 45 minutes. Concentrated vector was stored at −80 C until further use.

Lentivirus vector titers were determined using limited dilution on Sup-T1 cells (ATCC) cultured in RPMI-1640 supplemented with 10% FBS. Vectors were 3-fold serial diluted then 50 uL of diluted vector was added to a flat bottom microtiter plate containing Sup-T1 cells. After 72 hours cells were harvested and analyzed via FACS using Protein-L for scFv expression. The titer in transducing units per mL (TU/mL) was calculated from the vector dilution in which percent positive expression in Sup-T1 cells was less than 20% but greater than 5% using the following equation:

$$TU/mL = (\% \text{ Positive}/100) \times 2E^4 \times \text{dilution factor} \times 20$$

T Cell Isolation and Viral Transduction into Primary T Cells

Normal donor T cells were isolated via MACS negative selection (Miltenyi pan T cell isolation kit) from human PBMC obtained from Cellular Technology Limited. Purified T cells were cultured in RPMI supplemented with 10% FBS, 100 U/ml penicillin, 100 μg/ml streptomycin, 10 mM HEPES and 1 mM non-essential amino acids and activated with Dynabeads human T-activator CD3/CD28 beads (Invitrogen) at a bead to cell ratio of 3:1. After 18-24 hours of activation T cells were transduced with lentiviral vectors at a multiplicity of infection (MOI) of 5. Transduced T cells were expanded every 2-3 days for 10 days maintaining a cell density of ~0.75 million per mL. Cells were aliquoted and cryogenically frozen.

Cytotoxicity and IL2 Assay

Transduced T cells were analyzed for their ability to kill target expressing cell lines as well as secretion of the cytokine IL2; used as a surrogate for proliferation. The target expressing cell lines Nalm6 (CD19), cultured in RPMI with 10% FBS and K562 (negative control), cultured in IMDM with 10% FBS, were all engineered to stably express firefly luciferase under puromycin selection. Briefly, thawed transduced T cells were analyzed via FACS for percent CAR expression. All constructs were normalized to 10% CAR positive expression by diluting with isolated, expanded, freeze/thawed untransduced T cells. Transduced normalized T cells were then cultured in 200 μL of media at various effector to target ratios, holding target cells constant at $2.5E^4$ cells/well. Target cells were plated alone without the presence of effector cells to determine maximum luminescence. After 18-20 hours 100 μL of culture supernatant was removed for subsequent 1L2 analysis and 100 μL of OneGlo (Promega) luciferase substrate was added to the remaining supernatant and cells. Luminescence was measured on an Envison plate reader after a 10 minute incubation. Percent specific lysis was calculated using the following equation:

$$\text{Specific lysis}(\%) = (1 - (\text{sample luminescence/average maximum/luminescence})) \times 100$$

The harvested supernatant was analyzed for the amount of the IL2 via MSD ELISA following the manufacturer's instructions.

Primary Human T-Cell Results

Figure 3:
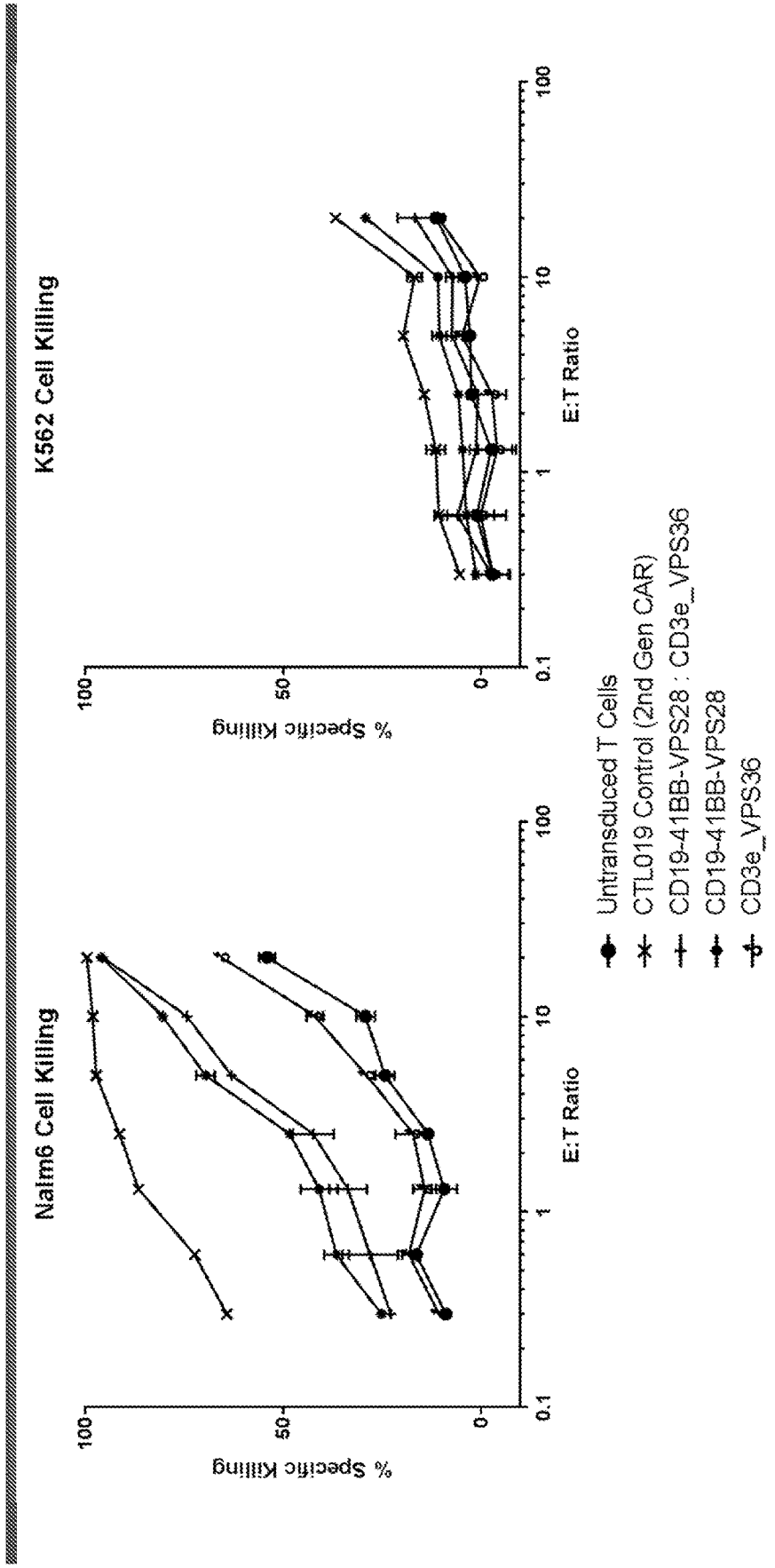
FIG. 3 is a pair of graphs showing percentage of the indicated cell killing in cells transfected with the indicated constructs as a function of transfection.
Figure 4:
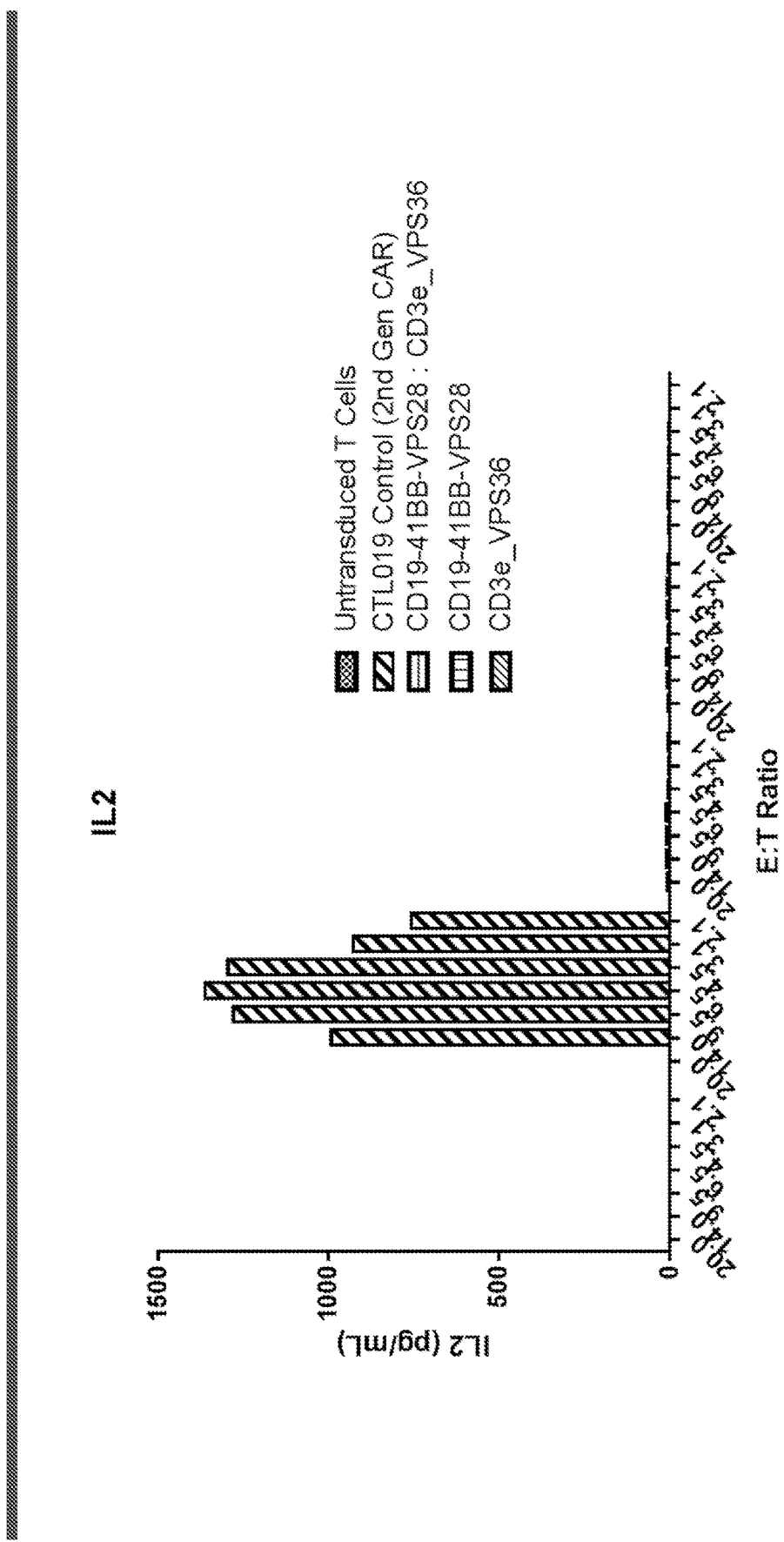
FIG. 4 is a graph showing concentration of IL-2 expression as a function of transfection in the indicated constructs.
Figure 5:
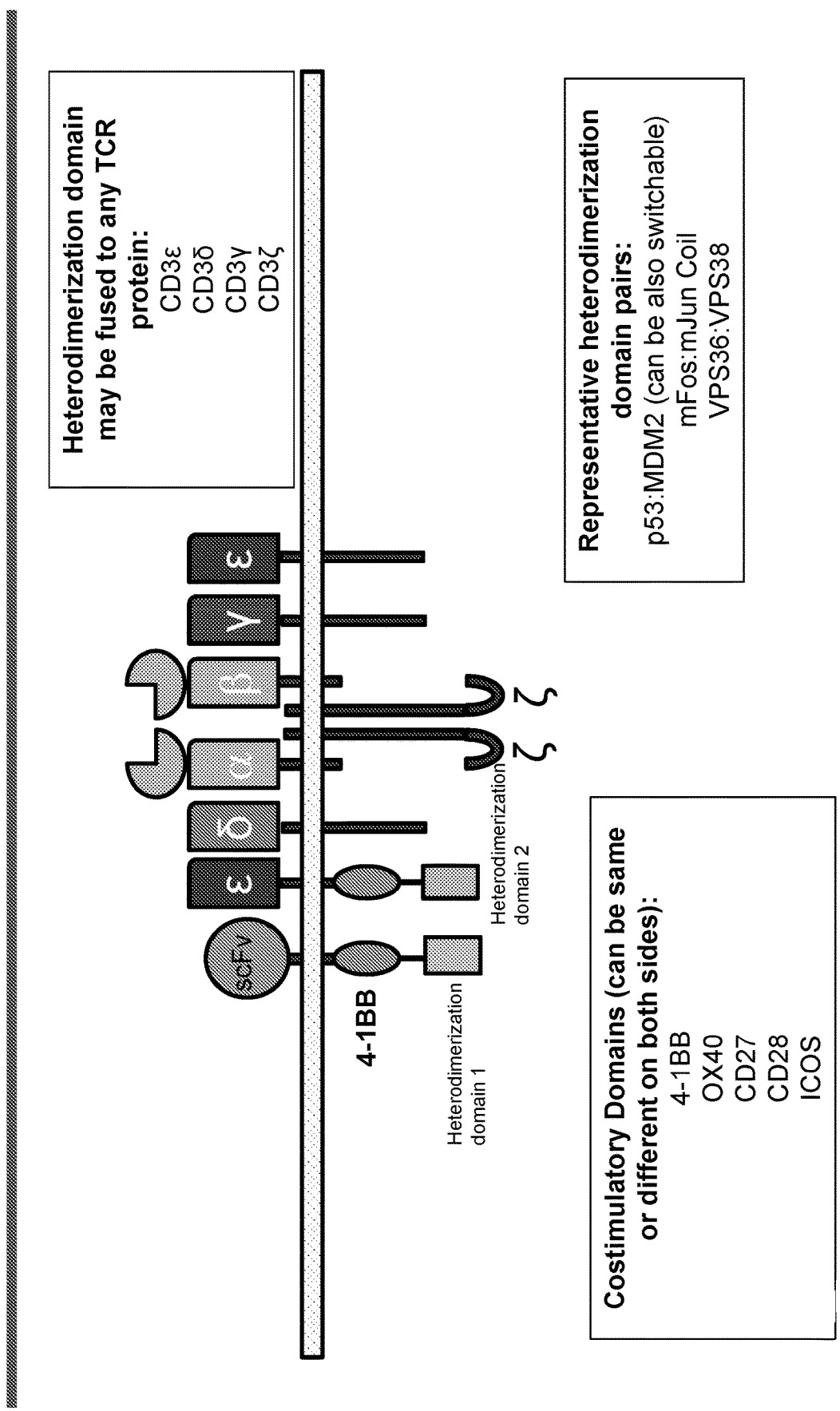
FIG. 5 is a schematic showing Constitutively Active TCR-based Chimeric Antigen Receptor (TCAR) with enhanced proliferation. A targeting and costimulatory domain are embedded into the TCR complex by fusion with an intracellular heterodimerization domain and co-transfection/co-transduction with the extracellular and transmembrane domains of an endogenous TCR complex member such as CD3 epsilon fused to a second costimulatory domain and a second heterodimerization domain. Unlike third generation CARs, this orientation provides for both costimulatory members to be membrane proximal and should further enhance proliferative capabilities.
Figure 6:
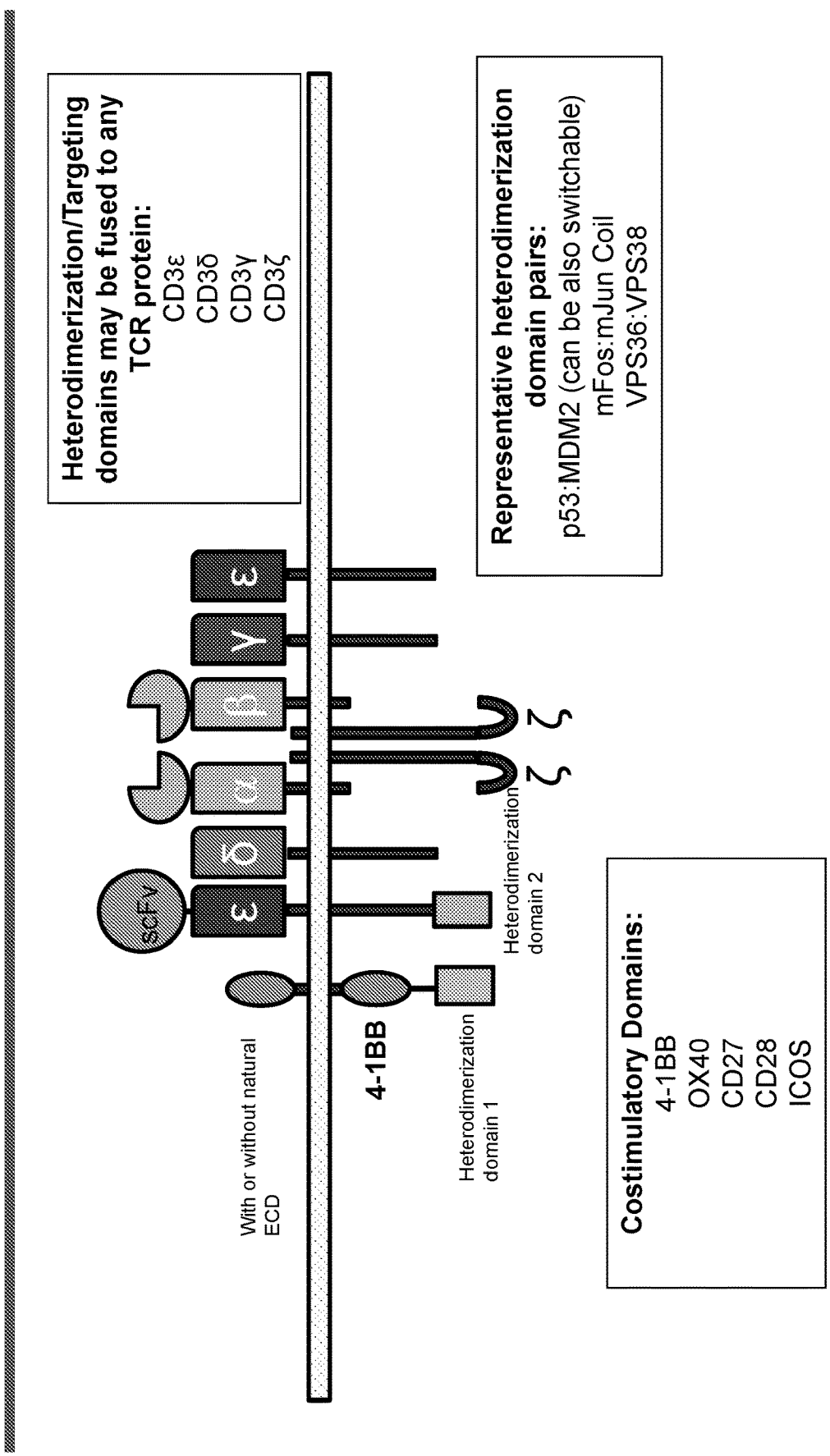
FIG. 6 is a schematic showing constitutively active TCR-based Chimeric Antigen Receptor (TCAR). A costimulatory receptor with or without its natural extracellular domain is embedded into the TCR complex by fusion with an intracellular heterodimerization domain and co-transfection/co-transduction with a targeting domain fused to an endogenous TCR complex member such as CD3 epsilon fused to a second intracellular heterodimerization domain.
Figure 7:
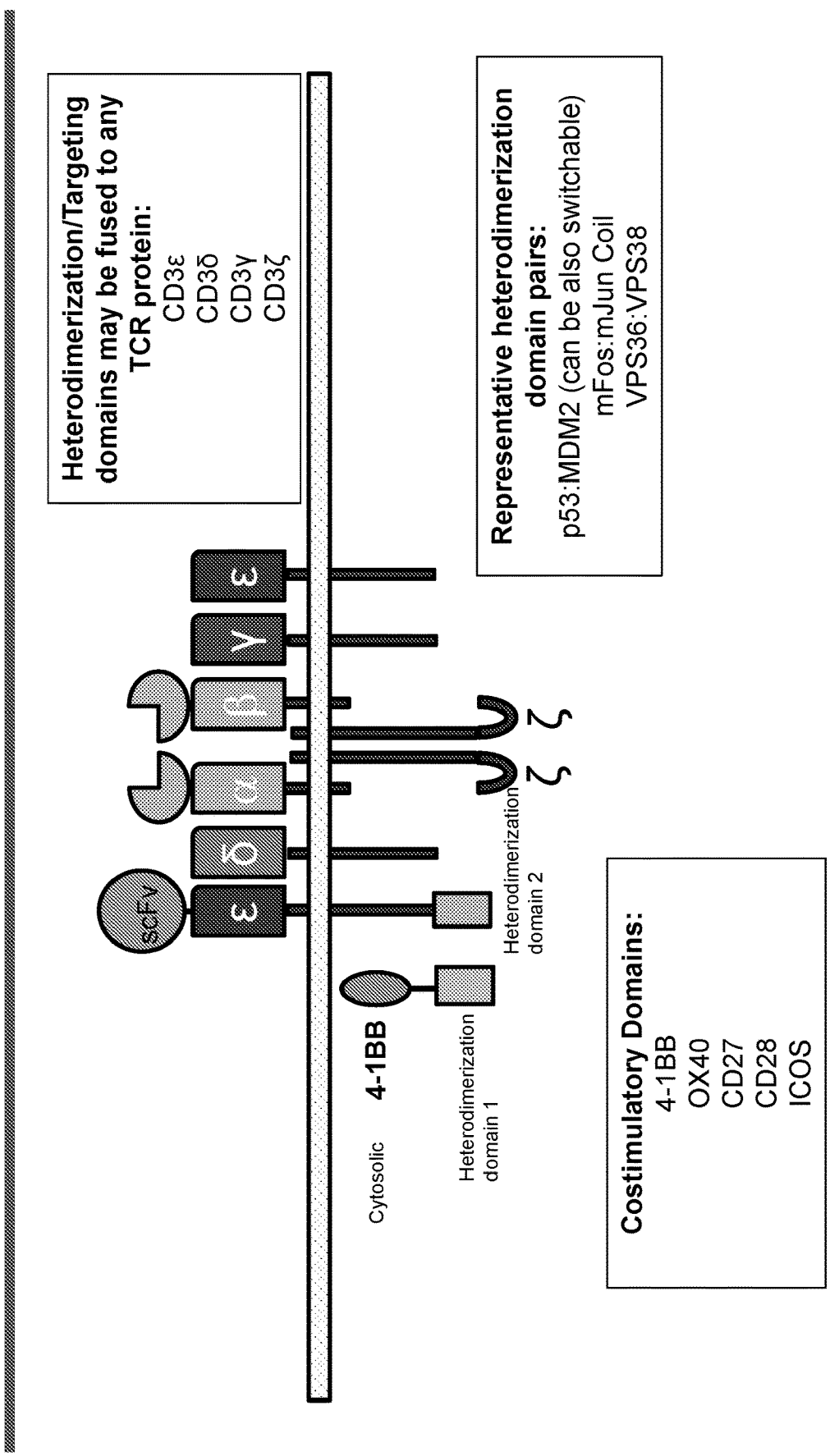
FIG. 7 is a schematic showing constitutively active TCR-based Chimeric Antigen Receptor (TCAR). A cytosolic costimulatory domain is embedded into the TCR complex by fusion with an intracellular heterodimerization domain and co-transfection/co-transduction with a targeting domain fused to an endogenous TCR complex member such as CD3 epsilon fused to a second intracellular heterodimerization domain.
Figure 8:
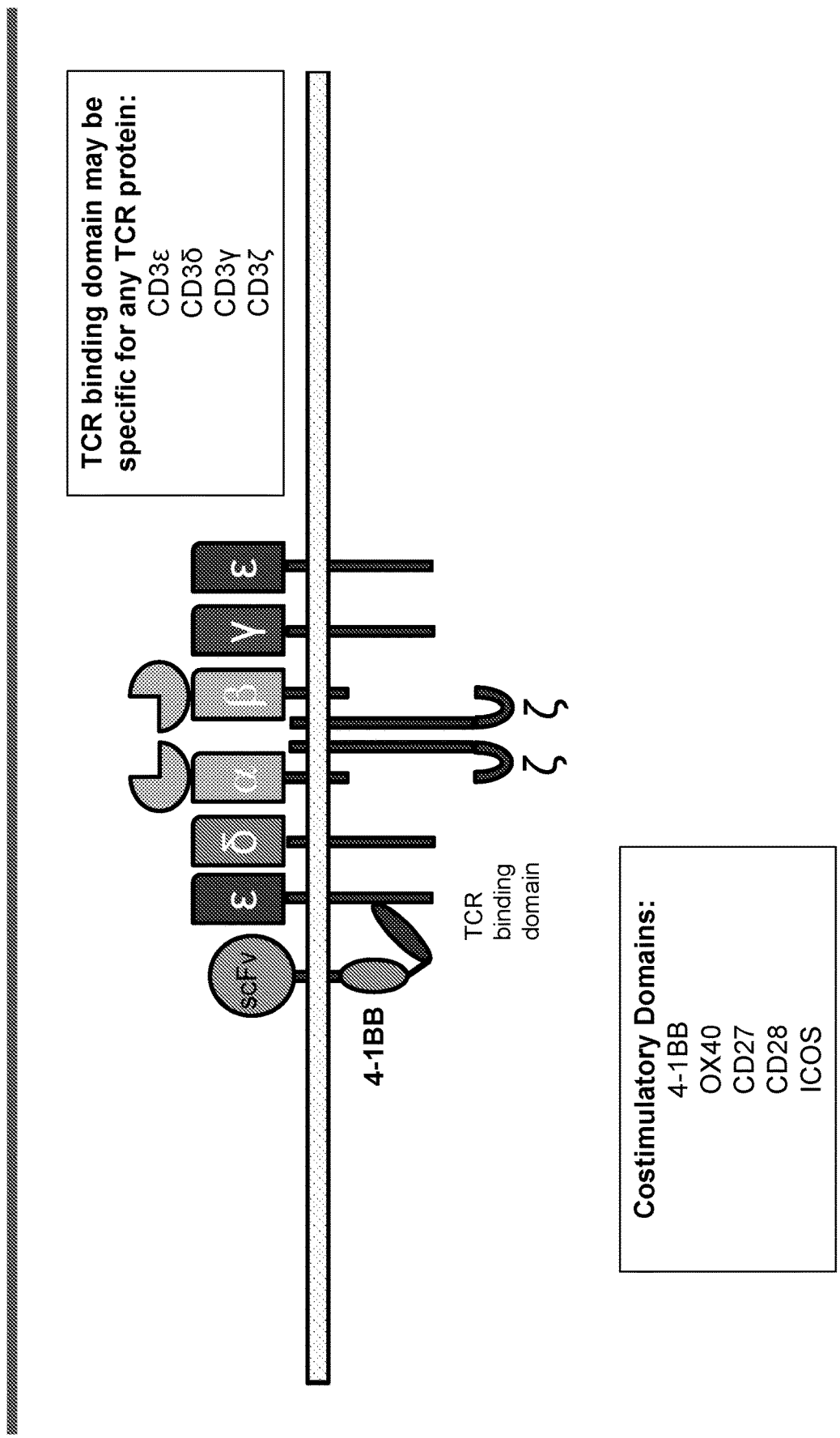
FIG. 8 is a schematic showing constitutively active TCR-based Chimeric Antigen Receptor (TCAR). A targeting and costimulatory domain are embedded into the TCR complex by fusion with an intracellular domain which binds to a member of the TCR complex.
Figure 9:
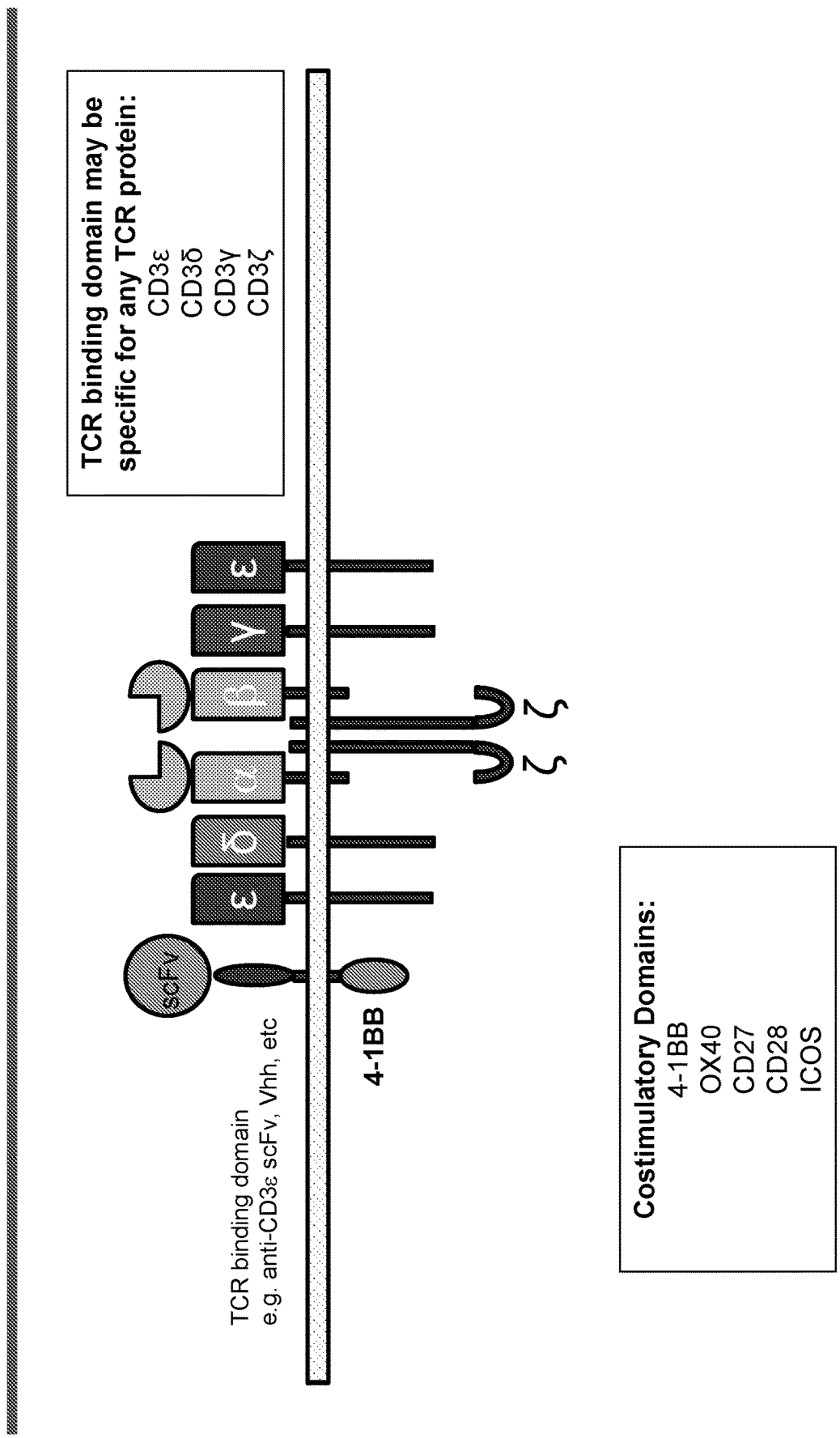
FIG. 9 is a schematic showing constitutively active TCR-based Chimeric Antigen Receptor (TCAR). A targeting and costimulatory domain are embedded into the TCR complex by fusion with an extracellular domain which binds to a member of the TCR complex.

FIG. 3 and FIG. 4 show the functional activity of "TCAR1" relative to the control CD19scFv-BBZ. As can be observed from both the redirected lysis assay and the IL2 expression results, TCAR1 demonstrated reduced functionality. It is not clear if both constructs were expressed in the T-cells under the transduction conditions; further optimizations may be needed to ensure simultaneous expression of both constructs containing both heterodimerization domains in the same cell. Additionally, further enhancements may be needed by optimizing the orientation of the heterodimerization domains via linker length or enhancing the affinity of the heterodimerization domains to one another. However, transient signaling results demonstrated the potential for these types of chimeric antigen receptors.

Example 2: Constitutively Active TCARs with Enhanced Proliferation Using Intracellular Heterodimerization Domains (FIGS. 5-9)

Synthesis of Constitutively Active TCAR Constructs with Multiple Costimulatory Domains Pairs of plasmid DNA will be synthesized externally by DNA2.0. The nominal non-regulatable CAR construct, CD19scFv-BBZ, SEQ ID NO: 1, will be used as a control.

"TCAR1" comprises a pair of constructs. In the first construct, the CD19 scFv was cloned with CD8 hinge and transmembrane domain followed by the costimulatory domain 4-1BB and the heterodimerization domain VPS28 at the C-terminus (SEQ ID NO: 2). The corresponding second construct was designed as above by fusing the heterodimerization domain VPS36 to a linker at the C-terminus of CD3 epsilon (SEQ ID NO:3). "TCAR3" (FIG. 5) comprises a pair of constructs. In the first construct, the CD19 scFv will be cloned with CD8 hinge and transmembrane domain followed by the costimulatory domain 4-1BB and the heterodimerization domain VPS28 at the C-terminus (SEQ ID NO: 2). The corresponding second construct will be designed by fusing the intracellular costimulatory domain of CD28 followed by VPS36 to the C-terminus of CD3 epsilon extracellular and transmembrane domains (SEQ ID NO:6).

CD3eECDTM-CD28-VPS36

(SEQ ID NO: 6)
<u>GSMQSGTHWRVLGLCLLSVGVWGQ</u>DGNEEMGGITQTPYKVSISGTTVIL

TCPQYPGSEILWQHNDKNIGGDEDDKNIGSDEDHLSLKEFSELEQSGYY

VCYPRGSKPEDANFYLYLRARVCENCMEMDVMSVATIVIVDICITGGLL

LLVYYWSRSKRSRLLHSDYMNMTPRRPGPTRKHYQPYAPPRDFAAYRSG

SGSGGSGSGGGSGSGSSGASADVVSTWVCPICMVSNETQGEFTKDTLPT

PICINCGVPADYELTKSSINCSNAIDPNANPRNQFG

Transfection of Jurkat reporter cell line and activation of NFAT.

Activation following target antigen engagement of the antigen binding domain will be measured with the Jurkat cells with NFAT-LUC reporter (JNL) reporter cell line as described in Example 1. The transfected cells will be added to the target plate with 100 µl per well. Luciferase One Glo reagent 100 µl will be added per well. The samples will be incubated for 5 min and then luminescence will be measured as described.

IL-2 Expression in Transfected Jurkat (JNL) Cells

Transfection of JNL cells and activation will be performed as described above in the JNL RGA assay excepting incubation which will be for 40-48 hours at 37° C., 5% $CO_2$. Measurement of secreted IL2 will be performed as described in Example 1.

Figure 10:
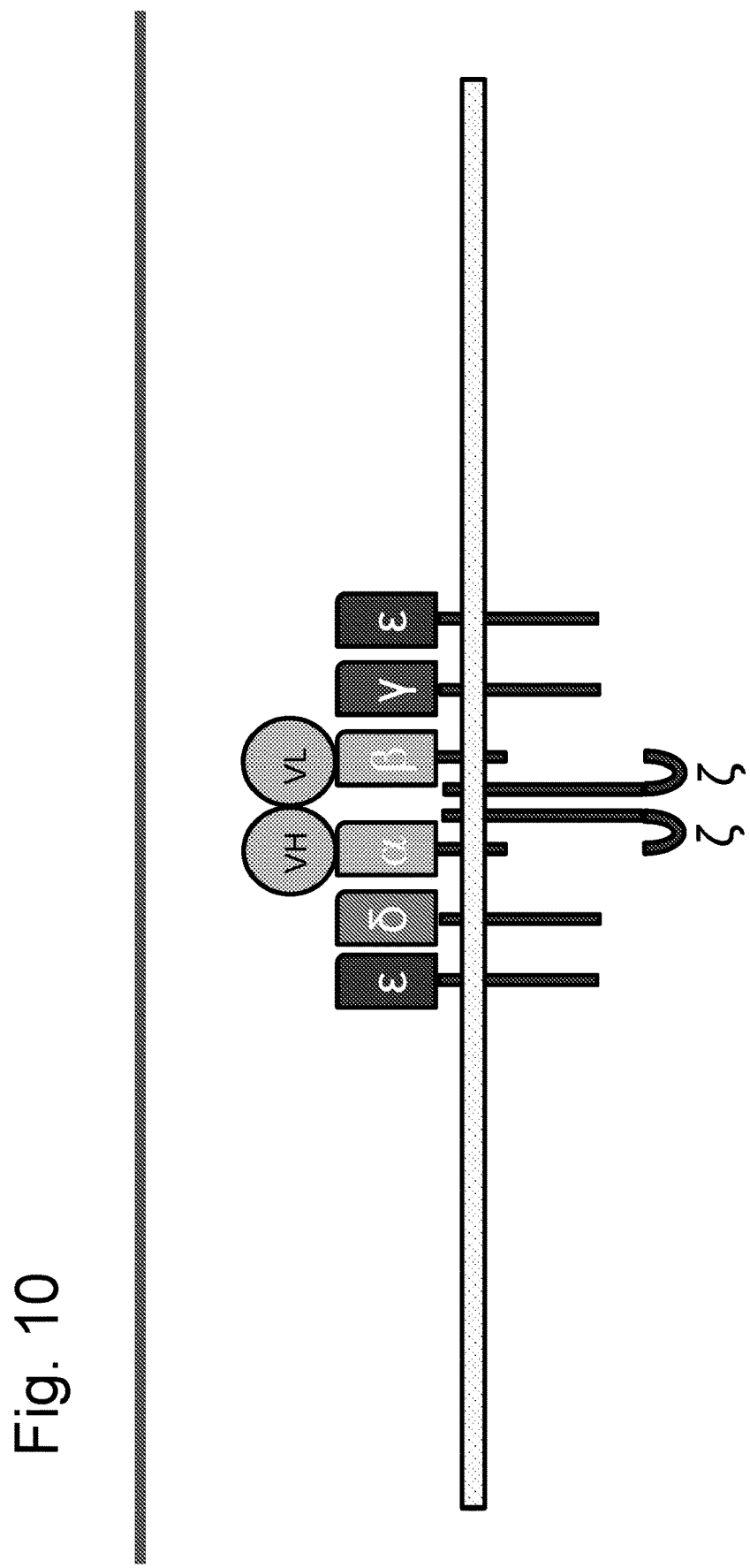
FIG. 10 is a schematic showing constitutively active Chimeric Antigen Receptor TCR fusion (fusTCAR). VL and Vh of a targeting domain derived from an antibody are embedded into the TCR complex by direct fusions to the endogenous truncated alpha and beta TCR.
Figure 11:
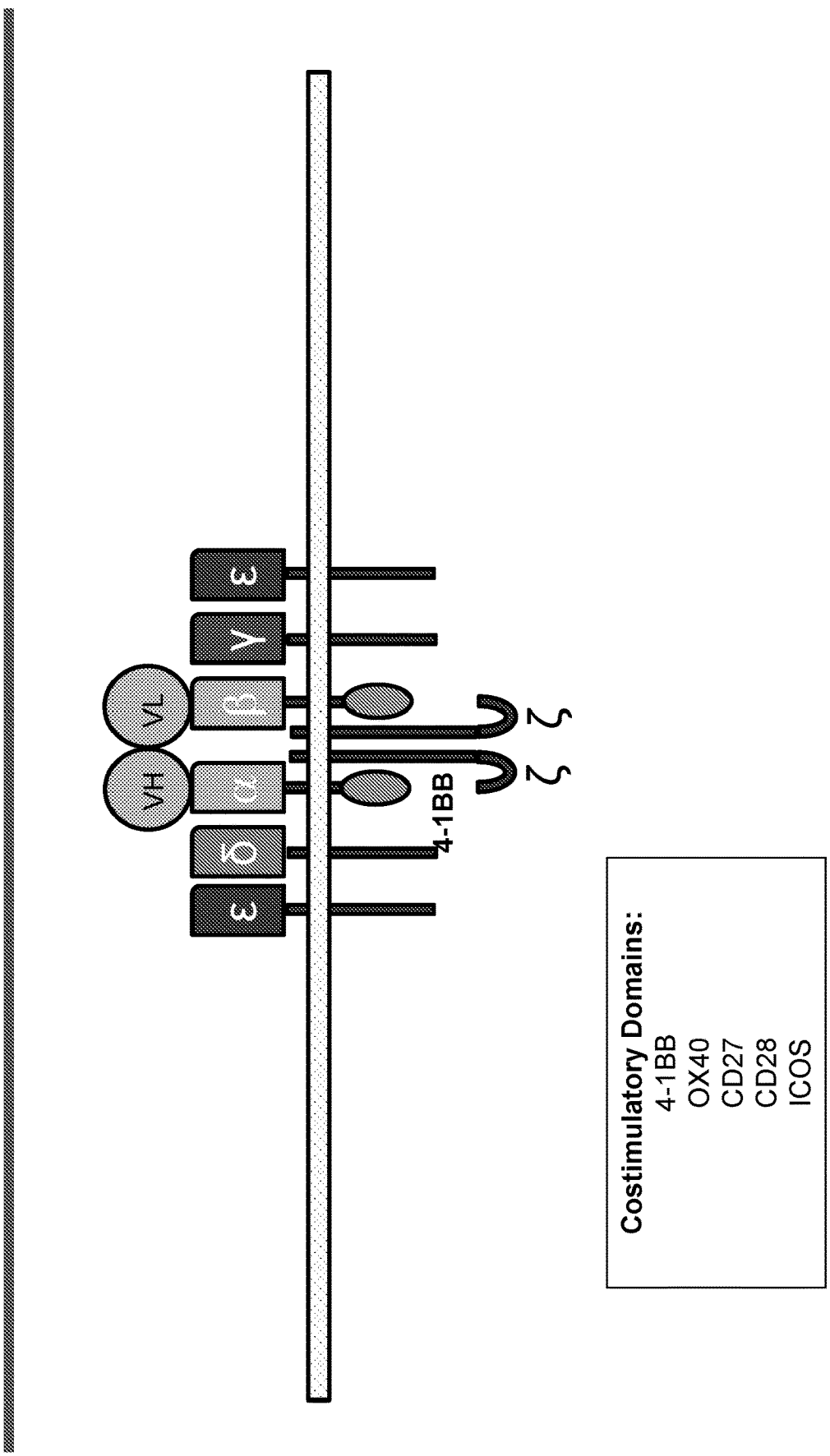
FIG. 11 is a schematic showing Constitutively Active Chimeric Antigen Receptor TCR fusion (fusTCAR). VL and Vh of a targeting domain derived from an antibody are embedded into the TCR complex by direct fusions to the endogenous truncated alpha and beta TCR followed by intracellular fusions of one or more costimulatory domains.

Example 3: Constitutively Active TCARs Fused into the TCR Complex Via CD3 Epsilon (fusTCAR) (FIGS. 10-11)

Transient Expression and Activation Assays

Synthesis of fusTCAR Constructs

Plasmid DNA were synthesized externally by DNA2.0. The nominal non-regulatable CAR construct, CD19scFv-BBZ, SEQ ID NO: 1, was used as a control. For the fusTCAR, the targeting domain can be fused directly to different members of TCR complex with or without additional intracellular co-stimulatory and signaling domains.

Figure 12:
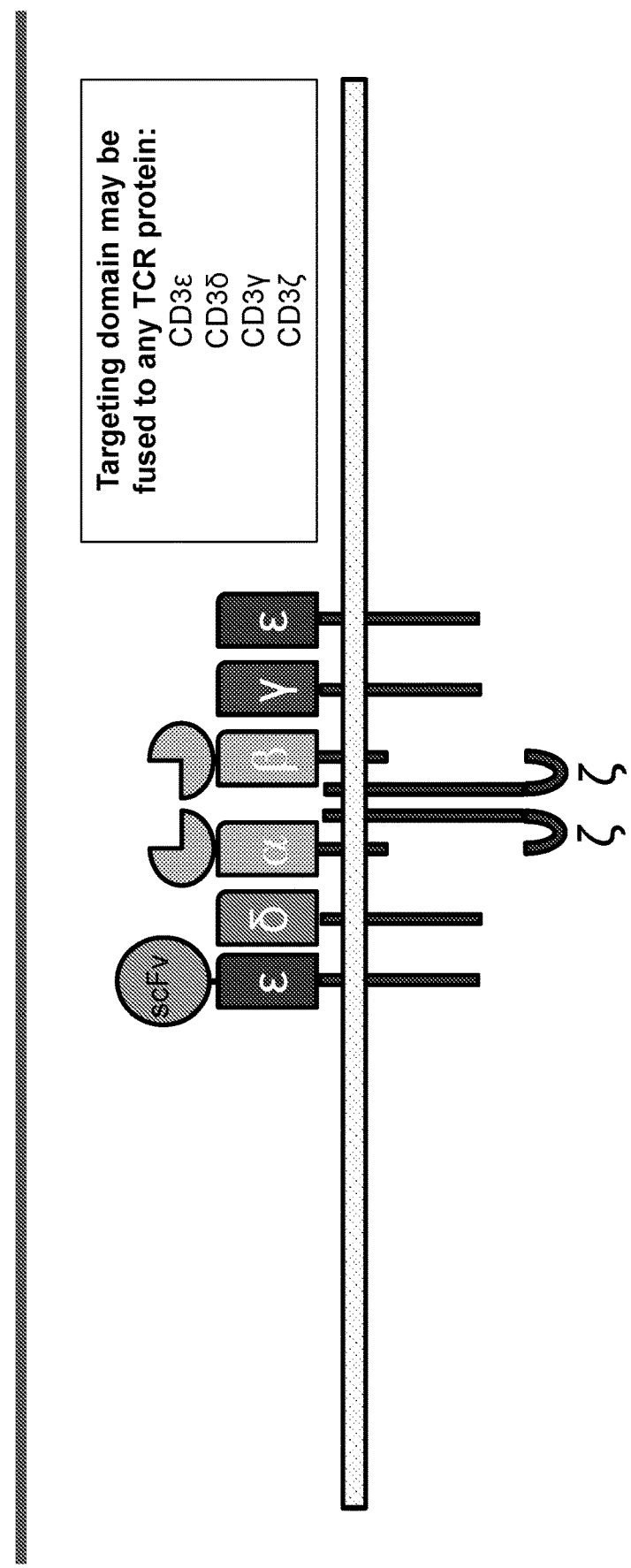
FIG. 12 is a schematic showing constitutively active Chimeric Antigen Receptor TCR fusion (fusTCAR). A targeting domain is embedded into the TCR complex by direct fusion to an endogenous TCR complex member such as CD3 epsilon.
Figure 13:
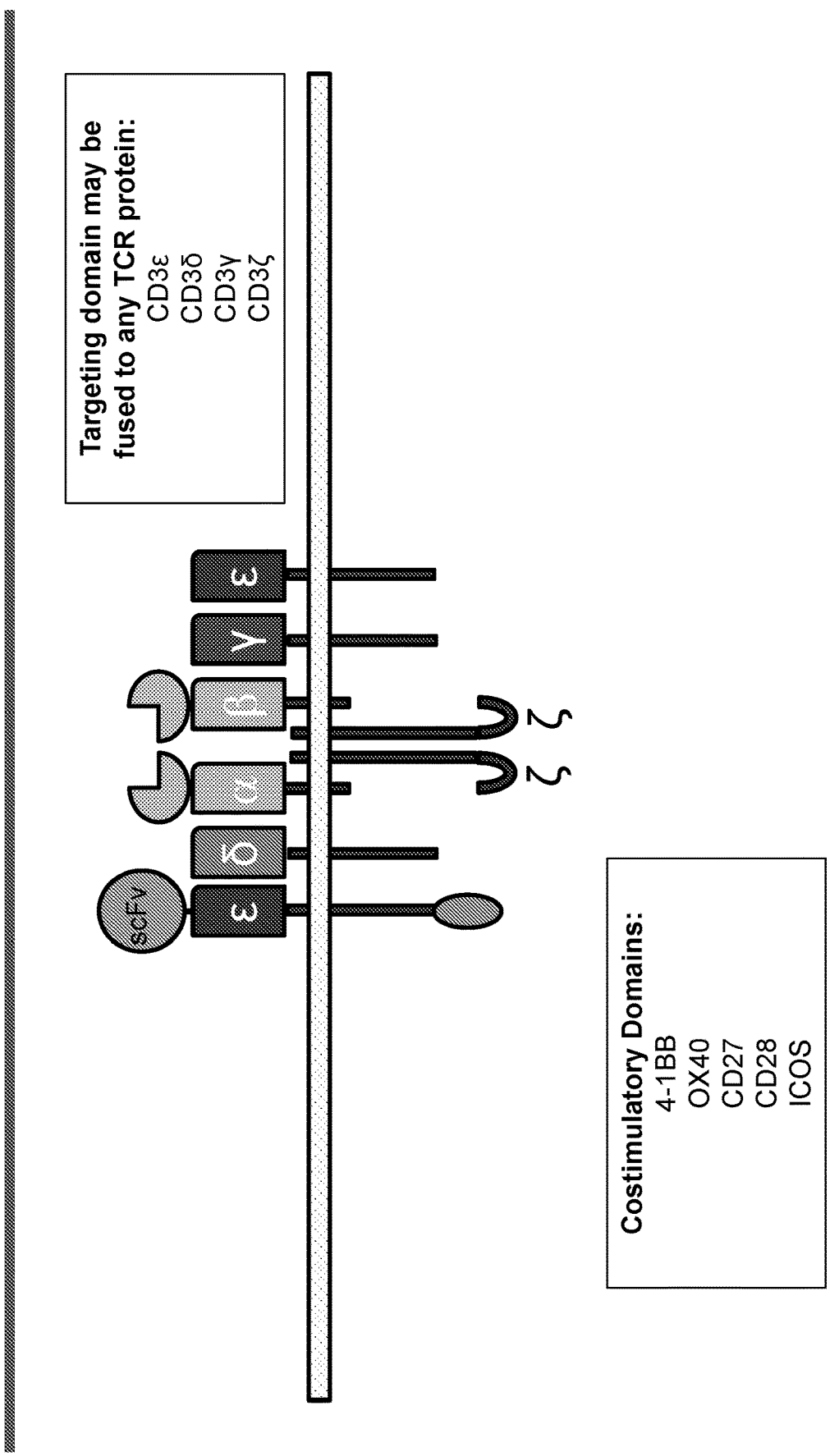
FIG. 13 is a schematic showing constitutively active Chimeric Antigen Receptor TCR fusion (fusTCAR). A targeting domain is embedded into the TCR complex by direct fusion to am endogenous TCR complex member such as CD3 epsilon followed by one or more intracellular co-stimulatory domains such as 4-1BB.
Figure 14:
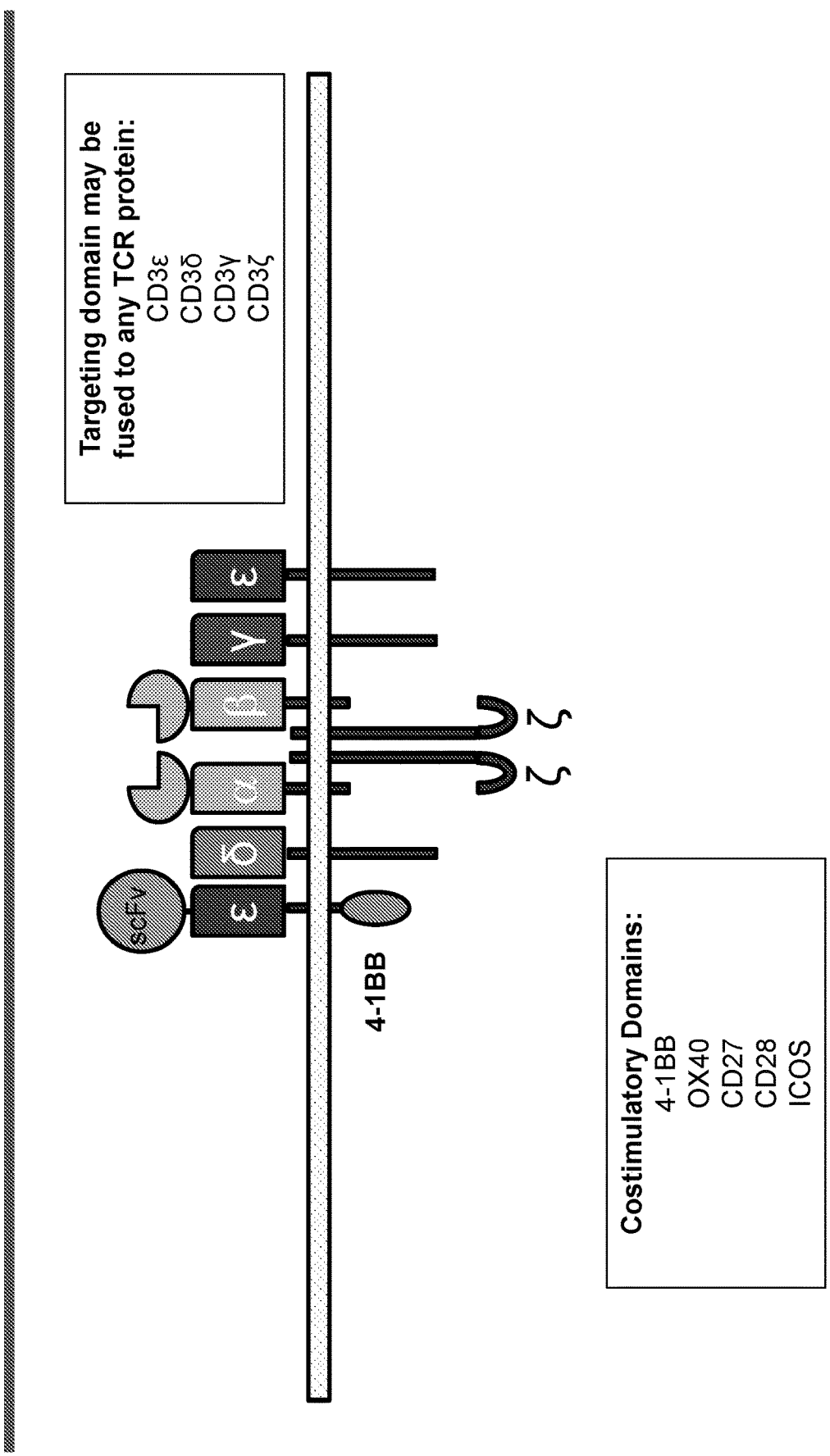
FIG. 14 is a schematic showing constitutively active Chimeric Antigen Receptor TCR fusion (fusTCAR). A targeting domain is embedded into the TCR complex by direct fusion to the extracellular and transmembrane domains of endogenous TCR complex member such as CD3 epsilon followed by one or more intracellular co-stimulatory domains such as 4-1BB.

In "fusTCAR1" (FIG. 12) the CD19 scFv was cloned as an N-terminal fusion to the complete CD3 epsilon protein (SEQ ID NO: 7). "FusTCAR2" (FIG. 13) was cloned as an N-terminal fusion to the complete CD3 epsilon protein followed by a C-terminal fusion of the intracellular costimulatory domain of 4-1BB (SEQ ID NO: 8) "FusTCAR3" (FIG. 14) lacks internal endogenous ITAM domains. CD19 scFv was cloned onto the N-terminus of the CD3 extracellular and transmembrane domains followed by the intracellular costimulatory domain 4-1BB (SEQ ID NO: 9).

CD19scFv-CD3e (Seq ID NO: 7)
<u>GSATMALPVTALLLPLALLLHAARP</u>EIVMTQSPATLSLSPGERATLSCR

ASQDISKYLNWYQQKPGQAPRLLIYHTSRLHSGIPARFSGSGSGTDYTL

TISSLQPEDFAVYFCQQGNTLPYTFGQGTKLEIKGGGGSGGGGSGGGGS

QVQLQESGPGLVKPSETLSLTCTVSGVSLPDYGVSWIRQPPGKGLEWIG

VIWGSETTYYSSSLKSRVTISKDNSKNQVSLKLSSVTAADTAVYYCAKH

YYYGGSYAMDYWGQGTLVTVSSGGGGSDGNEEMGGITQTPYKVSISGTT

VILTCPQYPGSEILWQHNDKNIGGDEDDKNIGSDEDHLSLKEFSELEQS

GYYVCYPRGSKPEDANFYLYLRARVCENCMEMDVMSVATIVIVDICITG

GLLLLVYYWSKNRKAKAKPVTRGAGAGGRQRGQNKERPPPVPNPDYEPI

RKGQRDLYSGLNQRRI

CD19scFv-CD3e-41BB (Seq ID NO: 8)
<u>GSATMALPVTALLLPLALLLHAARP</u>EIVMTQSPATISLSPGERATLSCR

ASQDISKYLNWYQQKPGQAPRLLIYHTSRLHSGIPARFSGSGSGTDYTL

TISSLQPEDFAVYFCQQGNTLPYTFGQGTKLEIKGGGGSGGGGSGGGGS

QVQLQESGPGLVKPSETLSLTCTVSGVSLPDYGVSWIRQPPGKGLEWIG

VIWGSETTYYSSSLKSRVTISKDNSKNQVSLKLSSVTAADTAVYYCAKH

YYYGGSYAMDYWGQGTLVTVSSGGGGSDGNEEMGGITQTPYKVSISGTT

VILTCPQYPGSEILWQHNDKNIGGDEDDKNIGSDEDHLSLKEFSELEQS

GYANCYPRGSKPEDANFYLYIRARVCENCMEMDVMSVATIVIVDICITG

GLLLLVYYWSKNRKAKAKPVTRGAGAGGRQRGQNKERPPPVPNPDYEPI

RKGQRDLYSGLNQRRIGSGSGGSKRGRKKLLYIFKQPEMRPVQTTQEED

GCSCREPEEEEGGCEL

CD19scFv-CD3eECDTM-41BB (Seq ID NO: 9)
<u>GSATMALPVTALLLPLALLLHAARP</u>TIVNTMSPATLSLSPGERAILSCR

ASQDISKYLNWYQQKPGQAPRLLIYHTSRLHSGIPARFSGSGSGTDYTL

TISSLQPEDFAVYFCQQGNTLPYIFGQGTKLEIKGGGGSGGGGSGGGGS

QVQLQESGPGLVKPSETLSLTCTVSGVSLPDYGVSWIRQPPGKGLEWIG

VIWGSETTYYSSSLKSRVTISKDNSKNQVSLKLSSVTAADTAVYYCAKH

YYYGGSYAMDYWGQGTLVTVSSGGGGSDGNEEMGGITQTPYKVSISGTT

VILTCPQYPGSEILWQHNDKNIGGDEDDKNIGSDEDHLSLKEFSELEQS

GYYVCYPRGSKPEDANFYINLRARVCENCMEMDVMSVATIVIVDICITG

GLLLLVYYWSKRGRKKLLYIFKQPFMRPVQTTQEEDGCSCRFPEEEEGG

CEL

Transfection of Jurkat Reporter Cell Line and Activation of NFAT.

Activation following target antigen engagement of the antigen binding domain was measured with the Jurkat cells with NFAT-LUC reporter (JNL) reporter cell line as described in Example 1. The transfected cells was added to the target plate with 100 µl per well. Luciferase One Glo reagent 100 µl was added per well. The samples were incubated for 5 min and then luminescence was measured as described.

IL-2 Expression in Transfected Jurkat (JNL) Cells

Transfection of JNL cells and activation was performed as described above in the JNL RGA assay excepting incubation which was for 40-48 hours at 37° C., 5% $CO_2$. Measurement of antigen-dependent IL2 expression was performed as described in Example 1.

Transient Expression Results

Figure 15:
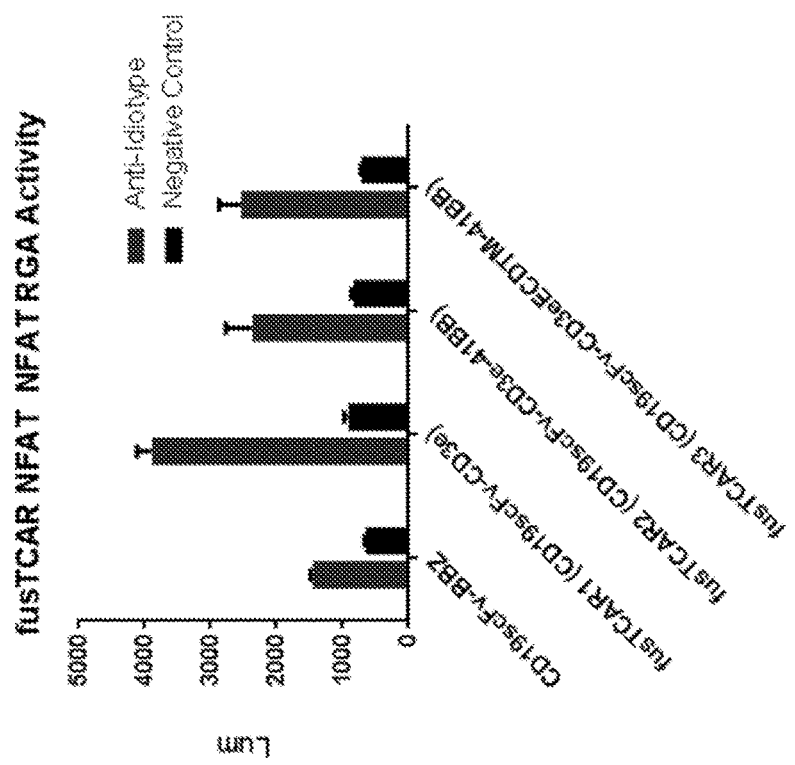
FIG. 15 is a graph showing JNL signaling and IL2 expression of activated fusTCARs.

Initial screening of fusTCAR1, fusTCAR2 and fusTCAR3 via transient transfection into JNL cells demonstrated antigen-dependent signaling as shown in FIG. 15. Importantly, signaling was still observed with fusTCAR3, which was truncated and lacked the ITAM signaling domain of CD3 epsilon. Transfection of a construct containing ITAM signaling domains is thus not a prerequisite for activity of fusTCARs. By associating the targeting domain with the TCR complex, signaling is mediated through all members of the complex and is not exclusively limited to that derived from a signaling domain fused to the targeting domain.

Production of Lentiviral Transduced Primary Human T-Cells

FusTCARs were also tested in primary human T-Cells for their activity. Prior to production of lentivirus additional constructs were also designed to confirm the dependence of functional ITAMS for in vitro activity of traditional CAR constructs and the independent activity for TCARs regardless of the presence or absence of functional ITAMS. Plasmid DNA were synthesized externally by DNA2.0. The first generation CAR design construct, CD19scFv-Zeta. SEQ ID No: 10, was synthesized; CD19 scFv was cloned as a N-terminal fusion to the CD8a linker and transmembrane domain followed by the intracellular signaling domain CD3zeta. A second construct (SEQ ID NO: 11) was similarly cloned, excepting that all intracellular tyrosine residues within CD3 zeta annotated to be phosphorylated were switched to phenylalanine in order to abbrogate intracellular phosphotyrosine signaling. As a combination of a intracellular costimulatory domain with intracellular signaling domain has previously been demonstrated to be beneficial for typical CAR constructs, a final construct was cloned whereby CD19 scFv was a N-terminal fusion to the CD8a linker and transmembrane domain followed by 4-1BB; no CD3 zeta signaling domain was included in this construct (SEQ ID NO: 12). Finally, an analogous fusTCAR was synthesized to CD19scFV-Zeta_7YtoF. "FusTCAR4" lacks internal endogenous ITAM domains. CD19scFv, SEQ ID NO: 13 was cloned as a N-terminal fusion to the complete CD3 epsilon protein except those tyrosines annotated to be phosphorylated were mutated to phenylalanine rendering the intrinsic signaling pathways associated with CD3 epsilon ITAMs inactive.

CD19scFv-Zeta (SEQ ID NO: 10)
<u>GSMALPVTALLLPLALLLHAARP</u>EIVMTQSPATLSLSPGERATLSCRAS

QDISKYLNWYQQKPGQAPRLLIYHTSRLHSGIPARFSGSGSGTDYTLTI

SSLQPEDFAVYFCQQGNTLPYTFGQGTKLEIKGGGGSGGGGSGGGGSGG

GGSQVQLQESGPGLVKPSETLSLTCTVSGVSLPDYGVSWIRQPPGKGLE

WIGVIWGSETTYYNSSLKSRVTISKDNSKNQVSLKLSSVTAADTAVYYC

AKHYYYGGSYAMDYWGQGTLVTVSSTTTPAPRPPTPAPTIASQPLSLRPE

ACRPAAGGAVHTRGLDFACDIYIWAPLAGTCGVLLLSLVITLYCRVKF

SRSADAPAYKQGQNQLYNELNLGRREEYDVLDKRRGRDPEMGGKPRRKN

PQEGLYNELQKDKMAEAYSEIGMKGERRRGKGHDGLYQGLSTATKDTYD

ALHMQALPPR

CD19scFv-Zeta_7YtoF (SEQ ID NO: 11)
<u>GSMALPVTALLLPLALLLHAARP</u>EIVMTQSPATLSLSPGERATLSCRAS

QDISKYLNWYQQKPGQAPRLLIYHTSRLHSGIPARFSGSGSGTDYTLTI

SSLQPEDFAVYKQQGNTLPYTFGQGTKLEIKGGGGSGGGGSGGGGSGGG

GSQVQLQESGPGINKPSETLSLTCTVSGVSLPDYGVSWIRQPPGKGLEW

IGVIWGSETTYYNSSLKSRVTISKDNSKNQVSLKLSSVTAADTAVYYCA

KHYYYGGSYAMDYWGQGTLVTVSSTTTPAPRPPTPAPTIASQPLSLRPE

ACRPAAGGAVHTRGLDFACDIYIWAPLAGTCGVLLLSLVITLYCRVKFS

RSADAPAFKQGQNQLFNELNLGRREEFDVLDKRRGRDPEMGGKPRRKNP

QEGLFNELQKDKMAEAFSEIGMKGERRRGKGHDGLFQGLSTATKDTFDA

LHMQALPPR

CD19scFv-BB (SEQ ID NO: 12)
<u>GSMALPVTALLLPLALLLHAARP</u>EIVMTQSPATLSLSPGERATLSCRAS

QDISKYLNWYQQKPGQAPRLLIYHTSRLHSGIPARFSGSGSGTDYTLTI

SSLQPEDFAVYFCQQGNTLPYTFGQGTKLEIKGGGGSGGGGSGGGGSGG

GGSQVQLQESGPGLVKPSETLSLTCPISGVSLPDYGVSWIRQPPGKGLE

WIGVIWGSETTYYNSSLKSRVTISKDNSKNQVSLKLSSVTAADTAVYYC

AKHYYYGGSYAMDYWGQGTINTYSSTITPAPRPPTPAPTIASQPLSLRP

EACRPAAGGAVHTRGLDFACDIYIWAPLAGTCGVLLLSLVITLYCKRGR

KKLLYIFKQPFMRPVQTTQEEDGCSCRFPEEEEGGCEL

CD19scFv-CD3e_2YtoF (SEQ ID NO: 13)
GSMALPVTALLLPLALLLHAARPEIVMTQSPATLSLSPGERATLSCRAS

QDISKYLNWYQQKPGQAPRIAIYHTSRLHSGIPARFSGSGSGTDYTLTI

SSLQPEDFAVYFCQQGNTLPYTFGQGTKLEIKGGGGSGGGGSGGGGSQV

QLQESGPGINKRSETLSLTCTVSGVSLPDYGVSWIRQPPGKGLEWIGVI

WGSETTYYSSSLKSRVTISKDNSKNQVSLKLSSVTAADTAVYYCAKHYY

YGGSYAMDYWGQGTLVTVSSGGGGSDGNEEMGGITQTPYKVSISGTTVI

LTCPQYPGSHILWQHNDKNIGGDEDDKNIGSDEDHLSLKEFSELEQSGY

YNTYPRGSKPEDANFYLYLRARATENCMEMDVMSVATIVIVDICITGGI

ILLVYYWSKNRKAKAKPVTRGAGAGGRQRGQNKERPPPVPNPDFEPIRK

GQRDLFSGLNQRRI

Lentivirus Production and Viral Transduction into Primary T Cells

As described in Example 1, lentivirus were produced and transduced into isolated primary human T-cells. Transduced T-cells and non-transduced control T-cells were expanded and frozen for subsequent analysis.

Cytotoxicity and IL2 Assay

Cytotoxicity and IL2 production induced by cross-linking primary human T-Cells to target tumor cells were assessed as described in Example 1.

Primary Human T-Cell Results

Figure 16:
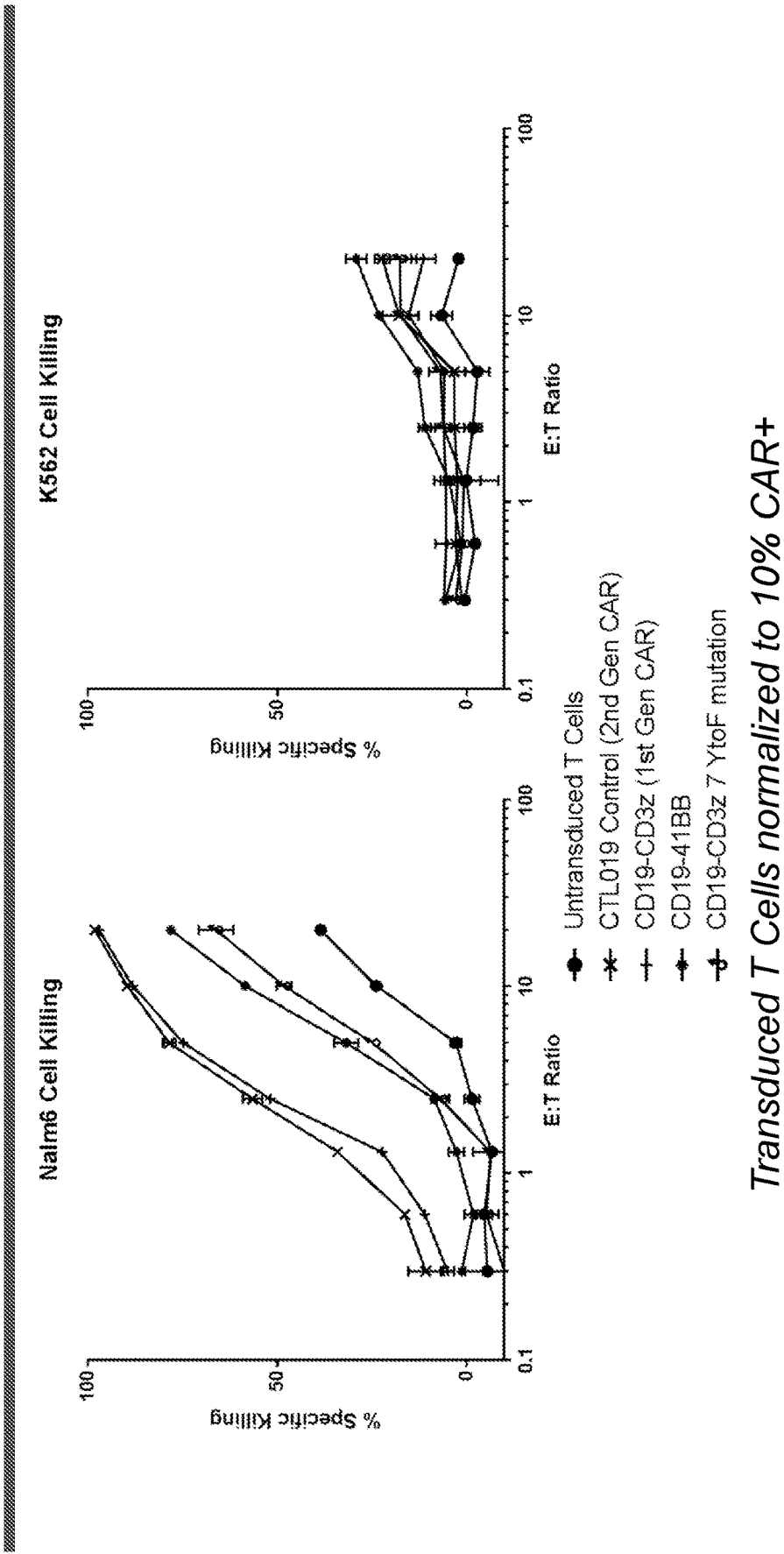
FIG. 16 is a series of graphs showing percentage of specific killing of the indicated cells by cells transfected with the indicated constructs as a function of transfection.
Figure 17:
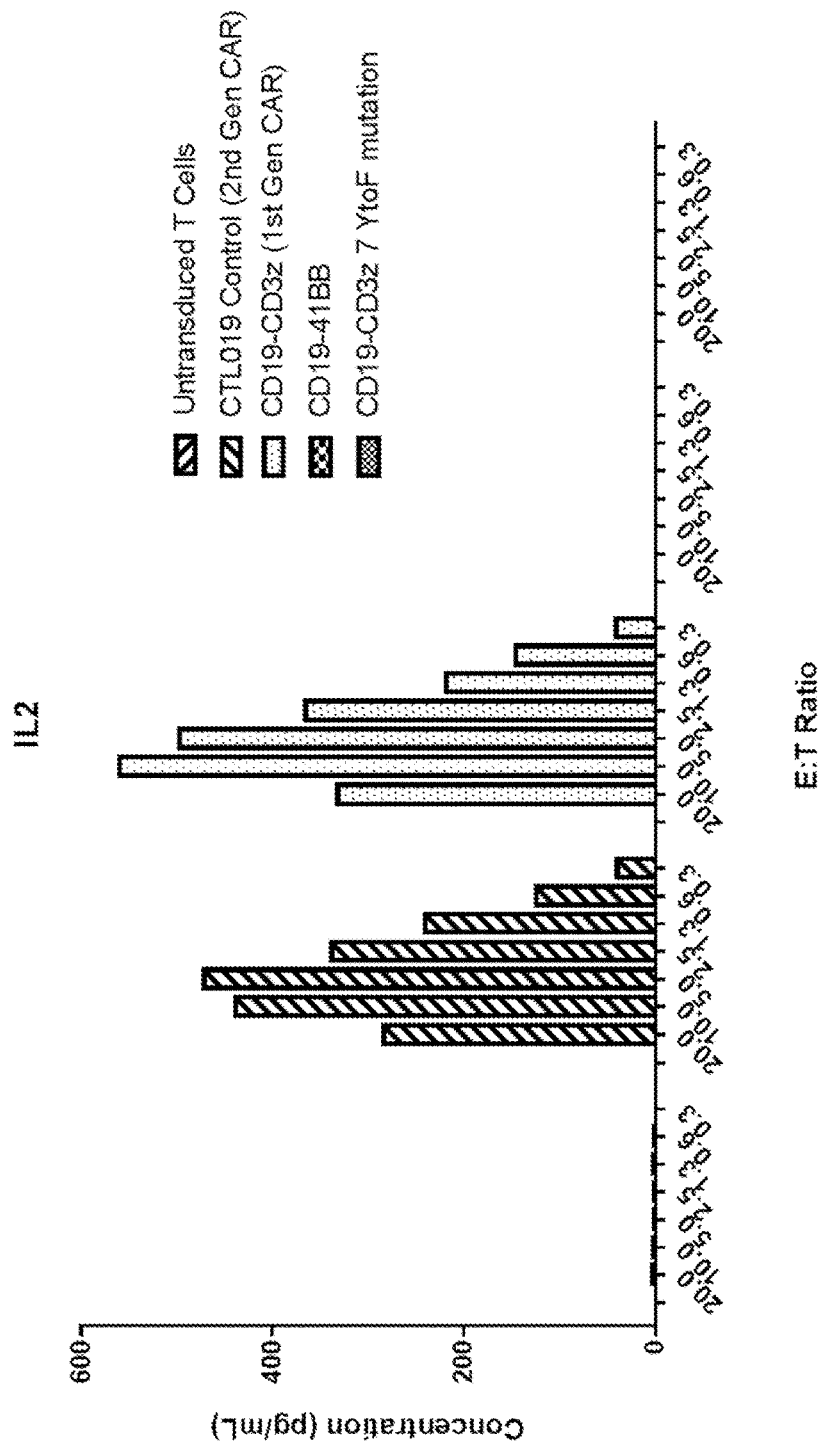
FIG. 17 is a graph showing expression of IL-2 as a function of transfection with the indicated constructs.
Figure 18:
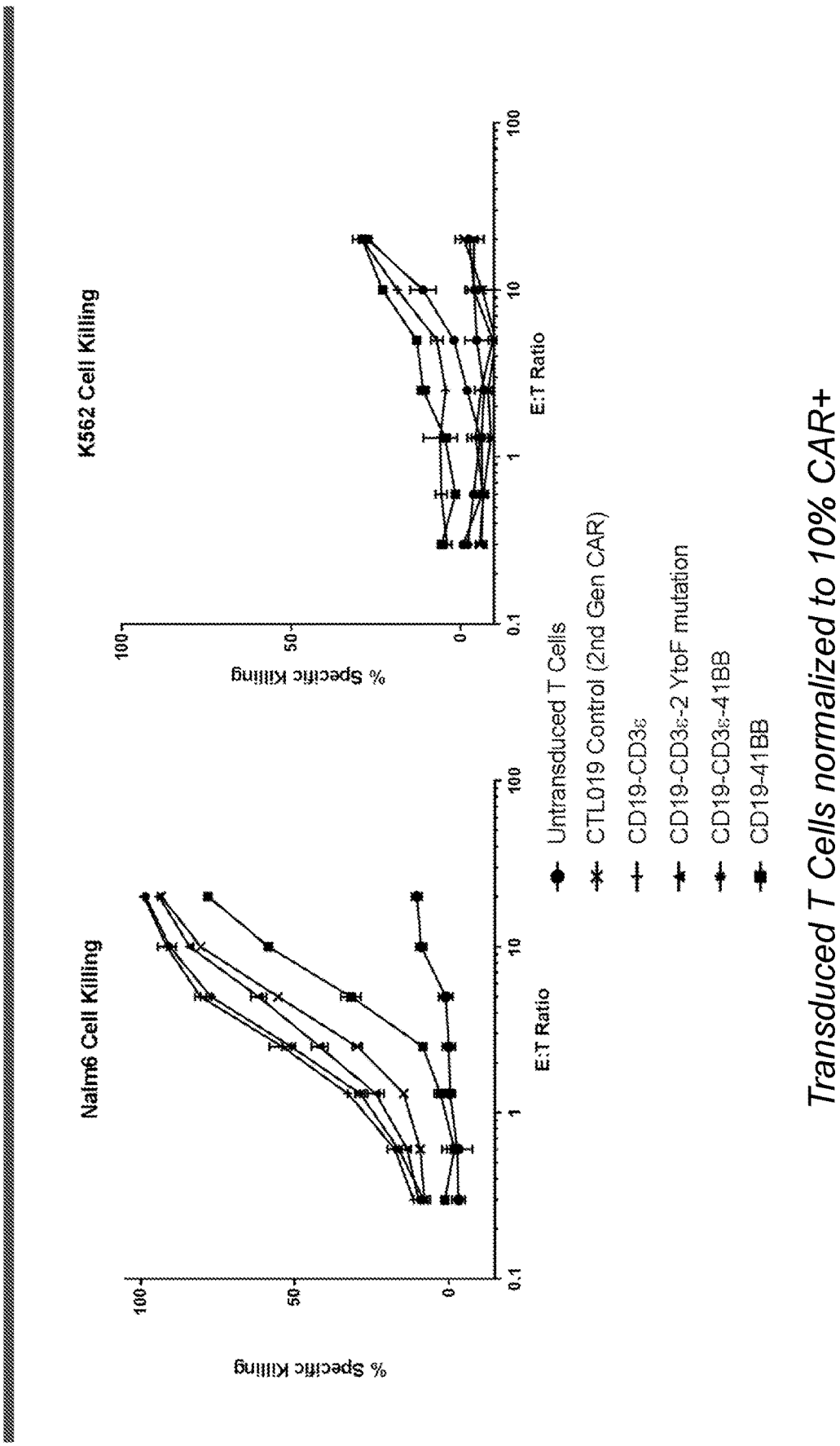
FIG. 18 is a pair of graphs showing percentage of the indicated cell killing in cells transfected with the indicated constructs as a function of transfection.
Figure 19:
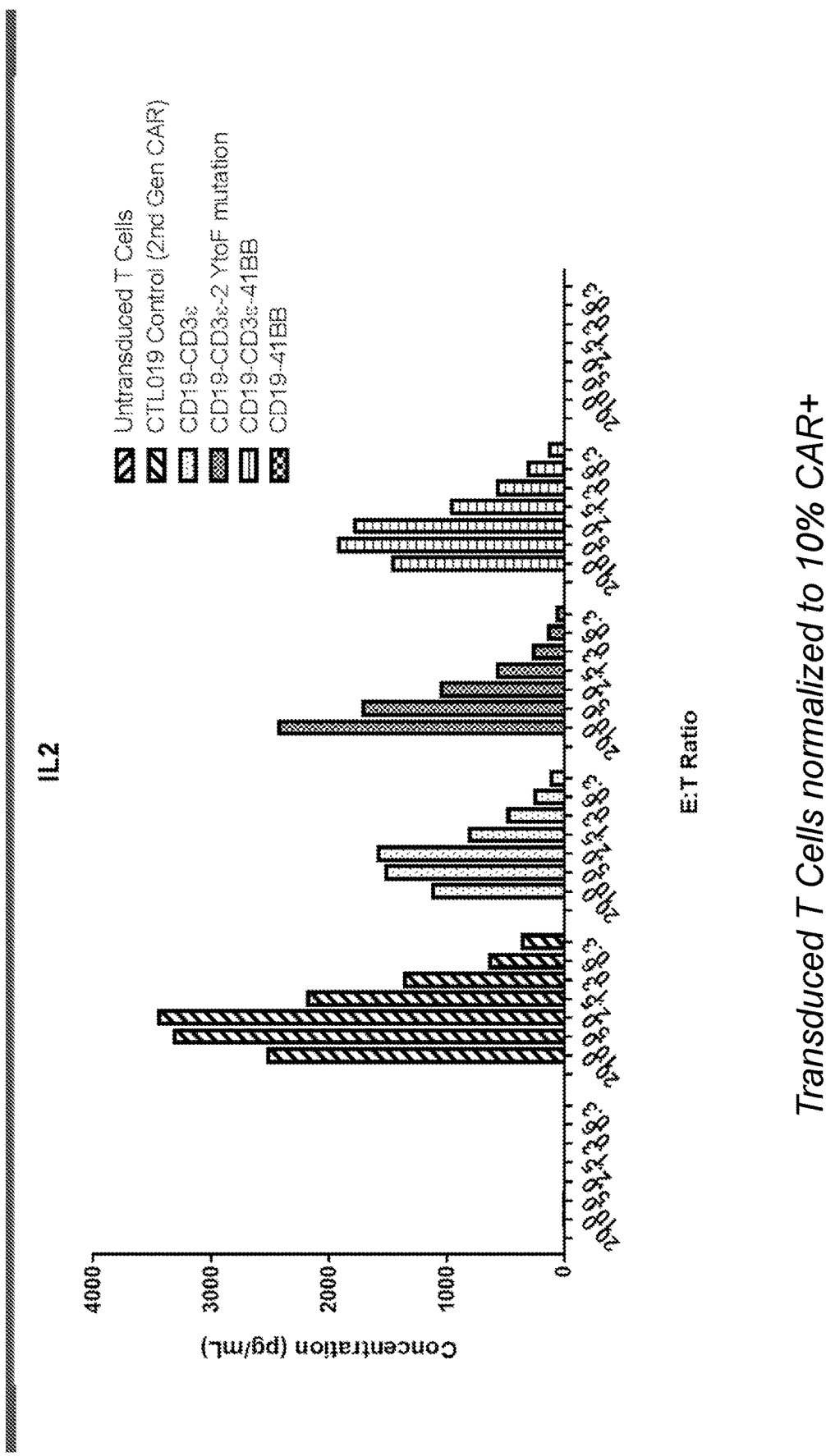
FIG. 19 is a graph showing concentration of IL-2 expression as a function of transfection in the indicated constructs.
Figure 20:
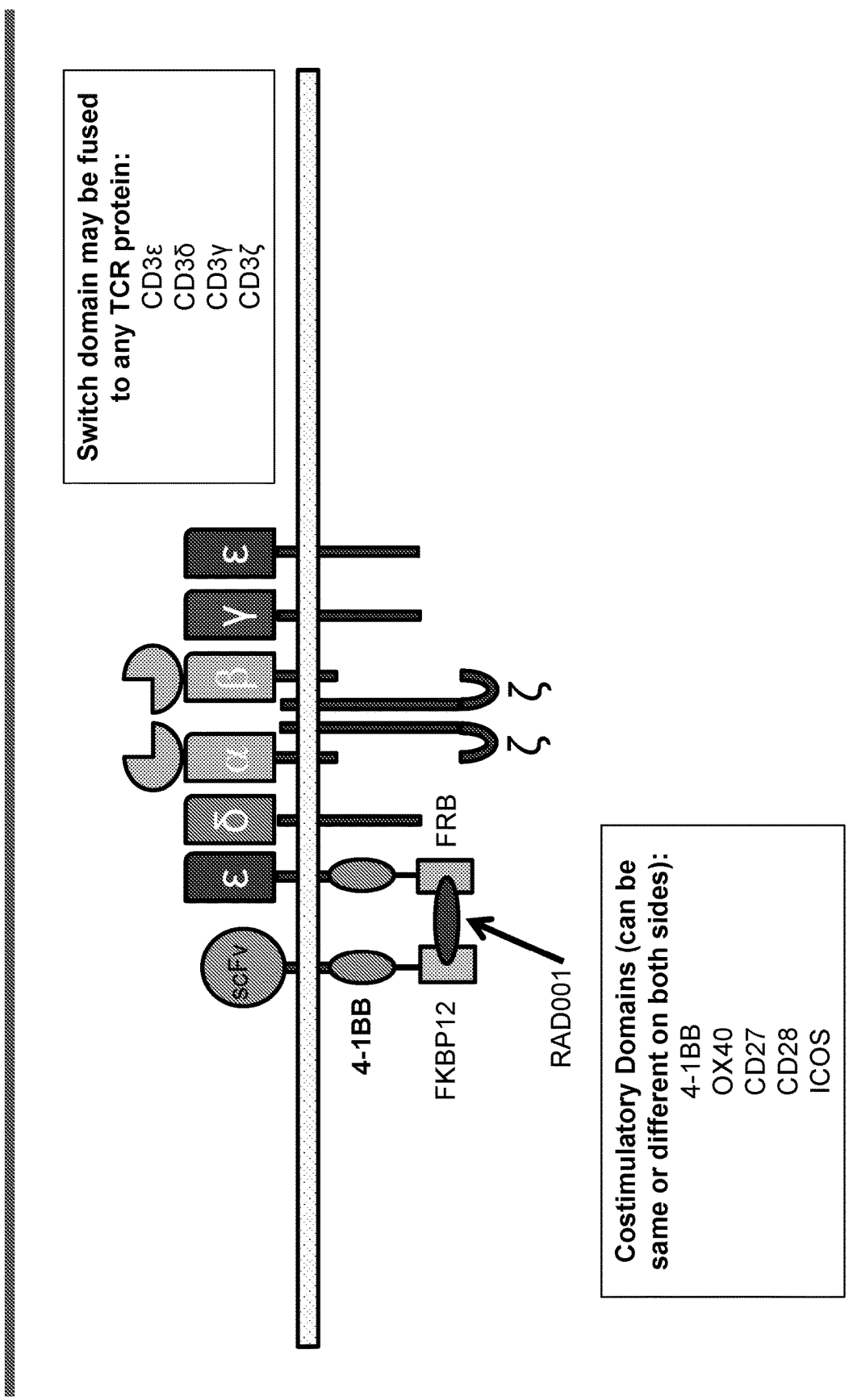
FIG. 20 is a schematic showing regulatable TCR-based Chimeric Antigen Receptor (rTCAR) with enhanced proliferation. A targeting and costimulatory domain are embedded into the TCR complex by fusion with an intracellular heterodimerization switch domain and co-transfection/co-transduction with the extracellular and transmembrane domains of an endogenous TCR complex member such as CD3 epsilon fused to a second costimulatory domain and a second heterodimerization switch domain. Signaling is induced upon addition of a switch molecule such as a rapalogue.
Figure 21:
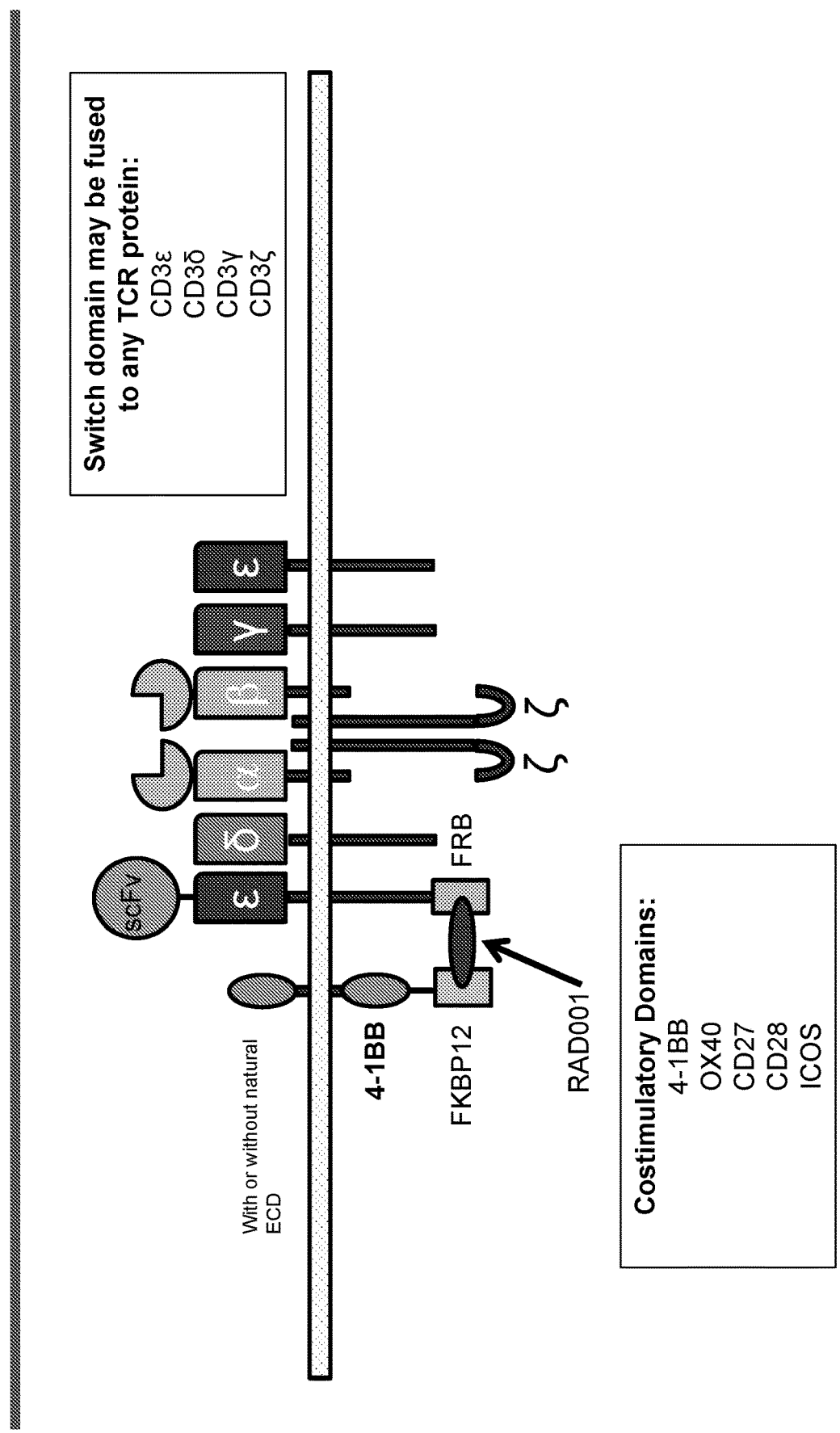
FIG. 21 is a schematic showing regulatable TCR-based Chimeric Antigen Receptor (rTCAR). A costimulatory receptor with or without its natural extracellular domain is embedded into the TCR complex by fusion with an intracellular heterodimerization switch domain and co-transfection/co-transduction with a targeting domain fused to an endogenous TCR complex member such as CD3 epsilon fused to a second intracellular heterodimerization switch domain. Proliferation is induced upon addition of a switch molecule such as a rapalogue.
Figure 22:
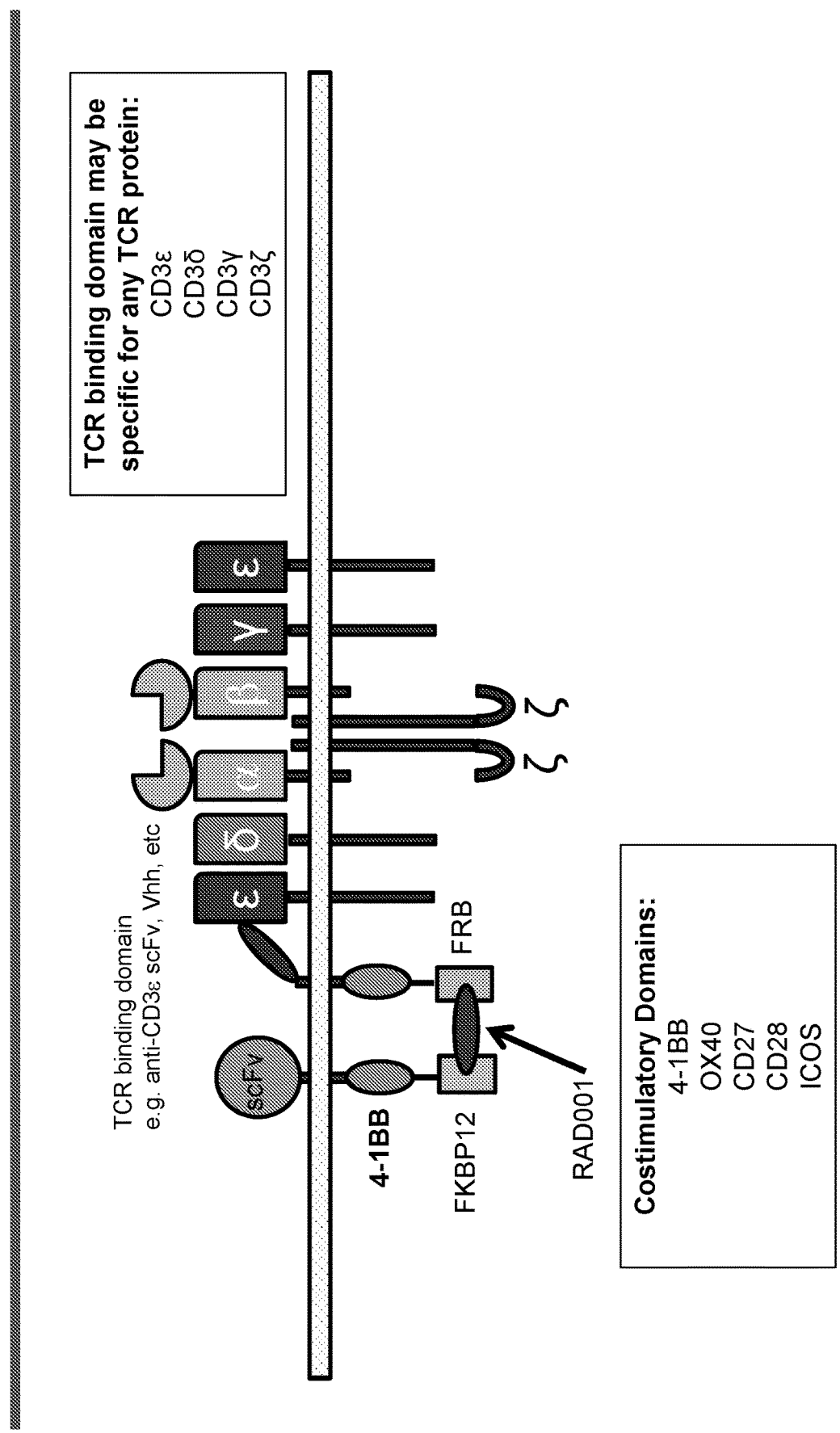
FIG. 22 is a schematic showing constitutively active TCR-based Chimeric Antigen Receptor (TCAR). A targeting and costimulatory domain are embedded into the TCR complex by fusion with an intracellular heterodimerization switch domain and co-transfection/co-transduction with an extracellular domain which binds to a member of the TCR complex fused to a transmembrane and intracellular domain of a costimulatory receptor and a second heterodimerization switch domain. Signaling is induced upon addition of a switch molecule such as a rapalogue.
Figure 23:
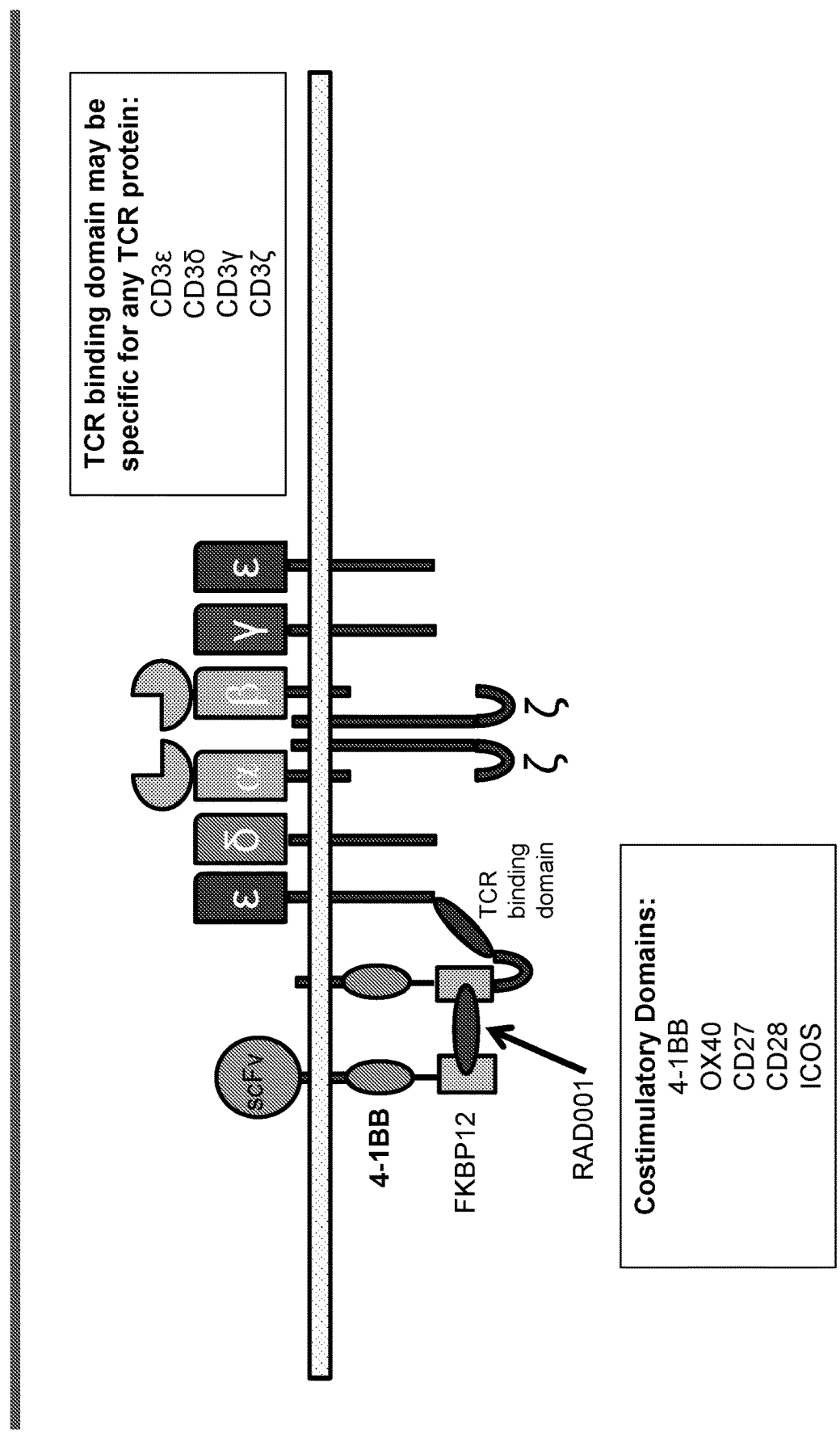
FIG. 23 is a schematic showing constitutively active TCR-based Chimeric Antigen Receptor (TCAR). A targeting and costimulatory domain are embedded into the TCR complex by fusion with an intracellular heterodimerization switch domain and co-transfection/co-transduction with a costimulatory receptor with or without its natural extracellular domain fused to a second heterodimerization switch domain and an intracellular domain which binds to a member of the TCR complex. Signaling is induced upon addition of a switch molecule such as a rapalogue.
Figure 24:
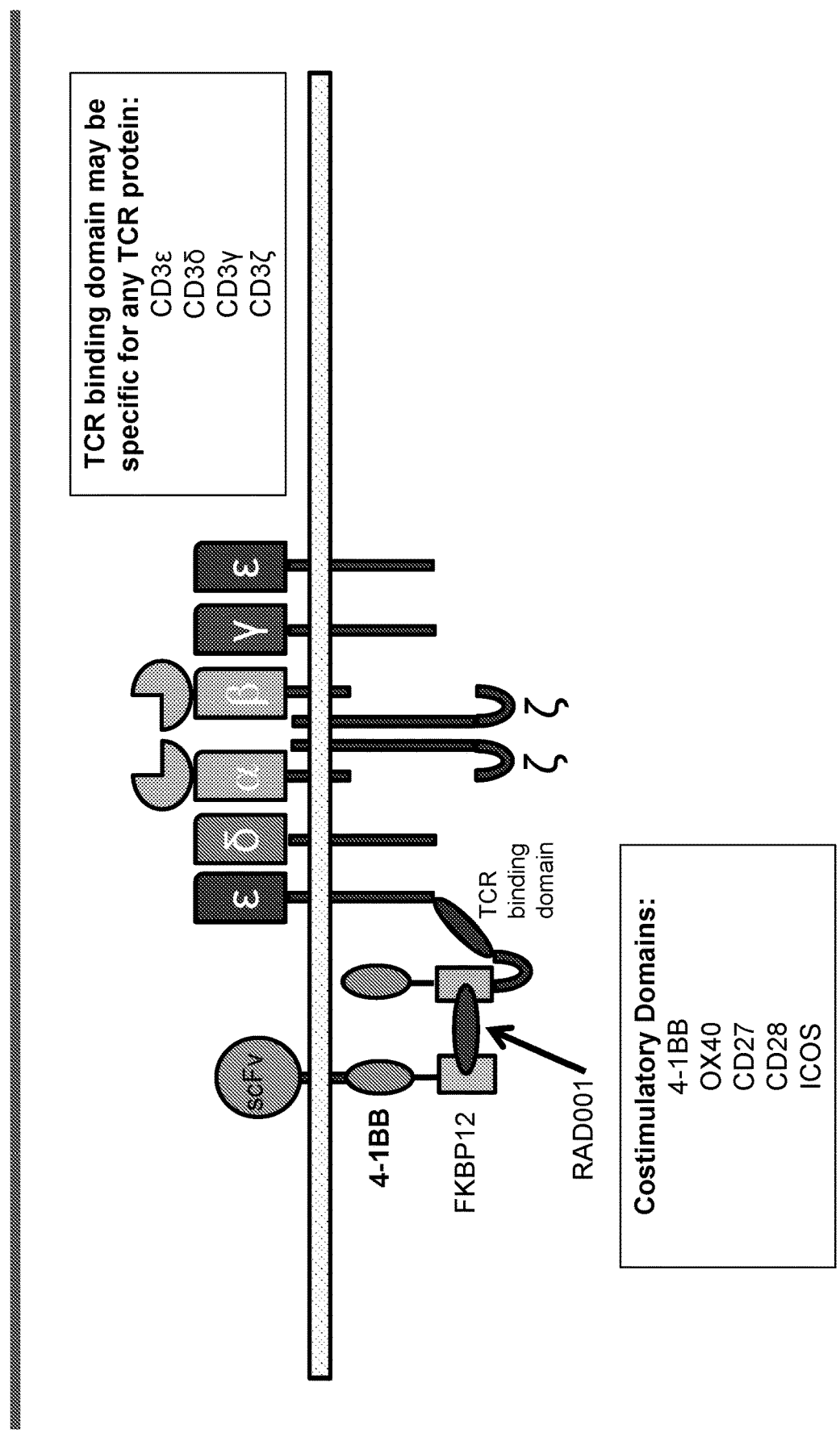
FIG. 24 is a schematic showing constitutively active TCR-based Chimeric Antigen Receptor (TCAR). A targeting and costimulatory domain are embedded into the TCR complex by fusion with an intracellular heterodimerization switch domain and co-transfection/co-transduction with a cytosolic costimulatory domain fused to a second heterodimerization switch domain and an intracellular domain which binds to a member of the TCR complex. Signaling is induced upon addition of a switch molecule such as a rapalogue.

As can be observed in FIG. 16 and FIG. 17, traditional CARs require functional endogenous ITAM signaling domains in order to induce maximal T-cell redirected lysis of the target cells and IL2 production. Constructs in which CD3 zeta was replaced with 41BB or were mutated to inactivate the ITAMS in CD3 zeta were deficient in both elements. In contrast, FIG. 18 and FIG. 19 demonstrate that fusTCAR activity is both specific and independent of endogenous functional ITAMs. Redirected lytic activity and IL2 secretion was observed regardless of the presence or absence or order of costimulatory domains. Furthermore, neither mutation of the key tyrosines involved in signaling nor complete removal of the intracellular domain of CD3 epsilon resulted in appreciable loss in functional in vitro activity of the TCARs.

Example 4: Regulatable TCARs Using Rapalogue Switch (rTCAR) (FIGS. 20-24)

Synthesis of Rapalogue Switch-Mediated rTCAR Constructs

Pairs of plasmid DNA were synthesized externally by DNA2.0. The nominal non-regulatable CAR construct, CD19scFv-BBZ, SEQ ID NO: 1, was used as a control. For the rTCAR, the various heterodimerization domains can be linked to different domains of the rTCAR constructs.

Figure 25:
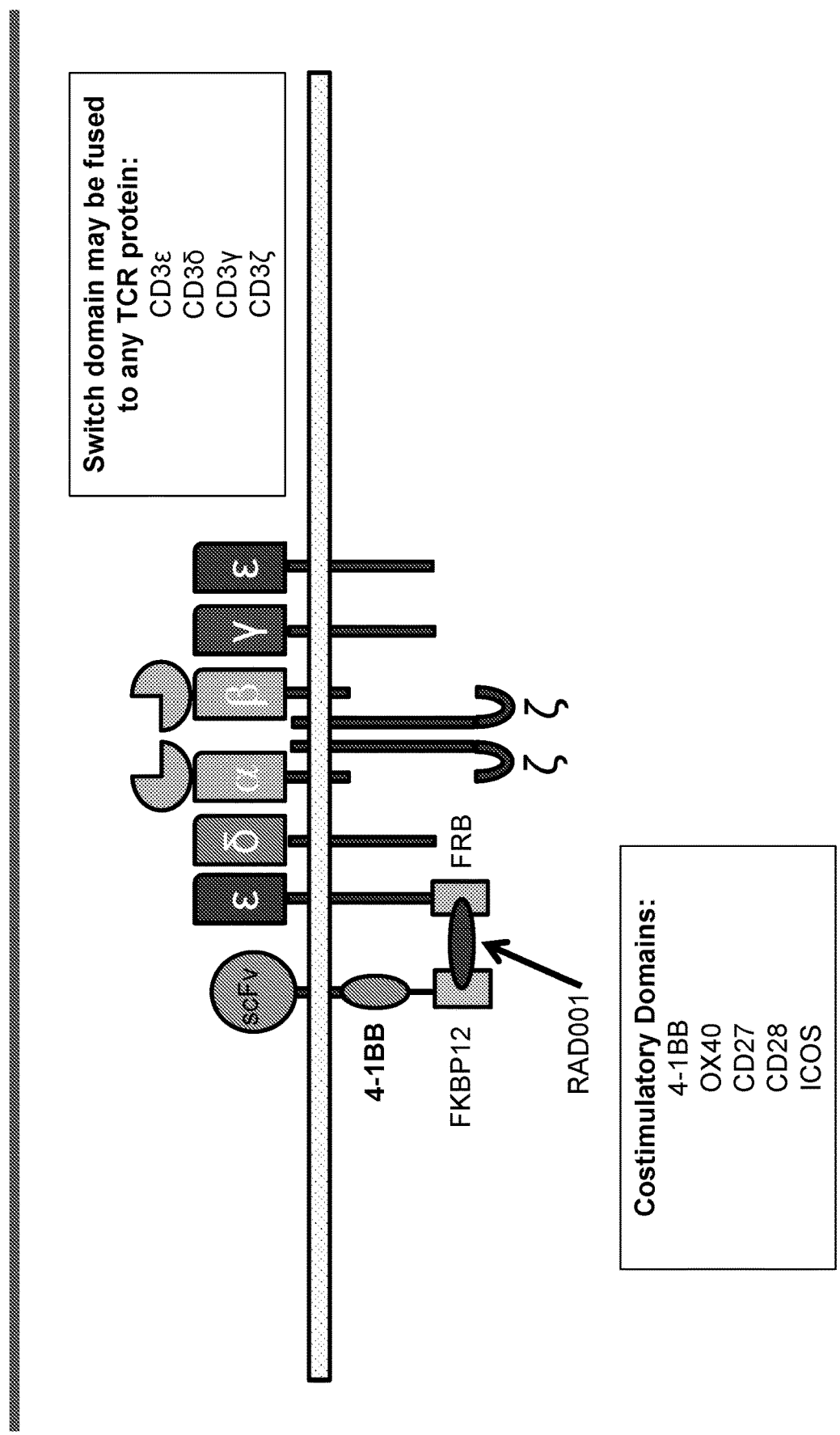
FIG. 25 is a schematic showing regulatable TCR-based Chimeric Antigen Receptor (TCAR). A targeting and costimulatory domain are embedded into the TCR complex by fusion with an intracellular heterodimerization switch domain and co-transfection/co-transduction with an endogenous TCR complex member such as CD3 epsilon fused to a second heterodimerization switch domain. Signaling is induced upon addition of a switch molecule such as a rapalogue.
Figure 26:
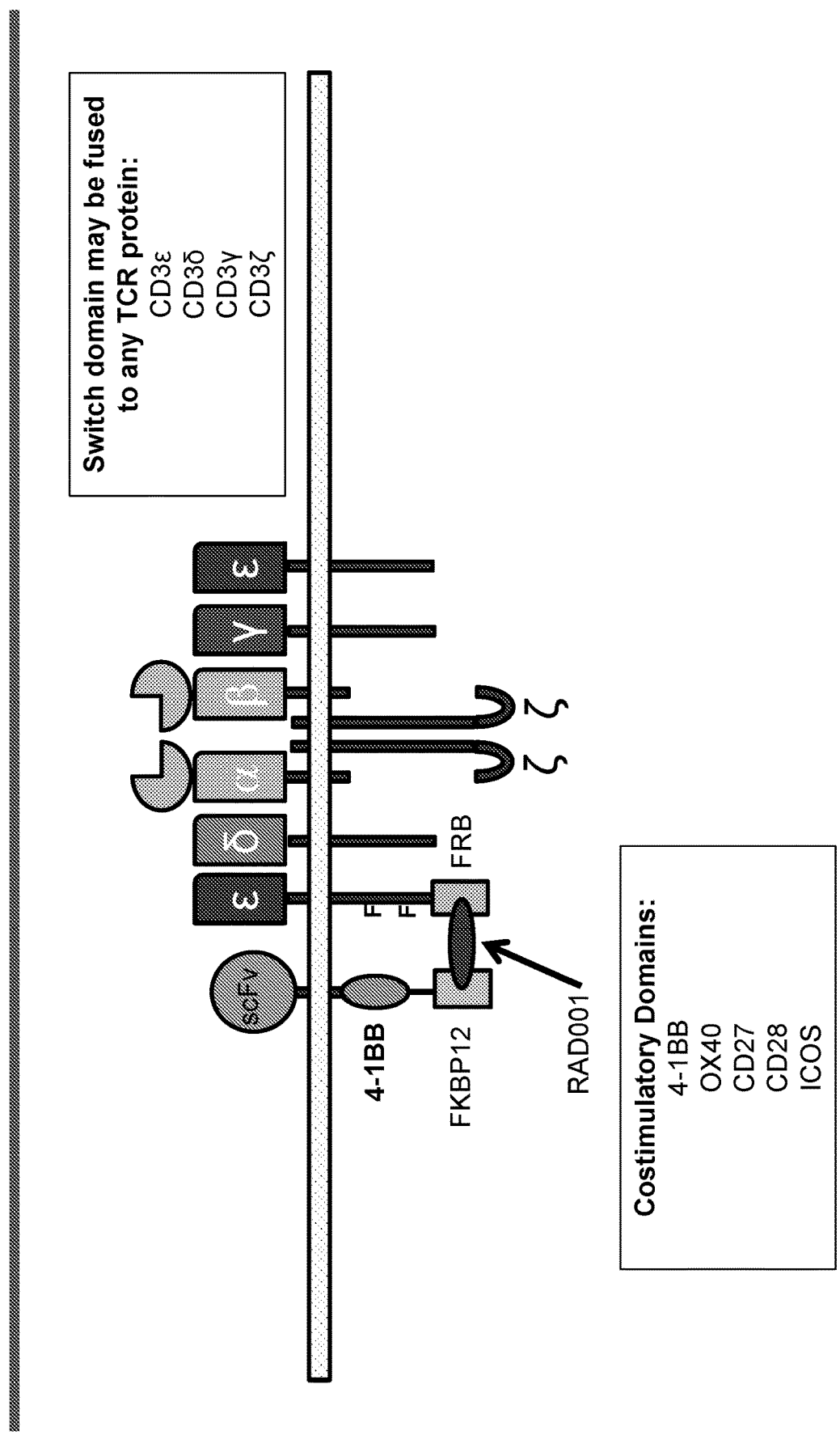
FIG. 26 is a schematic showing regulatable TCR-based Chimeric Antigen Receptor (rTCAR). A targeting and costimulatory domain are embedded into the TCR complex by fusion with an intracellular heterodimerization switch domain and co-transfection/co-transduction with an endogenous TCR complex member such as CD3 epsilon fused to a second heterodimerization switch domain. Signaling is induced upon addition of a switch molecule such as a rapalogue. ITAM domain from the CD3 epilson fusion was mutated to phenylalanine to demonstrate signaling was induced by other members of the TCR complex.

"rTCAR 1" (FIG. 25) comprises a pair of constructs. In the first construct, the CD19 scFv was cloned with CD8 hinge and transmembrane domain followed by the costimulatory domain 4-1BB and FKBP at the C-terminus (SEQ ID NO: 14). The corresponding second construct was designed by fusing a mutated FRB domain with enhanced affinity to RAD001 to a linker at the C-terminus of CD3 epsilon (SEQ ID NO: 15). "rTCAR2" (FIG. 26) comprises a pair of constructs. In the first construct, the CD19 scFv was cloned with CD8 hinge and transmembrane domain followed by the costimulatory domain 4-1BB and FKBP at the C-terminus (SEQ ID NO: 14). The corresponding second construct was designed by fusing a mutated FRB domain with enhanced affinity to RAD001 to a linker at the C-terminus of CD3 epsilon; additionally the two tyrosines within the ITAM domain of CD3 epsilon were mutated to phenylalanine to remove intrinsic signaling pathway from CD3 epsilon and demonstrate that signaling was mediated from the entire TCR complex (SEQ ID NO: 16).

CD19scFV-BB-FKBP
(SEQ ID NO: 14)
GSATMALPVTALLLPLALLLHAARPEIVMTQSPATLSLSPGERATLSCR

ASQDISKYLNWYQQKPGQAPRLLIYHTSRLHSGIPARFSGSGSGTDYTL

TISSLQPEDFAVYFCQQGNTLPYTFGQGTKLEIKGGGSGGGGSGGGGS

QVQLQESGPGLVKPSETLSLTCTVSGVSLPDYGVSWIRQPPGKGLEWIG

VIWGSETTYYSSSLKSRVTISKDNSKNQVSLKLSSVTAADTAVYYCAKH

YYYGGSYAMDYWGQGTLVTVSSTTTPAPRPPTPAPTIASQPLSLRPEAC

RPAAGGAVHTRGLDFACDIYIWAPLAGTCGVLLLSLVITLYCSLKRGRK

KLLYIFKQPFMRPVQTTQEEDGCSCRFPEEEEGGCELMGVQVETISIPG

DGRTFPKRGQTCVVHYTGMLEDGKKFDSSRDRNKPFKFMLGKQEVIRGW

EEGVAQMSVGQRAKLTISPDYAYGATGHPGIIPPHATLVFDVELLKLE

CD3e-FRBmutant
(SEQ ID NO: 15)
GSMQSGTHWRVLGLCLLSVGVWGQDGNEEMGGITQTPYKVSISGTTVIL

TCPQYPGSEILWQHNDKNIGGDEDDKNIGSDEDHLSLKEFSELEQSGYY

VCYPRGSKPEDANFYLYLRARVCENCMEMDVMSVATIVIVDICITGGLL

LLVYYWSKNRKAKAKPVTRGAGAGGRQRGQNKERPPPVPNPDYEPIRKG

QRDLYSGLNQRRIGSGSGGSILWHEMWHEGLIEASRLYFGERNVKGMFE

VLEPLHAMMERGPQTLKETSFNQAYGRDLMEAQEWCRKYMKSGNVKDLL

QAWDLYYHVFRRISK

CD3e-YtoFdouble-FRBmutant
(SEQ ID NO: 16)
GSMQSGTHWRVLGLCLLSVGVWGQDGNEEMGGITQTPYKVSISGTTVIL

TCPQYPGSEILWQHNDKNIGGDEDDKNIGSDEDHLSLKEFSELEQSGYY

VCYPRGSKPEDANFYLYLRARVCENCMEMDVMSVATIVIVDICITGGLL

LLVYYWSKNRKAKAKPVTRGAGAGGRQRGQNKERPPPVPNPDFEPIRKG

QRDLFSGLNQRRIGSGSGGSILWHEMWHEGLIEASRLYFGERNVKGMFE

VLEPLHAMMERGPQTLKETSFNQAYGRDLMEAQEWCRKYMKSGNVKDLL

QAWDLYYHVFRRISK

Dose Response of Rapalogue on NFAT Activation

The ability of RCAR constructs to demonstrate rapalogue-dependent signal activation following target antigen engagement of the antigen binding domain was measured with the Jurkat cells with NFAT-LUC reporter (JNL) reporter cell line as described in Example 1. The transfected cells were added to the target plate with 100 µl per well and co-incubated with varying concentrations of RAD001 for 18 hrs. Luciferase One Glo reagent 100 µl was added per well. The samples were incubated for 5 min and then luminescence was measured as described.

IL-2 Expression in Transfected Jurkat (JNL) Cells

Transfection of JNL cells and activation were performed as described above in the JNL RGA assay excepting incubation which was for 40 hours at 37° C., 5% $CO_2$. Measurement of secreted IL2 was performed as described in Example 1.

Results

Figure 27:
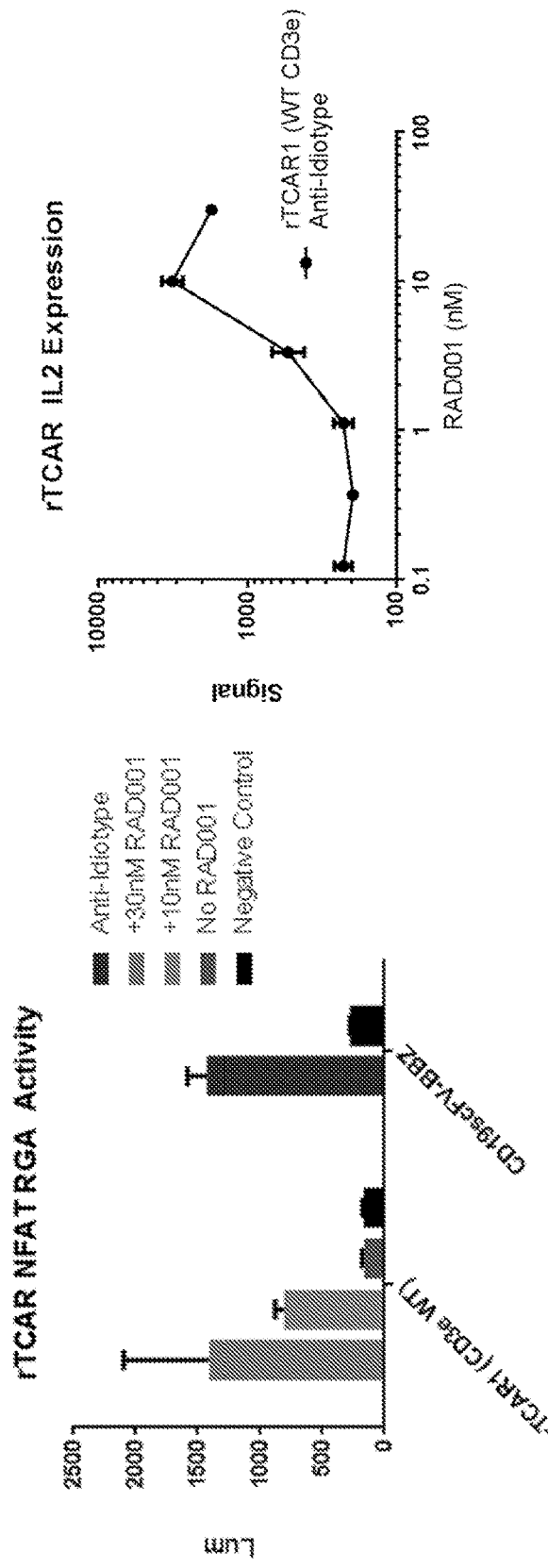
FIG. 27 is a series of graphs showing JNL signaling and IL2 expression of antigen activated FKBP/FRP rTCARs induced with RAD001.
Figure 28:
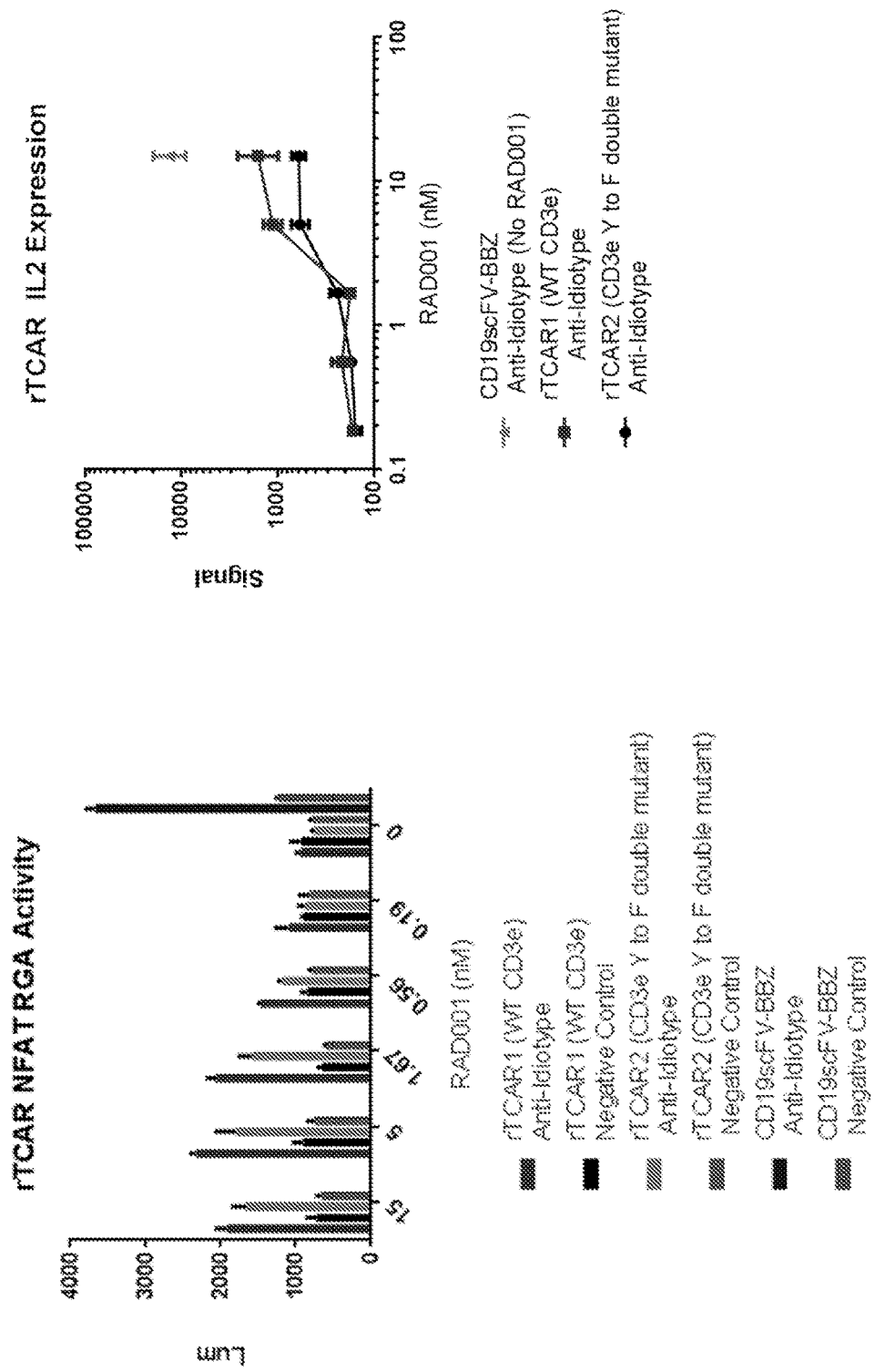
FIG. 28 is a series of graphs showing a comparison of JNL signaling and IL2 expression for Rapalogue-mediated antigen activated FKBP/FRP rTCARs with and without knock-out of CD3e ITAM signaling.

Initial screening of rTCAR1 via transient transfection into JNL cells demonstrated RAD001-mediated and antigen-dependent signaling and IL2 expression as shown in FIG. 27. In a subsequent experiment, rTCAR1 was compared to rTCAR2 in which the ITAM signaling of the transiently transfected CD3 epsilon was abrogated by mutation of the corresponding tyrosines to phenylalanine. A dose response with RAD001 was observed for rTCAR1 and rTCAR2 in both the reporter gene assay as well as in antigen-induced IL2 expression (FIG. 28), albeit with reduced signal and expression for rTCAR2 as would be expected. Transfection of a construct containing ITAM signaling domains is thus not a prerequisite for activity of rTCARs. By associating the targeting domain with the TCR complex, signaling is mediated through all members of the complex and is not exclusively limited to that derived from a signaling domain fused to the targeting domain.

Example 6: Constitutively Active TCARs Fused into the TCR Complex Via Truncated CD3 Epsilon Extracellular Domains (fusTCAR)

Crystal structures of CD3 epsilon and gamma in complex with the Fab fragment of the anti-CD3 monoclonal antibody OKT3 (Kjer-Nielsen et. al., 2004) and CD3 epsilon and delta in complex with the scFv of the anti-CD3 monoclonal Ab UCHT1 (Amett et. al., 2004) have been reported. These structures demonstrate that the interaction of epsilon with other accessory proteins is mediated through a beta sheet proximal to the membrane. Thus, fusion of a targeting domain to a truncated form of the CD3 epsilon extracellular domain comprised of the sequence containing the beta sheet may be the only prerequisite for fusTCAR activity.

Transient Expression

Synthesis of fusTCAR Constructs

Plasmid DNA was synthesized externally by DNA2.0. The nominal non-regulatable CAR construct, CD19scFv-BBZ, SEQ ID NO: 1, was used as a control.

In "fusTCAR5" the CD19 scFv was cloned as an N-terminal fusion to an N-terminally truncated form of CD3 epsilon extracellular and transmembrane domains followed by the intracellular costimulatory domain 4-1BB (SEQ ID NO: 17). "FusTCAR 6", "fusTCAR7" and "fusTCAR8" was cloned similarly to "fusTCAR5" to elucidate the role of the two membrane proximal cysteines in CD3 epsilon which do not appear to be involved in intramolecular disulfide bonding in mediating the interaction with other TCR complex members. For "fusTCAR6" (SEQ ID No: 18), the first cysteine was mutated to serine. In "fusTCAR7" (SEQ ID NO: 19), the second cysteine was mutated to serine. Finally, for "fusTCAR8" (SEQ ID NO: 20), both cysteines were mutated to serine. All four constructs in this example lack intrinsic intracellular ITAM signaling domains.

```
CD19scFv-CD3e_minimalECDTM-41BB
                                (Seq ID NO: 17)
GSATMALPVTALLLPLALLLHAARPEIVMTQSPATLSLSPGERATLSCR

ASQDISKYLNWYQQKPGQAPRLLIYHTSRLHSGIPARFSGSGSGTDYTL

TISSLQPEDFAVYFCQQGNTLPYTFGQGTKLEIKGGGGSGGGGSGGGGS

QVQLQESGPGLVKPSETLSLTCTVSGVSLPDYGVSWIRQPPGKGLEWIG

VIWGSETTYYSSSLKSRVTISKDNSKNQVSLKLSSVTAADTAVYYCAKH

YYYGGSYAMDYWGQGTLVTVSSGGGGSPEDANFYLYLRARVCENCMEMD

VMSVATIVIVDICITGGLLLLVYYWSKRGRKKLLYIFKQPFMRPVQTTQ

EEDGCSCRFPEEEEGGCEL

CD19scFv-CD3e_minimalECD-1stCystoSer-TM-41BB
                                (Seq ID NO: 18)
GSATMALPVTALLLPLALLLHAARPEIVMTQSPATLSLSPGERATLSCR

ASQPISKYLNWYQQKPGQAPRLLIYHTSRLHSGIPARFSGSGSGTDYTL

TISSLQPEDFAVYFCQQGNTLPYTFGQGTKLEIKGGGGSGGGGSGGGGS

QVQLQESGPGINKPSEILSLTCTVSGVSLPDYGVSWIRQPPGKGLEWIG

VIWGSETIYYSSSLKSRVTISKDNSKNQVSLKLSSVTAADTAVYYCAKH

YYYGGSYAMDYWGQGTLVTVSSGGGGSPEDANFYLYLRARVSENCMEMD

VMSVATIVIVDICITGGLLLLVYYWSKRGRKKLLYIFKQPFMRPVQTTQ

EEDGCSCRFPEEEEGGCEL

CD19scFv-CD3e_minimalECDTM-2ndCystoSer-TM-41BB
                                (Seq ID NO: 19)
GSATMALPVTALLLPLALLLHAARPEIVMTQSPATLSLSPGERATLSCR

ASQDISKYLNWYQQKPGQAPRLLIYHTSRLHSGIPARFSGSGSGTDYTL

TISSLQPEDFAVYFCQQGNTLPYTFGQGTKLEIKGGGGSGGGGSGGGGSQ

VQLQESGPGLVKPSETLSLTCTVSGVSLPDYGVSWIRQPPGKGLEWIGV

IWGSETTYYSSSLKSRVTISKDNSKNQVSLKLSSVTAADTAVYYCAKHY

YYGGSYAMDYWGQGTLVTVSSGGGGSPEDANFYLYLRARVCENSMEMDV

MSVATIVIVDICITGGLLLLVYYWSKRGRKKLLYIFKQPFMRPVQTTQE

EDGCSCRFPEEEEGGCEL

CD19scFv-CD3e_minimalECDTM-2xCystoSer-TM-41BB
                                (Seq ID NO: 20)
GSATMALPVTALLLPLALLLHAARPEIVMTQSPATLSLSPGERATLSCR

ASQDISKYLNWYQQKPGQAPRLLIYHTSRLHSGIPARFSGSGSGTDYTL

TISSLQPEDFAVYFCQQGNTLPYTFGQGTKLEIKGGGGSGGGGSGGGGS

QVQLQESGPGLVKPSETLSLTCTVSGVSLPDYGVSWIRQPPGKGLEWIG

VIWGSETTYYSSSLKSRVTISKDNSKNQVSLKLSSVTAADTAVYYCAKH

YYYGGSYAMDYWGQGTLVTVSSGGGGSPEDANFYLYLRARVSENSMEMD

VMSVATIVIVDICITGGLLLLVYYWSKRGRKKLLYIFKQPFMRPVQTTQ

EEDGCSCRFPEEEEGGCEL
```

Transfection of Jurkat Reporter Cell Line and Activation of NFAT.

Activation following target antigen engagement of the antigen binding domain was measured with the Jurkat cells with NFAT-LUC reporter (JNL) reporter cell line as described in Example 1. The transfected cells was added to the target plate with 100 μl per well. Luciferase One Glo reagent 100 μl was added per well. The samples were incubated for 5 min and then luminescence was measured as described.

Transient Expression Results

Target dependent signaling was not observed in transient expressed fusTCAR using the truncated extracellular domains. Subsequent FACs analysis demonstrated that there was no detectable expression of the constructs on the cell surface.

Production of Lentiviral Transduced Primary Human T-Cells

To determine if low expression was unique to the reporter cell line, a single representative truncated fusion construct, fusTCAR6, was also tested in primary human T-Cells for activity relative to Cd19scFv-BBZ.

Lentivirus Production and Viral Transduction into Primary T Cells

As described in Example 1, lentivirus were produced and transduced into isolated primary human T-cells. Transduced T-cells and non-transduced control T-cells were expanded and frozen for subsequent analysis.

Cytotoxicity and IL2 Assay

Cytotoxicity and IL2 production induced by cross-linking primary human T-Cells to target tumor cells were assessed as described in Example 1.

Primary Human T-Cell Results

Figure 29:
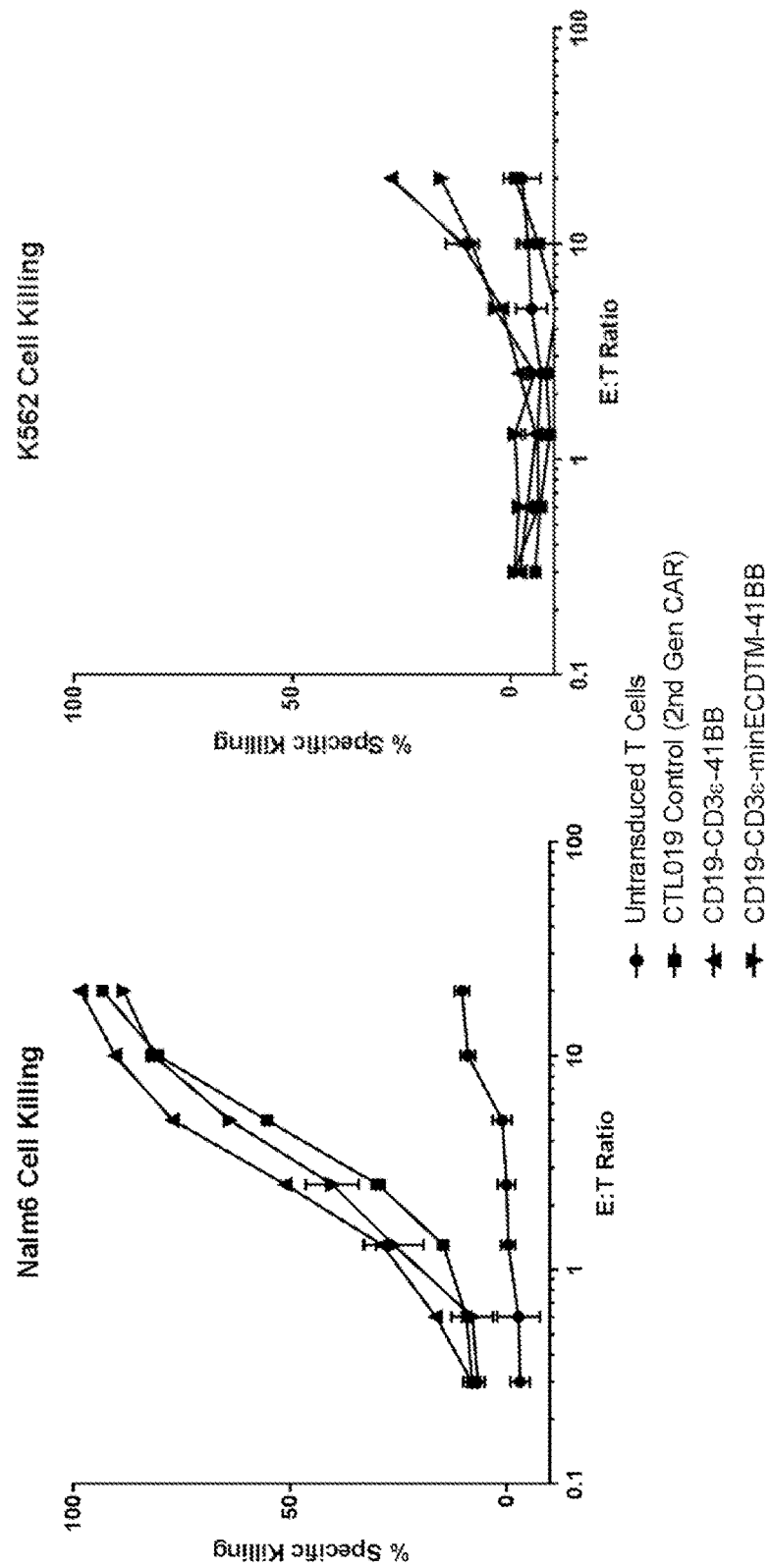
FIG. 29 is a pair of graphs showing percentage of the indicated cell killing in cells transfected with the indicated constructs as a function of transfection.
Figure 30:
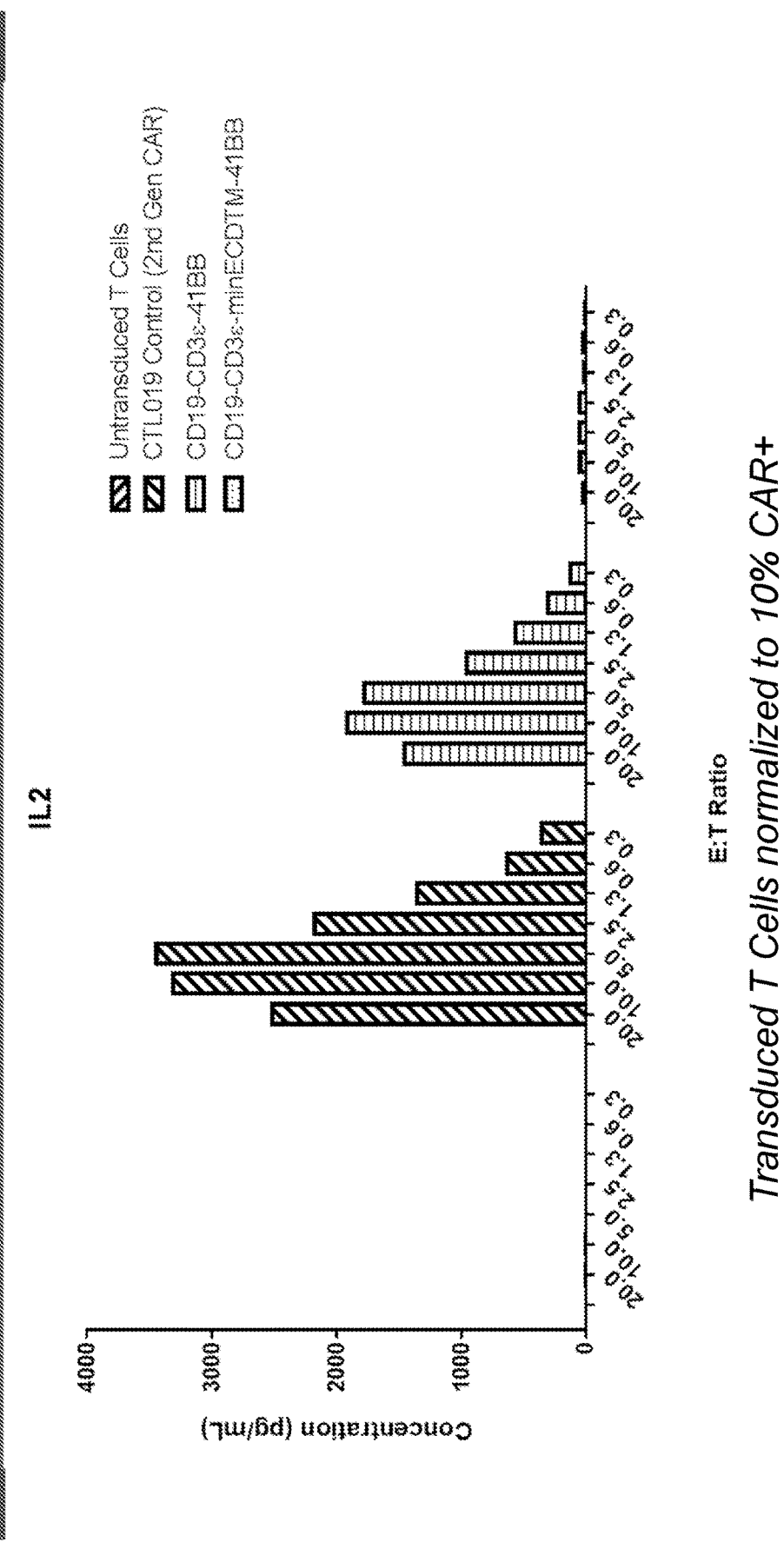
FIG. 30 is a graph showing concentration of IL-2 expression as a function of transfection in the indicated constructs.

As can be observed in FIG. 29, fusTCAR6 demonstrated comparable cytolytic activity relative to the control CD19scFv-BBZ CAR. Important to note that redirected lytic activity was observed despite the absence of ITAM signaling domains. In contrast, as shown in FIG. 30, fusTCAR6 resulted in reduced IL2 expression. Additional optimization of the construct is necessary to either stabilize the beta sheet or improve the interaction of the truncated CD3 epsilon with the remaining endogenous components of TCR. Nonetheless, the results demonstrated that the entire extracellular domain of the extracellular region of CD3 epsilon is not required to maintain cytolytic activity.

Example 7: Constitutively Active TCARs Fused into the TCR Complex Via CD3 Epsilon with Alternative Costimulatory Domains Traditional CARs have demonstrated to be functional with alternative costimulatory domains other than 4-1BB.

Production of Lentiviral Transduced Primary Human T-Cells

Synthesis of fusTCAR Constructs

Plasmid DNA will be synthesized externally by DNA2.0. The nominal non-regulatable CAR construct, CD19scFv-BBZ, SEQ ID NO: 1, will be used as a control and "fusCAR3" will be used as the TCAR control (SEQ ID NO: 9).

In fusTCAR listed in the table below the CD19 scFv will be cloned as an N-terminal fusion to the CD3 epsilon extracellular and transmembrane domains followed by intracellular costimulatory domains as specified. "FusTCAR9" to "fusTCAR13" lack intrinsic intracellular ITAM signaling domains.

| "FusTCAR" | Costimulatory Domain | SEQ ID NO |
| --- | --- | --- |
| fusTCAR9 | CD27 | 21 |
| fusTCAR10 | CD28 | 22 |
| fusTCAR11 | OX40 | 23 |
| fusTCAR12 | ICOS | 24 |
| fusTCAR13 | CD2 | 25 |

CD19scFv-CD3eECDTM-CD27
(SEQ ID NO: 21)
GSMALPVTALLLPLALLLHAARPEIVMTQSPATLSLSPGERATLSCRAS
QDISKYLNWYQQKPGQAPRLLIYHTSRLHSGIPARFSGSGSGTDYTLTI
SSLQPEDFAVYFCQQGNTLPYTFGQGTKLEIKGGGGSGGGGSGGGGSQV
QLQESGPGLVKPSETLSLTCTVSGVSLPDYGVSWIRQPPGKGLEWIGVI
WGSETTYYSSSLKSRVTISKDNSKNQVSLKLSSVTAADTAVYYCAKHYY
YGGSYAMDYWGQGTLVTVSSGGGGSDGNEEMGGITQTPYKVSISGTTVI
LTCPQYPGSEILWQHNDKNIGGDEDDKNIGSDEDHLSLKEFSELEQSGY
YVCYPRGSKPEDANFYLYLRARVCENCMEMDVMSVATIVIVDICITGGL
LLLVYYWSQRRKYRSNKGESPVEPAEPCHYSCPREEEGSTIPIQEDYRK
PEPACSP

CD19scFv-CD3eECDTM-CD28
(SEQ ID NO: 22)
GSMALPVTALLLPLALLLHAARPEIVMTQSPATLSLSPGERATLSCRAS
QDISKYLNWYQQKPGQAPRLLIYHTSRLHSGIPARFSGSGSGTDYTLTI
SSLQPEDFAVYFCQQGNTLPYTFGQGTKLEIKGGGGSGGGGSGGGGSQV
QLQESGPGLVKPSETLSLTCTVSGVSLPDYGVSWIRQPPGKGLEWIGVI
WGSETTYYSSSLKSRVTISKDNSKNQVSLKLSSVTAADTAVYYCAKHYY
YGGSYAMDYWGQGTLVTVSSGGGGSDGNEEMGGITQTPYKVSISGTTVI
LTCPQYPGSEILWQHNDKNIGGDEDDKNIGSDEDHLSLKERSELEQSGY
YVCYPRGSKPEDANFYLYLRARVCENCMEMDVMSVATIVIVDICITGGL
LLLVYYWSRSKRSRLLHSDYMNMTPRRPGPTRKHYQPYAPPRDFAAYRS

CD19scFv-CD3eECDTM-OX40
(SEQ ID NO: 23)
GSMALPVTALLLPLALLLHAARPEIVMTQSPATLSLSPGERATLSCRAS
QDISKYLNWYQQKPGQAPRLLIYHTSRLHSGIPARFSGSGSGTDYTLTI
SSLQPEDFAVYFCQQGNTLPYTFGQGTKLEIKGGGGSGGGGSGGGGSQV
QLQESGPGLVKPSETLSLTCTVSGVSLPDYGVSWIRQPPGKGLEWIGVI
WGSEITYYSSSLKSRVTISKDNSKNQVSLKLSSVTAADTAVYYCAKHYY
YGGSYAMDYWGQGTLVTVSSGGGGSDGNEEMGGITQTPYKVSISGTTVI
LTCPQYPGSEILWQHNDKNIGGDEDDKNIGSDEDHLSLKEFSELEQSGY
YVCYPRGSKPEDANFYLYLRARVCENCMEMDVMSVATIVIVDICITGGL
LLLVYYWSRRDQRLPPDAHKPPGGGSFRTPIQEEQADAHSTLAKI

CD19scFv-CD3eECDTM-ICOS
(SEQ ID NO: 24)
GSMALPVTALLLPLALLLHAARPEIVMTQSPATLSLSPGERATLSCRAS
QDISKYLNWYQQKPGQAPRLLIYHTSRLHSGIPARFSGSGSGTDYTLTI
SSLQPEDFAVYFCQQGNTLPYTFGQGTKLEIKGGGGSGGGGSGGGGSQV
QLQESGPGLVKPSETLSLTCTVSGVSLPDYGVSWIRQPPGKGLEWIGVI
WGSETTYYSSSLKSRVTISKDNSKNQVSLKLSSVTAADTAVYYCAKHYY
YGGSYAMDYWGQGTLVTVSSGGGGSDGNEEMGGITQTPYKVSISGTTVI
LTCPQYPGSEILWQHNDKNIGGDEDDKNIGSDEDHLSLKEFSELEQSGY
YVCYPRGSKPEDANFYLYLRARVCENCMEMDVMSVATIVIVDICITGGL
LLLVYYWSTKKKYSSSVHDPNGEYMFMRAVNTAKKSRLTDVTL

CD19scFv-CD3eECDTM-CD2
(SEQ ID NO: 25)
GSMALPVTALLLPLALLLHAARPEIVMTQSPATLSLSPGERATLSCRAS
QDISKYLNWYQQKPGQAPRLLIYHTSRLHSGIPARFSGSGSGTDYTLTI
SSLQPEDFAVYFCQQGNTLPYTFGQGTKLEIKGGGGSGGGGSGGGGSQV
QLQESGPGLVKPSETLSLTCTVSGVSLPDYGVSWIRQPPGKGLEWIGVI
WGSETTYYSSSLKSRVTISKDNSKNQVSLKLSSVTAADTAVYYCAKHYY
YGGSYAMDYWGQGTLVTVSSGGGGSDGNEEMGGITQTPYKVSISGTTVI
LTCPQYPGSEILWQHNDKNIGGDEDDKNIGSDEDHLSIKEFSELEQSGY
YVCYPRGSKPEDANFYINLRARVCENCMEMDVMSVATIVIVDICITGGL
LLLVYYWSKRKKQRSRRNDEELETRAHRVATEERGRKPHQIPASTPQNP
ATSQHPPPPPGHRSQAPSHRPPPPGHRVQHQPQKRPPAPSGTQVHQQKG
PPLPRPRVQPKPPHGAAENSLSPSSN

Lentivirus Production and Viral Transduction into Primary T Cells

As described in Example 1, lentivirus were produced and transduced into isolated primary human T-cells. Transduced T-cells and non-transduced control T-cells were expanded and frozen for subsequent analysis.

Cytotoxicity and IL2 Assay cytotoxicity and IL2 production induced by cross-linking primary human T-Cells to target tumor cells were assessed as described in Example 1.

Primary Human T-Cell Results

Figure 31:
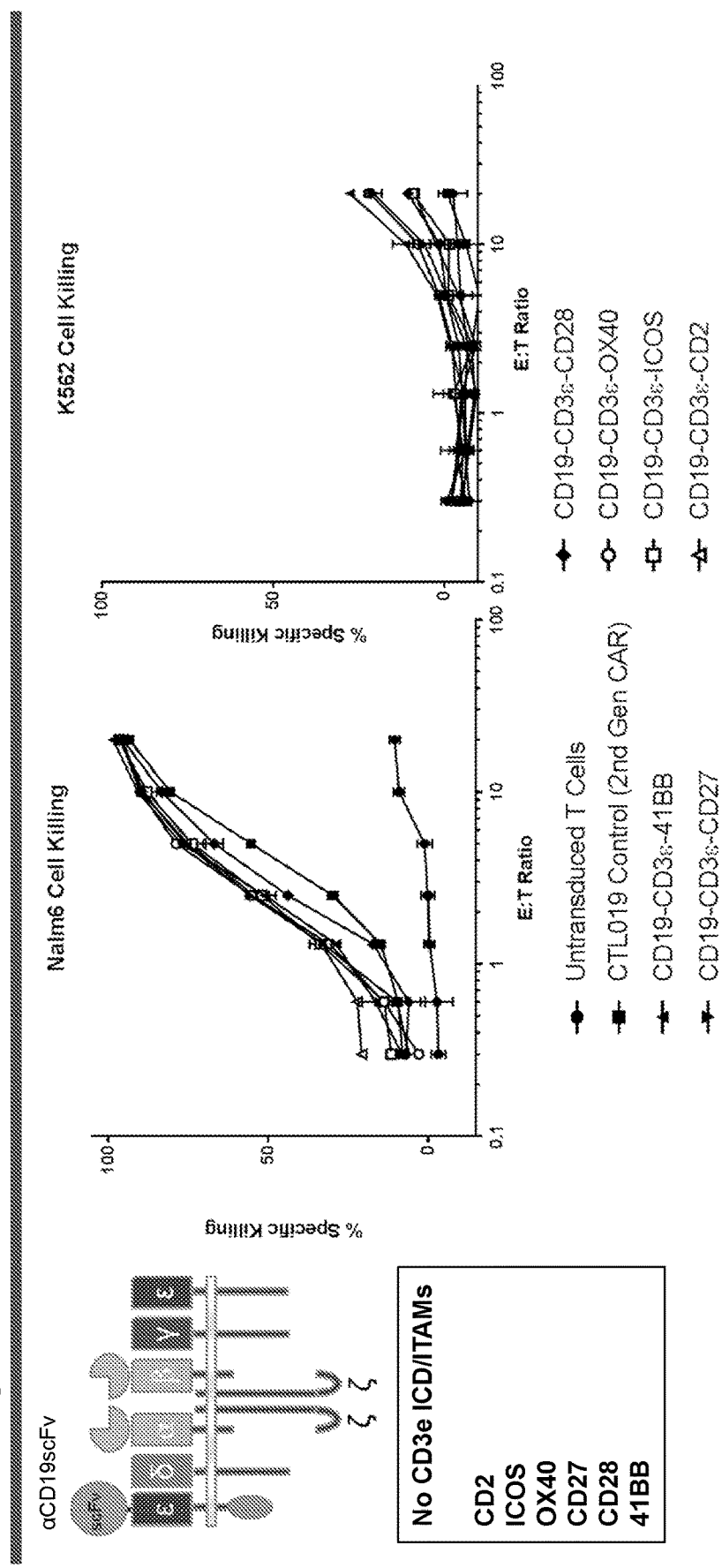
FIG. 31 is a pair of graphs showing percentage of the indicated cell killing in cells transfected with the indicated constructs as a function of transfection.
Figure 32:
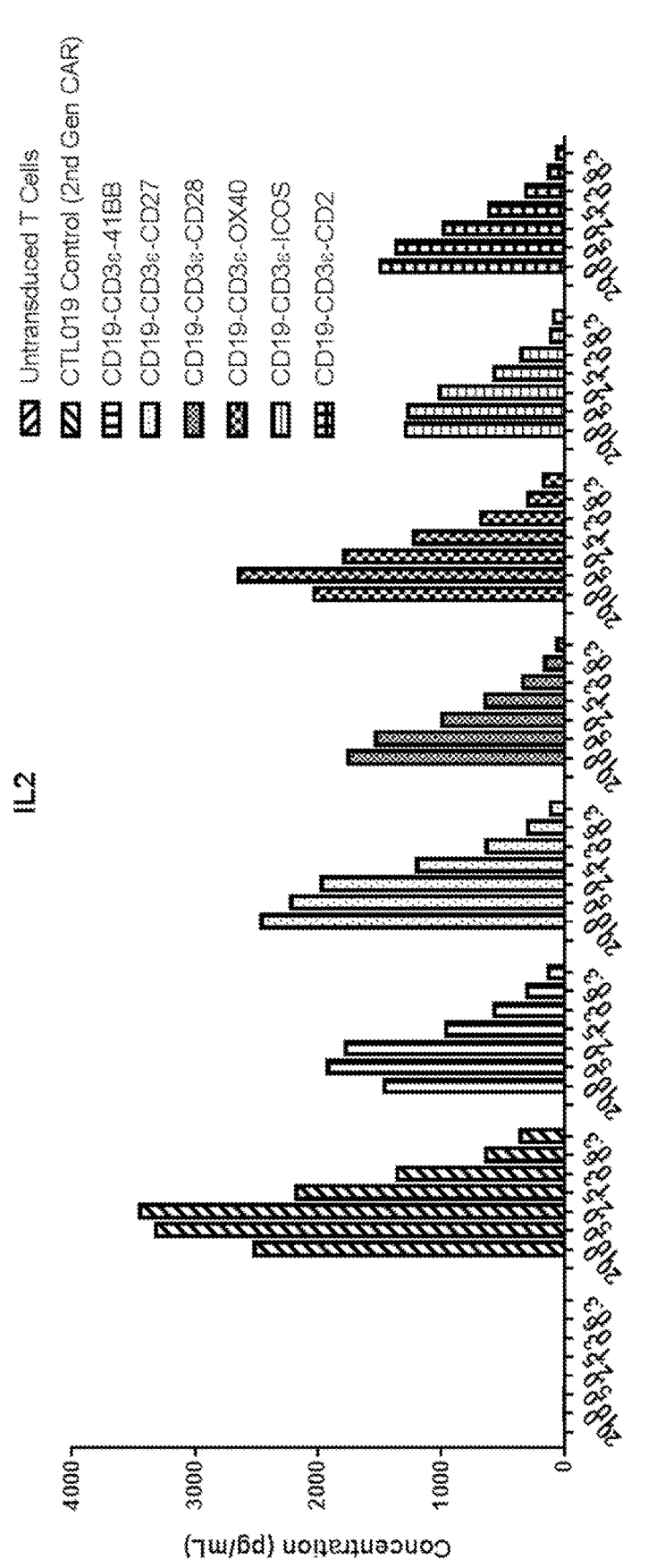
FIG. 32 is a graph showing concentration of IL-2 expression as a function of transfection in the indicated constructs.

FIG. 31 and FIG. 32 demonstrate that fusTCARs may be employed with any costimulatory domain and still retain target dependent cytolytic activity and induce IL2 expression despite the lack of ITAM domains within the constructs.

Example 8: Constitutively Active TCARs Fused into the TCR Complex Via CD3 Gamma, CD3 Delta and CD3 Zeta (fusTCAR)

Given the complex multi-protein architecture of the TCR complex, activity for TCARs may not be limited to covalent and non-covalent fusions with CD3 epsilon; non-covalent and covalent fusions with other accessory proteins in the complex such as for examples CD3 gamma, CD3 delta and CD3 zeta may also produce active TCARs. Additionally, as immunological synapse may be mediated by the distance between the target cells and the T-Cells, it may become necessary to mediate the optimal length by using different length linkers between the tumor targeting arm and the fusion with these accessory proteins.

Transient Expression and Activation Assays
Synthesis of fusTCAR Constructs

Plasmid DNA will be synthesized externally by DNA2.0. The nominal non-regulatable CAR construct, CD19scFv-BBZ, SEQ ID NO: 1, will be used as a control.

In "fusTCAR14" the CD19 scFv will be cloned as an N-terminal fusion with 2×G4S linker (SEQ ID NO: 62) to the CD3 delta extracellular and transmembrane domains followed by the intracellular costimulatory domain 4-1BB (SEQ ID NO: 26). Similarly, "fusTCAR15" (SEQ ID NO: 27) will be cloned excepting with 4×G4S linker (SEQ ID NO: 45) between the scFv and the CD3 epsilon extracellular domain.

In "fusTCAR16" the CD19 scFv was cloned as an N-terminal fusion to the CD3 delta extracellular and transmembrane domains followed by the intracellular costimulatory domain 4-1BB (SEQ ID NO: 28). "fusTCAR17" (SEQ ID NO: 29) and "fusCAR18" (SEQ ID NO: 30) were cloned similarly excepting with 2×G4S (SEQ ID NO: 62) and 4×G4S (SEQ ID NO: 45) linkers, respectively, between the scFv and the CD3 delta extracellular domain.

In "fusTCAR19" the CD19 scFv was cloned as an N-terminal fusion to the CD3 gamma extracellular and transmembrane domains followed by the intracellular costimulatory domain 4-1BB (SEQ ID NO: 31). "fusTCAR20" (SEQ ID NO: 32) and "fusTCAR21" (SEQ ID NO: 33) were cloned similarly excepting with 2×G4S(SEQ ID NO: 62) and 4×G4S (SEQ ID NO: 45) linkers, respectively, between the scFv and the CD3 gamma extracellular domain.

CD19scFv-CD3e_2G4S_ECDTM-41BB (Seq ID NO: 26/ "2G4S" disclosed as SEQ ID NO: 62)
GSMALPVTALLLPLALLLHAARPEIVMTQSPATLSLSPGERATLSCRAS
QDISKYLNWYQQKPGQAPRLLIYHTSRLHSGIPARFSGSGSGTDYTLTI
SSLQPEDFAVYFCQQGNTLPYTFGQGTKLEIKGGGGSGGGGSGGGGSQV
QLQESGPGINKRSETLSLTCTVSGVSLPDYGVSWIRQPPGKGLEWIGVI
WGSETTYYSSSLKSRVTISKDNSKNQVSLKLSSVTAADTAVYYCAKHYY
YGGSYAMDYWGQGTLVTVSSGGGGSGGGGSDGNEEMGGITQTPYKVSIS
GTTVILTCPQYPGSEILWQHNDKNIGGDEDDKNIGSDEDHLSLKEFSEL
EQSGYYVCYPRGSKPEDANFYLYLRARVCENCMEMDVMSVATIVIVDIC
ITGGLLLLVYYWSKRGRKKLLYIFKQPFMRPVQTTQEEDGCSCRFPEEE
EGGCEL CD19scFv-CD3e_4G4S_ECDTM-41BB (Seq ID NO: 27/ "4G4S" disclosed as SEQ ID NO: 45)
GSMALPVTALLLPLALLLHAARPEIVMTQSPATLSLSPGERATLSCRAS
QDISKYLNWYQQKPGQAPRLLIYHTSRLHSGIPARFSGSGSGTDYTLTI
SSLQPEDFANYECQQGNTLPYTEGQGTKLEIKGGGGSGGGGSGGGGSQV
QLQESGPGLVKPSETLSLTCTVSGVSLPDYGVSWIRQPPGKGLEWIGVI
WGSETTYYSSSLKSRVTISKDNSKNQVSLKLSSVTAADTAVYYCAKHYY
YGGSYAMDYWGQGTLVTVSSGGGGSGGGGSGGGGSGGGGSDGNEEMGGI
TQTPYKVSISGTTVILTCPQYPGSEILWQHNDKNIGGDEDDKNIGSDED
HLSLKEFSELEQSGYYVCYPRGSKPEDANFYLYLRARVCENCMEMDVMS
VATIVIVDICITGGLLLLVYYWSKRGRKKLLYIFKQPFMRPVQTTQEED
GCSCRFPEEEEGGCEL CD19scFv-CD3d_ECDTM-41BB
(Seq ID NO: 28)
GSATMALPVTALLLPLALLLHAARPEIVMTQSPATLSLSPGERATLSCR
ASQDISKYLNWYQQKPGQAPRLLIYHTSRLHSGIPARFSGSGSGTDYTL
TISSLQPEDFAVYFCQQGNTLPYTFGQGTKLEIKGGGGSGGGGSGGGGS
QVQLQESGPGLVKPSETLSLTCTVSGVSLPDYGVSWIRQPPGKGLEWIG
VIWGSETTYYSSSLKSRVTISKDNSKNQVSLKLSSVTAADTAVYYCAKH
YYYGGSYAMDYWGQGTLVTVSSGGGGSFKIPIEELEDRVFVNCNTSITW
VEGTVGTLLSDITRLDLGKRILDPRGIYRCNGTDIYKDKESTVQVHYRM
CQSCVELDPATVAGIIVTDVIATLLLALGVFCFAKRGRKKLLYIFKQPF
MRPVQTTQEEDGCSCRFPEEEEGGCEL CD19scFv-CD3d_2G4S_ECDTM-41BB (Seq ID NO: 29/ "2G4S" disclosed as SEQ ID NO: 62)
GSMALPVTALLLPLALLLHAARPEIVMTQSPATLSLSPGERATLSCRAS
QDISKYLNWYQQKPGQAPRLLIYHTSRLHSGIPARESGSGSGTDYTLTI
SSLQPEDFAVYFCQQGNTLPYTFGQGTKLEIKGGGGSGGGGSGGGGSQV
QLQESGPGLVKPSETLSLTCTVSGVSLPDYGVSWIRQPPGKGLEWIGVI
WGSETTYYSSSLKSRVTISKDNSKNQVSLKLSSVTAADTAVYYCAKHYY
YGGSYAMDYWGQGTLVTVSSGGGGSGGGGSFKIPIEELEDRVEVNCNTS
ITWYEGTVGTLLSDITRLDLGKRILDPRGIYRCNGTDIYKDKESTVQVF
IYIRMICQSCVELDPATVAGIIVTDVIATLLLAUNECEAKRGRKKLLYI
FKQPFMRPVQTTQEEDGCSCRFPEEEEGGCEL CD19scFv-CD3d_4G4S_ECDTM-41BB (Seq ID NO: 30/ "4G4S" disclosed as SEQ ID NO: 45)
GSMALPVTALLLPLALLLHAARPEIVMTQSPATLSLSPGERATLSCRAS
QDISKYLNWYQQKPGQAPRLLPMTSRLFISGIPARFSGSGSGTDYTLTI
SSLQPEDFAVYFCQQGNTLPYTFGQGTKLEIKGGGGSGGGGSGGGGSQV
QLQESGPGLVKPSETLSLTCTVSGVSLPDYGVSWIRQPPGKGLEWIGVI
WGSETTYYSSSIXSPNTISKDNSKNQVSLKLSSVTAADTAVYYCAKHYY
YGGSYNNIDYWGQGILVTVSSGGGGSGGGGSGGGGSGGGGSFRIPIEEL
EDRVFVNCNTSITWVEGTVGTLLSDITRLDLGKRILDPRGIYRCNGTDI
YKDKESTVQVHYRMCQSCVELDPATVAGIIVTDVIATLLLALGVFCFAK
RGRKKLLYIFKQPFMRPVQTTQEEDGCSCRFPEEEEGGCEL CD19scFv-CD3gECDTM-41BB
(Seq ID NO: 31)
GSATMALPVTALLLPLALLLHAARPEIVMTQSPATLSLSPGERATLSCR
ASQDISKYLNWYQQKPGQAPRLLIYHTSRLHSGIPARFSGSGSGTDYTL
TISSLQPEDFAVYFCQQGNTLPYTFGQGTKLEIKGGGGSGGGGSGGGGS
QVQLQESGPGLVKPSETLSLTCTVSGVSLPDYGVSWIRQPPGKGLEWIG

```
VIWGSETTYYSSSLKSRVTISKDNSKNQVSLKLSSVTAADTAVYYCAKH

YYYGGSYAMDYWGQGTLVTVSSGGGGSQSIKGNHLVKVYDYQEDGSVLL

TCDAEAKNITWFKDGKMIGFLTEDKKKWNLGSNAKDPRGMYQCKGSQNK

SKPLQVYYRMCQNCIELNAATISGFLFAEIVSIFVLAVGVYFIAKRGRK

KLLYIFKQPFMRPVQTTQEEDGCSCRFPEEEEGGCEL

CD19scFv-2G4S_CD3gECDTM-41BB (Seq ID NO: 32/
"2G4S" disclosed as SEQ ID NO: 62)
GSMALPVTALLLPLALLLHAARPEIVMTQSPATLSLSPGERATLSCRAS

QPISKYLNWYQQKPGQAPRLLIYHTSRLHSGIPARFSGSGSGTDYTLTI

SSLQPEDFAVYFCQQGNTLPYITGQGTKLEIKGGGGSGGGGSGGGGSQV

QLQESGPGLVKPSETLSLTCTVSGVSLPDYGVSWIRQPPGKGLEWIGVI

NVGSETTYYSSSLKSRVTISKDNSKNQVSLKLSSVTAADTAWYCAKHYY

YGGSYAMDYWGQGTLVTVSSGGGGSGGGGSQSIKGNHLVKVYDYQEDGS

VLLTCDAEAKNITWFKDGKMIGFLTEDKKKWNLGSNAKDPRGMYQCKGS

QNKSKPLQVYYRMCQNCIELNAATISGFLFAEIVSIFVLAVGVYFIAKR

GRKKLLYIFKQPFMRPVQTTQEEDGCSCRFPEEEEGGCEL

CD19scFv-4G4S_CD3gECDTM-41BB (Seq ID NO: 33/
"4G4S" disclosed as SEQ ID NO: 45)
GSMALPVTALLLPLALLLHAARPEIVMTQSPATLSLSPGERATLSCRAS

QDISKYLNWYQQKPGQAPRLLIYHTSRLHSGIPARFSGSGSGTDYTLTI

SSLQPEDFAVYFCQQGNTLPYTFGQGTKLEIKGGGGSGGGGSGGGGSQV

QLQESGPGLVKPSETLSLTCTVSGVSLPDYGVSWIRQPPGKGLEWIGVI

WGSETTYYSSSLKSRVTISKDNSKNQVSLKLSSVTAADTAVYYCAKHYY

YGGSYAMDYWGQGTLVTVSSGGGGSGGGGSGGGGSGGGGSQSIKGNHLV

KVYDYQEDGSVLLTCDAEAKNITWFKDGKMIGFLTEDKKKWNLGSNAKD

PRGMYQCKGSQNKSKPLQVYYRMCQNCIELNAATISGFLFAEIVSIFVL

AVGVYFIAKRGRKKLLYIFKQPFMRPVQTTQEEDGCSCRFPEEEEGGCE

L
```

Transfection of Jurkat Reporter Cell Line and Activation of NFAT.

Activation following target antigen engagement of the antigen binding domain was measured with the Jurkat cells with NFAT-LUC reporter (JNL) reporter cell line as described in Example 1. The transfected cells were added to the target plate with 100 µl per well. Luciferase One Glo reagent 100 µl was added per well. The samples were incubated for 5 min and then luminescence was measured as described.

Transient Transfection Results

Figure 33:
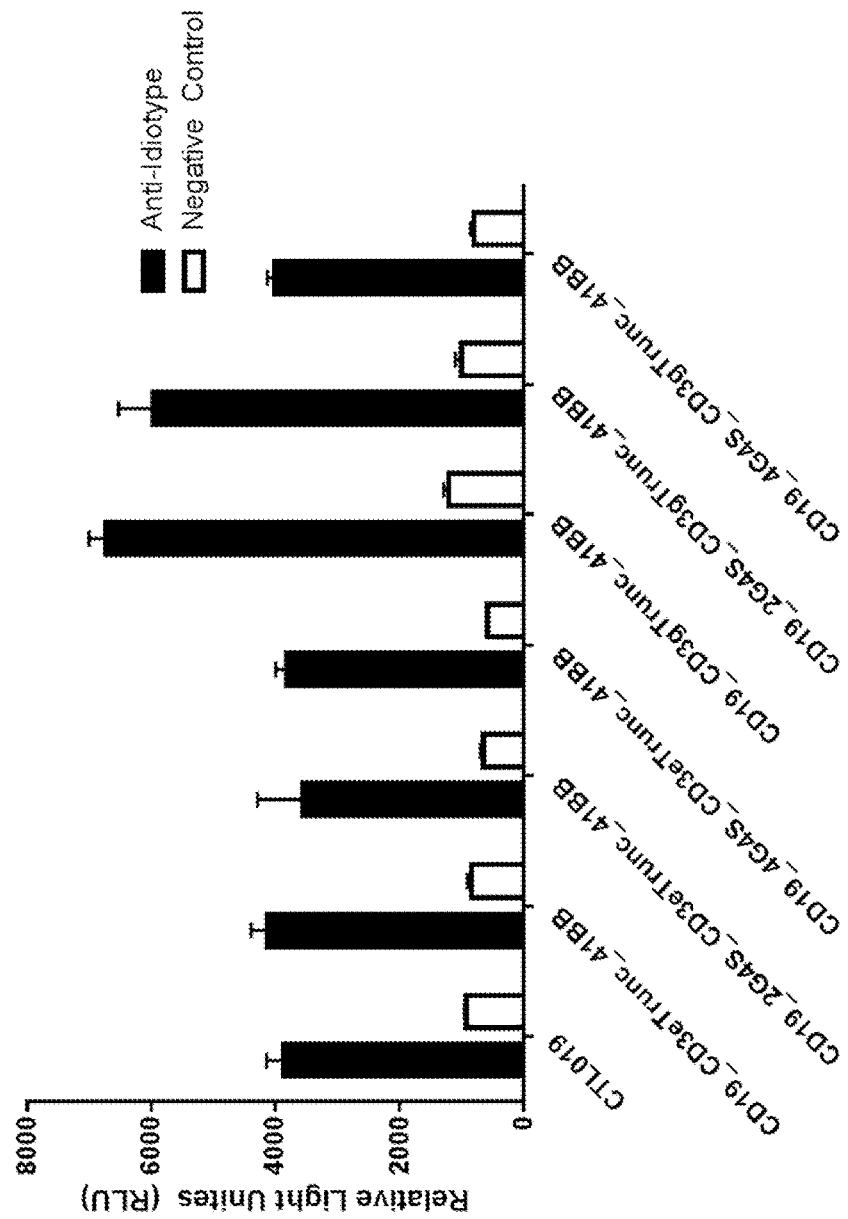
FIG. 33 is a graph showing light intensity as generated by an NFAT reporter gene system. The anti-idiotype antibody binds the expressed scFv.

FIG. 33 demonstrates that TCARs are functional and result in signaling via the NFAT pathway regardless of whether CD3 epsilon or CD3 gamma was used for the fusion in the construct. Additionally, linkers of various lengths may be employed to fuse the binding domain to the remainder of the TCAR in order to obtain the desired results. Constructs fused to CD3 delta did not transiently express on the cell surface of the reporter cells based upon FACS so a determination could not be made as to their suitability based upon this approach and evaluation was instead performed in primary human T-cells.

Production of Lentiviral Transduced Primary Human T-Cells

FusTCARs were also tested in primary human T-Cells for their activity. Prior to production of lentivirus an additional construct was also designed to test if the extracellular and transmembrane domains of CD3 zeta could be used in the absence of its intracellular domain. Plasmid DNA was synthesized externally by DNA2.0. In "fusTCAR22" the CD19 scFv was cloned as an N-terminal fusion to the CD3 zeta extracellular and transmembrane domains followed by the intracellular costimulatory domain 4-1BB (SEQ ID NO: 34).

```
CD19scFv-CD3zECDTM-41BB
                                           (Seq ID NO: 34)
GSMALPVTALLLPLALLLHAARPEIVMTQSPATLSC

RASQDISKYLNWYQQKPGQAPRLLIYHTSRLHSGIPARFSGSGSGT

DYTLTISSLQPEDFAVYFCQQGNTLPYTFGQGTKLEIKGGGGSGGG

GSGGGGSQVQLQESGPGLVKPSETLSLTCTVSGVSLPDYGVSWIRQ

PPGKGLEWIGVIWGSETTYYSSSLKSRVTISKDNSKNQVSLKLSSV

TAADTAVYYCAKHYYYGGSYAMDYWGQGTLVTVSSGGGGSQSFGLL

DPKLCYLLDGILFIYGVILTALFLKRGRKKLLYIFKQPFMRPVQTT

QEEDGCSCRFPEEEEGGCEL
```

Lentivirus Production and Viral Transduction into Primary T Cells

As described in Example 1, lentivirus were produced for fusTCAR3, fusTCAR16, fusTCAR19 and fusTCAR22 and transduced into isolated primary human T-cells. Transduced T-cells and non-transduced control T-cells were expanded and frozen for subsequent analysis.

Cytotoxicity and IL2 Assay

Cytotoxicity and IL2 production induced by cross-linking primary human T-Cells to target tumor cells were assessed as described in Example 1.

Primary Human T-Cell Results

Figure 34:
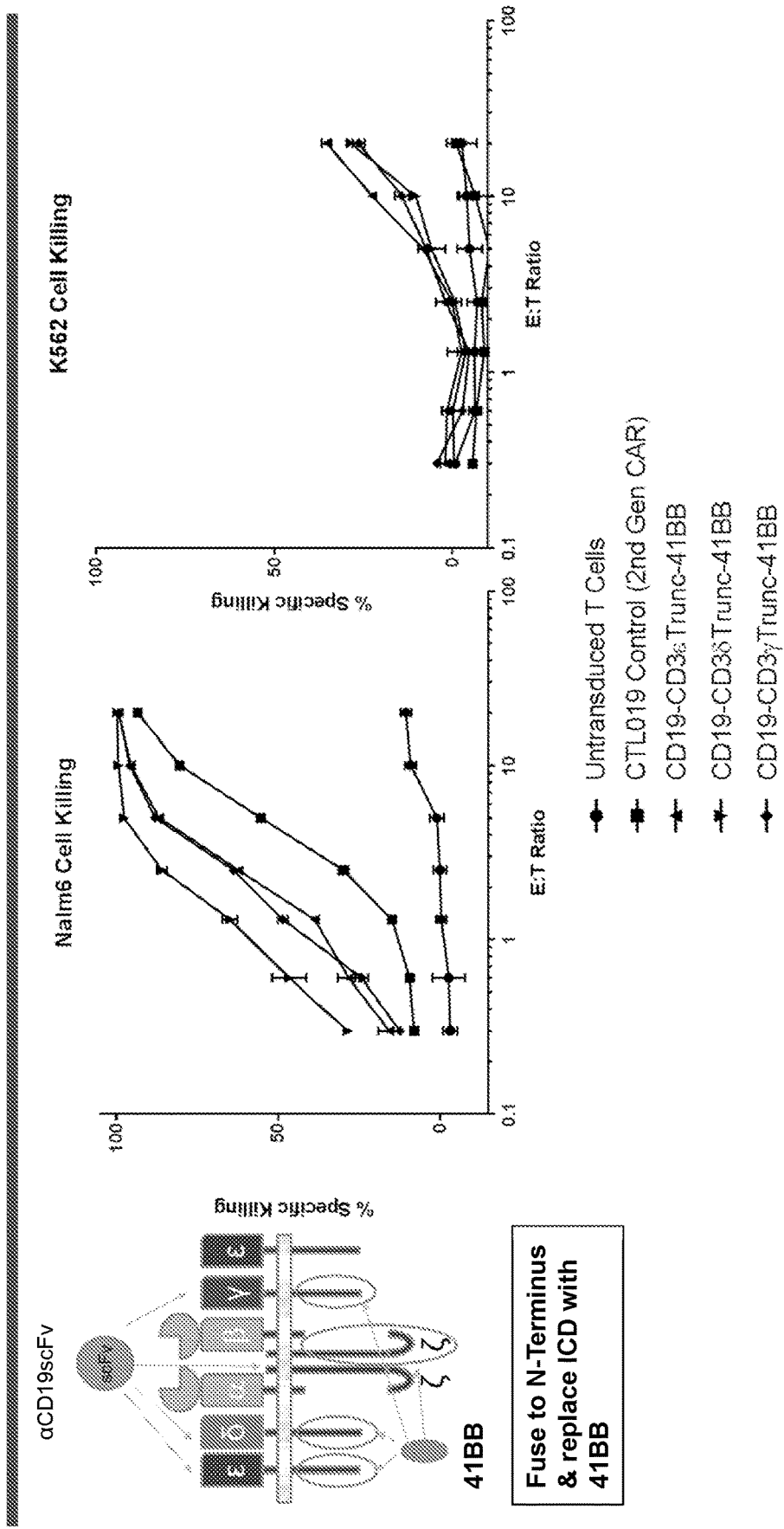
FIG. 34 is a pair of graphs showing percentage of the indicated cell killing in cells transfected with the indicated constructs as a function of transfection.
Figure 35:
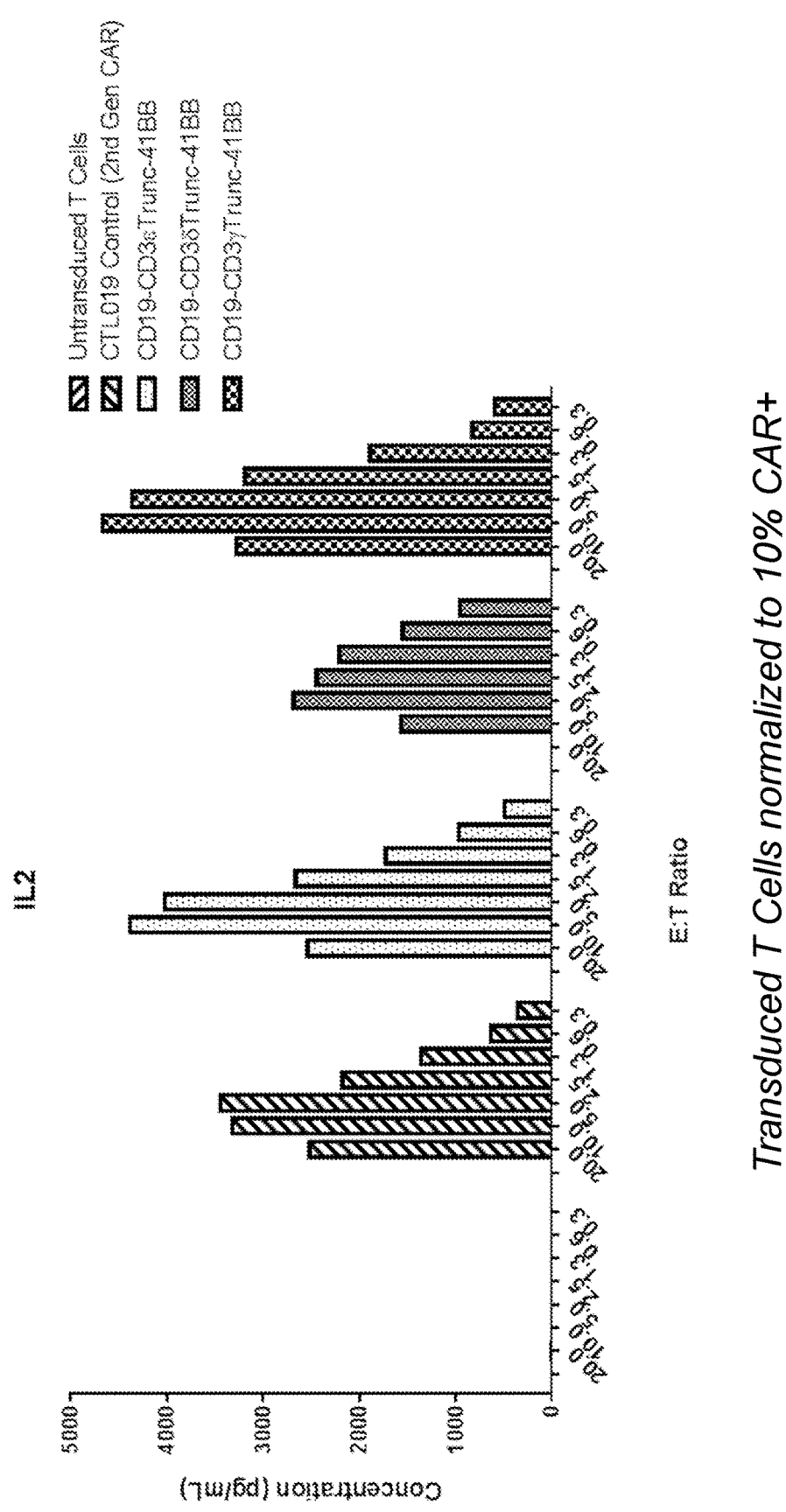
FIG. 35 is a graph showing concentration of IL-2 expression as a function of transfection in the indicated constructs.
Figure 36:
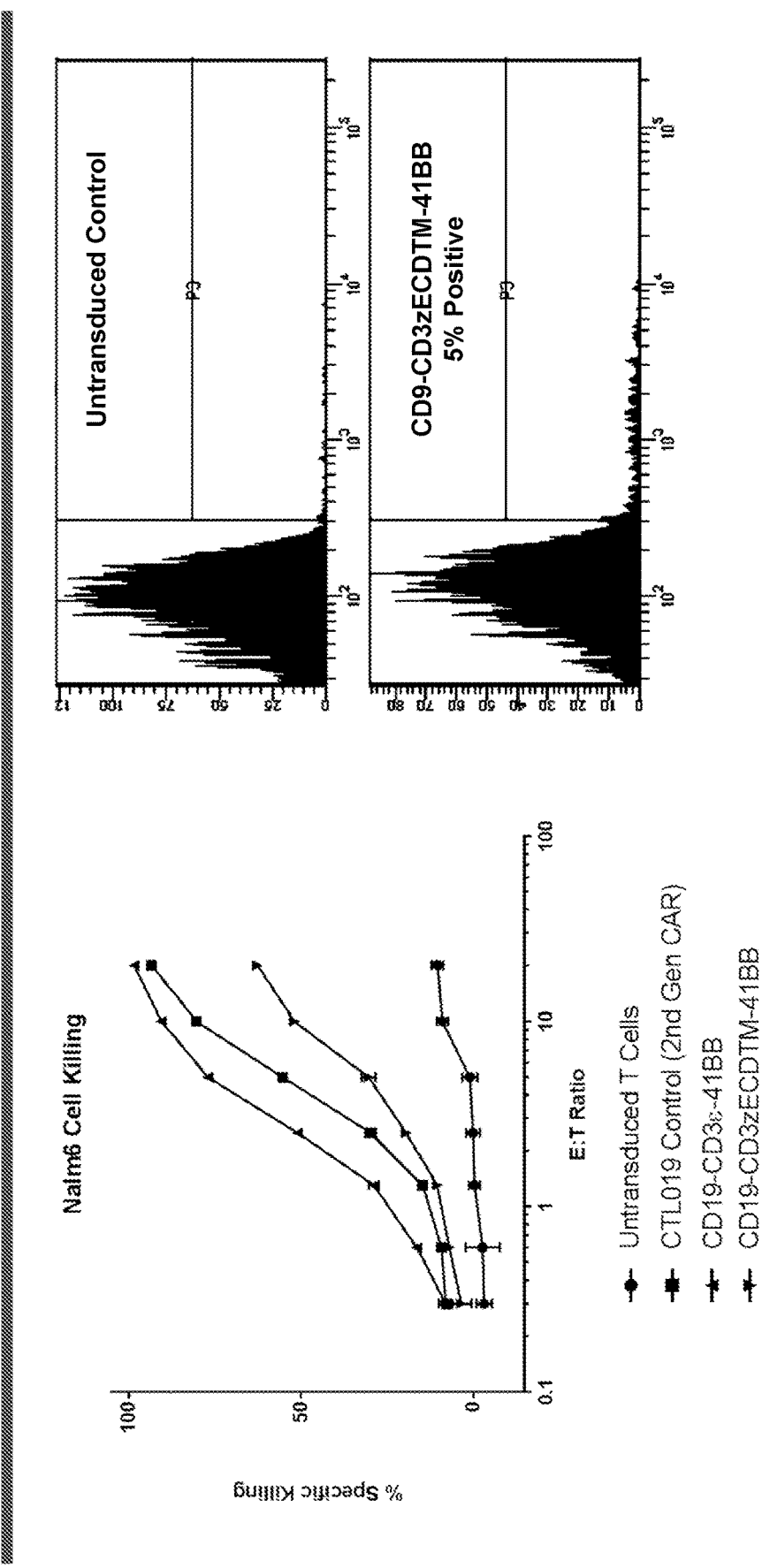
FIG. 36, left panel, is a graph showing percentage of the indicated cell killing in cells transfected with the indicated constructs as a function of transfection.

As can be observed in FIG. 34 and FIG. 35, fusTCARs on CD3 epsilon. CD3 gamma and CD3 delta demonstrated appreciable activity relative to the control CD19scFv-BBZ CAR. Important to note that redirected lytic activity and IL2 secretion was observed despite the absence of ITAM signaling domains. In contrast, as shown in FIG. 36, fusTCAR on CD3 zeta resulted in reduced lytic activity. FACS analysis demonstrated low cell surface expression for this construct likely due to the architecture of the TCR and the addition of the tumor targeting domain; additional optimization of the construct design is necessary to improve expression and maximize activity.

Example 9: Constitutively Active TCARs Fused into the TCR Complex Via CD3 Epsilon with Alternative Binding Domains TCARs should demonstrate broad applicability against solid as well as hematological tumors using a variety of binding domains and target antigens. Mesothelin is one antigen of interest expressed on a broad range of tumor types.

Synthesis of fusTCAR Constructs

Plasmid DNA will be synthesized externally by DNA2.0. The nominal non-regulatable CAR construct, MSLN5scFv-BBZ. SEQ ID NO: 35, will be used as a control.

In "fusTCAR23" the CD19 scFv will be cloned as an N-terminal fusion with G4S linker (SEQ ID NO: 52) to the CD3 epsilon extracellular and transmembrane domains followed by the intracellular costimulatory domain 4-1BB (SEQ ID NO: 36). "FusTCAR25" was cloned similarly excepting CD8a linker was used to fuse to the N-terminus of CD3 epsilon extracellular and transmembrane domains follower by 4-1BB (SEQ ID NO: 37) "FusTCAR25" was cloned as an N-terminal fusion with G4S linker (SEQ ID NO: 52) to the CD3 epsilon extracellular and transmembrane domains followed by the intracellular costimulatory domain CD27 (SEQ ID NO: 38) "FusTCAR23," "fusTCAR24" and "fusTCAR25" lack intrinsic intracellular ITAM signaling domains.

```
MSLN5scFv-BBZ
                                         (SEQ ID NO: 35)
GSMALPVTALLLPLALLLHAARPQVQLVQSGAEVEKPGASVKVSCK

ASGYTFTDYYMHWVRQAPGQGLEWMGWINPNSGGTNYAQKFQGRVT

MTRDTSISTAYMELSRLRSDDTAVYYCASGWDFDYWGQGTLVTVSS

GGGGSGGGGSGGGGSGGGGSDIVMTQSPSSLSASVGDRVTITCRAS

QSIRYYLSWYQQKPGKAPKLLIYTASILQNGVPSRFSGSGSGTDFT

LTISSLQPEDFATYYCLQTYTTPDFGPGTKVEIKTTTPAPRPPTPA

PTIASQPLSLRPEACRPAAGGAVHTRGLDFACDIYIWAPLAGTCGV

LLLSLVITLYCKRGRKKLLYIFKQPFMRPVQTTQEEDGCSCRFPEE

EEGGCELRVKFSRSADAPAYKQGQNQLYNELNLGRREEYDVLDKRR

GRDPEMGGKPRRKNPQEGLYNELQKDKMAEAYSEIGMKGERRRGKG

HDGLYQGLSTATKDTYDALHMQALPPR

MSLN5scFv-CD3eECDTM-41BB
                                         (SEQ ID NO: 36)
GSMALPVTALLLPLALLLHAARPQVQLVQSGAEVEKPGASVKVSCK

ASGYTFTDYYMHWVRQAPGQGLEWMGWINPNSGGTNYAQKFQGRVT

MTRDTSISTAYMELSRLRSDDTAVYYCASGWDFDYWGQGTINTVSS

GGGGSGGGGSGGGGSGGGGSDIVMTQSPSSESASVGDRVTITCRAS

QSIRYYLSWYQQKPGKAPKLLIYTASILQNGVPSRFSGSGSGTDFT

LTISSLQPEDFATYYCLQTYTTPDFGPGTKVEIKGGGGSDGNEEMG

GITQTPYKVSISGTTVILTCPQYPGSEILWQHDKNIGGDEDDKNIG

SDEDHLSLKEFSELEQSGYYVCYPRGSKPEDANFYLYLRARVCENC

MEMDVMSVATIVIVDICITGGLLLLVYYWSKRGRKKLLYIFKQPFM

RPVQTTQEEDGCSCRFPEEEEGGCEL

MSLN5scFv-CD8hinge-CD3eECDTM-41BB
                                         (SEQ ID NO: 37)
GSMALPVTALLLPLALLLHAARPQVQLVQSGAEVEKPGASVKVSCK

ASGYTFTDYYMHWVRQAPGQGLEWMGWINPNSGGTNYAQKFQGRVT

MTRDTSISTAYMELSRLRSDDTAVYYCASGWDFDYWGQGTLVTVSS

GGGGSGGGGSGGGGSGGGGSDIVMTQSPSSLSASVGDRVTITCRAS

QSIRYYLSWYQQKPGKAPKLLIYTASILQNGVPSRFSGSGSGTDFT

LTISSLQPEDFATYYCLQTYTTPDFGPGTKVEIKTTTPAPRPPTPA

PTIASQPLSLRPEASRPAAGGAVHTRGLDTGGGSDGNEEMGGITQT

PYKVSISGTTVILTCPQYPGSEILWQHDKNIGGDEDDKNIGSDED

HLSLKEFSELEQSGYYVCYPRGSKPEDANFYLYLRARVCENCMEMD

VMSVATIVIVDICITGGLLLLVYYWSKRGRKKLLYIFKQPFMRPVQ

TTQEEDGCSCRFPEEEEGGCEL

MSLN5scFv-CD3eECDTM-CD27
                                         (SEQ ID NO: 38)
GSMALPVTALLLPLALLLHAARPQVQLVQSGAEVEKPGASVKVSCK

ASGYTFTDYYMHWVRQAPGQGLEWMGWINPNSGGTNYAQKFQGRVT

MTRDTSISTAYMELSRLRSDDTAVYYCASGWDFDYWGQGTLVTVSS

GGGGSGGGGSGGGGSGGGGSDIVMTQSPSSLSASVGDRVTITCRAS

QSIRYYLSWYQQKPGKAPKLLIYTASILQNGVPSRFSGSGSGTDFT

LTISSLQPEDFATYYCLQTYTTPDFGPGTKVEIKGGGGSDGNEEMG

GITQTPYKVSISGTTVILTCPQYPGSEILWQHNDKNIGGDEDDKNI

GSDEDHLSLKEFSELEQSGYYVCYPRGSKPEDANFYLYLRARVCEN

CMEMDVMSVATIVIVDICITGGLLLLVYYWSQRRKYRSNKGESPVE

PAEPCHYSCPREEEGSTIPIQEDYRKPEPACSP
```

Lentivirus Production and Viral Transduction into Primary T Cells

As described in Example 1, lentivirus were produced and transduced into isolated primary human T-cells. Transduced T-cells and non-transduced control T-cells were expanded and frozen for subsequent analysis.

Cytotoxicity and IL2 Assay

Cytotoxicity and IL2 production induced by cross-linking primary human T-Cells to target tumor cells were assessed as described in Example 1. OVCAR8, naturally overexpressing mesothelin and transduced with firefly luciferase, was substituted as the target cell line.

Primary Human T-Cell Results

Figure 37:
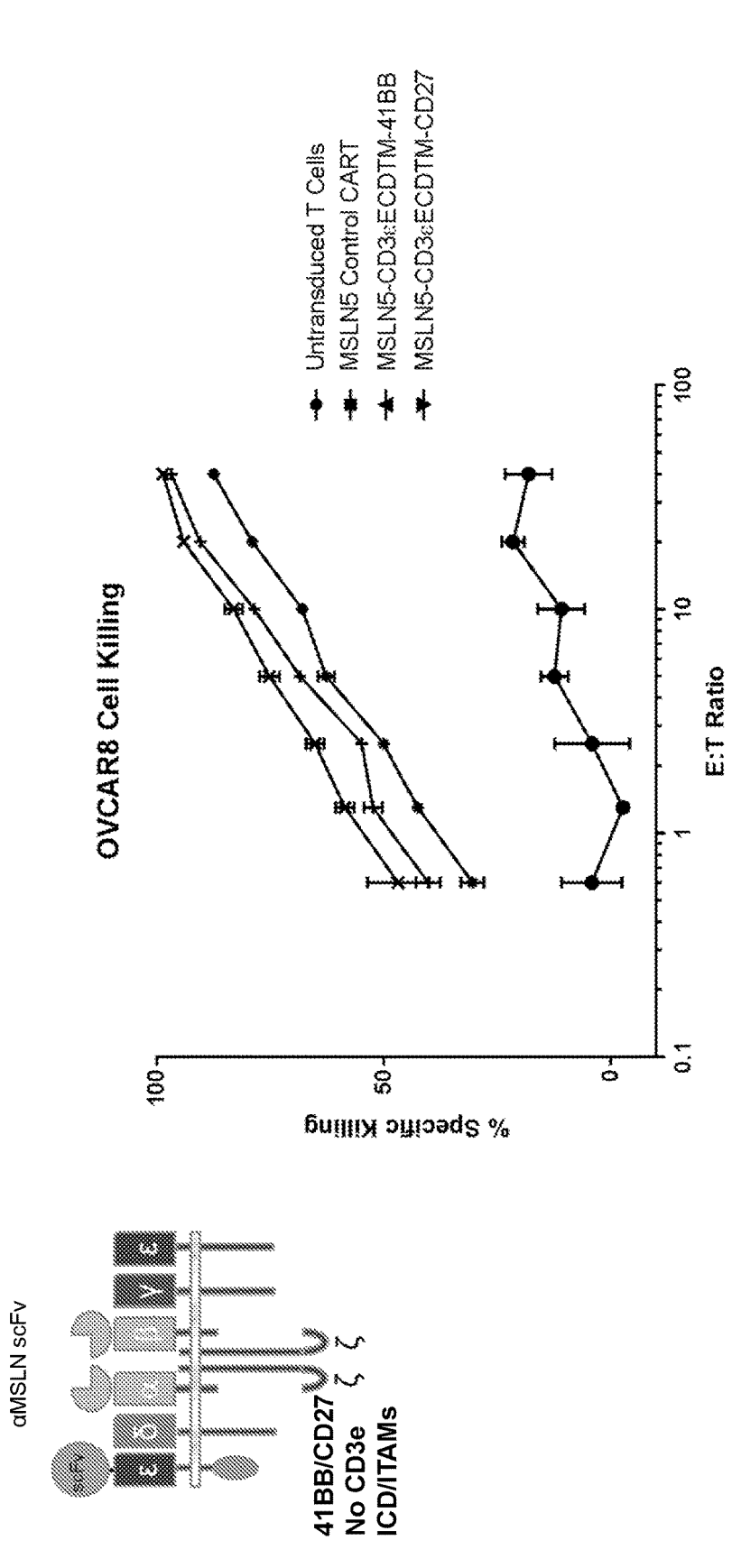
FIG. 37 is a graph showing percentage of the indicated cell killing in cells transfected with the indicated constructs as a function of transfection.
Figure 38:
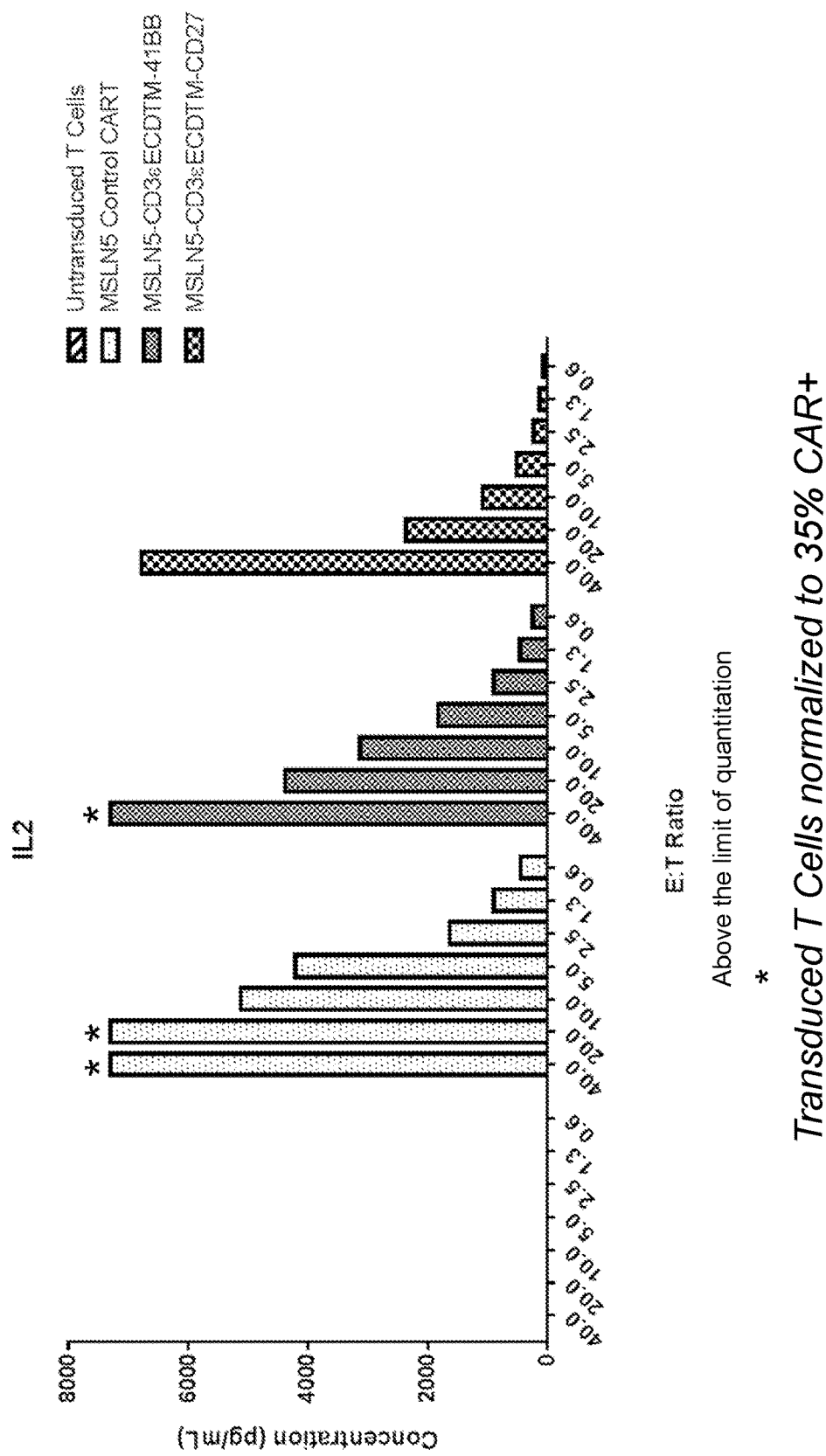
FIG. 38 is a graph showing concentration of IL-2 expression as a function of transfection in the indicated constructs.
Figure 39:
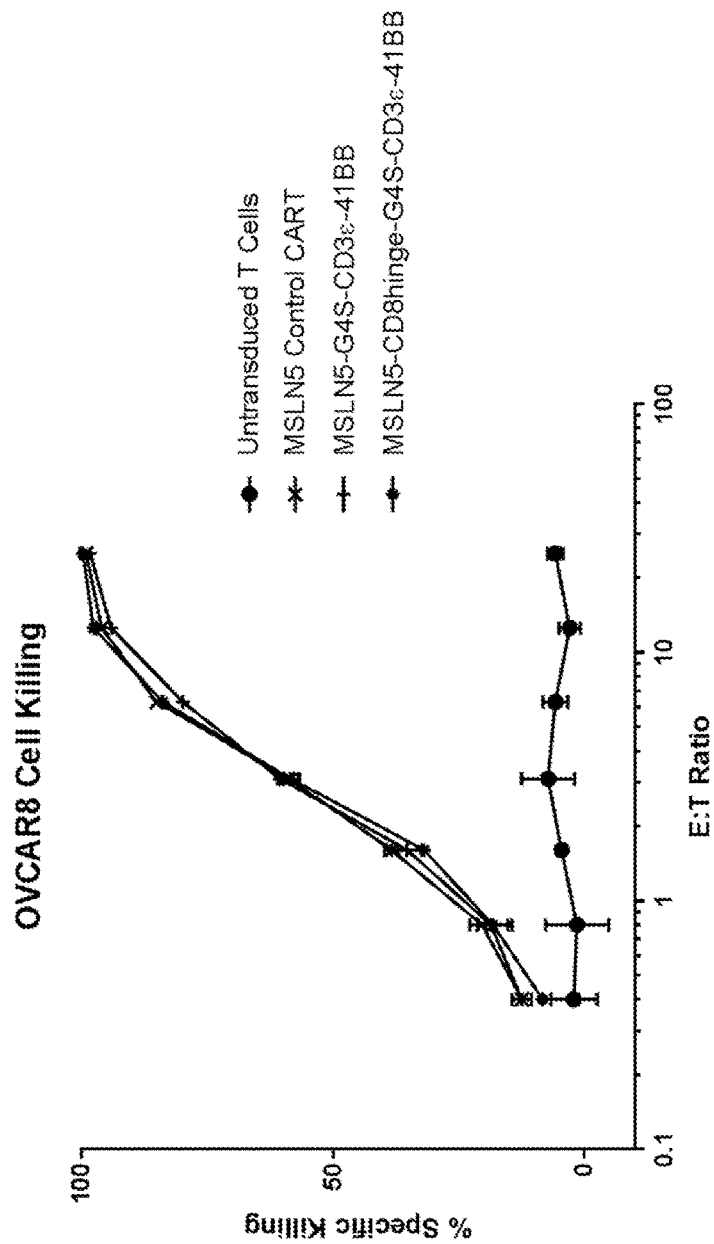
FIG. 39 is a graph showing percentage of the indicated cell killing in cells transfected with the indicated constructs as a function of transfection.
Figure 40:
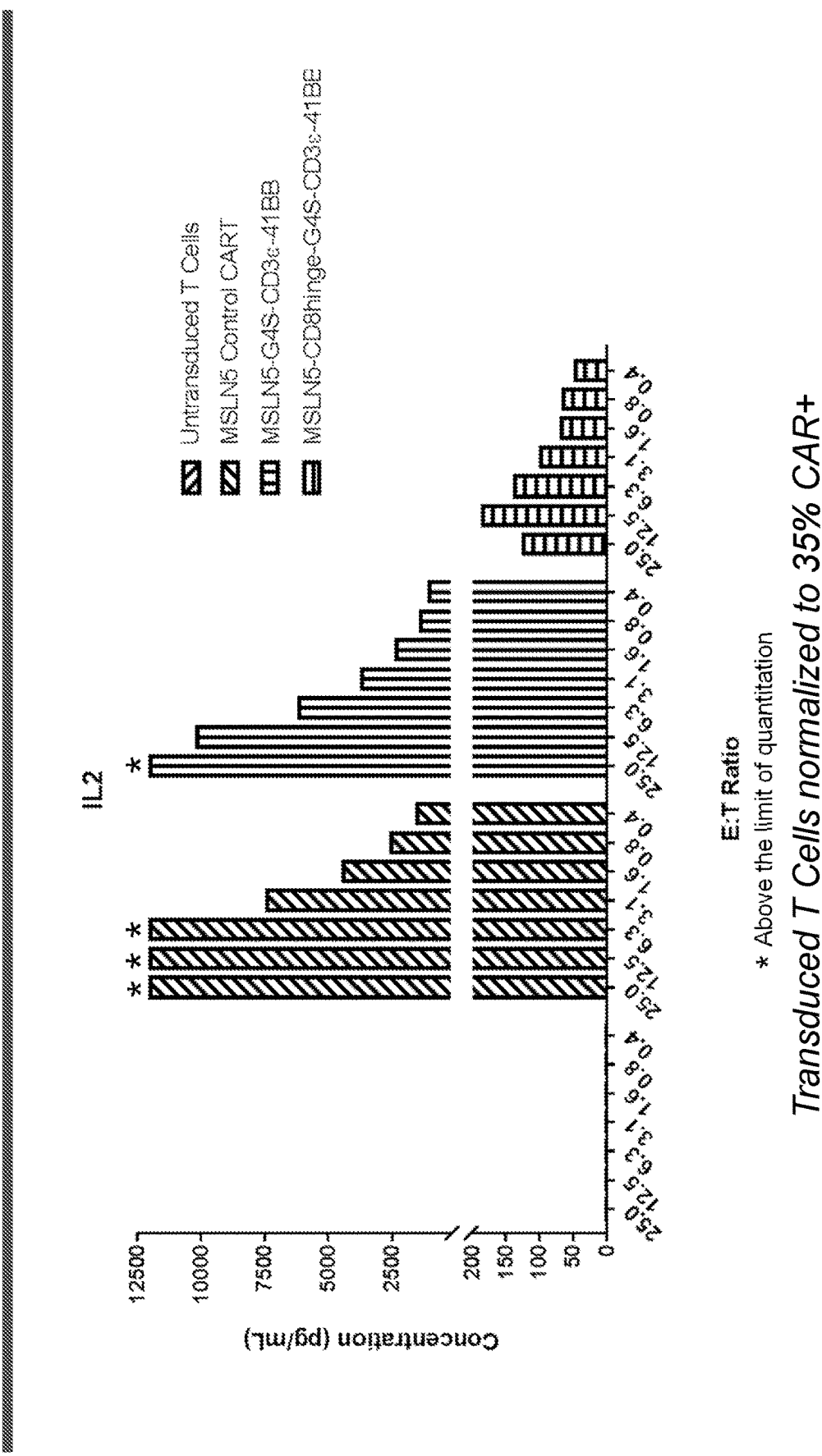
FIG. 40 is a graph showing concentration of IL-2 expression as a function of transfection in the indicated constructs.

Similar to the other examples utilizing CD19-targeting TCARS, TCARs targeting mesothelin antigen are potent cytotoxic molecules. Cytotoxic activity and IL2 expression upon engagement (FIGS. 37 and 38, respectively) did not require ITAMs as a prerequisite for activity and both CD27 and 4-1BB intracellular costimulatory domains demonstrated good functional activity. As shown in FIGS. 39 and 40, the linker between the tumor targeting domain and the TCR accessory protein can modulate the functional activity of TCARs and can be adjusted to obtain the desired characteristics.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. A combination of chimeric membrane proteins, comprising a first chimeric membrane protein and a second chimeric membrane protein,
wherein the first chimeric membrane protein comprises a first antigen binding domain, a CD3 gamma, delta, or epsilon domain and an intracellular co-stimulatory domain, wherein the second chimeric membrane protein comprises a second antigen binding domain, a CD3 gamma, delta, or epsilon domain and an intracellular co-stimulatory domain,
wherein said CD3 domain of the first or second chimeric membrane protein comprises an extracellular domain derived from the extracellular domain of CD3 gamma, delta, or epsilon and said intracellular co-stimulatory domain of the first or second chimeric membrane protein is not derived from CD3 gamma, delta, or epsilon, and
wherein the first and the second chimeric membrane proteins lack an ITAM signaling domain.

2. A combination of chimeric membrane proteins, comprising a first chimeric membrane protein and a second chimeric membrane protein,
wherein the first chimeric membrane protein comprises a CD3 gamma, delta, or epsilon domain and a first intracellular dimerization domain, wherein said CD3 gamma, delta, or epsilon domain comprises an extracellular domain derived from the extracellular domain of CD3 gamma, delta, or epsilon,
wherein the second chimeric membrane protein comprises an extracellular antigen binding domain, an intracellular costimulatory domain and a second intracellular dimerization domain, and
wherein the first and the second chimeric membrane proteins lack an ITAM signaling domain.

3. The combination of chimeric membrane proteins of claim 2, wherein said first chimeric membrane protein further comprises an intracellular co-stimulatory domain.

4. The combination of chimeric membrane proteins of claim 1, wherein said CD3 gamma, delta, or epsilon domain of the first or second chimeric protein comprises the entire CD3 gamma, delta, or epsilon extracellular domain.

5. The combination of chimeric membrane proteins of claim 1, wherein said first or second chimeric protein does not comprise any intracellular domain derived from CD3 gamma, delta, or epsilon.

6. The combination of chimeric membrane proteins of claim 1, wherein the antigen binding domain of the first or second chimeric membrane protein is located N-terminal to said CD3 gamma, delta, or epsilon domain.

7. A cell comprising the combination of chimeric membrane proteins of claim 2.

8. A nucleic acid construct encoding the combination of chimeric membrane proteins of claim 2.

9. The nucleic acid construct of claim 8, wherein said nucleic acid construct is mRNA.

10. A vector comprising the nucleic acid construct of claim 8, wherein said vector is a lentiviral, adenoviral, or retroviral vector.

11. The cell of claim 7, wherein said extracellular antigen binding domain of said second chimeric protein comprises the antigen binding domain of an antibody or fragment thereof.

12. The cell of claim 7, wherein said first and second dimerization domains make up a heterodimerization pair and heterodimerize when expressed in said cell.

13. The cell of claim 12, wherein the heterodimerization domain pairs are selected from the group consisting of: FKBP and FRB, p53 and MDM2, mFos and mJun Coils, and VPS36 and VPS28, GyrB-GyrB based switch, and a GAI-GID1 based switch.

14. The cell of claim 7, wherein said first and second dimerization domain make up a heterodimerization pair and heterodimerize when expressed in said cell only in the presence of a dimerization compound.

15. The cell of claim 13, wherein one of said first and second dimerization domains comprises a rapamycin analog binding sequence having at least 85% identity with FRB and the other dimerization domain comprises a rapamycin analog binding sequence having at least 85% identity with FKBP.

16. The cell of claim 15, wherein one of said first and second dimerization domains comprises a rapamycin analog binding sequence from FKBP.

17. The cell of claim 15, wherein one of said first and second dimerization domain comprises a rapamycin analog binding sequence from FRB.

18. The cell of claim 7, wherein said cell is selected from an NK cell or T cell.

19. The vector of claim 10, wherein, upon expression of said first and second chimeric proteins, said proteins are expressed as a single mRNA transcript.

20. The vector of claim 19, wherein the nucleic acid sequences encoding said first and second chimeric proteins are separated by a nucleic acid encoding a self-cleavage site or an internal ribosomal entry site.

21. The combination of chimeric membrane proteins of claim 1, wherein the intracellular co-stimulatory domain of the first or second chimeric membrane protein is a functional signaling domain of a protein selected from the group consisting of: an MEW class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, ICAM-1, LFA-1 (CD11a/CD18), 4-1BB (CD137), B7-H3, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

22. A method of treating a subject with a proliferative disorder, said method comprising administering the cell of claim 7, wherein the cell is a T cell or NK cell.

23. The method of claim 22, wherein said cell is autologous or allogeneic to said subject.

24. The method of claim 22, wherein said subject is a human.

25. The combination of chimeric membrane proteins of claim 3, wherein said first chimeric membrane protein further comprises an antigen binding domain.

26. A cell comprising the combination of chimeric membrane proteins of claim 1.

27. A nucleic acid construct encoding the combination chimeric membrane proteins of claim 1.

28. A vector comprising the nucleic acid construct of claim 27, wherein said vector is a lentiviral, adenoviral, or retroviral vector.

29. The cell of claim 7, wherein the antigen binding domain is chosen from CD19, CD123, CD22, CD30, CD171, CS-1, CLL-1 (CLECL1), CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, PRSS21, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRCSD, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, legumain, HPV E6, E7, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, or IGLL1.

30. The combination of chimeric membrane proteins of claim 25, wherein the intracellular co-stimulatory domain is a functional signaling domain of a protein selected from the group consisting of: an MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, ICAM-1, LFA-1 (CD11a/CD18), 4-1BB (CD137), B7-H3, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

31. A method of treating a subject with a proliferative disorder, said method comprising administering the cell of claim 26, wherein the cell is a T cell or NK cell.

32. The cell of claim 7, wherein said first and second chimeric proteins both comprise an intracellular co-stimulatory domain derived from the same protein or different endogenous proteins.

33. The cell of claim 26, wherein said cell is selected from an NK cell or T cell.

34. The combination of chimeric membrane proteins of claim 25, wherein the antigen binding domain of the first chimeric membrane protein binds to a tumor antigen chosen from CD19, CD123, CD22, CD30, CD171, CS-1, CLL-1 (CLECL1), CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, PRSS21, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, legumain, HPV E6, E7, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, or IGLL1.

35. The combination of chimeric membrane proteins of claim 25, wherein the antigen binding domain of the first chimeric membrane protein is located N-terminal to said CD3 gamma, delta, or epsilon domain.

36. The combination of chimeric membrane proteins of claim 1, wherein the antigen binding domain of the first or second chimeric membrane protein binds to a tumor antigen chosen from CD19, CD123, CD22, CD30, CD171, CS-1, CLL-1 (CLECL1), CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, PRSS21, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMW-MAA, o-acetyl-GD2, Folate receptor beta, TEM1/CD248, TEM7R, CLDN6, TSHR, GPRCSD, CXORF61, CD97, CD179a, ALK, Polysialic acid, PLAC1, GloboH, NY-BR-1, UPK2, HAVCR1, ADRB3, PANX3, GPR20, LY6K, 0101E2, TARP, WT1, NY-ESO-1, LAGE-1a, legumain, HPV E6, E7, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, or IGLL1.

37. The combination of chimeric membrane proteins of claim 2, wherein said CD3 gamma, delta, or epsilon domain comprises the entire CD3 gamma, delta, or epsilon extracellular domain.

38. The combination of chimeric membrane proteins of claim 2, wherein the first or the second chimeric membrane protein does not comprise any intracellular domain derived from CD3 gamma, delta, or epsilon.

39. The combination of chimeric membrane proteins of claim 21, wherein the extracellular domain of the first or the second chimeric membrane protein comprises the extracellular domain of CD3 epsilon and the intracellular co-stimulatory domain comprises the 4-1BB signaling domain.

40. The combination of chimeric membrane proteins of claim 30, wherein the extracellular domain comprises the extracellular domain of CD3 epsilon and the intracellular co-stimulatory domain comprises the 4-1BB signaling domain.

41. The combination of chimeric membrane proteins of claim 1, wherein the intracellular co-stimulatory domains of the first and second chimeric proteins are derived from the same protein.

42. The combination of chimeric membrane proteins of claim 1, wherein the intracellular co-stimulatory domains of the first and second chimeric proteins are derived from different endogenous proteins.

43. The combination of chimeric membrane proteins of claim 3, wherein the intracellular co-stimulatory domains of the first and second chimeric proteins are derived from the same protein.

44. The combination of chimeric membrane proteins of claim 3, wherein the intracellular co-stimulatory domains of the first and second chimeric proteins are derived from different endogenous proteins.

\* \* \* \* \*